(12) United States Patent
Close et al.

(10) Patent No.: US 7,981,874 B2
(45) Date of Patent: Jul. 19, 2011

(54) PHOSPHORUS DERIVATIVES AS HISTONE DEACETYLASE INHIBITORS

(75) Inventors: Joshua Close, Franklin, MA (US); Jonathan Grimm, Newton, MA (US); Richard W. Heidebrecht, Jr., Brookline, MA (US); Solomon Kattar, Arlington, MA (US); Thomas A. Miller, Brookline, MA (US); Karin M. Otte, Newton Center, MA (US); Scott Peterson, Somerville, MA (US); Phieng Siliphaivanh, Brookline, MA (US); Paul J. Tempest, Brookline, MA (US); Kevin J. Wilson, West Newton, MA (US); David J. Witter, Norfolk, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 262 days.

(21) Appl. No.: 12/309,459

(22) PCT Filed: Jul. 16, 2007

(86) PCT No.: PCT/US2007/016123
§ 371 (c)(1),
(2), (4) Date: Jan. 16, 2009

(87) PCT Pub. No.: WO2008/010985
PCT Pub. Date: Jan. 24, 2008

(65) Prior Publication Data
US 2009/0270351 A1    Oct. 29, 2009

Related U.S. Application Data

(60) Provisional application No. 60/832,014, filed on Jul. 20, 2006, provisional application No. 60/920,541, filed on Mar. 28, 2007.

(51) Int. Cl.
| | |
|---|---|
| *A61K 31/662* | (2006.01) |
| *A61K 31/683* | (2006.01) |
| *A61K 31/67* | (2006.01) |
| *A61K 31/675* | (2006.01) |
| *A61K 31/4747* | (2006.01) |
| *A61K 31/4545* | (2006.01) |
| *A61K 31/4436* | (2006.01) |
| *A61K 31/415* | (2006.01) |
| *A61K 31/427* | (2006.01) |
| *C07F 9/28* | (2006.01) |
| *C07F 9/53* | (2006.01) |
| *C07F 9/40* | (2006.01) |
| *C07F 9/32* | (2006.01) |
| *C07F 9/6571* | (2006.01) |
| *C07F 9/6584* | (2006.01) |
| *C07D 333/20* | (2006.01) |
| *C07D 277/50* | (2006.01) |
| *C07D 231/40* | (2006.01) |
| *C07D 221/20* | (2006.01) |
| *C07F 9/58* | (2006.01) |
| *C07F 9/59* | (2006.01) |

(52) U.S. Cl. ........ 514/110; 514/119; 514/336; 514/370; 514/407; 514/438; 544/1; 546/16; 546/19; 546/22; 548/193; 548/371.4; 549/6

(58) Field of Classification Search ...... 549/6; 548/193, 548/371.4; 546/16, 19, 21, 22; 544/1; 514/110, 514/119, 336, 370, 407, 438; 558/70, 73, 558/81, 190
See application file for complete search history.

(56) References Cited

U.S. PATENT DOCUMENTS

| | | |
|---|---|---|
| 3,339,999 A | 9/1967 | Wick et al. |
| 4,079,049 A | 3/1978 | Ramsay et al. |
| 4,971,957 A | 11/1990 | Tsutsumi et al. |
| 5,369,108 A | 11/1994 | Breslow et al. |
| 5,700,811 A | 12/1997 | Breslow et al. |
| 5,932,616 A | 8/1999 | Breslow et al. |
| 6,087,367 A | 7/2000 | Breslow et al. |
| 6,511,990 B1 | 1/2003 | Breslow et al. |
| 2003/0139404 A1 | 7/2003 | Haag et al. |
| 2004/0142953 A1 | 7/2004 | Delorme et al. |

(Continued)

FOREIGN PATENT DOCUMENTS

DE         1265896        4/1968

(Continued)

OTHER PUBLICATIONS

Schafer et al. Drug Discovery Today 2008, 13 (21/22), 913-916.*

(Continued)

*Primary Examiner* — Jason M Nolan
(74) *Attorney, Agent, or Firm* — Li Su; David A. Muthard

(57) ABSTRACT

The present invention relates to a novel class of phosphorus derivatives. The phosphorus compounds can be used to treat cancer. The phosphorus compounds can also inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases. The present invention further provides pharmaceutical compositions comprising the phosphorus derivatives and safe dosing regimens of these pharmaceutical compositions, which are easy to follow, and which result in a therapeutically effective amount of the phosphorus derivatives in vivo.

17 Claims, No Drawings

U.S. PATENT DOCUMENTS

| | | |
|---|---|---|
| 2004/0192744 A1 | 9/2004 | Haag et al. |
| 2005/0288282 A1 | 12/2005 | Delorme et al. |

FOREIGN PATENT DOCUMENTS

| | | |
|---|---|---|
| EP | 1378510 | 1/2004 |
| EP | 1541574 | 6/2005 |
| GB | 894 960 A | 4/1962 |
| GB | 1 021 194 A | 3/1966 |
| JP | 6-306089 | 11/1994 |
| JP | 11335375 | 12/1999 |
| WO | WO01/30780 | 5/2001 |
| WO | WO01/38322 | 5/2001 |
| WO | WO02/47679 | 6/2002 |
| WO | WO03/013484 | 2/2003 |
| WO | WO03/024448 | 3/2003 |
| WO | WO03/075929 | 9/2003 |
| WO | WO03/076395 | 9/2003 |
| WO | WO03/076422 | 9/2003 |
| WO | WO03/087057 | 10/2003 |
| WO | WO03/092686 | 11/2003 |
| WO | WO2004/058234 | 7/2004 |
| WO | WO2004/062601 | 7/2004 |
| WO | WO2004/069823 | 8/2004 |
| WO | WO2005/030704 | 4/2005 |
| WO | WO2005/030705 | 4/2005 |
| WO | WO2005/092899 | 10/2005 |
| WO | WO 2005/120515 | 12/2005 |

OTHER PUBLICATIONS

Horig et al. Journal of Translational Medicine 2004, 2(44).*
Heidbrecht et al. Bioorganic & Medicinal Chemistry Letters 2009, 19, 2053-2058.*
Lane et al. Journal of Clinical Oncology 2009, 27(32), 5459-5468.*
Bolden et al. Nature Reviews Drug Discovery 2006, 5, 769-784.*
Raposo, C. et al., Journal of the Chemical Society. Perkin Transactions 1, Chemical Society, Letchworth, GB., vol. 15, pp. 2113-2116 (1994).

* cited by examiner

US 7,981,874 B2

PHOSPHORUS DERIVATIVES AS HISTONE DEACETYLASE INHIBITORS

PRIORITY CLAIM

This application is a §371 application of PCT/US07/016123 that was filed on Jul. 16, 2007, which claims priority from the U.S. Provisional Application Numbers 60/832,014, filed on Jul. 20, 2006, and 60/920,541, filed Mar. 28, 2007, now expired.

FIELD OF THE INVENTION

The present invention relates to a novel class of phosphorus derivatives. The phosphorus compounds can be used to treat cancer. The phosphorus compounds can also inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention can also be useful in the prevention and treatment of TRX-mediated diseases, such as autoimmune, allergic and inflammatory diseases, and in the prevention and/or treatment of diseases of the central nervous system (CNS), such as neurodegenerative diseases.

BACKGROUND OF THE INVENTION

Compounds having a hydroxamic acid moiety have been shown to possess useful biological activities. For example, many peptidyl compounds possessing a hydroxamic acid moiety are known to inhibit matrix metalloproteinases (MMPs), which are a family of zinc endopeptidases. The MMPs play a key role in both physiological and pathological tissue degradation. Therefore, peptidyl compounds that have the ability to inhibit the action of MMPs show utility for the treatment or prophylaxis of conditions involving tissue breakdown and inflammation. Further, compounds having a hydroxamic acid moiety have been shown to inhibit histone deacetylases (HDACs), based at least in part on the zinc binding property of the hydroxamic acid group.

The inhibition of HDACs can repress gene expression, including expression of genes related to tumor suppression. Inhibition of histone deacetylase can lead to the histone deacetylase-mediated transcriptional repression of tumor suppressor genes. For example, inhibition of histone deacetylase can provide a method for treating cancer, hematological disorders, such as hematopoiesis, and genetic related metabolic disorders. More specifically, transcriptional regulation is a major event in cell differentiation, proliferation, and apoptosis. There are several lines of evidence that histone acetylation and deacetylation are mechanisms by which transcriptional regulation in a cell is achieved (Grunstein, M., Nature, 389: 349-52 (1997)). These effects are thought to occur through changes in the structure of chromatin by altering the affinity of histone proteins for coiled DNA in the nucleosome. There are five types of histones that have been identified. Histones H2A, $H_2B$, H3 and H4 are found in the nucleosome, and H1 is a linker located between nucleosomes. Each nucleosome contains two of each histone type within its core, except for H1, which is present singly in the outer portion of the nucleosome structure. It is believed that when the histone proteins are hypoacetylated, there is a greater affinity of the histone to the DNA phosphate backbone. This affinity causes DNA to be tightly bound to the histone and renders the DNA inaccessible to transcriptional regulatory elements and machinery.

The regulation of acetylated states occurs through the balance of activity between two enzyme complexes, histone acetyl transferase (HAT) and histone deacetylase (HDAC). The hypoacetylated state is thought to inhibit transcription of associated DNA. This hypoacetylated state is catalyzed by large multiprotein complexes that include HDAC enzymes. In particular, HDACs have been shown to catalyze the removal of acetyl groups from the chromatin core histones.

It has been shown in several instances that the disruption of HAT or HDAC activity is implicated in the development of a malignant phenotype. For instance, in acute promyelocytic leukemia, the oncoprotein produced by the fusion of PML and RAR alpha appears to suppress specific gene transcription through the recruitment of HDACs (Lin, R. J. et al., Nature 391:811-14 (1998)). In this manner, the neoplastic cell is unable to complete differentiation and leads to excess proliferation of the leukemic cell line.

U.S. Pat. Nos. 5,369,108, 5,932,616, 5,700,811, 6,087,367 and 6,511,990, disclose hydroxamic acid derivatives useful for selectively inducing terminal differentiation, cell growth arrest or apoptosis of neoplastic cells. In addition to their biological activity as antitumor agents, these hydroxamic acid derivatives have recently been identified as useful for treating or preventing a wide variety of thioredoxin (TRX)-mediated diseases and conditions, such as inflammatory diseases, allergic diseases, autoimmune diseases, diseases associated with oxidative stress or diseases characterized by cellular hyperproliferation (U.S. application Ser. No. 10/369, 094, filed Feb. 15, 2003). Further, these hydroxamic acid derivatives have been identified as useful for treating diseases of the central nervous system (CNS) such as neurodegenerative diseases and for treating brain cancer (See, U.S. application Ser. No. 10/273,401, filed Oct. 16, 2002).

The inhibition of HDAC by the hydroxamic acid containing compound suberoylanilide hydroxamic acid (SAHA) disclosed in the above referenced U.S. patents, is thought to occur through direct interaction with the catalytic site of the enzyme as demonstrated by X-ray crystallography studies (Finnin, M. S. et al., Nature 401:188-193 (1999)). The result of HDAC inhibition is not believed to have a generalized effect on the genome, but rather, only affects a small subset of the genome (Van Lint, C. et al., Gene Expression 5:245-53 (1996)). Evidence provided by DNA microarrays using malignant cell lines cultured with a HDAC inhibitor shows that there are a finite (1-2%) number of genes whose products are altered. For example, cells treated in culture with HDAC inhibitors show a consistent induction of the cyclin-dependent kinase inhibitor p21 (Archer, S. Shufen, M. Shei, A., Hodin, R. PNAS 95:6791-96 (1998)). This protein plays an important role in cell cycle arrest. HDAC inhibitors are thought to increase the rate of transcription of p21 by propagating the hyperacetylated state of histones in the region of the p21 gene, thereby making the gene accessible to transcriptional machinery. Genes whose expression is not affected by HDAC inhibitors do not display changes in the acetylation of regional associated histones (Dressel, U. et al., Anticancer Research 20(2A): 1017-22 (2000)).

Further, hydroxamic acid derivatives such as SAHA have the ability to induce tumor cell growth arrest, differentiation and/or apoptosis (Richon et al., Proc. Natl. Acad. Sci. USA, 93:5705-5708 (1996)). These compounds are targeted towards mechanisms inherent to the ability of a neoplastic cell to become malignant, as they do not appear to have toxicity in doses effective for inhibition of tumor growth in animals (Cohen, L. A. et al., Anticancer Research 19:4999-5006 (1999)).

In view of the wide variety of applications for compounds containing hydroxamic acid moieties, the development of new inhibitors having improved properties, for example, increased potency or increased bioavailability is highly desirable.

SUMMARY OF THE INVENTION

The present invention relates to a novel class of phosphorus derivatives. The phosphorus compounds can be used to treat cancer. The phosphorus compounds can also inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention may also useful in the prevention and treatment of TRX-mediated diseases, such as autoimmune, allergic and inflammatory diseases, and in the prevention and/or treatment of diseases of the central nervous system (CNS), such as neurodegenerative diseases. The present invention further provides pharmaceutical compositions comprising the phosphorus derivatives, and safe, dosing regimens of these pharmaceutical compositions, which are easy to follow, and which result in a therapeutically effective amount of the phosphorus derivatives in vivo.

It has been unexpectedly discovered that certain phosphorus derivatives show improved activity as histone deacetylase (HDAC) inhibitors.

The present invention thus relates to compounds represented by Formula I and pharmaceutically acceptable salts, solvates and hydrates thereof, as detailed herein.

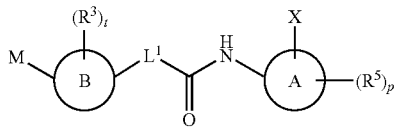

DETAILED DESCRIPTION OF THE INVENTION

The present invention relates to a novel class of phosphorus derivatives. In one embodiment, the phosphorus derivatives can inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating cancer in a subject. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases.

It has been unexpectedly and surprisingly discovered that certain phosphorus derivatives, show improved activity as histone deacetylase (HDAC) inhibitors.

Compounds

The present invention relates to compounds represented by Formula I:

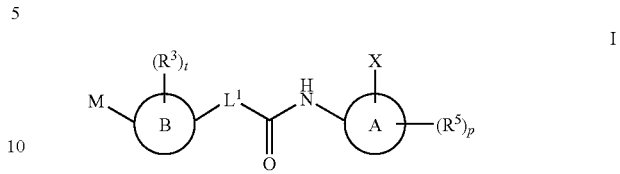

Wherein
Ring A is a 5- to 6-membered heteroaryl or 6-membered aryl;
With the proviso that Ring A is not tetrahydro-dioxo-pyrimidinyl;
Ring B is heteroaryl or aryl;
M is selected from:

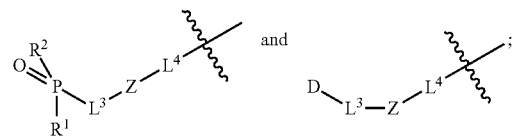

D is a P(O) containing heterocyclyl, wherein the heterocyclyl is optionally substituted with at least one $R^{11}$;
$R^1$ and $R^2$ are independently selected from —OR, —NR$^7$R$^8$, substituted or unsubstituted $C_1$-$C_{10}$ alkyl, substituted or unsubstituted $C_1$-$C_{10}$ alkenyl, substituted or unsubstituted $C_1$-$C_{10}$ alkynyl, substituted or unsubstituted $C_3$-$C_{10}$ cycloalkyl, —(CR$^a_2$)$_r$R$^9$, —ORC(O)OR, —O(CR$^a_2$)$_r$R$^9$, —O(CR$^a_2$)$_r$C(O)NR$^7$R$^8$, —O(CR$^a_2$)$_r$ NR$^7$R$^8$, and —O(CR$^a_2$)$_r$OR;
or $R^1$ and $R^2$ together with the phosphorous atom to which they are attached form a phosphorous-containing heterocyclic ring, wherein the heterocyclic ring is optionally substituted with at least one $R^{11}$;
or $R^2$ and $R^6$ together with the phosphorous and C atom to which they are respectively attached, form a heterocyclic ring, wherein the heterocyclic ring is optionally substituted with at least one $R^{11}$;
or $R^1$ and $R^4$ together with the phosphorous and C atom to which they are respectively attached, form a heterocyclic ring, wherein the heterocyclic ring is optionally substituted with at least one $R^{11}$;
$R^3$ is independently selected from hydrogen, —OR, —NR$^7$R$^8$, —NO$_2$, —CN, —C(O)NR$^7$R$^8$, —NR$^7$R$^8$C(O)R, C(O), $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O) O—, $C_1$-$C_7$ alkyl-C(=O)—, $C_1$-$C_7$ alkynyl, halo, hydroxyalkoxy, $C_1$-$C_7$ alkyl-NHSO$_2$—, $C_1$-$C_7$ alkyl-SO$_2$NH—, $C_1$-$C_7$ alkylsulfonyl, $C_1$-$C_7$ alkylamino or di($C_1$-$C_7$)alkylimino;
$R^4$ and $R^6$ are independently of each other hydrogen, —OR, —NR$^7$R$^8$, halo, —CN, —C(O)NR$^7$R$^8$, —NR$^7$R$^8$C (O)R, —C(O)OR, —P(O)(OR)$_2$, oxo, substituted or unsubstituted $C_1$-$C_6$ alkyl, substituted or unsubstituted $C_1$-$C_4$ alkenyl, substituted or unsubstituted $C_1$-$C_4$ alkynyl, substituted or unsubstituted cycloalkyl, substituted or unsubstituted heteroaryl, substituted or unsubstituted heterocyclic or substituted or unsubstituted aryl;
or $R^4$ and $R^6$ together with the C atom to which they are attached form a heterocyclic or carbocyclic ring, which can be optionally substituted with at least one $R^{11}$;

$R^5$ is independently selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-NHSO$_2$—, $C_1$-$C_7$ alkyl-SO$_2$NH—, $C_1$-$C_7$ alkylsulfonyl, $C_1$-$C_7$ alkylamino or di($C_1$-$C_7$)alkylamino or $L^2$-$R^9$, $R^7$ and $R^8$ are independently selected from hydrogen, $C_1$-$C_7$ alkyl, —C(O)O—$C_1$-$C_7$alkyl, —P(O)$CR^a{}_2$, —P(O)(OR)$_2$, —(CR$^a{}_2$)$_r$heteroaryl, —(CR$^a{}_2$)$_r$heterocyclic, —(CR$^a{}_2$)$_r$$C_3$-$C_8$ cycloalkyl and —(CR$^a{}_2$)$_r$aryl, where alkyl, heteroaryl, heterocyclic, aryl or cycloalkyl is optionally substituted with at least one $R^{11}$;

$R^9$ is independently selected from hydrogen, $C_1$-$C_7$ alkyl, heteroaryl, heterocyclic, aryl, and $C_3$-$C_8$ cycloalkyl, where alkyl, heteroaryl, heterocyclic, aryl or cycloalkyl is optionally substituted with at least one $R^{11}$;

$R^{11}$ is independently selected from OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-NHSO$_2$—, $C_1$-$C_7$ alkyl-SO$_2$NH—, $C_1$-$C_7$ alkylsulfonyl, $C_1$-$C_7$ alkylamino or di($C_1$-$C_7$)alkylamino;

R is independently H, $C_1$-$C_7$ alkyl, or $C_3$-$C_{10}$ cycloalkyl, where alkyl or cycloalkyl is optionally substituted with at least one $R^{11}$;

$R^a$ is independently selected from H and $C_1$-$C_7$ alkyl, where $C_1$-$C_7$ alkyl is optionally substituted with at least one $R^{11}$;

$L^1$ is (CH$_2$)$_r$, ethenyl or cyclopropyl;

$L^2$ is independently selected from a bond, $C_1$-$C_4$ alkylene, $C_1$-$C_4$ alkynyl, $C_1$-$C_4$ alkenyl, —O—, —S—, —N—, —C(=O)NH—, —NHC(=O)—, —NHC(=O)NH—, —SO$_2$NH—, —NHSO$_2$—, —SO$_2$—, —C(=O)— or —C(=O)O—;

$L^3$ is a bond, —(CR$^a{}_2$)$_r$C(O)(CR$^a{}_2$)$_r$—, —(CR$^a{}_2$)$_r$O(CR$^a{}_2$)$_r$—, —(CR$^a{}_2$)$_r$C(O)NR$^7$(CR$^a{}_2$)$_r$—, —(CR$^a{}_2$)$_r$NR$^7$C(O)(CR$^a{}_2$)$_r$—, —(CR$^a{}_2$)$_r$NR$^7$C(O)NR$^7$(CR$^a{}_2$)$_r$—, —(CR$^a{}_2$)$_r$OC(O)NR$^7$(CR$^a{}_2$)$_r$—, —(CR$^a{}_2$)$_r$NR$^7$C(O)O(CR$^a{}_2$)$_r$ or —(CR$^a{}_2$)$_r$NR$^7$(CR$^a{}_2$)$_r$—, —(CR$^4$R$^6$)$_n$—;

$L^4$ is a bond, —(CR$^a{}_2$)$_r$C(O)(CR$^a{}_2$)$_r$—, —(CR$^a{}_2$)$_r$O(CR$^a{}_2$)$_r$—, —(CR$^a{}_2$)$_r$C(O)NR$^7$(CR$^a{}_2$)$_r$—, —(CR$^a{}_2$)$_r$NR$^7$C(O)(CR$^a{}_2$)$_r$—, —(CR$^a{}_2$)$_r$NR$^7$C(O)NR$^7$(CR$^a{}_2$)$_r$—, —(CR$^a{}_2$)$_r$OC(O)NR$^7$(CR$^a{}_2$)$_r$—, —(CR$^a{}_2$)$_r$NR$^7$C(O)O(CR$^a{}_2$)$_r$ or —(CR$^a{}_2$)$_r$NR$^7$(CR$^a{}_2$)$_r$—, —(CR$^4$R$^6$)$_n$—;

X is SH or $NH_2$;

Z is a bond, heteroaryl, heterocyclic, aryl, or $C_3$-$C_8$ cycloalkyl, where heteroaryl, heterocyclic, aryl or cycloalkyl is optionally substituted with at least one $R^{11}$;

n is 0, 1, 2, 3 or 4;

p is 1, 2, 3 or 4;

r is independently 0, 1, 2 or 3;

t is 1, 2, 3, or 4;

or a stereoisomer or pharmaceutically acceptable salt thereof.

In another embodiment of the invention,

Ring A is a 5- to 6-membered heteroaryl or 6-membered aryl;

With the proviso that Ring A is not tetrahydro-dioxo-pyrimidinyl;

Ring B is heteroaryl or aryl;

M is selected from:

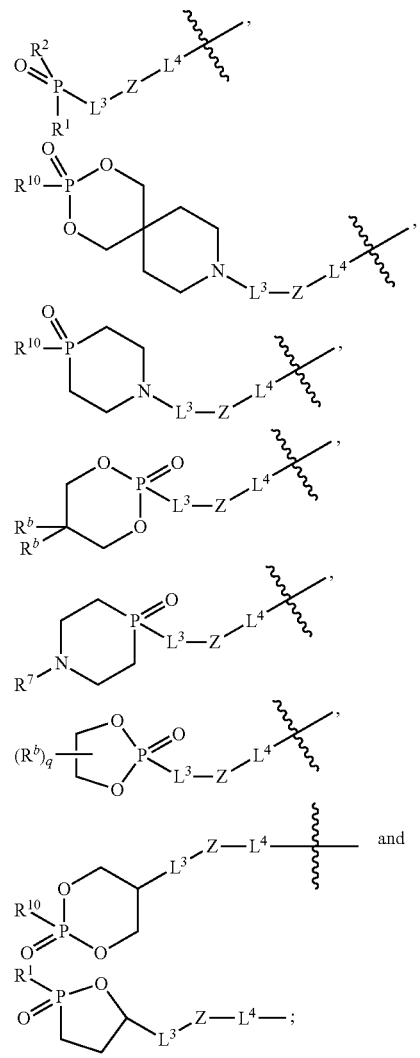

$R^1$ and $R^2$ are independently selected from —OR, —NR$^7$R$^8$, substituted or unsubstituted $C_1$-$C_{10}$ alkyl, substituted or unsubstituted $C_1$-$C_{10}$ alkenyl, substituted or unsubstituted $C_1$-$C_{10}$ alkynyl, substituted or unsubstituted $C_3$-$C_{10}$ cycloalkyl, —(CR$^a{}_2$)$_r$R$^9$, —ORC(O)OR, —O(CR$^a{}_2$)$_r$R$^9$, —O(CR$^a{}_2$)$_r$C(O)NR$^7$R$^8$, —O(CR$^a{}_2$), NR$^7$R$^8$, and —O(CR$^a{}_2$)$_r$OR;

or $R^1$ and $R^2$ together with the phosphorous atom to which they are attached form a phosphorous-containing heterocyclic ring, optionally substituted with at least one $R^{11}$;

or $R^2$ and $R^6$ together with the phosphorous and C atom to which they are respectively attached, form a heterocyclic ring, optionally substituted with at least one $R^{11}$;

or $R^1$ and $R^4$ together with the phosphorous and C atom to which they are respectively attached, form a heterocyclic ring, optionally substituted with at least one $R^{11}$;

$R^3$ is independently selected from hydrogen, —OR, —NR$^7$R$^8$, —NO$_2$, —CN, —C(O)NR$^7$R$^8$, —NR$^7$R$^8$C(O)R, C(O), $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-NHSO$_2$—, $C_1$-$C_7$ alkyl-SO$_2$NH—, $C_1$-$C_7$ alkylsulfonyl, $C_1$-$C_7$ alkylamino or di($C_1$-$C_7$)alkylamino;

R⁴ and R⁶ are independently of each other hydrogen, —OR, —NR⁷R⁸, halo, —CN, —C(O)NR⁷R⁸, —NR⁷R⁸C(O)R, —C(O)OR, —P(O)(OR)₂, oxo, substituted or unsubstituted C₁-C₆ alkyl, substituted or unsubstituted C₁-C₄ alkenyl, substituted or unsubstituted C₁-C₄ alkynyl, substituted or unsubstituted cycloalkyl, substituted or unsubstituted heteroaryl, substituted or unsubstituted heterocyclic or substituted or unsubstituted aryl;

or R⁴ and R⁶ together with the C atom to which they are attached form a heterocyclic or carbocyclic ring, optionally substituted with at least one R¹¹;

R⁵ is independently selected from hydrogen, OH, NH₂, nitro, CN, amide, carboxyl, C₁-C₇ alkoxy, C₁-C₇ alkyl, C₁-C₇ haloalkyl, C₁-C₇ haloalkyloxy, C₁-C₇ hydroxyalkyl, C₁-C₇ alkenyl, C₁-C₇ alkyl-C(=O)O—, C₁-C₇ alkyl-C(=O)—, C₁-C₇ alkynyl, halo, hydroxyalkoxy, C₁-C₇ alkyl-NHSO₂—, C₁-C₇ alkyl-SO₂NH—, C₁-C₇ alkylsulfonyl, C₁-C₇ alkylamino or di(C₁-C₇)alkylamino or L²-R⁹, R⁷ and R⁸ are independently selected from hydrogen, C₁-C₇ alkyl, —C(O)O—C₁-C₇alkyl, —P(O)CR^a₂, —P(O)(OR)₂, —(CR^a₂)ᵣheteroaryl, —(CR^a₂)ᵣheterocyclic, —(CR^a₂)ᵣC₃-C₈ cycloalkyl and —(CR^a₂)ᵣaryl, where alkyl, heteroaryl, heterocyclic, aryl or cycloalkyl is optionally substituted with at least one R¹¹;

R⁹ is independently selected from hydrogen, C₁-C₇ alkyl, heteroaryl and aryl, where alkyl, heteroaryl or aryl is optionally substituted with at least one R¹¹;

R¹⁰ is independently selected from hydrogen, C₁-C₇ alkyl, —(CR^a₂)ᵣheteroaryl, —(CR^a₂)ᵣheterocyclic, —(CR^a₂)ᵣC₃-C₈ cycloalkyl and —(CR^a₂)ᵣaryl, where alkyl, heteroaryl, heterocyclic, aryl or cycloalkyl is optionally substituted with at least one R¹¹;

R¹¹ is independently selected from OH, NH₂, nitro, CN, amide, carboxyl, C₁-C₇ alkoxy, C₁-C₇ alkyl, C₁-C₇ haloalkyl, C₁-C₇ haloalkyloxy, C₁-C₇ hydroxyalkyl, C₁-C₇ alkenyl, C₁-C₇ alkyl-C(=O)O—, C₁-C₇ alkyl-C(=O)—, C₁-C₇ alkynyl, halo, hydroxyalkoxy, C₁-C₇ alkyl-NHSO₂—, C₁-C₇ alkyl-SO₂NH—, C₁-C₇ alkylsulfonyl, C₁-C₇ alkylamino or di(C₁-C₇)alkylamino;

R is independently H, C₁-C₇ alkyl, or C₃-C₁₀ cycloalkyl, where alkyl or cycloalkyl is optionally substituted with at least one R¹¹;

R^a is independently selected from H and C₁-C₇ alkyl, where C₁-C₇ alkyl is optionally substituted with at least one R¹¹;

R^b is independently selected from H and C₁-C₇ alkyl, where C₁-C₇ alkyl is optionally substituted with at least one R¹¹;

L¹ is (CH₂)ᵣ, ethenyl or cyclopropyl;

L² is independently selected from a bond, C₁-C₄ alkylene, C₁-C₄ alkynyl, C₁-C₄ alkenyl, —O—, —S—, —N—, —C(=O)NH—, —NHC(=O)—, —NHC(=O)NH—, —SO₂NH—, —NHSO₂—, —SO₂—, —C(=O)— or —C(=O)O—;

L³ is a bond, —(CR^a₂)ᵣC(O)(CR^a₂)ᵣ—, —(CR^a₂)ᵣO(CR^a₂)ᵣ—, (CR^a₂)ᵣC(O)NR⁷(cR^a₂)ᵣ—, —(CR^a₂)ᵣNR⁷C(O)(CR^a₂)ᵣ—, —(CR^a₂)ᵣNR⁷C(O)NR⁷(CR^a₂)ᵣ—, —(CR^a₂)ᵣC(O)NR⁷(CR^a₂)ᵣ—, —(CR^a₂)ᵣNR⁷C(O)O(CR^a₂)ᵣ— or —(CR^a₂)ᵣNR⁷(CR^a₂)ᵣ—, —(CR⁴R⁶)ₙ—;

L⁴ is a bond, —(CR^a₂)ᵣC(O)(CR^a₂)ᵣ—, —(CR^a₂)ᵣO(CR^a₂)ᵣ—, —(CR^a₂)ᵣC(O)NR⁷(CR^a₂)ᵣ—, —(CR^a₂)ᵣNR⁷C(O)(CR^a₂)ᵣ—, —(CR^a₂)ᵣNR⁷C(O)NR⁷(CR^a₂)ᵣ—, —(CR^a₂)ᵣOC(O)NR⁷(CR^a₂)ᵣ—, —(CR^a₂)ᵣNR⁷C(O)O(CR^a₂)ᵣ or —(CR^a₂)ᵣNR⁷(CR^a₂)ᵣ—, —(CR⁴R⁶)ₙ—;

X is SH or NH₂;

Z is a bond, heteroaryl, heterocyclic, aryl, or C₃-C₈ cycloalkyl, where heteroaryl, heterocyclic, aryl or cycloalkyl is optionally substituted with at least one R¹¹;

n is 0, 1, 2, 3 or 4;
p is 1, 2, 3 or 4;
q is 1 or 2;
r is independently 0, 1, 2 or 3;
t is 1, 2, 3, or 4;
or a stereoisomer or pharmaceutically acceptable salt thereof.

In another embodiment of the invention,
Ring A is a 5- to 6-membered heteroaryl or 6-membered aryl;
With the proviso that Ring A is not tetrahydro-dioxo-pyrimidinyl;
Ring B is heteroaryl or aryl;
M is selected from:

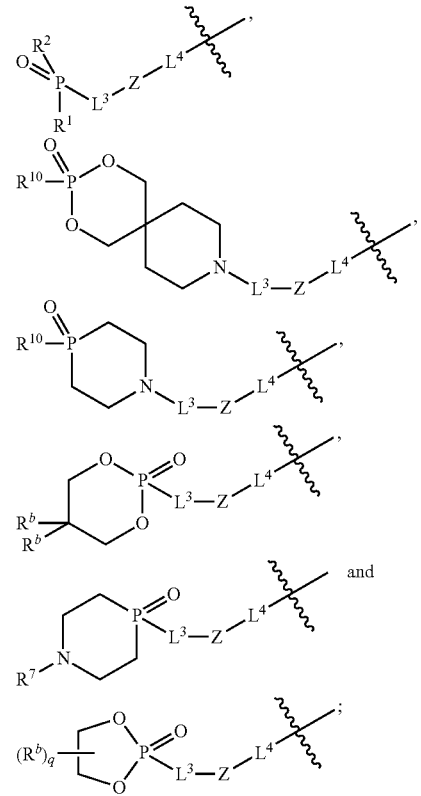

R¹ and R² are independently selected from —OR, —NR⁷R⁸, substituted or unsubstituted C₁-C₁₀ alkyl, substituted or unsubstituted C₁-C₁₀ alkenyl, substituted or unsubstituted C₁-C₁₀ alkynyl, substituted or unsubstituted C₃-C₁₀ cycloalkyl, —(CR^a₂)ᵣR⁹, —ORC(O)OR, —O(CR^a₂)ᵣR⁹, —O(CR^a₂)ᵣC(O)NR⁷R⁸, —O(CR^a₂)ᵣNR⁷R⁸, and —O(CR^a₂)ᵣOR;

or R¹ and R² together with the phosphorous atom to which they are attached form a phosphorous-containing heterocyclic ring;

or R² and R⁶ together with the phosphorous and C atom to which they are respectively attached, form a heterocyclic ring;

or R¹ and R⁴ together with the phosphorous and C atom to which they are respectively attached, form a heterocyclic ring;

R³ is independently selected from hydrogen, —OR, —NR⁷R⁸, —NO₂, —CN, —C(O)NR⁷R⁸, —NR⁷R⁸C(O)R, C(O), C₁-C₇ alkyl, C₁-C₇ haloalkyl, C₁-C₇ haloalkyloxy, C₁-C₇ hydroxyalkyl, C₁-C₇ alkenyl, C₁-C₇ alkyl-C(=O)O—, C₁-C₇ alkyl-C(=O)—, C₁-C₇ alkynyl, halo, hydroxyalkoxy, C₁-C₇ alkyl-NHSO₂—, C₁-C₇ alkyl-SO₂NH—, C₁-C₇ alkylsulfonyl, C₁-C₇ alkylamino or di(C₁-C₇)alkylamino;

R⁴ and R⁶ are independently of each other hydrogen, —OR, —NR⁷R⁸, halo, —CN, —C(O)NR⁷R⁸, —NR⁷R⁸C(O)R, —C(O)OR, —P(O)(OR)₂, oxo, substituted or unsubstituted C₁-C₆ alkyl, substituted or unsubstituted C₁-C₄ alkenyl, substituted or unsubstituted C₁-C₄ alkynyl, substituted or unsubstituted cycloalkyl, substituted or unsubstituted heteroaryl, substituted or unsubstituted heterocyclic or substituted or unsubstituted aryl;

or R⁴ and R⁶ together with the C atom to which they are attached form a heterocyclic or carbocyclic ring;

R⁵ is independently selected from hydrogen, OH, NH₂, nitro, CN, amide, carboxyl, C₁-C₇ alkoxy, C₁-C₇ alkyl, C₁-C₇ haloalkyl, C₁-C₇ haloalkyloxy, C₁-C₇ hydroxyalkyl, C₁-C₇ alkenyl, C₁-C₇ alkyl-C(=O)O—, C₁-C₇ alkyl-C(=O)—, C₁-C₇ alkynyl, halo, hydroxyalkoxy, C₁-C₇ alkyl-NHSO₂—, C₁-C₇ alkyl-SO₂NH—, C₁-C₇ alkylsulfonyl, C₁-C₇ alkylamino or di(C₁-C₇)alkylamino or L²-R⁹, R⁷ and R⁸ are independently selected from hydrogen, C₁-C₇ alkyl, —(CRᵃ₂)ᵣheteroaryl, —(CRᵃ₂)ᵣheterocyclic, —(CRᵃ₂)ᵣC₃-C₈ cycloalkyl and —(CRᵃ₂)ᵣaryl, where alkyl, heteroaryl, heterocyclic, aryl or cycloalkyl is optionally substituted with at least one R¹¹;

R⁹ is independently selected from hydrogen, C₁-C₇ alkyl, heteroaryl, heterocyclic, aryl, and C₃-C₈ cycloalkyl, where alkyl, heteroaryl, heterocyclic, aryl or cycloalkyl is optionally substituted with at least one R¹¹;

R¹⁰ is independently selected from hydrogen, C₁-C₇ alkyl, —(CRᵃ₂)ᵣheteroaryl, —(CRᵃ₂)ᵣheterocyclic, —(CRᵃ₂)ᵣC₃-C₈ cycloalkyl and —(CRᵃ₂)ᵣaryl, where alkyl, heteroaryl, heterocyclic, aryl or cycloalkyl is optionally substituted with at least one R¹¹;

R¹¹ is independently selected from OH, NH₂, nitro, CN, amide, carboxyl, C₁-C₇ alkoxy, C₁-C₇ alkyl, C₁-C₇ haloalkyl, C₁-C₇ haloalkyloxy, C₁-C₇ hydroxyalkyl, C₁-C₇ alkenyl, C₁-C₇ alkyl-C(=O)O—, C₁-C₇ alkyl-C(=O)—, C₁-C₇ alkynyl, halo, hydroxyalkoxy, C₁-C₇ alkyl-NHSO₂—, C₁-C₇ alkyl-SO₂NH—, C₁-C₇ alkylsulfonyl, C₁-C₇ alkylamino or di(C₁-C₇)alkylamino;

R is independently H, C₁-C₇ alkyl, or C₃-C₁₀ cycloalkyl, where alkyl or cycloalkyl is optionally substituted with at least one R¹¹;

Rᵃ is independently selected from H and C₁-C₇ alkyl, where C₁-C₇ alkyl is optionally substituted with at least one R¹¹;

Rᵇ is independently selected from H and C₁-C₇ alkyl, where C₁-C₇ alkyl is optionally substituted with at least one R¹¹;

L¹ is (CH₂)ᵣ, ethenyl or cyclopropyl;

L² is independently selected from a bond, C₁-C₄ alkylene, C₁-C₄ alkynyl, C₁-C₄ alkenyl, —O—, —S—, —N—, —C(=O)NH—, —NHC(=O)—, —NHC(=O)NH—, —SO₂NH—, —NHSO₂—, —SO₂—, —C(=O)— or —C(=O)O—;

L³ is a bond, —(CRᵃ₂)ᵣC(O)—, —(CRᵃ₂)ᵣO—, —(CRᵃ₂)ᵣC(O)NR⁷—, —(CRᵃ₂)ᵣNR⁷C(O)—, —(CRᵃ₂)ᵣNR⁷C(O)NR⁷—, —(CR)OC(O)NR⁷—, —(CRᵃ₂)ᵣNR⁷C(O)O—, —(CRᵃ₂)ᵣNR⁷—, or —(CR⁴R⁶)ₙ—;

L⁴ is a bond, —(CRᵃ₂)ᵣC(O)—, —(CRᵃ₂)ᵣO—, —(CRᵃ₂)ᵣC(O)NR⁷—, —(CRᵃ₂)ᵣNR⁷C(O)—, —(CRᵃ₂)ᵣNR⁷C(O)NR⁷—, —(CRᵃ₂)ᵣOC(O)NR⁷—, —(CRᵃ₂)ᵣNR⁷C(O)O—, —(CRᵃ₂)ᵣNR⁷— or —(CR⁴R⁶)ₙ—;

X is SH or NH₂;

Z is a bond, heteroaryl, heterocyclic, aryl, or C₃-C₈ cycloalkyl, where heteroaryl, heterocyclic, aryl or cycloalkyl is optionally substituted with at least one R¹¹;

n is 0, 1, 2, 3 or 4;

p is 1, 2, 3 or 4;

q is 1 or 2;

r is independently 0, 1, 2 or 3;

t is 1, 2, 3, or 4;

or a stereoisomer or pharmaceutically acceptable salt thereof.

In another embodiment of the invention,

Ring A is a 5- to 6-membered heteroaryl or 6-membered aryl;
With the proviso that Ring A is not tetrahydro-dioxo-pyrimidinyl;
Ring B is heteroaryl or aryl;
M is selected from:

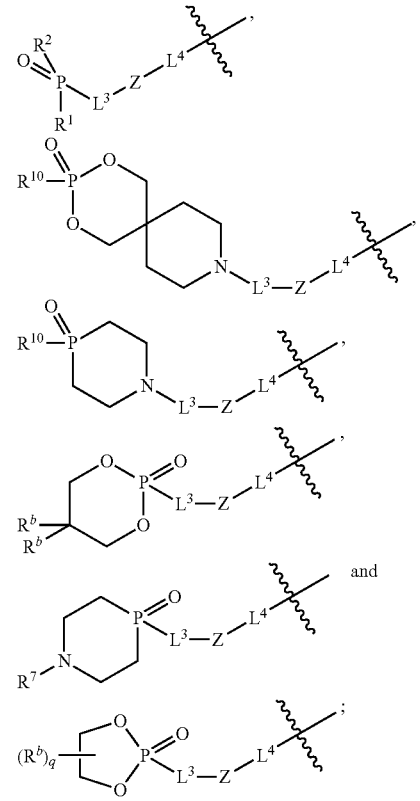

R¹ and R² are independently selected from —OR, —NR⁷R⁸, unsubstituted C₁-C₁₀ alkyl, unsubstituted C₃-C₁₀ cycloalkyl, —(CRᵃ₂)ᵣR⁹, —ORC(O)OR, —O(CRᵃ₂)ᵣR⁹, —O(CRᵃ₂)ᵣC(O)NR⁷R⁸, —O(CRᵃ₂)ᵣNR⁷R⁸, and —O(CRᵃ₂)ᵣOR;

or R¹ and R² together with the phosphorous atom to which they are attached form a phosphorous-containing heterocyclic ring;

R³ is hydrogen;

R⁴ and R⁶ are independently of each other hydrogen, —OR, —NH₂, halo, —CN, —C(O)NH₂, —NH₂C(O)R, —C(O)OR, —P(O)(OR)₂, oxo, unsubstituted C₁-C₆ alkyl;

R⁵ is L²-R⁹;

R⁷ and R⁸ are independently selected from hydrogen, C₁-C₇ alkyl, —(CRᵃ₂)ᵣheteroaryl, —(CRᵃ₂)ᵣheterocyclic, —(CRᵃ₂)ᵣC₃-C₈ cycloalkyl and —(CRᵃ₂)ᵣaryl, where alkyl, heteroaryl, heterocyclic, aryl or cycloalkyl is optionally substituted with at least one R¹¹;

$R^9$ is independently selected from hydrogen, $C_1$-$C_7$ alkyl, heteroaryl and aryl, where heteroaryl, aryl or alkyl is optionally substituted with at least one $R^{11}$;

$R^{10}$ is independently selected from unsubstituted $C_1$-$C_7$ alkyl or unsubstituted aryl;

$R^{11}$ is independently selected from $C_1$-$C_7$ alkyl, halo, $CF_3$, OH or $C_1$-$C_7$ alkoxy;

R is independently H, $C_1$-$C_7$ alkyl, or $C_3$-$C_{10}$ cycloalkyl, where alkyl or cycloalkyl is optionally substituted with at least one $R^{11}$;

$R^a$ is independently selected from H and $C_1$-$C_7$ alkyl, where $C_1$-$C_7$ alkyl is optionally substituted with at least one $R^{11}$;

$R^b$ is independently selected from H and $C_1$-$C_7$ alkyl, where $C_1$-$C_7$ alkyl is optionally substituted with at least one $R^{11}$;

$L^1$ is $(CH_2)_r$ or ethenyl;

$L^2$ is a bond;

$L^3$ is a bond, —$(CR^a_2)_rO$—, —$(CR^a_2)_rC(O)$—, —$(CR^a_2)_rNR^7$—, —$(CR^4R^6)_n$—;

$L^4$ is a bond or —$(CR^4R^6)_n$—;

X is $NH_2$;

Z is a bond, heteroaryl, heterocyclic, aryl, or $C_3$-$C_8$ cycloalkyl, where heteroaryl, heterocyclic, aryl or cycloalkyl is optionally substituted with at least one $R^{11}$;

n is 0, 1 or 2;

p is 1, 2, 3 or 4;

q is 1 or 2;

r is independently 0, 1, 2 or 3;

t is 1, 2, 3, or 4;

or a stereoisomer or pharmaceutically acceptable salt thereof.

In another embodiment of the invention, compounds are represented by Formula IA,

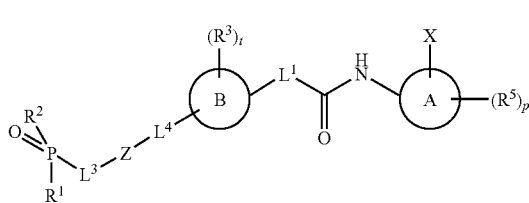

IA

Ring A is a 5- to 6-membered heteroaryl or 6-membered aryl;

With the proviso that Ring A is not tetrahydro-dioxo-pyrimidinyl;

Ring B is heteroaryl or aryl;

$R^1$ and $R^2$ are independently selected from —OR, —$NR^7R^8$, substituted or unsubstituted $C_1$-$C_{10}$ alkyl, substituted or unsubstituted $C_1$-$C_{10}$ alkenyl, substituted or unsubstituted $C_1$-$C_{10}$ alkynyl, substituted or unsubstituted $C_3$-$C_{10}$ cycloalkyl, —$(CR^a_2)_rR^9$, —$ORC(O)OR$, —$O(CR^a_2)_rR^9$, —$O(CR^a_2)_rC(O)NR^7R$, —$O(CR^a_2)_rNR^7R^8$, and —$O(CR^a_2)_rOR$;

$R^3$ is independently selected from hydrogen, —OR, —$NR^7R^8$, —$NO_2$, —CN, —$C(O)NR^7R^8$, —$NR^7R^8C(O)R$, $C(O)$, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-NHSO$_2$—, $C_1$-$C_7$ alkyl-SO$_2$NH—, $C_1$-$C_7$ alkylsulfonyl, $C_1$-$C_7$ alkylamino or di($C_1$-$C_7$)alkylamino;

$R^4$ and $R^6$ are independently of each other hydrogen, —OR, —$NR^7R^8$, halo, —CN, —$C(O)NR^7R^8$, —$NR^7R^8C(O)R$, —$C(O)OR$, —$P(O)(OR)_2$, oxo, substituted or unsubstituted $C_1$-$C_6$ alkyl, substituted or unsubstituted $C_1$-$C_4$ alkenyl, substituted or unsubstituted $C_1$-$C_4$ alkynyl, substituted or unsubstituted cycloalkyl, substituted or unsubstituted heteroaryl, substituted or unsubstituted heterocyclic or substituted or unsubstituted aryl;

$R^5$ is independently selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-NHSO$_2$—, $C_1$-$C_7$ alkyl-SO$_2$NH—, $C_1$-$C_7$ alkylsulfonyl, $C_1$-$C_7$ alkylamino or di($C_1$-$C_7$)alkylamino or $L^2$-$R^9$, $R^7$ and $R^8$ are independently selected from hydrogen, $C_1$-$C_7$ alkyl, —$(CR^a_2)_t$heteroaryl, —$(CR^a_2)_t$heterocyclic, —$(CR^a_2)_tC_3$-$C_8$ cycloalkyl and —$(CR^a_2)_t$aryl, where alkyl, heteroaryl, heterocyclic, aryl or cycloalkyl is optionally substituted with at least one $R^{11}$;

$R^9$ is independently selected from hydrogen, $C_1$-$C_7$ alkyl, heteroaryl, heterocyclic, aryl, and $C_3$-$C_8$ cycloalkyl, where alkyl, heteroaryl, heterocyclic, aryl or cycloalkyl is optionally substituted with at least one $R^{11}$;

$R^{11}$ is independently selected from OH, NIH2, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-NHSO$_2$—, $C_1$-$C_7$ alkyl-SO$_2$NH—, $C_1$-$C_7$ alkylsulfonyl, $C_1$-$C_7$ alkylamino or di($C_1$-$C_7$)alkylamino;

R is independently H, $C_1$-$C_7$ alkyl, or $C_3$-$C_{10}$ cycloalkyl, where alkyl or cycloalkyl is optionally substituted with at least one $R^{11}$;

$R^a$ is independently selected from H and $C_1$-$C_7$ alkyl, where $C_1$-$C_7$ alkyl is optionally substituted with at least one $R^{11}$;

$L^1$ is $(CH_2)_r$, ethenyl or cyclopropyl;

$L^2$ is independently selected from a bond, $C_1$-$C_4$ alkylene, $C_1$-$C_4$ alkynyl, $C_1$-$C_4$ alkenyl, —O—, —S—, —N—, —C(=O)NH—, —NHC(=O)—, —NHC(=O)NH—, —SO$_2$NH—, —NHSO$_2$—, —SO$_2$—, —C(=O)— or —C(=O)O—;

$L^3$ is a bond, —$(CR^a_2)_rC(O)$—, —$(CR^a_2)_rO$—, —$(CR^a_2)_rC(O)NR^7$—, —$(CR^a_2)_rNR^7C(O)$—, —$(CR^a_2)_rNR^7C(O)NR^7$—, —$(CR^a_2)_rOC(O)NR^7$—, —$(CR^a_2)_rNR^7C(O)O$— or —$(CR^a_2)_rNR^7$—, —$(CR^4R^6)_n$—;

$L^4$ is a bond, —$(CR^a_2)_rC(O)$—, —$(CR^a_2)_rO$—, —$(CR^a_2)_rC(O)NR^7$—, —$(CR^a_2)_rNR^7C(O)$—, —$(CR^a_2)_rNR^7C(O)NR^7$—, —$(CR^a_2)_rOC(O)NR^7$—, —$(CR^a_2)_rNR^7C(O)O$— or —$(CR^a_2)_rNR^7$—, —$(CR^4R^6)_n$—;

X is SH or $NH_2$;

Z is a bond, heteroaryl, heterocyclic, aryl, or $C_3$-$C_8$ cycloalkyl, where heteroaryl, heterocyclic, aryl or cycloalkyl is optionally substituted with at least one $R^{11}$;

n is 0, 1, 2, 3 or 4;

p is 1, 2, 3 or 4;

r is independently 0, 1, 2 or 3;

t is 1, 2, 3, or 4;

or a stereoisomer or pharmaceutically acceptable salt thereof.

In another embodiment of the invention under Formula IA, Ring A is a 5- to 6-membered heteroaryl or 6-membered aryl;

With the proviso that Ring A is not tetrahydro-dioxo-pyrimidinyl;

Ring B is heteroaryl or aryl;

$R^1$ and $R^2$ are independently selected from —OR, —$NR^7R^8$, unsubstituted $C_1$-$C_{10}$ alkyl, unsubstituted $C_3$-$C_{10}$ cycloalkyl, —$(CR^a_2)_tR^9$, —$ORC(O)OR$, —$O(CR^a_2)_tR^9$, —$O(CR^a_2)_rC(O)NR^7R^8$, —$O(CR^a_2)_rNR^7R^8$, and —$O(CR^a_2)_rOR$;

$R^3$ is hydrogen;

$R^4$ and $R^6$ are independently of each other hydrogen, —OR, —$NH_2$, halo, —CN, —C(O)$NH_2$, —$NH_2$C(O)R, —C(O)OR, —P(O)(OR)$_2$, oxo, unsubstituted $C_1$-$C_6$ alkyl;

$R^5$ is L-$R^9$;

$R^7$ and $R^8$ are independently selected from hydrogen, $C_1$-$C_7$ alkyl, —(C$R^a{}_2$)$_r$heteroaryl, —(C$R^a{}_2$)$_r$heterocyclic, —(C$R^a{}_2$)$_r$$C_3$-$C_8$ cycloalkyl and —(C$R^a{}_2$)$_r$aryl, where alkyl, heteroaryl, heterocyclic, aryl or cycloalkyl is optionally substituted with at least one $R^{11}$;

$R^9$ is independently selected from hydrogen, $C_1$-$C_7$ alkyl, heteroaryl and aryl, where heteroaryl, aryl or alkyl is optionally substituted with at least one $R^{11}$;

$R^{11}$ is independently selected from $C_1$-$C_7$ alkyl, halo, $CF_3$, OH or $C_1$-$C_7$ alkoxy;

R is independently H, $C_1$-$C_7$ alkyl, or $C_3$-$C_{10}$ cycloalkyl, where alkyl or cycloalkyl is optionally substituted with at least one $R^{11}$;

$R^a$ is independently selected from H and $C_1$-$C_7$ alkyl, where $C_1$-$C_7$ alkyl is optionally substituted with at least one $R^{11}$;

$L^1$ is (C$H_2$)$_r$ or ethenyl;

$L^2$ is a bond;

$L^3$ is a bond, —(C$R^a{}_2$)$_r$C(O)—, —(C$R^a{}_2$)$_r$O—, —(C$R^a{}_2$)$_r$C(O)N$R^7$—, —(C$R^a{}_2$)$_r$N$R^7$C(O)—, —(C$R^a{}_2$)$_r$N$R^7$C(O)N$R^7$—, —(C$R^a{}_2$)$_r$OC(O)N$R^7$—, —(C$R^a{}_2$)$_r$N$R^7$C(O)O— or (C$R^a{}_2$)$_r$N$R^7$—, —(C$R^4R^6$)$_n$—;

$L^4$ is a bond, —(C$R^a{}_2$)$_r$C(O)—, —(C$R^a{}_2$)$_r$O—, —(C$R^a{}_2$)$_r$C(O)N$R^7$—, —(C$R^a{}_2$)$_r$N$R^7$C(O)—, —(C$R^a{}_2$)$_r$N$R^7$C(O)N$R^7$—, —(C$R^a{}_2$)$_r$OC(O)N$R^7$—, —(C$R^a{}_2$)$_r$N$R^7$C(O)O— or —(C$R^a{}_2$)$_r$N$R^7$—, —(C$R^4R^6$)$_n$—;

X is $NH_2$;

Z is a bond, heteroaryl, heterocyclic, aryl, or $C_3$-$C_8$ cycloalkyl, where heteroaryl, heterocyclic, aryl or cycloalkyl is optionally substituted with at least one $R^{11}$;

n is 0, 1 or 2;

p is 1, 2, 3 or 4;

r is independently 0, 1, 2 or 3;

t is 1, 2, 3, or 4;

or a stereoisomer or pharmaceutically acceptable salt thereof.

In another embodiment of the invention under Formula IA, Ring A is phenyl, pyridyl or pyrimidinyl;

Ring B is heteroaryl or aryl;

$R^1$ and $R^2$ are independently selected from —OR, unsubstituted $C_1$-$C_{10}$ alkyl, unsubstituted $C_3$-$C_{10}$ cycloalkyl, —(C$R^a{}_2$)$_r$$R^9$ or —O(C$R^a{}_2$)$_r$$R^9$;

$R^3$ is hydrogen;

$R^4$ and $R^6$ are independently of each other hydrogen, —OR, —$NH_2$, halo, —CN, —C(O)$NH_2$, —$NH_2$C(O)R, —C(O)OR, —P(O)(OR)$_2$, oxo, unsubstituted $C_1$-$C_6$ alkyl;

$R^5$ is $L^2$-$R^9$;

$R^9$ is independently selected from hydrogen, $C_1$-$C_7$ alkyl, heteroaryl and aryl, where heteroaryl, aryl or alkyl is optionally substituted with at least one $R^{11}$;

$R^{11}$ is independently selected from $C_1$-$C_7$ alkyl, halo, haloalkyl, OH or $C_1$-$C_7$ alkoxy;

R is independently H, $C_1$-$C_7$ alkyl, or $C_3$-$C_{10}$ cycloalkyl, where alkyl or cycloalkyl is optionally substituted with at least one $R^{11}$;

$R^a$ is independently selected from H and $C_1$-$C_7$ alkyl, where $C_1$-$C_7$ alkyl is optionally substituted with at least one $R^{11}$;

$L^1$ is (C$H_2$)$_r$ or ethenyl;

$L^2$ is a bond;

$L^3$ is a bond, —(C$R^a{}_2$)$_r$C(O)N$R^7$—, —(C$R^a{}_2$)$_r$N$R^7$C(O)—, —(C$R^a{}_2$)$_r$N$R^7$C(O)N$R^7$—, —(C$R^a{}_2$)$_r$OC(O)N$R^7$—, —(C$R^a{}_2$)$_r$N$R^7$C(O)O— or —(C$R^a{}_2$)$_r$N$R^7$— or —(C$R^4R^6$)$_n$—;

$L^4$ is a bond or —(C$R^4R^6$)$_n$—;

X is $NH_2$;

Z is a bond;

n is 0, 1 or 2;

p is 1;

r is independently 0, 1, 2 or 3;

t is 1, 2, 3, or 4;

or a stereoisomer or pharmaceutically acceptable salt thereof.

In another embodiment of the invention under Formula IB,

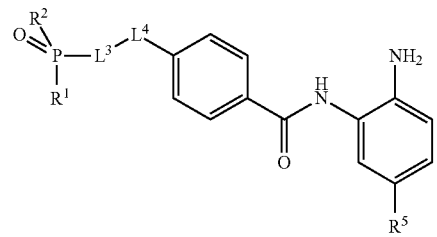

IB $R^1$ and $R^2$ are independently selected from —OR or unsubstituted $C_1$-$C_4$ alkyl;

$R^4$ and $R^6$ are hydrogen;

$R^5$ is $L^2$-$R^9$;

$R^9$ is independently selected from hydrogen, unsubstituted or substituted heteroaryl, or unsubstituted or substituted aryl;

$R^a$ is independently selected from H and unsubstituted $C_1$-$C_4$ alkyl;

R is unsubstituted $C_1$-$C_4$ alkyl;

$L^3$ is —(C$R^a{}_2$)$_r$C(O)N$R^7$—, —(C$R^a{}_2$)$_r$OC(O)N$R^7$—, or —(C$R^a{}_2$)$_r$N$R^7$—;

$L^4$ is a bond or —(C$R^4R^6$)$_n$—;

n is 0, 1 or 2;

r is independently 0, 1, 2 or 3;

or a stereoisomer or pharmaceutically acceptable salt thereof.

In another embodiment of the above embodiments,

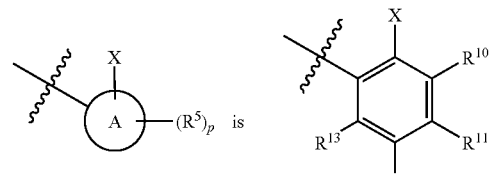

$R^{10}$, $R^{11}$, and $R^{13}$ are independently of each other hydrogen or fluoro. $R^{12}$ is hydrogen, substituted or unsubstituted phenyl or substituted or unsubstituted thienyl and X is amino.

In another embodiment of the above embodiments, the

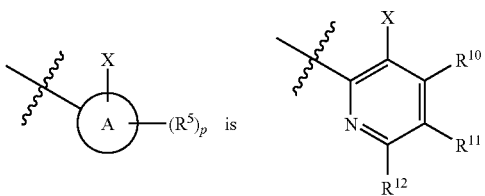 is 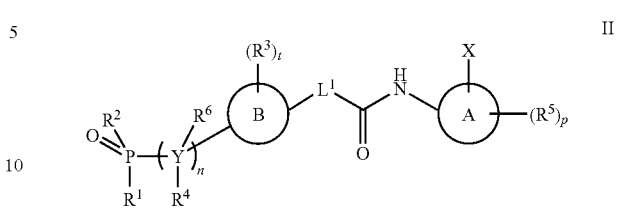

$R^{10}$ and $R^{11}$ are independently of each other hydrogen or fluoro;

$R^{12}$ is hydrogen, substituted or unsubstituted phenyl or substituted or unsubstituted thienyl and X is amino.

In another embodiment of the above embodiments, $R^{12}$ is

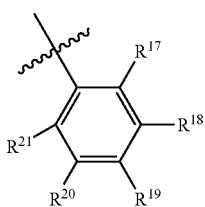

$R^{17}$ and $R^{21}$ are independently selected from hydrogen or fluoro;

$R^{18}$, $R^{19}$ or $R^{20}$ are independently selected from hydrogen, halo, methyl, methoxy or halomethyl.

In another embodiment of the above embodiments, $R^{12}$ is

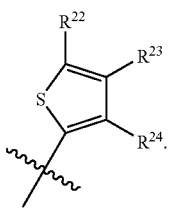

$R^{22}$, $R^{21}$ and $R^{24}$ are independently selected from hydrogen, methyl, amino, hydroxyl, and halo.

In another embodiment of the above embodiments, $R^{12}$ is

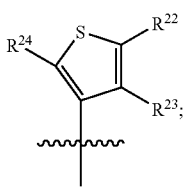

$R^{22}$, $R^{23}$ and $R^{24}$ are independently selected from hydrogen, methyl, amino, hydroxyl and halo.

In another embodiment of the above embodiments, Ring B is selected from phenyl, benzothiophenyl, benzofuranyl, thiazolyl, benzothiazolyl, furanyl, pyridyl, pyrimidyl, quinolinyl, thiophenyl, benzodioxyl, benzooxadiazolyl, quinoxalinyl, benzotriazolyl, benzoimidazolyl or benzooxazolyl.

In another embodiment, compounds of the instant invention are represented by Formula II:

wherein $R^1$ and $R^2$ are independently selected from OH, $NR^7R^8$, substituted or unsubstituted $C_1$-$C_{10}$ alkyl, substituted or unsubstituted $C_1$-$C_{10}$ alkenyl, substituted or unsubstituted $C_1$-$C_{10}$ alkynyl, substituted or unsubstituted $C_1$-$C_{10}$ alkoxy, substituted or unsubstituted cycloalkyl, substituted or unsubstituted heteroaryl, substituted or unsubstituted heterocyclic or substituted or unsubstituted aryl;

or $R^1$ and $R^2$ together with the phosphorous atom to which they are attached form a phosphorous-containing heterocyclic ring;

or $R^2$ and $R^6$ together with the phosphorous and Y atom to which they are respectively attached, form a heterocyclic ring;

or $R^1$ and $R^4$ together with the phosphorous and Y atom to which they are respectively attached, form a heterocyclic ring;

$R^3$ is selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-$NHSO_2$—, $C_1$-$C_7$ alkyl-$SO_2NH$—, $C_1$-$C_7$ alkylsulfonyl, $C_1$-$C_7$ alkylamino or di($C_1$-$C_7$)alkylamino;

$R^4$ and $R^6$ are independently of each other hydrogen, OH, $NR^7R^8$, halo or substituted or unsubstituted $C_1$-$C_4$ alkyl, substituted or unsubstituted $C_1$-$C_4$ alkenyl, substituted or unsubstituted $C_1$-$C_4$ alkynyl, substituted or unsubstituted cycloalkyl, substituted or unsubstituted heteroaryl, substituted or unsubstituted heterocyclic or substituted or unsubstituted aryl;

or $R^4$ and $R^6$ together with the Y atom to which they are attached form a heterocyclic or carbocyclic ring;

$R^5$ is selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-$NHSO_2$—, $C_1$-$C_7$ alkyl-$SO_2NH$—, $C_1$-$C_7$ alkylsulfonyl, $C_1$-$C_7$ alkylamino or di($C_1$-$C_7$)alkylamino or $L^2$-$R^9$, wherein $R^9$ is substituted or unsubstituted heteroaryl, substituted or unsubstituted heterocyclic, substituted or unsubstituted aryl, substituted or unsubstituted $C_3$-$C_8$ cycloalkyl, $L^2$ is selected from a bond, $C_1$-$C_4$ alkylene, $C_1$-$C_4$ alkynyl, $C_1$-$C_4$ alkenyl, —O—, —S—, —N—, —C(=O)NH—, —NHC(=O)—, —NHC(=O)NH—, —$SO_2NH$—, —$NHSO_2$—, —$SO_2$—, —C(=O)— or —C(=O)O—;

$R^7$ and $R^8$ are independently selected from hydrogen, substituted or unsubstituted $C_1$-$C_{10}$ alkyl, substituted or unsubstituted cycloalkyl, substituted or unsubstituted heteroaryl, substituted or unsubstituted heterocyclic or substituted or unsubstituted aryl;

Ring A is a 5- to 6-membered heteroaryl or 6-membered aryl;

Ring B is heteroaryl or aryl;

n is 0, 1, 2, 3 or 4;

p is 1, 2, 3 or 4;

t is 1, 2, 3 or 4;

$L^1$ is $(CH_2)_r$, ethenyl or cyclopropyl, wherein r is 0, 1 or 2;

X is SH or $NH_2$;

Y is C or N;

With the proviso that Ring A is not tetrahydro-dioxo-pyrimidinyl; or a stereoisomer or pharmaceutically acceptable salt thereof.

In one embodiment, the substitution of $R^1$ and $R^2$ for $C_1$-$C_{10}$ alkoxy, $C_1$-$C_{10}$ alkyl, cycloalkyl, heteroaryl, heterocyclic or aryl groups are selected from OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-$NHSO_2$—, $C_1$-$C_7$ alkyl-$SO_2NH$—, $C_1$-$C_7$ alkylsulfonyl, $C_1$-$C_7$ alkylamino or di($C_1$-$C_7$)alkylamino. In another embodiment, the substitution of $R^1$ and $R^2$ for $C_1$-$C_{10}$ alkoxy, $C_1$-$C_{10}$ alkyl, cycloalkyl, heteroaryl, heterocyclic or aryl groups are selected from hydrogen, OH, $NH_2$, nitro, CN, amide, carboxy or halo. In one embodiment, the substitution of $R^1$ and $R^2$ for $C_1$-$C_{10}$ alkoxy, $C_1$-$C_{10}$ alkyl, cycloalkyl, heteroaryl, heterocyclic or aryl groups are selected from substituted or unsubstituted $C_1$-$C_{10}$ alkyl, substituted or unsubstituted cycloalkyl, substituted or unsubstituted heteroaryl, substituted or unsubstituted heterocyclic or substituted or unsubstituted aryl.

In one embodiment, compounds of the invention are represented by Formula II, wherein $R^1$ and $R^2$ are independently selected from OH, $NR^7R^8$, substituted or unsubstituted $C_1$-$C_4$ alkyl, substituted or unsubstituted $C_1$-$C_4$ alkoxy, substituted or unsubstituted heteroaryl or substituted or unsubstituted aryl;

or $R^1$ and $R^2$ together with the phosphorous atom to which they are attached form a phosphorous-containing heterocyclic ring;

$R^3$ is selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-$NHSO_2$—, $C_1$-$C_7$ alkyl-$SO_2NH$—, $C_1$-$C_7$ alkylsulfonyl, $C_1$-$C_7$ alkylamino or di($C_1$-$C_7$)alkylamino;

$R^4$ and $R^6$ are independently of each other hydrogen, OH, $NH_2$, halo or unsubstituted $C_1$-$C_4$ alkyl;

or $R^4$ and $R^6$ together with the Y atom to which they are attached form a heterocyclic or carbocyclic ring;

$R^5$ is selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-$NHSO_2$—, $C_1$-$C_7$ alkyl-$SO_2NH$—, $C_1$-$C_7$ alkylsulfonyl, $C_1$-$C_7$ alkylamino or di($C_1$-$C_7$)alkylamino or $L^2$-$R^9$, wherein $R^9$ is substituted or unsubstituted heteroaryl, substituted or unsubstituted aryl, $L^2$ is selected from a bond, $C_1$-$C_4$ alkylene, $C_1$-$C_4$ alkynyl, $C_1$-$C_4$ alkenyl, —O—, —S—, —N—, —C(=O)NH—, —NHC(=O)—, —NHC(=O)NH—, —$SO_2NH$—, —$NHSO_2$—, —$SO_2$—, —C(=O)— or —C(=O)O—;

$R^7$ and $R^8$ are independently selected from hydrogen, substituted or unsubstituted $C_1$-$C_4$ alkyl, substituted or unsubstituted heteroaryl or substituted or unsubstituted aryl;

Ring A is a 5- to 6-membered monocyclic heteroaryl or 6-membered monocyclic aryl;

Ring B is heteroaryl or aryl;

n is 0, 1, 2, 3 or 4;

p is 1, 2, 3 or 4;

t is 1, 2, 3 or 4;

$L^1$ is $(CH_2)_r$, ethenyl or cyclopropyl, wherein r is 0, 1 or 2;

X is SH or $NH_2$;

Y is C or N;

With the proviso that Ring A is not tetrahydro-dioxo-pyrimidinyl.

In one embodiment of the above mentioned embodiments, the

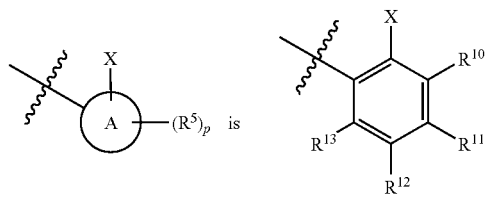

$R^{10}$, $R^{11}$ and $R^{13}$ are independently of each other selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-$NHSO_2$—, $C_1$-$C_7$ alkyl-$SO_2NH$—, $C_1$-$C_7$ alkylsulfonyl, $C_1$-$C_7$ alkylamino or di($C_1$-$C_7$)alkylamino;

$R^{12}$ is selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-$NHSO_2$—, $C_1$-$C_7$ alkyl-$SO_2NH$—, $C_1$-$C_7$ alkylsulfonyl, $C_1$-$C_7$ alkylamino or di($C_1$-$C_7$)alkylamino or $L^2$-$R^9$, wherein $R^9$ is substituted or unsubstituted heteroaryl, substituted or unsubstituted aryl, $L^2$ is selected from a bond, $C_1$-$C_4$ alkylene, $C_1$-$C_4$ alkynyl, $C_1$-$C_4$ alkenyl, —O—, —S—, —N—, —C(=O)NH—, —NHC(=O)—, —NHC(=O)NH—, —$SO_2NH$—, —$NHSO_2$—, —$SO_2$—, —C(=O)— or —C(=O)O—.

In one embodiment, the substitution on $R^9$ is selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-$NHSO_2$—, $C_1$-$C_7$ alkyl-$SO_2NH$—, $C_1$-$C_7$ alkylsulfonyl, $C_1$-$C_7$ alkylamino or di($C_1$-$C_7$)alkylamino. In another embodiment, the substitution on $R^9$ is selected from hydrogen, OH, $NH_2$, nitro, CN, amide, carboxyl, methoxy, methyl, halomethyl and halo.

In one embodiment, $R^{10}$, $R^{11}$ and $R^{13}$ are independently of each other hydrogen or fluoro.

In one embodiment, $R^{12}$ is hydrogen, substituted or unsubstituted phenyl or substituted or unsubstituted thienyl and X is amino.

In one embodiment, $R^{12}$ is

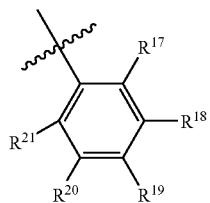

$R^{17}$ and $R^{21}$ are independently selected from hydrogen or fluoro;

$R^{18}$, $R^{19}$ or $R^{20}$ are independently selected from hydrogen, halo, methyl, methoxy or halomethyl.

In one embodiment, $R^{17}$, $R^{18}$, $R^9$, $R^{20}$ and $R^{21}$ are hydrogen.

In one embodiment of the above mentioned embodiments, the

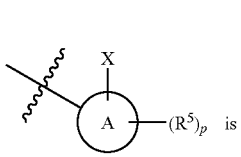 is 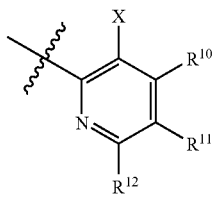

$R^{10}$ and $R^{11}$ are independently of each other selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-$NHSO_2$—, $C_1$-$C_7$ alkyl-$SO_2NH$—, $C_1$-$C_7$ alkylsulfonyl, $C_1$-$C_7$ alkylamino or di($C_1$-$C_7$)alkylamino;

$R^{12}$ is selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-$NHSO_2$—, $C_1$-$C_7$ alkyl-$SO_2NH$—, $C_1$-$C_7$ alkylsulfonyl, $C_1$-$C_7$ alkylamino or di($C_1$-$C_7$)alkylamino or $L^2$-$R^9$, wherein $R^9$ is substituted or unsubstituted heteroaryl, substituted or unsubstituted aryl, $L^2$ is selected from a bond, $C_1$-$C_4$ alkylene, $C_1$-$C_4$ alkynyl, $C_1$-$C_4$ alkenyl, —O—, —S—, —N—, —C(=O)NH—, —NHC(=O)—, —NHC(=O)NH—, —$SO_2NH$—, —$NHSO_2$—, —$SO_2$—, —C(=O)— or —C(=O)O—.

In one embodiment, the substitution on $R^9$ is selected from hydrogen, OH, $NH_2$, nitro, CN, amide, carboxyl, $C_1$-$C_7$alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-$NHSO_2$—, $C_1$-$C_7$ alkyl-$SO_2NH$—, $C_1$-$C_7$ alkylsulfonyl, $C_1$-$C_7$ alkylamino or di($C_1$-$C_7$)alkylamino. In another embodiment, the substitution on $R^9$ is selected from hydrogen, OH, $NH_2$, nitro, CN, amide, carboxyl, methoxy, methyl, halomethyl and halo.

In one embodiment, $R^{10}$ and $R^{11}$ are independently of each other hydrogen or fluoro.

In one embodiment, $R^{12}$ is hydrogen, substituted or unsubstituted phenyl or substituted or unsubstituted thienyl and X is amino.

In one embodiment, $R^{12}$ is

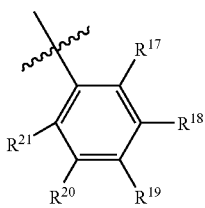

$R^{17}$ and $R^{21}$ are independently selected from hydrogen or fluoro;

$R^{18}$, $R^{19}$ or $R^{20}$ are independently selected from hydrogen, halo, methyl, methoxy or halomethyl.

In one embodiment, $R^{17}$, $R^{18}$, $R^{19}$, $R^{20}$ and $R^{21}$ are hydrogen.

In one embodiment, $R^{12}$ is methyl or halo substituted or unsubstituted thienyl.

In one embodiment, $R^{12}$ is

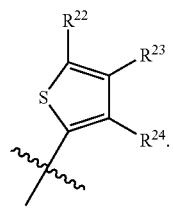

$R^{22}$, $R^{23}$ and $R^{24}$ are independently selected from hydrogen, methyl, amino, hydroxyl, and halo.

In one embodiment, $R^{12}$ is

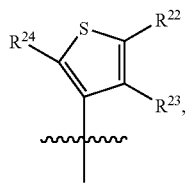

$R^{22}$, $R^{23}$ and $R^{24}$ are independently selected from hydrogen, methyl, amino, hydroxyl and halo.

In one embodiment, $R^{22}$, $R^{23}$ and $R^{24}$ are hydrogen.

In one embodiment of the above embodiments,

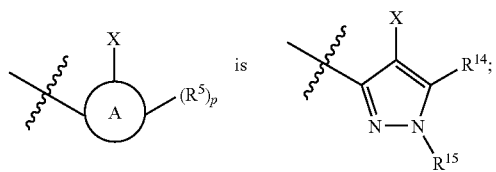

X is SH or $NH_2$;

$R^{14}$ is selected from hydrogen or halo;

$R^{15}$ is selected from hydrogen, $C_1$-$C_7$ alkyl, or $L^3$-$R^{16}$, wherein $R^{16}$ is substituted or unsubstituted heteroaryl, substituted or unsubstituted aryl, $L^3$ is selected from a bond or $C_1$-$C_4$ alkylene.

In one embodiment, $R^{14}$ and $R^{15}$ are hydrogen.

In one embodiment, $R^{15}$ is

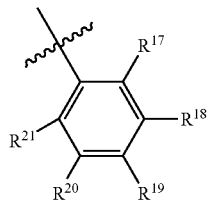

$R^{17}$ and $R^{21}$ are independently selected from hydrogen or fluoro;

$R^{18}$, $R^{19}$ or $R^{20}$ are independently selected from hydrogen, halo, methyl, methoxy or halomethyl.

In one embodiment, $R^{17}$, $R^{18}$, $R^{19}$, $R^{20}$ and $R^{21}$ are hydrogen.

In one embodiment of the above mentioned embodiments, $R^1$ and $R^2$ are independently selected from OH, unsubstituted $C_1$-$C_4$ alkoxy, or unsubstituted aryl;

$R^3$ is hydrogen;

$R^4$ and $R^6$ are independently of each other hydrogen, OH, $NH_2$, F or methyl;

Ring B is phenyl;

n is 0 or 1;

$L^1$ is $(CH_2)_r$, wherein r is 0.

Specific embodiments depicting non-limiting Examples of the phosphorus derivatives of the above Formulas are provided in the Experimental Section hereinbelow.

Specific examples of the compounds of the instant invention include:

Diethyl [4-({[2-amino-5-(2-thienyl)phenyl]amino}carbonyl)phenyl]phosphonate;
Diethyl[4-({[2-amino-5-(3-thienyl)phenyl]amino}carbonyl)phenyl]phosphonate;
Diethyl (4-{[(4-aminobiphenyl-3-yl)amino]carbonyl}phenyl)phosphonate;
Diethyl(4-{[(4-amino-1-phenyl-1H-pyrazol-3-yl)amino]carbonyl}phenyl)phosphonate;
Ethyl hydrogen [4-({[2-amino-5-(2-thienyl)phenyl]amino}carbonyl)phenyl]phosphonate;
Ethyl hydrogen (4-{[(4-amino-1-phenyl-1H-pyrazol-3-yl)amino]carbonyl}phenyl)phosphonate;
Methyl [4-({[2-amino-5-(2-thienyl)phenyl]amino}carbonyl)phenyl]phenylphosphinate;
Methyl [4-({[2-amino-5-(3-thienyl)phenyl]amino}carbonyl)phenyl]phenylphosphinate;
Methyl (4-{[(4-aminobiphenyl-3-yl)amino]carbonyl}phenyl)phenylphosphinate;
Ethyl[4-({[2-amino-5-(2-thienyl)phenyl]amino}carbonyl)phenyl]methylphosphinate;
Ethyl [4-({[2-amino-5-(2-thienyl)phenyl]amino}carbonyl)phenyl]phenylphosphinate;
Ethyl (4-{[(4-aminobiphenyl-3-yl)amino]carbonyl}phenyl)methylphosphinate;
Methyl[4-({[2-amino-5-(2-thienyl)phenyl]amino}carbonyl)phenyl]methylphosphinate;
2-(ethylsulfonyl)ethyl [4-({[2-amino-5-(2-thienyl)phenyl]amino}carbonyl)phenyl]methylphosphinate;
3-hydroxy-3-methylbutyl [4-({[2-amino-5-(2-thienyl)phenyl]amino}carbonyl)phenyl]methylphosphinate;
Cyclobutyl [4-({[2-amino-5-(2-thienyl)phenyl]amino}carbonyl)phenyl]methylphosphinate;
Ethyl [4-({[2-amino-5-(2-thienyl)phenyl]amino}carbonyl)phenyl]ethylphosphinate;
Ethyl [5-({[2-amino-5-(2-thienyl)phenyl]amino}carbonyl)pyridin-2-yl]methylphosphinate;
N-(2-Amino-5-thiophen-2-yl-phenyl)-4-(diisopropyl-phosphinoyl)-benzamide;
N-[2-Amino-5-(2-thienyl)phenyl]-4-[(1-methyl-4-oxido-1,4-azaphosphinan-4-yl)methyl]benzamide;
N-(2-Amino-5-thiophen-2-yl-phenyl)-4-(dimethyl-phosphinoyl)-benzamide;
N-(2-Amino-5-phen-2-yl-phenyl)-4-(dimethyl-phosphinoyl)-benzamide;
[4-(2-Amino-5-thiophen-2-yl-phenylcarbamoyl)-benzyl]-phosphonic acid dimethyl ester;
[4-(2-Amino-5-thiophen-2-yl-phenylcarbamoyl)-benzyl]-phosphonic acid diethyl ester;
[4-(2-Amino-5-thiophen-2-yl-phenylcarbamoyl)-benzyl]-phosphonic acid monomethyl ester;
[4-(2-Amino-5-thiophen-2-yl-phenylcarbamoyl)-benzyl]-phosphonic acid monoethyl ester;
[4-(4-Amino-5-phenyl-2H-pyrazol-3-ylcarbamoyl)-benzyl]-phosphonic acid dimethyl ester;
[4-(2-Amino-5-thiophen-3-yl-phenylcarbamoyl)-benzyl]-phosphonic acid diethyl ester;
[4-(2-Amino-5-thiophen-2-yl-phenylcarbamoyl)-benzyl]-phosphonic acid diethyl ester;
N-[2-amino-5-(2-thienyl)phenyl]-4-[(5,5-dimethyl-2-oxido-1,3,2-dioxaphosphinan-2-yl)methyl]benzamide;
Diisopropyl [4-({[2-amino-5-(2-thienyl)phenyl]amino}carbonyl)benzyl]phosphonate;
Diethyl [3-({[2-amino-5-(2-thienyl)phenyl]amino}carbonyl)benzyl]phosphonate;
Methyl tetrahydro-2H-pyran-4-ylmethyl[4-({[2-amino-5-(2-thienyl)phenyl]amino}carbonyl)benzyl]phosphonate;
Methyl P-[4-({[2-amino-5-(2-thienyl)phenyl]amino}carbonyl)benzyl]-N-1,3-thiazol-2-ylphosphonamidoate;
Ethyl {[[4-({[2-amino-5-(2-thienyl)phenyl]amino}carbonyl)benzyl](methoxy)phosphoryl]oxy}acetate;
Diethyl (4-{[(4-aminobiphenyl-3-yl)amino]carbonyl}benzyl)phosphonate;
Methyl pyridin-3-ylmethyl[4-({[2-amino-5-(2-thienyl)phenyl]amino}carbonyl)benzyl]phosphonate;
Methyl P-[4-({[2-amino-5-(2-thienyl)phenyl]amino}carbonyl)benzyl]-N-benzylphosphonamidoate;
Methyl P-[4-({[2-amino-5-(2-thienyl)phenyl]amino}carbonyl)benzyl]-N-(pyridin-3-ylmethyl)phosphonamidoate;
Dibenzyl[4-({[2-amino-5-(2-thienyl)phenyl]amino}carbonyl)benzyl]phosphonate;
2-amino-2-oxoethyl methyl[4-({[2-amino-5-(2-thienyl)phenyl]amino}carbonyl)benzyl]phosphonate;
2-amino-2-methylpropyl methyl[4-({[2-amino-5-(2-thienyl)phenyl]amino}carbonyl)benzyl]phosphonate;
3-hydroxy-3-methylbutyl methyl[4-({[2-amino-5-(2-thienyl)phenyl]amino}carbonyl)benzyl]phosphonate;
Tetraethyl {[4-({[2-amino-5-(2-thienyl)phenyl]amino}carbonyl)phenyl]methylene}bis(phosphonate);
Diethyl [[4-({[2-amino-5-(2-thienyl)phenyl]amino}carbonyl)phenyl](cyano)methyl]phosphonate;
Methyl [4-({[2-amino-5-(2-thienyl)phenyl]amino}carbonyl)phenyl](diethoxyphosphoryl)acetate;
Methyl 3-[4-({[2-amino-5-(2-thienyl)phenyl]amino}carbonyl)phenyl]-2-(dimethoxyphosphoryl)propanoate;
Diethyl {2-[4-({[2-amino-5-(2-thienyl)phenyl]amino}carbonyl)phenyl]-1-cyanoethyl}phosphonate;
Tetraethyl {2-[4-({[2-amino-5-(2-thienyl)phenyl]amino}carbonyl)phenyl]ethane-1,1-diyl}bis(phosphonate);
Diethyl {2-amino-1-[4-({[2-amino-5-(2-thienyl)phenyl]amino}carbonyl)benzyl]-2-oxoethyl}phosphonate;
[4-(2-Amino-5-thiophen-2-yl-phenylcarbamoyl)-benzyl]-phenyl-phosphinic acid methyl ester;
[4-(2-Amino-5-thiophen-2-yl-phenylcarbamoyl)-benzyl]-phenyl-phosphinic acid;
[4-(2-Amino-5-thiophen-3-yl-phenylcarbamoyl)-benzyl]-phenyl-phosphinic acid methyl ester;
[4-(4-Amino-1-phenyl-1H-pyrazol-3-ylcarbamoyl)-benzyl]-phenyl-phosphinic acid methyl ester;
[4-(2-Amino-5-thiophen-2-yl-phenylcarbamoyl)-benzyl]-methyl-phosphinic acid ethyl ester;
[4-(4-Amino-biphenyl-3-ylcarbamoyl)-benzyl]-methyl-phosphinic acid ethyl ester;

[4-(4-Amino-biphenyl-3-ylcarbamoyl)-benzyl]-methyl-phosphinic acid ethyl ester;
[4-(4-Amino-biphenyl-3-ylcarbamoyl)-benzyl]-methyl-phosphinic acid ethyl ester;
[4-(2-Amino-5-thiophen-2-yl-phenylcarbamoyl)-benzyl]-methyl-phosphinic acid cyclobutyl ester;
Methyl [4-({[2-amino-5-(2-thienyl)-phenyl]amino}-carbonyl)benzyl-methylphosphinate; Isopropyl [4-({[2-amino-5-(2-thienyl)-phenyl]amino}-carbonyl)benzyl]-methylphosphinate;
N-[2-Amino-5-(2-thienyl)phenyl]-4-({methyl[(pyridin-3-ylmethyl)amino]-phosphoryl}methyl)-benzamide;
Pyridin-3-ylmethyl [4-({[2-amino-5-(2-thienyl)phenyl]amino}-carbonyl)benzyl]methyl-phosphinate;
Methyl [4-({[2-amino-5-(2-thienyl)-phenyl]amino}-carbonyl)benzyl]-ethylphosphinate;
Ethyl [4-({[2-amino-5-(2-thienyl)-phenyl]amino}-carbonyl)benzyl]-ethylphosphinate;
Isopropyl [4-({[2-amino-5-(2-thienyl)-phenyl]amino}-carbonyl)benzyl]-ethylphosphinate;
Cyclobutyl [4-({[2-amino-5-(2-thienyl)-phenyl]amino}-carbonyl)benzyl]-ethylphosphinate;
N-[2-Amino-5-(2-thienyl)phenyl]-4-({ethyl[(pyridin-3-ylmethyl)amino]-phosphoryl}methyl)-benzamide;
Pyridin-3-ylmethyl [4-({[2-amino-5-(2-thienyl)phenyl]amino}-carbonyl)benzyl]ethyl-phosphinate;
Cyclobutyl [4-({[2-amino-5-(2-thienyl)phenyl]amino}carbonyl)benzyl]phenylphosphinate;
Methyl [4-({[2-amino-5-(2-thienyl)phenyl]amino}carbonyl)benzyl](4-fluorophenyl)phosphinate;
Methyl [3-({[2-amino-5-(2-thienyl)phenyl]amino}carbonyl)benzyl]phenylphosphinate;
Isopropyl [3-({[2-amino-5-(2-thienyl)phenyl]amino}carbonyl)benzyl]methylphosphinate;
Methyl [3-({[2-amino-5-(2-thienyl)phenyl]amino}carbonyl)benzyl]ethylphosphinate;
Ethyl[4-({[2-amino-5-(2-thienyl)phenyl]amino}carbonyl)benzyl]phenylphosphinate;
Isopropyl[4-({[2-amino-5-(2-thienyl)phenyl]amino}carbonyl)benzyl]phenylphosphinate;
2,2,2-trifluoroethyl[4-({[2-amino-5-(2-thienyl)phenyl]amino}carbonyl)benzyl]phenylphosphinate;
Ethyl[4-({[2-amino-5-(2-thienyl)phenyl]amino}carbonyl)benzyl]isopropylphosphinate;
Ethyl[4-({[2-amino-5-(2-thienyl)phenyl]amino}carbonyl)benzyl]cyclopropylphosphinate;
3-hydroxy-3-methylbutyl[4-({[2-amino-5-(2-thienyl)phenyl]amino}carbonyl)benzyl]phenylphosphinate;
2-amino-2-methylpropyl[4-({[2-amino-5-(2-thienyl)phenyl]amino}carbonyl)benzyl]phenylphosphinate;
2-amino-2-oxoethyl[4-({[2-amino-5-(2-thienyl)phenyl]amino}carbonyl)benzyl]phenylphosphinate;
Methyl [4-({[2-amino-5-(2-thienyl)phenyl]amino}carbonyl)benzyl]cyclopropylphosphinate;
Methyl (S)-[4-({[2-amino-5-(2-thienyl)phenyl]amino}carbonyl)benzyl]methylphosphinate;
Methyl (R)-[4-({[2-amino-5-(2-thienyl)phenyl]amino}carbonyl)benzyl]methylphosphinate;
Methyl (4-{[(4-aminobiphenyl-3-yl)amino]carbonyl}benzyl)methylphosphinate;
3-hydroxy-3-methylbutyl [4-({[2-amino-5-(2-thienyl)phenyl]amino}carbonyl)benzyl]ethylphosphinate;
3-hydroxy-3-methylbutyl [4-({[2-amino-5-(2-thienyl)phenyl]amino}carbonyl)benzyl]methylphosphinate;
2-(ethylsulfonyl)ethyl[4-({[2-amino-5-(2-thienyl)phenyl]amino}carbonyl)benzyl]methylphosphinate;
Diethyl {[5-({[2-amino-5-(2-thienyl)phenyl]amino}carbonyl)pyridin-2-yl]methyl}phosphonate;
Diethyl {[5-({[2-amino-5-(3-thienyl)phenyl]amino}carbonyl)pyridin-2-yl]methyl}phosphonate;
Methyl {[5-({[2-amino-5-(2-thienyl)phenyl]amino}carbonyl)pyridin-2-yl]methyl}phenylphosphinate;
Methyl {[5-({[2-amino-5-(3-thienyl)phenyl]amino}carbonyl)pyridin-2-yl]methyl}phenylphosphinate;
{([4-(2-Amino-5-thiophen-2-yl-phenylcarbamoyl)-phenyl]-hydroxy-methyl}-phosphonic acid dimethyl ester;
{1-[4-(2-Amino-5-thiophen-2-yl-phenylcarbamoyl)-phenyl]-1-fluoro-ethyl}-phosphonic acid dimethyl ester;
{1-[4-(2-Amino-5-thiophen-3-yl-phenylcarbamoyl)-phenyl]-1-fluoro-ethyl}-phosphonic acid dimethyl ester;
{1-[4-(4-Amino-biphenyl-3-ylcarbamoyl)-phenyl]-1-fluoro-ethyl}-phosphonic acid dimethyl ester;
{[4-(2-Amino-5-thiophen-3-yl-phenylcarbamoyl)-phenyl]-hydroxy-methyl}-phosphonic acid dimethyl ester;
{[4-(4-Amino-biphenyl-3-ylcarbamoyl)-phenyl]-hydroxy-methyl}-phosphonic acid dimethyl ester;
{[4-(2-Amino-5-thiophen-2-yl-phenylcarbamoyl)-phenyl]-fluoro-methyl}-phosphonic acid dimethyl ester;
{Amino-[4-(2-amino-5-thiophen-2-yl-phenylcarbamoyl)-phenyl]-methyl}-phosphonic acid dimethyl ester;
{[4-(2-Amino-5-thiophen-2-yl-phenylcarbamoyl)-phenyl]-hydroxy-methyl}-phenyl-phosphinic acid ethyl ester;
{1-[4-(2-Amino-5-thiophen-2-yl-phenylcarbamoyl)-phenyl]-1-fluoro-ethyl}-phenyl-phosphinic acid methyl ester;
{1-[4-(2-Amino-5-thiophen-3-yl-phenylcarbamoyl)-phenyl]-1-fluoro-ethyl}-phenyl-phosphinic acid methyl ester;
{1-[4-(4-Amino-biphenyl-3-ylcarbamoyl)-phenyl]-1-fluoro-ethyl}-phenyl-phosphinic acid methyl ester;
{[4-(2-Amino-5-thiophen-3-yl-phenylcarbamoyl)-phenyl]-hydroxy-methyl}-phenyl-phosphinic acid ethyl ester;
{[4-(4-Amino-biphenyl-3-ylcarbamoyl)-phenyl]-hydroxy-methyl}-phenyl-phosphinic acid ethyl ester;
N-(2-Amino-5-thiophen-2-yl-phenyl)-4-(diisopropyl-phosphinoylmethyl)-benzamide;
N-(2-Amino-5-thiophen-2-yl-phenyl)-4-(diethyl-phosphinoylmethyl)-benzamide;
N-(2-Amino-5-thiophen-2-yl-phenyl)-4-(dimethyl-phosphinoylmethyl)-benzamide;
N-[2-Amino-5-(2-thienyl)phenyl]-3-[(diethylphosphoryl)methyl]benzamide;
N-[2-amino-5-(2-thienyl)phenyl]-4-[2-(dimethylphosphoryl)ethyl]benzamide;
Ethyl-{2-[4-({[2-amino-5-(2-thienyl)phenyl]amino}carbonyl)phenyl]ethyl}methyl phosphinate;
N-[2-Amino-5-(2-thienyl)phenyl]-4-[(3-methyl-3-oxido-2,4-dioxa-9-aza-3-phosphaspiro[5.5]undec-9-yl)methyl]benzamide;
N-[2-Amino-5-(2-thienyl)phenyl]-4-[(3-methyl-3-oxido-2,4-dioxa-9-aza-3-phosphaspiro[5.5]undec-9-yl)carbonyl]benzamide;
N-[2-Amino-5-(2-thienyl)phenyl]-6-(3-methyl-3-oxido-2,4-dioxa-9-aza-3-phospaspiro[5.5]undec-9-yl)nicotinamide;
N-[2-amino-5-(2-thienyl)phenyl]-6-{2-[bis(dimethylamino)phosphoryl]-2,8-diazaspiro[4.5]dec-8-yl}nicotinamide;
N-[2-Amino-5-(2-thienyl)phenyl]-4-[(4-oxido-4-phenyl-1,4-azaphosphinan-1-yl)methyl]benzamide;
N-(2-Amino-5-(2-thienyl)phenyl]-4-[(4-oxido-4-phenyl-1,4-azaphosphinan-1-yl)carbonyl]benzamide;
N-[2-Amino-5-(2-thienyl)phenyl]-6-(4-oxido-4-phenyl-1,4-azaphosphinan-1-yl)nicotinamide;

N-[2-Amino-5-(2-thienyl)phenyl]-4-[(4-ethyl-4-oxido-1,4-azaphosphinan-1-yl)methyl]benzamide;
N-[2-Amino-5-(2-thienyl)phenyl]-4-[(4-ethyl-4-oxido-1,4-azaphosphinan-1-yl)carbonyl]benzamide;
N-[2-Amino-5-(2-thienyl)phenyl]-6-(4-ethyl-4-oxido-1,4-azaphosphinan-1-yl)nicotinamide;
N-(4-aminobiphenyl-3-yl)-4-[(4-oxido-4-phenyl-1,4-azaphosphinan-1-yl)methyl]benzamide;
N-[2-amino-5-(2-thienyl)phenyl]-4-[2-(4-oxido-4-phenyl-1,4-azaphosphinan-1-yl)ethyl]benzamide;
N-[2-amino-5-(2-thienyl)phenyl]-4-[2-(4-ethyl-4-oxido-1,4-azaphosphinan-1-yl)ethyl]benzamide;
N-[2-amino-5-(2-thienyl)phenyl]-4-[2-(4-oxido-4-phenyl-1,4-azaphosphinan-1-yl)-2-oxoethyl]benzamide;
N-[2-amino-5-(2-thienyl)phenyl]-4-[2-(4-ethyl-4-oxido-1,4-azaphosphinan-1-yl)-2-oxoethyl]benzamide;
N-[2-amino-5-(2-thienyl)phenyl]-4-{[[2-(dimethylphosphoryl)ethyl] (methyl)amino]methyl}benzamide;
N-[2-amino-5-(2-thienyl)phenyl]-4-{[[2-(diisopropylphosphoryl)ethyl](methyl)amino]methyl}benzamide;
N-[2-amino-5-(2-thienyl)phenyl]-4-{[[2-(diphenylphosphoryl)ethyl](methyl)amino]ethyl}benzamide;
N-[2-amino-5-(2-thienyl)phenyl]-6-[[2-(dimethylphosphoryl)ethyl]amino]nicotinamide;
N-[2-amino-5-(2-thienyl)phenyl]-6-[[2-(diisopropylphosphoryl)ethyl](methyl)amino]nicotinamide;
N-[2-amino-5-(2-thienyl)phenyl]-6-[[2-(diphenylphosphoryl)ethyl](methyl)amino]nicotinamide;
N'-[2-amino-5-(2-thienyl)phenyl]-N-[2-(dimethylphosphoryl)ethyl]-N-methylterephthalamide;
N'[2-amino-5-(2-thienyl)phenyl]-N-[2-(diisopropylphosphoryl)ethyl]-N-methylterephthalamide;
N'-[2-amino-5-(2-thienyl)phenyl]-N-[2-(diphenylphosphoryl)ethyl]-N-methylterephthalamide;
N-[2-amino-5-(2-thienyl)phenyl]-6-{[2-(diisopropylphosphoryl)ethyl]amino}nicotinamide;
N-[2-amino-5-(2-thienyl)phenyl]-N'-[2-(diisopropylphosphoryl)ethyl]terephthalamide;
N-[2-amino-5-(2-thienyl)phenyl]-4-({[2-(diisopropylphosphoryl)ethyl]amino}methyl)benzamide;
N-[2-amino-5-(2-thienyl)phenyl]-N'-[2-(dimethylphosphoryl)ethyl]terephthalamide;
N-[2-amino-5-(2-thienyl)phenyl]-4-({[2-(dimethylphosphoryl)ethyl]amino}methyl)benzamide;
Methyl (4-{[(4-aminobiphenyl-3-yl)amino]carbonyl}benzyl)[2-(dimethylphosphoryl)ethyl]carbamate;
Diethyl {1-[5-({[2-amino-5-(2-thienyl)phenyl]amino}carbonyl)pyridin-2-yl]piperidin-4-yl}phosphonate;
Diethyl (1-{[4-({[2-amino-5-(2-thienyl)phenyl]amino}carbonyl)phenyl]methyl}piperidin-4-yl) phosphonate;
Diethyl (1-{[4-({[2-amino-5-(2-thienyl)phenyl]amino}carbonyl)phenyl]carbonyl}piperidin-4-yl)phosphonate;
[4-({[2-amino-5-(2-thienyl)phenyl]amino}carbonyl)phenyl]methyl dimethylphosphinate;
2-[4-({[2-amino-5-(2-thienyl)phenyl]amino}carbonyl)phenyl]ethyl methylphosphonate;
[4-({[2-amino-5-(2-thienyl)phenyl]amino}carbonyl)phenyl]methyl ethylmethylphosphonate;
[4-({[2-amino-5-(2-thienyl)phenyl]amino}carbonyl)phenyl]methyl methylphenylphosphonate;
N-[2-amino-5-(2-thienyl)phenyl]-4-({[(4R,5R)-4,5-dimethyl-2-oxido-1,3,2-dioxaphospholan-2-yl]oxy}methyl)benzamide;
4-({[2-amino-5-(2-thienyl)phenyl]amino}carbonyl)benzyl dimethylphosphate;
1-[4-({[2-amino-5-(2-thienyl)phenyl]amino}carbonyl)phenyl]ethyl ethyl methylphosphonate;
1-[4-({[2-amino-5-(2-thienyl)phenyl]amino}carbonyl)phenyl]ethyl methyl methylphosphonate;
1-[4-({[2-amino-5-(2-thienyl)phenyl]amino}carbonyl)phenyl]ethyl methyl phenylphosphonate;
4-({[2-amino-5-(2-thienyl)phenyl]amino}carbonyl)benzyl ethylphenylphosphonate;
2-[4-({[2-amino-5-(2-thienyl)phenyl]amino}carbonyl)phenyl]ethyl dimethylphosphinate;
2-[4-({[2-amino-5-(2-thienyl)phenyl]amino}carbonyl)phenyl]ethyl methyl methylphosphonate;
1-[4-({[2-amino-5-(2-thienyl)phenyl]amino}carbonyl)phenyl]-2,2,2-trifluoro-1-(trifluoromethyl)ethyl dimethylphosphinate;
4-({[2-amino-5-(2-thienyl)phenyl]amino}carbonyl)phenyl dimethylphosphinate; (4-{[(4-aminobiphenyl-3-yl)amino]carbonyl}phenyl)methyldimethylphosphinate;
1-[4-({[2-amino-5-(2-thienyl)phenyl]amino}carbonyl)phenyl]ethyldiethylphosphinate;
4-({[2-amino-5-(2-thienyl)phenyl]amino}carbonyl)benzyldiethylphosphinate;
1-[4-({[2-amino-5-(2-thienyl)phenyl]amino}carbonyl)phenyl]ethyldimethylphosphinate;
4-({[2-amino-5-(2-thienyl)phenyl]amino}carbonyl)benzyldiisopropylphosphinate;
1-[4-({[2-amino-5-(2-thienyl)phenyl]amino}carbonyl)phenyl]ethyldiisopropylphosphinate;
Dimethyl [4-({[2-amino-5-(2-thienyl)phenyl]amino}carbonyl)benzyl]amidophosphate;
N-[2-amino-5-(2-thienyl)phenyl]-4-({[(4R,5R)-4,5-dimethyl-2-oxido-1,3,2-dioxaphospholan-2-yl]amino}methyl)benzamide;
N-[2-amino-5-(2-thienyl)phenyl]-4-({[bis(dimethylamino)phosphoryl]amino}methyl)benzamide;
Dimethyl [4-({[2-amino-5-(2-thienyl)phenyl]amino}carbonyl)phenyl]amidophosphate;
Diethyl [4-({[2-amino-5-(2-thienyl)phenyl]amino}carbonyl)phenyl]amidophosphate;
Dimethyl [4-({[2-amino-5-(2-thienyl)phenyl]amino}carbonyl)phenyl]amidophosphate;
Dimethyl [4-({[2-amino-5-(2-thienyl)phenyl]amino}carbonyl)phenyl]methylamidophosphate;
Dimethyl (4-{[(4-aminobiphenyl-3-yl)amino]carbonyl}phenyl]methylamidophosphate;
N-[2-amino-5-(2-thienyl)phenyl]-4-[bis(dimethylphosphoryl)amino]benzamide;
Dimethyl {[({[4-({[2-amino-5-(2-thienyl)phenyl]amino}carbonyl)benzyl]amino}carbonyl) oxy]methyl}phosphonate;
4-(dimethylphosphoryl)benzyl (4-{[(4-aminobiphenyl-3-yl)amino]carbonyl}benzyl)carbamate;
[5-(dimethylphosphoryl)pyridin-3-yl]methyl [4-({[2-amino-5-(2-thienyl)phenyl]amino}carbonyl)benzyl]carbamate;
Diethyl ({[(4-{[(4-aminobiphenyl-3-yl)amino]carbonyl}phenyl)methyl][(methyloxy)carbonyl]amino}methyl)phosphonate;
Diethyl {[({[4-({[2-amino-5-(2-thienyl)phenyl]amino}carbonyl)benzyl]amino}carbonyl) oxy]methyl}phosphonate;
Dimethyl {[({[4-({[2-amino-5-(2-thienyl)phenyl]amino}carbonyl)benzyl]amino}carbonyl) oxy]methyl}phosphonate;

Methyl {[({[4-({[2-amino-5-(2-thienyl)phenyl]amino}carbonyl)benzyl]amino}carbonyl)oxy]methyl}methylphosphinate;

Ethyl {[({[4-({[2-amino-5-(2-thienyl)phenyl]amino}carbonyl)benzyl]amino}carbonyl)oxy]methyl}methylphosphinate;

Ethyl {[({[4-({[2-amino-5-(2-thienyl)phenyl]amino}carbonyl)benzyl]amino}carbonyl)oxy]methyl}ethylphosphinate; (dimethylphosphoryl)methyl [4-({[2-amino-5-(2-thienyl)phenyl]amino}carbonyl)benzyl]carbamate;

Diethyl (4-{[4-({[2-amino-5-(2-thienyl)phenyl]amino}carbonyl)benzoyl]amino}phenyl)phosphonate;

Diethyl [({[4-({[2-amino-5-(2-thienyl)phenyl]amino}carbonyl)phenyl]carbonyl}amino)methyl]phosphonate;

Diethyl [({[4-({[2-amino-5-(2-thienyl)phenyl]amino}carbonyl)phenyl]methyl}amino) methyl]phosphonate;

N-[2-amino-5-(2-thienyl)phenyl]-4-[(2s)-2-oxido-2-phenyl-1,3,2-dioxaphosphinan-5-yl]benzamide;

N-[2-amino-5-(2-thienyl)phenyl]-4-[(2r)-2-oxido-2-phenyl-1,3,2-dioxaphosphinan-5-yl]benzamide;

N-[2-amino-5-(2-thienyl)phenyl]-4-[(2s)-2-methyl-2-oxido-1,3,2-dioxaphosphinan-5-yl]benzamide;

N-[2-amino-5-(2-thienyl)phenyl]-4-[(2)-2-methyl-2-oxido-1,3,2-dioxaphosphinan-5-yl]benzamide;

Dimethyl [3-((1E)-3-{[2-amino-5-(2-thienyl)phenyl]amino}-3-oxoprop-1-en-1-yl)phenyl]phosphonate;

Ethyl [3-((1E)-3-{[2-amino-5-(2-thienyl)phenyl]amino}-3-oxoprop-1-en-1-yl)phenyl]methylphosphinate;

Ethyl {3-[4-({[2-({[(1,1-dimethylethyl)oxy]carbonyl}amino)-5-(2-thienyl)phenyl]amino}carbonyl)phenyl]-3-oxopropyl}methylphosphinate;

N-[2-amino-5-(2-thienyl)phenyl]-4-(2-methyl-2-oxido-1,2-oxaphospholan-5-yl)benzamide or the pharmaceutically acceptable salt or stereoisomer thereof.

Chemical Definitions

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on.

When used in the phrases "alkylaryl", "alkylcycloalkyl" and "alkylheterocyclyl" the term "alkyl" refers to the alkyl portion of the moiety and does not describe the number of atoms in the aryl and heteroaryl portion of the moiety. In an embodiment, if the number of carbon atoms is not specified, the "alkyl" of "alkylaryl", "alkylcycloalkyl" and "alkylheterocyclyl" refers to $C_1$-$C_{12}$ alkyl and in a further embodiment, refers to $C_1$-$C_6$ alkyl.

The term "cycloalkyl" means a monocyclic saturated or unsaturated aliphatic hydrocarbon group having the specified number of carbon atoms. The cycloalkyl is optionally bridged (i.e., forming a bicyclic moiety), for example with a methylene, ethylene or propylene bridge. The bridge may be optionally substituted or branched. The cycloalkyl may be fused with an aryl group such as phenyl, and it is understood that the cycloalkyl substituent is attached via the cycloalkyl group. For example, "cycloalkyl" includes cyclopropyl, methyl-cyclopropyl, 2,2-dimethyl-cyclobutyl, 2-ethyl-cyclopentyl, cyclohexyl, cyclopentenyl, cyclobutenyl and so on.

In an embodiment, if the number of carbon atoms is not specified, "alkyl" refers to $C_1$-$C_{12}$ alkyl and in a further embodiment, "alkyl" refers to $C_1$-$C_6$ alkyl. In an embodiment, if the number of carbon atoms is not specified, "cycloalkyl" refers to $C_3$-$C_{10}$ cycloalkyl and in a further embodiment, "cycloalkyl" refers to $C_3$-$C_7$ cycloalkyl. In an embodiment, examples of "alkyl" include methyl, ethyl, n-propyl, i-propyl, n-butyl, t-butyl and i-butyl.

The term "alkylene" means a hydrocarbon diradical group having the specified number of carbon atoms. For example, "alkylene" includes —$CH_2$—, —$CH_2CH_2$— and the like. In an embodiment, if the number of carbon atoms is not specified, "alkylene" refers to $C_1$-$C_{12}$ alkylene and in a further embodiment, "alkylene" refers to $C_1$-$C_6$ alkylene.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylenearyl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

"Aryl" is intended to mean any stable monocyclic, bicyclic or tricyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

In one embodiment, "aryl" is an aromatic ring of 6 to 14 carbons atoms, and includes a carbocyclic aromatic group fused with a 5- or 6-membered cycloalkyl group such as indan. Examples of carbocyclic aromatic groups include, but are not limited to, phenyl, naphthyl, e.g. 1-naphthyl and 2-naphthyl; anthracenyl, e.g. 1-anthracenyl, 2-anthracenyl; phenanthrenyl; fluorenonyl, e.g. 9-fluorenonyl, indanyl and the like. A carbocyclic aromatic group is optionally substituted with a designated number of substituents, described below.

The term heteroaryl, as used herein, represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

Heteroaryl groups within the scope of this definition include but are not limited to acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. Additional examples of heteroaryl include, but are not limited to pyridyl, e.g., 2-pyridyl (also referred to as α-pyridyl), 3-pyridyl (also referred to as β-pyridyl) and 4-pyridyl (also referred to as γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazoyl, 4-oxazoyl and 5-oxazoyl; isoxazoyl; pyrrolyl; pyridazinyl; pyrazinyl and the like. Heterocyclic aromatic (or heteroaryl) as defined above may be optionally substituted with a designated number of substituents, as described below for aromatic groups.

In an embodiment, "heteroaryl" may also include a "fused polycyclic aromatic", which is a heteroaryl fused with one or more other heteroaryl or nonaromatic heterocyclic ring. Examples include, quinolinyl and isoquinolinyl, e.g. 2-quinolinyl, 3-quinolinyl, 4-quinolinyl, 5-quinolinyl, 6-quinolinyl, 7-quinolinyl and 8-quinolinyl, 1-isoquinolinyl, 3-quinolinyl, 4-isoquinolinyl, 5-isoquinolinyl, 6-isoquinolinyl, 7-isoquinolinyl and 8-isoquinolinyl; benzofuranyl, e.g. 2-benzofuranyl and 3-benzofuranyl; dibenzofuranyl, e.g. 2,3-dihydrobenzofuranyl; dibenzothiophenyl; benzothienyl, e.g. 2-benzothienyl and 3-benzothienyl; indolyl, e.g. 2-indolyl and 3-indolyl; benzothiazolyl, e.g., 2-benzothiazolyl; benzooxazolyl, e.g., 2-benzooxazolyl; benzimidazolyl, e.g. 2-benzoimidazolyl; isoindolyl, e.g. 1-isoindolyl and 3-isoindolyl; benzotriazolyl; purinyl; thianaphthenyl, pyrazinyland the like. Fused polycyclic aromatic ring systems may optionally be substituted with a designated number of substituents, as described herein.

The term "heterocycle" or "heterocyclyl" as used herein is intended to mean monocyclic, spirocyclic, bicyclic or tricyclic ring of up to 7 atoms in each ring, wherein each ring is aromatic or non-aromatic and contains carbon and from 1 to 4 heteroatoms selected from the group consisting of O, N, P and S. A nonaromatic heterocycle may be fused with an aromatic aryl group such as phenyl or aromatic heterocycle.

"Heterocyclyl" therefore includes the above mentioned heteroaryls, as well as dihydro and tetrahydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In an embodiment, "heterocycle" (also referred to herein as "heterocyclyl"), is a monocyclic, spirocyclic, bicyclic or tricyclic saturated or unsaturated ring of 5- to 14-ring atoms of carbon and from one to four heteroatoms selected from O, N, S or P. Examples of heterocyclic rings include, but are not limited to: pyrrolidinyl, piperidinyl, morpholinyl, thiamorpholinyl, piperazinyl, dihydrofuranyl, tetrahydrofuranyl, dihydropyranyl, tetrahydrodropyranyl, dihydroquinolinyl, tetrahydroquinolinyl, dihydroisoquinolinyl, tetrahydroisoquinolinyl, dihydropyrazinyl, tetrahydropyrazinyl, dihydropyridyl, tetrahydropyridyl and the like.

An "alkylaryl group" (arylalkyl) is an alkyl group substituted with an aromatic group, for example, a phenyl group. Another example of an alkylaryl group is a benzyl group. Suitable aromatic groups are described herein and suitable alkyl groups are described herein. Suitable substituents for an alkylaryl group are described herein.

An "alkyheterocyclyl" group" is an alkyl group substituted with a heterocyclyl group. Suitable heterocyclyl groups are described herein and suitable alkyl groups are described herein. Suitable substituents for an alkyheterocyclyl group are described herein.

An "alkycycloalkyl group" is an alkyl group substituted with a cycloalkyl group. Suitable cycloalkyl groups are described herein and suitable alkyl groups are described herein. Suitable substituents for an alkycycloalkyl group are described herein.

An "aryloxy group" is an aryl group that is attached to a compound via an oxygen (e.g., phenoxy).

An "alkoxy group" (alkyloxy), as used herein, is a straight chain or branched $C_1$-$C_{12}$ or cyclic $C_3$-$C_{12}$ alkyl group that is connected to a compound via an oxygen atom. Examples of alkoxy groups include but are not limited to methoxy, ethoxy and propoxy.

An "arylalkoxy group" (arylalkyloxy) is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

An "alkylamino group" as used herein, is an alkyl group that is attached to a compound via a nitrogen.

As used herein, an "arylalkylamino group" is an arylalkyl group that is attached to a compound via a nitrogen on the alkyl portion of the arylalkyl.

An "alkylsulfonyl group" as used herein, is an alkyl group that is attached to a compound via the sulfur of a sulfonyl group.

As used herein, many moieties or groups are referred to as being either "substituted or unsubstituted". When a moiety is referred to as substituted, it denotes that any portion of the moiety that is known to one skilled in the art as being available for substitution can be substituted. The phrase "optionally substituted with one or more substituents" means, in one embodiment, one substituent, two substituents, three substituents, four substituents or five substituents. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents are: alkyl, alkenyl or alkynyl groups (which can also be substituted, with one or more substituents), alkoxy groups (which can be substituted), a halogen or halo group (F, Cl, Br, I), hydroxy, nitro, oxo, —CN, —COH, —COOH, amino, azido, N-alkylamino or N,N-dialkylamino (in which the alkyl groups can also be substituted), N-arylamino or N,N-diarylamino (in which the aryl groups can also be substituted), esters (—C(O)—OR, where R can be a group such as alkyl, aryl, etc., which can be substituted), ureas (—NHC(O)—NHR, where R can be a group such as alkyl, aryl, etc., which can be substituted), carbamates (—NHC(O)—OR, where R can be a group such as alkyl, aryl, etc., which can be substituted), sulfonamides (—NHS(O)$_2$R, where R can be a group such as alkyl, aryl, etc., which can be substituted), alkylsulfonyl (which can be substituted), S(O)$_2$, aryl (which can be substituted), cycloalkyl (which can be substituted) alkylaryl (which can be substituted), alkylheterocyclyl (which can be substituted), alkylcycloalkyl (which can be substituted), and aryloxy (which can be substituted).

In an embodiment of the instant invention, Ring A is selected from phenyl or pyrazolyl. In an embodiment of the instant invention, Ring A is phenyl. In an embodiment of the instant invention, Ring A is pyridyl. In an embodiment of the instant invention, Ring A is pyrimidinyl.

In one embodiment of Formula I or the above mentioned embodiments, Ring B is selected from phenyl, benzothiophenyl, benzofuranyl, thiazolyl, benzothiazolyl, furanyl, pyridyl, pyrimidyl, quinolinyl, thiophenyl, benzodioxyl, benzooxadiazolyl, quinoxalinyl, benzotriazolyl, benzoimidazolyl or benzooxazolyl. In another embodiment, Ring B is phenyl, benzothiophenyl, thiophenyl or pyridyl. In a further embodiment, Ring B is phenyl or pyridyl. In a further embodiment, Ring B is phenyl.

In an embodiment of the instant invention, M is

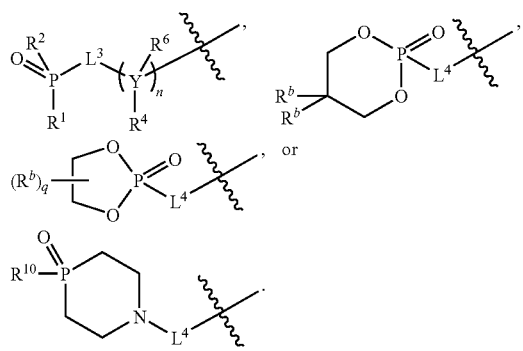

In another embodiment, M is

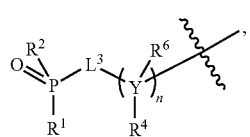

In another embodiment, M is

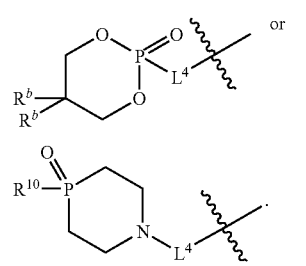

In another embodiment, M is

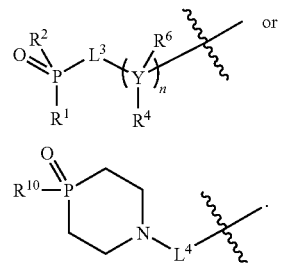

In another embodiment, M is selected from:

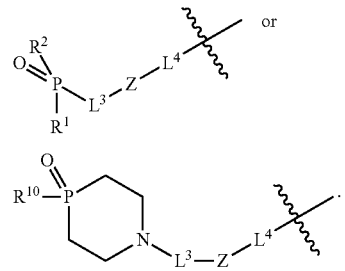

In another embodiment, M is

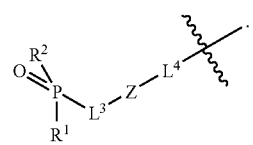

In another embodiment, M is selected from:

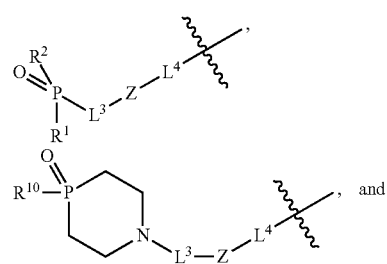

-continued

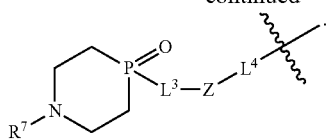

In an embodiment of the instant invention, Y is C; $R^4$ and $R^6$ are hydrogen; n is 0 or 1;

In an embodiment of the instant invention, $R^1$ and $R^2$ are independently selected from substituted or unsubstituted $C_1$-$C_{10}$ alkyl or substituted or unsubstituted $C_1$-$C_{10}$ alkyl. In another embodiment of the instant invention, $R^1$ and $R^2$ are independently selected from substituted or unsubstituted $C_1$-$C_4$ alkyl or substituted or unsubstituted $C_1$-$C_4$ alkoxy. In another embodiment of the instant invention, $R^1$ and $R^2$ are independently selected from unsubstituted $C_1$-$C_4$ alkyl or unsubstituted $C_1$-$C_4$ alkoxy.

In an embodiment of the instant invention, $R^5$ is H, $C_1$-$C_7$ alkyl, or $L^2$-$R^9$. In another embodiment, $R^5$ is $L^2$-$R^9$. In another embodiment, $R^5$ is $L^2$-$R^9$, where $L^2$ is a bond or $C_1$-$C_4$ alkylene and $R^9$ is substituted or unsubstituted heteroaryl, substituted or unsubstituted heterocyclic or substituted or unsubstituted aryl. In another embodiment, $R^5$ is $L^2$-$R^9$, where $L^2$ is a bond and $R^9$ is thienyl or phenyl.

In an embodiment of the instant invention, $R^7$ is H, $C_1$-$C_7$ alkyl, —$(CR^a{}_2)_r$heteroaryl, —$(CR^a{}_2)_r$heterocyclic, and —$(CR^a{}_2)_r$aryl.

In an embodiment of the instant invention, $R^8$ is H, $C_1$-$C_7$ alkyl, —$(CR^a{}_2)_r$heteroaryl, —$(CR^a{}_2)_r$heterocyclic, and —$(CR^a{}_2)_r$aryl.

In an embodiment of the instant invention, $R^9$ is substituted or unsubstituted heteroaryl, substituted or unsubstituted heterocyclic and substituted or unsubstituted aryl. In another embodiment, $R^9$ is substituted or unsubstituted pyranyl, substituted or unsubstituted thiazolyl, substituted or unsubstituted pyridinyl and substituted or unsubstituted phenyl.

In another embodiment of this invention, $R^{10}$ is $C_1$-$C_7$ alkyl, aryl or heteroaryl.

In another embodiment of this invention, $R^{10}$ is $C_1$-$C_7$ alkyl or aryl.

In another embodiment of this invention, $R^{11}$ is independently selected from $C_1$-$C_7$ alkyl, halo, $CF_3$, OH, $C_1$-$C_7$ alkoxy.

In an embodiment of this invention, $L^1$ is a bond.

In an embodiment of this invention, $L^2$ is a bond.

In one embodiment, $L^3$ is a bond, unsubstituted or substituted $C_1$-$C_7$ alkyl, —C(O)—, —O—, —C(O)$NR^7$—, —$NR^7$C(O)—, —$NR^7$C(O)$NR^7$—, —OC(O)$NR^7$—, —$NR^7$C(O)O— or —$NR^7$—, where alkyl is optionally substituted with at least one $R^{11}$. In another embodiment, $L^3$ is —$(CR^a{}_2)_r$C(O)$NR^7$—, —$(CR^a{}_2)_r$$NR^7$C(O)—, —$(CR^a{}_2)_r$OC(O)$NR^7$—, —$(CR^a{}_2)_r$$NR^7$C(O)O— or —$(CR^a{}_2)_r$$NR^7$— In another embodiment, $L^3$ is —$(CR^a{}_2)_r$$NR^7$C(O)—, —$(CR^a{}_2)_r$OC(O)$NR^7$—, or —$(CR^a{}_2)_r$$NR^7$— In a further embodiment, $L^3$ is —$(CR^a{}_2)_r$OC(O)$NR^7$—, or —$(CR^a{}_2)_r$$NR^7$— In a further embodiment, $L^3$ is —$CH_2$—OC(O)$NR^7$—, or —$CH_2NR^7L^3$ is a bond, unsubstituted or substituted $C_1$-$C_7$ alkyl, —C(O)—, —O—, or —$NR^7$—, where alkyl is optionally substituted with at least one $R^{11}$. In another embodiment, $L^3$ is a bond. In another embodiment, $L^3$ is —O—. In another embodiment, $L^3$ is $(CH_2)_n$.

In one embodiment, $L^4$ is $(CH_2)_n$. In another embodiment, $L^4$ is $CH_2$. In another embodiment, $L^4$ is a bond.

In an embodiment, X is $NH_2$.

In an embodiment of the instant invention, Y is C.

In an embodiment, Z is a bond, heteroaryl or heterocyclic, where heteroaryl, heterocyclic is optionally substituted with at least one $R^{11}$. In an embodiment, Z is a bond.

In an embodiment of this invention, variable n is 0, 1, or 2.

In an embodiment of this invention, variable r is 0, 1, or 2

In an embodiment of this invention, variable t is 1 and $R^3$ is H.

Stereochemistry

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the HDAC inhibitors of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

This invention is also intended to encompass pro-drugs of the phosphorus derivatives disclosed herein. A prodrug of any of the compounds can be made using well-known pharmacological techniques.

This invention, in addition to the above listed compounds, is intended to encompass the use of homologs and analogs of such compounds. In this context, homologs are molecules having substantial structural similarities to the above-described compounds and analogs are molecules having substantial biological similarities regardless of structural similarities.

Pharmaceutically Acceptable Salts

The phosphorus derivatives described herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts organic and inorganic acids, for example, acid addition salts which may, for example, be hydrochloric acid, sulphuric acid, methanesulphonic acid, fumaric acid, maleic acid, succinic acid, acetic acid, benzoic acid, oxalic acid, citric acid, tartaric acid, carbonic acid, phosphoric acid, trifluoroacetic acid, formic acid and the like. Pharmaceutically acceptable salts can also be prepared from by treatment with inorganic bases, for example, sodium, potassium, ammonium, calcium, or ferric hydroxides, and such organic bases as isopropylamine, trimethylamine, 2-ethylamino ethanol, histidine, procaine, and the like. Pharmaceutically acceptable salts can also be formed from elemental anions such as chlorine, bromine and iodine.

The active compounds disclosed can, as noted above, also be prepared in the form of their hydrates. The term "hydrate" includes but is not limited to hemihydrate, monohydrate, dihydrate, trihydrate, tetrahydrate and the like.

The active compounds disclosed can, as noted above, also be prepared in the form of a solvate with any organic or inorganic solvent, for example alcohols such as methanol, ethanol, propanol and isopropanol, ketones such as acetone, aromatic solvents and the like.

The active compounds disclosed can also be prepared in any solid or liquid physical form. For example, the compound can be in a crystalline form, in amorphous form, and have any particle size. Furthermore, the compound particles may be micronized, or may be agglomerated, particulate granules, powders, oils, oily suspensions or any other form of solid or liquid physical form.

The compounds of the present invention may also exhibit polymorphism. This invention further includes different polymorphs of the compounds of the present invention. The term "polymorph" refers to a particular crystalline state of a substance, having particular physical properties such as X-ray diffraction, IR spectra, melting point, and the like.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

Methods of Treatment

The invention also relates to methods of using the phosphorus derivatives described herein. As demonstrated herein, the phosphorus derivatives of the present invention are useful for the treatment of cancer. In addition, there is a wide range of other diseases for which phosphorus derivatives may be found useful. Non-limiting examples are thioredoxin (TRX)-mediated diseases as described herein, and diseases of the central nervous system (CNS) as described herein.

1. Treatment of Cancer

As demonstrated herein, the phosphorus derivatives of the present invention are useful for the treatment of cancer. Accordingly, in one embodiment, the invention relates to a method of treating cancer in a subject in need of treatment comprising administering to said subject a therapeutically effective amount of the phosphorus derivatives described herein.

The term "cancer" refers to any cancer caused by the proliferation of neoplastic cells, such as solid tumors, neoplasms, carcinomas, sarcomas, leukemias, lymphomas and the like. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma; and Adrenal glands: neuroblastoma. Thus, the term "cancerous cell" as provided herein, includes a cell afflicted by any one of the above-identified conditions.

In an embodiment, the instant compounds are useful in the treatment of cancers that include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

2. Treatment of Thioredoxin (TRX)-Mediated Diseases

In another embodiment, the phosphorus derivatives are used in a method of treating a thioredoxin (TRX)-mediated disease or disorder in a subject in need thereof, comprising administering to the subject a therapeutically effective amount of one or more of the phosphorus compounds described herein.

Examples of TRX-mediated diseases include, but are not limited to, acute and chronic inflammatory diseases, autoimmune diseases, allergic diseases, diseases associated with oxidative stress, and diseases characterized by cellular hyperproliferation.

Non-limiting examples are inflammatory conditions of a joint including rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation); hemohorragic shock; hyperalgesia: inflammatory bowel disease; multiple sclerosis; myopathies (e.g., muscle protein metabolism, esp. in sepsis); osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes. Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

3. Treatment of Diseases of the Central Nervous System (CNS)

In another embodiment, the phosphorus derivatives are used in a method of treating a disease of the central nervous system in a subject in need thereof comprising administering to the subject a therapeutically effective amount of any one or more of the phosphorus compounds described herein.

In a particular embodiment, the CNS disease is a neurodegenerative disease. In a further embodiment, the neurodegenerative disease is an inherited neurodegenerative disease, such as those inherited neurodegenerative diseases that are polyglutamine expansion diseases. Generally, neurodegenerative diseases can be grouped as follows:

I. Disorders characterized by progressive dementia in the absence of other prominent neurologic signs, such as Alzheimer's disease; Senile dementia of the Alzheimer type; and Pick's disease (lobar atrophy).

II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy).

III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome.

IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders).

V. Syndrome of central autonomic nervous system failure (Shy-Drager syndrome).

VI. Syndromes of muscular weakness and wasting without sensory changes (motomeuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia.

VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy.

VIII. Syndromes of progressive visual loss such as pigmentary degeneration of the retina (retinitis pigmentosa), and hereditary optic atrophy (Leber's disease).

Definitions

The term "treating" in its various grammatical forms in relation to the present invention refers to preventing (i.e., chemoprevention), curing, reversing, attenuating, alleviating, minimizing, suppressing or halting the deleterious effects of a disease state, disease progression, disease causative agent (e.g., bacteria or viruses) or other abnormal condition. For example, treatment may involve alleviating a symptom (i.e., not necessary all symptoms) of a disease or attenuating the progression of a disease. Because some of the inventive methods involve the physical removal of the etiological agent, the artisan will recognize that they are equally effective in situations where the inventive compound is administered prior to, or simultaneous with, exposure to the etiological agent (prophylactic treatment) and situations where the inventive compounds are administered after (even well after) exposure to the etiological agent.

Treatment of cancer, as used herein, refers to partially or totally inhibiting, delaying or preventing the progression of cancer including cancer metastasis; inhibiting, delaying or preventing the recurrence of cancer including cancer metastasis; or preventing the onset or development of cancer (chemoprevention) in a mammal, for example a human.

As used herein, the term "therapeutically effective amount" is intended to encompass any amount that will achieve the desired therapeutic or biological effect. The therapeutic effect is dependent upon the disease or disorder being treated or the biological effect desired. As such, the therapeutic effect can be a decrease in the severity of symptoms associated with the disease or disorder and/or inhibition (partial or complete) of progression of the disease. The amount needed to elicit the therapeutic response can be determined based on the age, health, size and sex of the subject. Optimal amounts can also be determined based on monitoring of the subject's response to treatment.

In the present invention, when the compounds are used to treat or prevent cancer, the desired biological response is partial or total inhibition, delay or prevention of the progression of cancer including cancer metastasis; inhibition, delay or prevention of the recurrence of cancer including cancer metastasis; or the prevention of the onset or development of cancer (chemoprevention) in a mammal, for example a human.

Furthermore, in the present invention, when the compounds are used to treat and/or prevent thioredoxin (TRX)-mediated diseases and conditions, a therapeutically effective amount is an amount that regulates, for example, increases, decreases or maintains a physiologically suitable level of TRX in the subject in need of treatment to elicit the desired therapeutic effect. The therapeutic effect is dependent upon the specific TRX-mediated disease or condition being treated. As such, the therapeutic effect can be a decrease in the severity of symptoms associated with the disease or disorder and/or inhibition (partial or complete) of progression of the disease or disease.

Furthermore, in the present invention, when the compounds are used to treat and/or prevent diseases or disorders of the central nervous system (CNS), a therapeutically effective amount is dependent upon the specific disease or disorder being treated. As such, the therapeutic effect can be a decrease in the severity of symptoms associated with the disease or disorder and/or inhibition (partial or complete) of progression of the disease or disorder.

In addition, a therapeutically effective amount can be an amount that inhibits histone deacetylase.

Further, a therapeutically effective amount, can be an amount that selectively induces terminal differentiation, cell growth arrest and/or apoptosis of neoplastic cells, or an amount that induces terminal differentiation of tumor cells.

The method of the present invention is intended for the treatment or chemoprevention of human patients with cancer. However, it is also likely that the method would be effective in the treatment of cancer in other subjects. "Subject", as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

Histone Deacetylases and Histone Deacetylase Inhibitors

As demonstrated herein, the phosphorus derivatives of the present invention show improved activity as histone deacetylase (HDAC) inhibitors. Accordingly, in one embodiment, the invention relates to a method of inhibiting the activity of histone deacetylase comprising contacting the histone deacetylase with an effective amount of one or more of the phosphorus compounds described herein.

Histone deacetylases (HDACs), as that term is used herein, are enzymes that catalyze the removal of acetyl groups from lysine residues in the amino terminal tails of the nucleosomal core hi stones. As such, HDACs together with histone acetyl transferases (HATs) regulate the acetylation status of histones. Histone acetylation affects gene expression and inhibitors of HDACs, such as the hydroxamic acid-based hybrid polar compound suberoylanilide hydroxamic acid (SAHA) induce growth arrest, differentiation and/or apoptosis of transformed cells in vitro and inhibit tumor growth in vivo. HDACs can be divided into three classes based on structural homology. Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Both Class I and II HDACs are inhibited by hydroxamic acid-based HDAC inhibitors, such as SAHA. Class III HDACs form a structurally distant class of NAD dependent enzymes that are related to the yeast SIR2 proteins and are not inhibited by hydroxamic acid-based HDAC inhibitors.

Histone deacetylase inhibitors or HDAC inhibitors, as that term is used herein are compounds that are capable of inhibiting the deacetylation of histones in vivo, in vitro or both. As such, HDAC inhibitors inhibit the activity of at least one histone deacetylase. As a result of inhibiting the deacetylation of at least one histone, an increase in acetylated histone occurs and accumulation of acetylated histone is a suitable biological marker for assessing the activity of HDAC inhibitors. Therefore, procedures that can assay for the accumulation of acetylated histones can be used to determine the HDAC inhibitory activity of compounds of interest. It is understood that compounds that can inhibit histone deacetylase activity can also bind to other substrates and as such can inhibit other biologically active molecules such as enzymes. It is also to be understood that the compounds of the present invention are capable of inhibiting any of the histone deacetylases set forth above, or any other histone deacetylases.

For example, in patients receiving HDAC inhibitors, the accumulation of acetylated histones in peripheral mononuclear cells as well as in tissue treated with HDAC inhibitors can be determined against a suitable control.

HDAC inhibitory activity of a particular compound can be determined in vitro using, for example, an enzymatic assays which shows inhibition of at least one histone deacetylase. Further, determination of the accumulation of acetylated histones in cells treated with a particular composition can be determinative of the HDAC inhibitory activity of a compound.

Assays for the accumulation of acetylated histones are well known in the literature. See, for example, Marks, P. A. et al., J. Natl. Cancer Inst., 92:1210-1215, 2000, Butler, L. M. et al., Cancer Res. 60:5165-5170 (2000), Richon, V. M. et al., Proc. Natl. Acad. Sci., USA, 95:3003-3007, 1998, and Yoshida, M. et al., J. Biol. Chem., 265:17174-17179, 1990.

For example, an enzymatic assay to determine the activity of an HDAC inhibitor compound can be conducted as follows. Briefly, the effect of an HDAC inhibitor compound on affinity purified human epitope-tagged (Flag) HDAC 1 can be assayed by incubating the enzyme preparation in the absence of substrate on ice for about 20 minutes with the indicated amount of inhibitor compound. Substrate ([$^3$H]acetyl-labelled murine erythroleukemia cell-derived histone) can be added and the sample can be incubated for 20 minutes at 37° C. in a total volume of 30 µL. The reaction can then be stopped and released acetate can be extracted and the amount of radioactivity release determined by scintillation counting. An alternative assay useful for determining the activity of an HDAC inhibitor compound is the "HDAC Fluorescent Activity Assay; Drug Discovery Kit-AK-500" available from BIOMOL Research Laboratories, Inc., Plymouth Meeting, Pa.

In vivo studies can be conducted as follows. Animals, for example, mice, can be injected intraperitoneally with an HDAC inhibitor compound. Selected tissues, for example, brain, spleen, liver etc, can be isolated at predetermined times, post administration. Histones can be isolated from tissues essentially as described by Yoshida et al., J. Biol. Chem. 265:17174-17179, 1990. Equal amounts of histones (about 1 µg) can be electrophoresed on 15% SDS-polyacrylamide gels and can be transferred to Hybond-P filters (available from Amersham). Filters can be blocked with 3% milk and can be probed with a rabbit purified polyclonal anti-acetylated histone H4 antibody (αAc-H4) and anti-acetylated histone H3 antibody (αAc-H3) (Upstate Biotechnology, Inc.). Levels of acetylated histone can be visualized using a horseradish peroxidase-conjugated goat anti-rabbit antibody (1:5000) and the SuperSignal chemiluminescent substrate (Pierce). As a loading control for the histone protein, parallel gels can be run and stained with Coomassie Blue (CB).

In addition, hydroxamic acid-based HDAC inhibitors have been shown to up regulate the expression of the $p21^{WAF1}$ gene. The $p_{21}^{WAF1}$ protein is induced within 2 hours of culture with HDAC inhibitors in a variety of transformed cells using standard methods. The induction of the $p21^{WAF1}$ gene is associated with accumulation of acetylated histones in the chromatin region of this gene. Induction of $p_{21}^{WAF1}$ can therefore be recognized as involved in the G1 cell cycle arrest caused by HDAC inhibitors in transformed cells.

Combination Therapy

The phosphorus compounds of the present invention can be administered alone or in combination with other therapies suitable for the disease or disorder being treated. Where separate dosage formulations are used, the phosphorus compound and the other therapeutic agent can be administered at essentially the same time (concurrently) or at separately staggered times (sequentially). The pharmaceutical combination is understood to include all these regimens. Administration in these various ways are suitable for the present invention as long as the beneficial therapeutic effect of the phosphorus compound and the other therapeutic agent are realized by the patient at substantially the same time. In an embodiment, such beneficial effect is achieved when the target blood level concentrations of each active drug are maintained at substantially the same time.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, agents that interfere with cell cycle checkpoints, agents that interfere with receptor tyrosine kinases (RTKs) and cancer vaccines. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, diethylstibestral, tamoxifen, raloxifene, idoxifene, LY353381, LY117081, toremifene, fluoxymestero, Ifulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

Other hormonal agents include: aromatase inhibitors (e.g., aminoglutethimide, anastrozole and tetrazole), luteinizing hormone release hormone (LHRH) analogues, ketoconazole, goserelin acetate, leuprolide, megestrol acetate and mifepristone.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylomithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofuilven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis [diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycanninomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonanide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNP11100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino] ethyl]-5-[4-hydrooxy-3,5-dimethoxyphenyl]-5,5a,6,8,8a,9-hexahydrofluro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678 and WO 03/39460 and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, SAHA, TSA, oxamflatin, PXD101, MG98, valproic acid and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, palti- trexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, 11-acetyl-8-(carbamoyloxymethyl)-4-formyl-6-methoxy)-4-oxa-1,1'-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589, 485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression.

Such agents include inhibitors of c-Kit, Eph, PDGF, Flt3 and c-Met. Further agents include inhibitors of RTKs shown as described by Bume-Jensen and Hunter, Nature, 411:355-365, 2001.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of CD20 (rituximab), inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272, and U.S. Pat. No. 5,932,598.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBRE® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Opthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet* 61:785-789, 1997) and Kufe et al (*Cancer Medicine,* 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), Duc-4, NF-1, NF-2, RB, WT1, BRCA1, BRCA2, a uPA/uPAR antagonist ("Adenovirus-Mediated Delivery of a uPA/uPAR Antagonist Suppresses Angiogenesis-Dependent Tumor Growth and Dissemination in Mice," *Gene Therapy, August* 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, bacillus Calmette-Guerin, octreotide, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to anastrozole, letrozole and exemestane.

A compound of the instant invention may also be useful for treating or preventing cancer in combination with siRNA therapeutics.

A compound of the instant invention may also be useful for treating or preventing cancer in combination with compounds which induce terminal differentiation of the neoplastic cells. Suitable differentiation agents include the compounds disclosed in any one or more of the following references.

a) Polar compounds (Marks et al (1987); Friend, C., Scher, W., Holland, J. W., and Sato, T. (1971) *Proc. Natl. Acad. Sci.* (USA) 68: 378-382; Tanaka, M., Levy, J., Terada, M., Breslow, R., Rifkind, R. A., and Marks, P. A. (1975) *Proc. Natl. Acad. Sci.* (USA) 72: 1003-1006; Reuben, R. C., Wife, R. L., Breslow, R., Rifkind, R. A., and Marks, P. A. (1976) *Proc. Natl. Acad. Sci.* (USA) 73: 862-866);

b) Derivatives of vitamin D and retinoic acid (Abe, E., Miyaura, C., Sakagami, H., Takeda, M., Konno, K., Yamazaki, T., Yoshika, S., and Suda, T. (1981) *Proc. Natl. Acad. Sci.* (USA) 78: 4990-4994; Schwartz, E. L., Snoddy, J. R., Kreutter, D., Rasmussen, H., and Sartorelli, A. C. (1983) *Proc. Am. Assoc. Cancer Res.* 24: 18; Tanenaga, K., Hozumi, M., and Sakagami, Y. (1980) *Cancer Res.* 40: 914-919);

c) Steroid hormones (Lotem, J. and Sachs, L. (1975) *Int. J. Cancer* 15: 731-740);

d) Growth factors (Sachs, L. (1978) *Nature (Lond.)* 274: 535, Metcalf, D. (1985) *Science,* 229: 16-22);

e) Proteases (Scher, W., Scher, B. M., and Waxman, S. (1983) *Exp. Hematol.* 11: 490-498; Scher, W., Scher, B. M., and Waxman, S. (1982) *Biochem. & Biophys. Res. Comm.* 109: 348-354);

f) Tumor promoters (Huberman, E. and Callaham, M. F. (1979) *Proc. Natl. Acad. Sci.* (USA) 76: 1293-1297; Lottem, J. and Sachs, L. (1979) *Proc. Natl. Acad. Sci.* (USA) 76: 5158-5162); and g) inhibitors of DNA or RNA synthesis (Schwartz, E. L. and Sartorelli, A. C. (1982) *Cancer Res.* 42: 2651-2655, Terada, M., Epner, E., Nudel, U., Salmon, J., Fibach, E., Rifkind, R. A., and Marks, P. A. (1978) *Proc. Natl. Acad. Sci.* (USA) 75: 2795-2799; Morin, M. J. and Sartorelli, A. C. (1984) *Cancer Res* 44: 2807-2812; Schwartz, E. L., Brown, B. J., Nierenberg, M., Marsh, J. C., and Sartorelli, A. C. (1983) Cancer Res. 43: 2725-2730; Sugano, H., Furusawa, M., Kawaguchi, T., and Ikawa, Y. (1973) Bibl. Hematol. 39: 943-954; Ebert, P. S., Wars, I., and Buell, D. N. (1976) *Cancer Res.* 36: 1809-1813; Hayashi, M., Okabe, J., and Hozumi, M. (1979) Gann 70: 235-238).

A compound of the instant invention may also be useful for treating or preventing cancer in combination with γ-secretase inhibitors.

Also included in the scope of the claims is a method of treating cancer that comprises administering a therapeutically effective amount of a compound of Formula I in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

The compounds of the instant invention are useful in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubexg); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megaceg); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vinorelbine (Navelbine®); zoledronate (Zometa®); and zoledronic acid (Zometa®).

The use of all of these approaches in combination with the phosphorus compounds described herein are within the scope of the present invention.

Dosages and Dosing Schedules

The dosage regimen utilizing the phosphorus derivatives of the present invention can be selected in accordance with a variety of factors including type, species, age, weight, sex and the type of cancer being treated; the severity (i.e., stage) of the disease to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

For oral administration, suitable daily dosages are for example between about 2-4000 mg administered orally once-daily, twice-daily or three times-daily, continuous (every day) or intermittently (e.g., 3-5 days a week). For example, when used to treat the desired disease, the dose of the phosphorus compound can range between about 2 mg to about 2000 mg per day.

The phosphorus derivative is administered once daily (QD), or divided into multiple daily doses such as twice daily (BID), and three times daily (TID). For administration once a day, a suitably prepared medicament would therefore contain all of the needed daily dose. For administration twice a day, a suitably prepared medicament would therefore contain half of the needed daily dose. For administration three times a day, a suitably prepared medicament would therefore contain one third of the needed daily dose.

In addition, the administration can be continuous, i.e., every day, or intermittently. The terms "intermittent" or "intermittently" as used herein means stopping and starting at either regular or irregular intervals. For example, intermittent administration of an HDAC inhibitor may be administration one to six days per week or it may mean administration in cycles (e.g., daily administration for two to eight consecutive weeks, then a rest period with no administration for up to one week) or it may mean administration on alternate days.

Typically, an intravenous formulation may be prepared which contains a concentration of the phosphorus derivative of between about 1.0 mg/mL to about 10 mg/mL. In one example, a sufficient volume of intravenous formulation can be administered to a patient in a day such that the total dose for the day is between about 1 and about 1500 mg/m$^2$.

Subcutaneous formulations, preferably prepared according to procedures well known in the art at a pH in the range between about 5 and about 12, also include suitable buffers and isotonicity agents, as described below. They can be formulated to deliver a daily dose of HDAC inhibitor in one or more daily subcutaneous administrations, e.g., one, two or three times each day.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

It should be apparent to a person skilled in the art that the various modes of administration, dosages and dosing schedules described herein merely set forth specific embodiments and should not be construed as limiting the broad scope of the invention. Any permutations, variations and combinations of the dosages and dosing schedules are included within the scope of the present invention.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

Pharmaceutical Compositions

The compounds of the invention, and derivatives, fragments, analogs, homologs pharmaceutically acceptable salts or hydrate thereof, can be incorporated into pharmaceutical compositions suitable for oral administration, together with a pharmaceutically acceptable carrier or excipient. Such compositions typically comprise a therapeutically effective amount of any of the compounds above, and a pharmaceutically acceptable carrier. In one embodiment, the effective amount is an amount effective to selectively induce terminal differentiation of suitable neoplastic cells and less than an amount which causes toxicity in a patient.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

In one embodiment, the pharmaceutical compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the phosphorus derivative active compound and the inert carrier or diluent, a hard gelatin capsule.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscannellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flowaids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The compounds of the present invention may be administered intravenously on the first day of treatment, with oral administration on the second day and all consecutive days thereafter.

The compounds of the present invention may be administered for the purpose of preventing disease progression or stabilizing tumor growth.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause unmanageable toxicity in the patient. In the certain embodiments, the amount of the compound that is administered to the patient is less than the amount that causes a concentration of the compound in the patient's plasma to equal or exceed the toxic level of the compound. In one embodiment, the concentration of the compound in the patient's plasma is maintained at about 10 nM. In another embodiment, the concentration of the compound in the patient's plasma is maintained at about 25 nM. In another embodiment, the concentration of the compound in the patient's plasma is maintained at about 50 nM. In another embodiment, the concentration of the compound in the patient's plasma is maintained at about 100 nM. In another embodiment, the concentration of the compound in the patient's plasma is maintained at about 500 nM. In another embodiment, the concentration of the compound in the patient's plasma is maintained at about 1000 nM. In another embodiment, the concentration of the compound in the patient's plasma is maintained at about 2500 nM. In another embodiment, the concentration of the compound in the patient's plasma is maintained at about 5000 nM. The optimal amount of the compound that should be administered to the patient in the practice of the present invention will depend on the particular compound used and the type of cancer being treated.

The instant invention also includes a pharmaceutical composition useful for treating or preventing cancer that comprises a therapeutically effective amount of a compound of Formula I and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

In Vitro Methods:

The present invention also provides methods of using the phosphorus derivatives of the present invention for inducing terminal differentiation, cell growth arrest and/or apoptosis of neoplastic cells thereby inhibiting the proliferation of such cells. The methods can be practiced in vivo or in vitro.

In one embodiment, the present invention provides in vitro methods for selectively inducing terminal differentiation, cell growth arrest and/or apoptosis of neoplastic cells, thereby inhibiting proliferation of such cells, by contacting the cells with an effective amount of any one or more of the phosphorus derivatives described herein.

In a particular embodiment, the present invention relates to an in vitro method of selectively inducing terminal differentiation of neoplastic cells and thereby inhibiting proliferation of such cells. The method comprises contacting the cells under suitable conditions with an effective amount of one or more of the phosphorus compounds described herein.

In another embodiment, the invention relates to an in vitro method of selectively inducing cell growth arrest of neoplastic cells and thereby inhibiting proliferation of such cells. The method comprises contacting the cells under suitable conditions with an effective amount of one or more of the phosphorus compounds described herein.

In another embodiment, the invention relates to an in vitro method of selectively inducing apoptosis of neoplastic cells and thereby inhibiting proliferation of such cells. The method comprises contacting the cells under suitable conditions with an effective amount of one or more of the phosphorus compounds described herein.

In another embodiment, the invention relates to an in vitro method of inducing terminal differentiation of tumor cells in a tumor comprising contacting the cells with an effective amount of any one or more of the phosphorus compounds described herein.

Although the methods of the present invention can be practiced in vitro, it is contemplated that the preferred embodiment for the methods of selectively inducing terminal differentiation, cell growth arrest and/or apoptosis of neoplastic cells, and of inhibiting HDAC will comprise contacting the cells in vivo, i.e., by administering the compounds to a subject harboring neoplastic cells or tumor cells in need of treatment.

Thus, the present invention provides in vivo methods for selectively inducing terminal differentiation, cell growth arrest and/or apoptosis of neoplastic cells in a subject, thereby inhibiting proliferation of such cells in the subject, by administering to the subject an effective amount of any one or more of the phosphorus derivatives described herein.

In a particular embodiment, the present invention relates to a method of selectively inducing terminal differentiation of neoplastic cells and thereby inhibiting proliferation of such cells in a subject. The method comprises administering to the subject an effective amount of one or more of the phosphorus derivatives described herein.

In another embodiment, the invention relates to a method of selectively inducing cell growth arrest of neoplastic cells and thereby inhibiting proliferation of such cells in a subject. The method comprises administering to the subject an effective amount of one or more of the phosphorus derivatives described herein.

In another embodiment, the invention relates to a method of selectively inducing apoptosis of neoplastic cells and thereby inhibiting proliferation of such cells in a subject. The method comprises administering to the subject an effective amount of one or more of the phosphorus derivatives described herein.

In another embodiment, the invention relates to a method of treating a patient having a tumor characterized by proliferation of neoplastic cells. The method comprises administering to the patient one or more of the phosphorus derivatives described herein. The amount of compound is effective to selectively induce terminal differentiation, induce cell growth arrest and/or induce apoptosis of such neoplastic cells and thereby inhibit their proliferation.

The invention is illustrated in the examples in the Experimental Details Section that follows. This section is set forth to aid in an understanding of the invention but is not intended to, and should not be construed to limit in any way the invention as set forth in the claims which follow thereafter.

EXPERIMENTAL DETAILS SECTION

Example 1

Synthesis

The compounds of the present invention were prepared by the general methods outlined in the synthetic schemes below, as exemplified below. In the following schemes, Ar may represent aryl or heteroaryl.

A/B. Preparation of Aryl Phosphonates/Phosphinates

Schemes 1 and 2 illustrate the use of nickel-catalyzed coupling to make the aryl-phosphorus bond and subsequent transformation to pharmaceutically useful compounds.

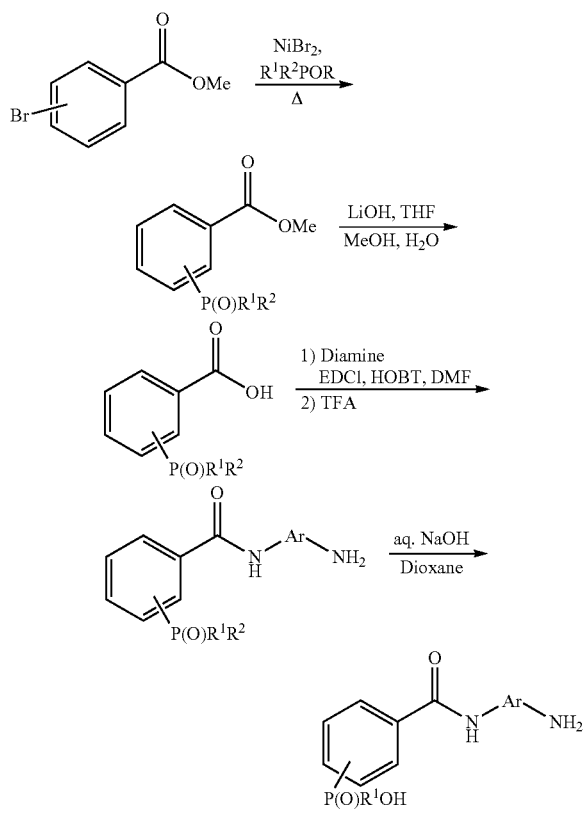

C. Preparation of Aryl Phosphine Oxides

Scheme 4 illustrates the synthetic route used to access aryl phosphine oxides.

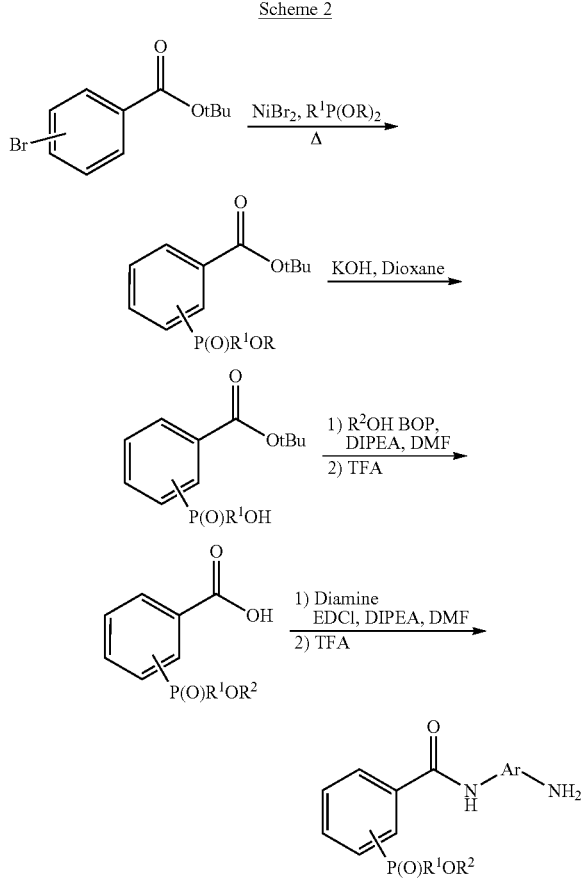

Scheme 2

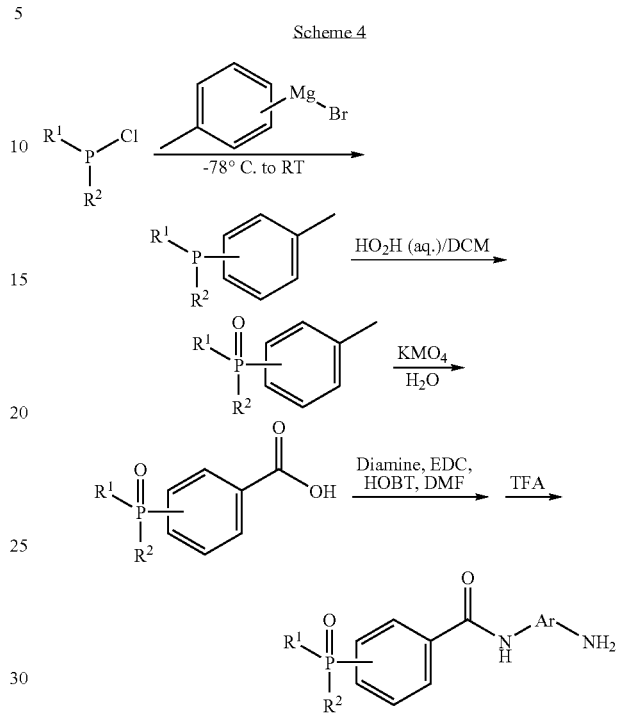

Scheme 4

Scheme 3 illustrates the synthetic route to make the heteroaryl-phosphorus bond and subsequent transformation to pharmaceutically useful compounds.

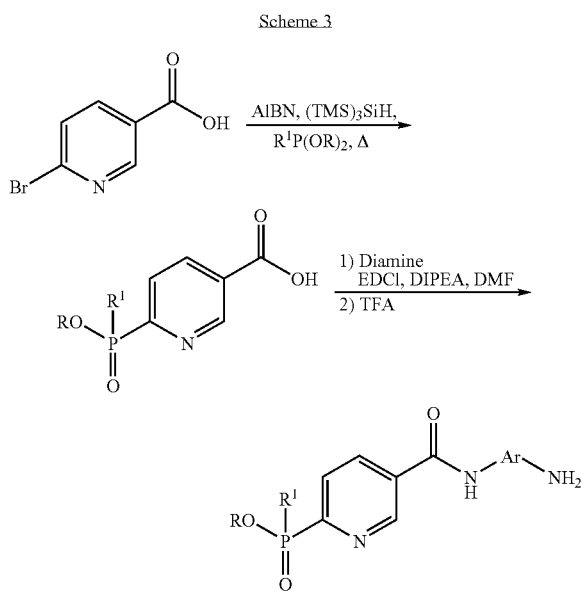

Scheme 3

Scheme 5 illustrates an alternative synthetic route to aryl phosphine oxides

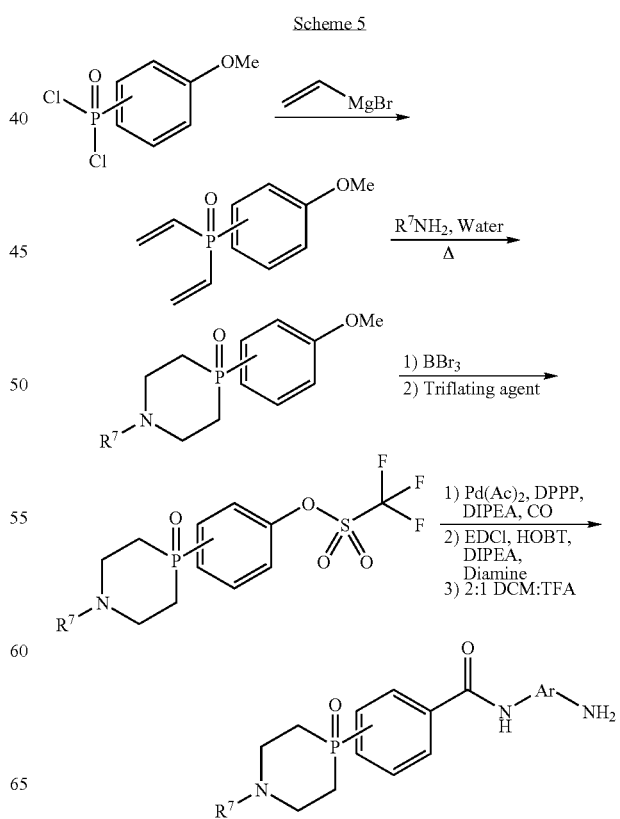

Scheme 5

D/E. Preparation of Alkyl Phosphonates/Phosphinates

Scheme 6 illustrates the use of an Arbuzov coupling to make the phosphorus carbon bond and subsequent transformations to pharmaceutically useful compounds.

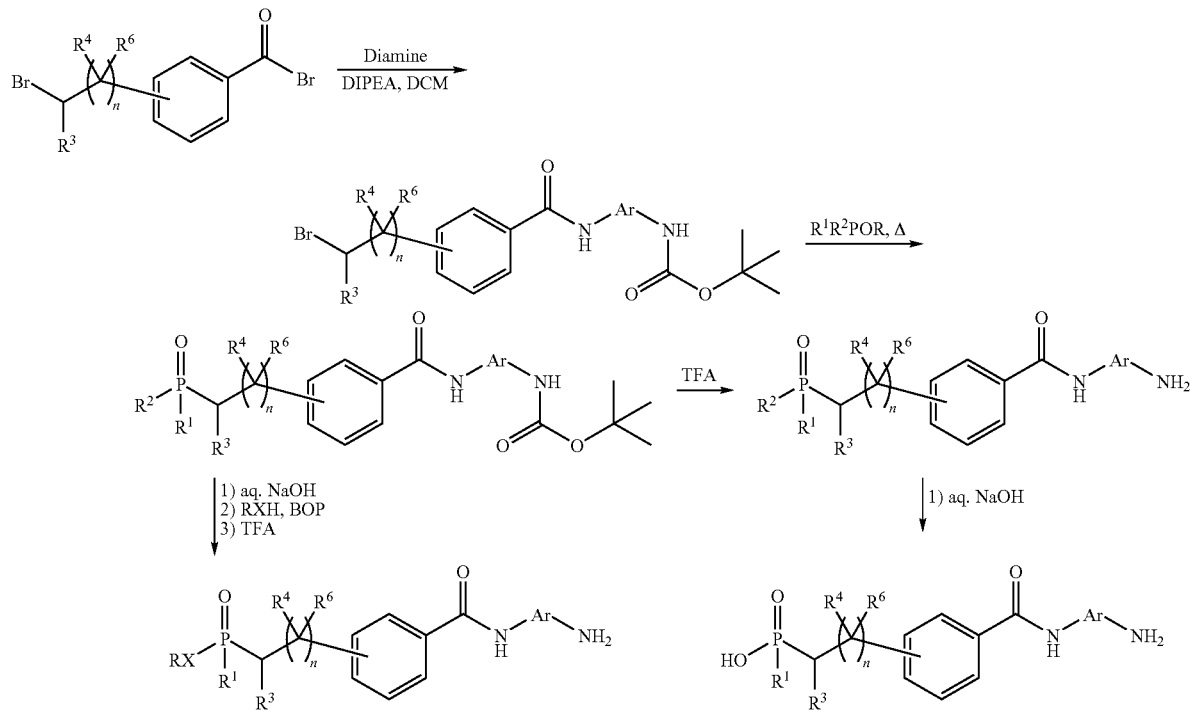

Scheme 7 illustrates an alternate synthetic route to access alkyl phosphonates or phosphinates with the Arbuzov coupling taking place earlier in the sequence, as well as, incorporating α-substitution.

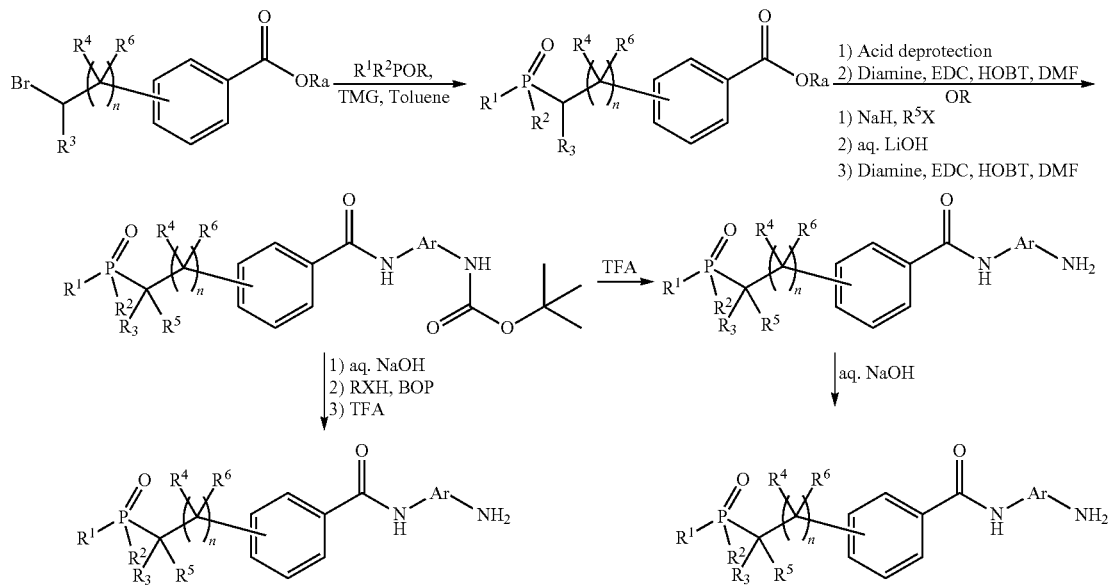

Scheme 8 illustrates an alternative synthetic route to alkyl phosphonates with α-substitution.
Scheme 9 illustrates an alternative synthetic route to phosphonates containing β-substitution.
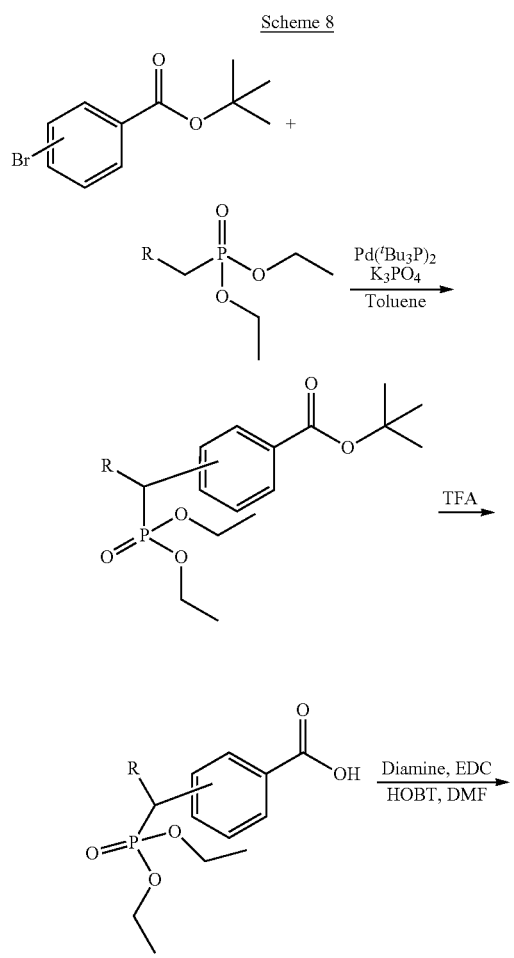
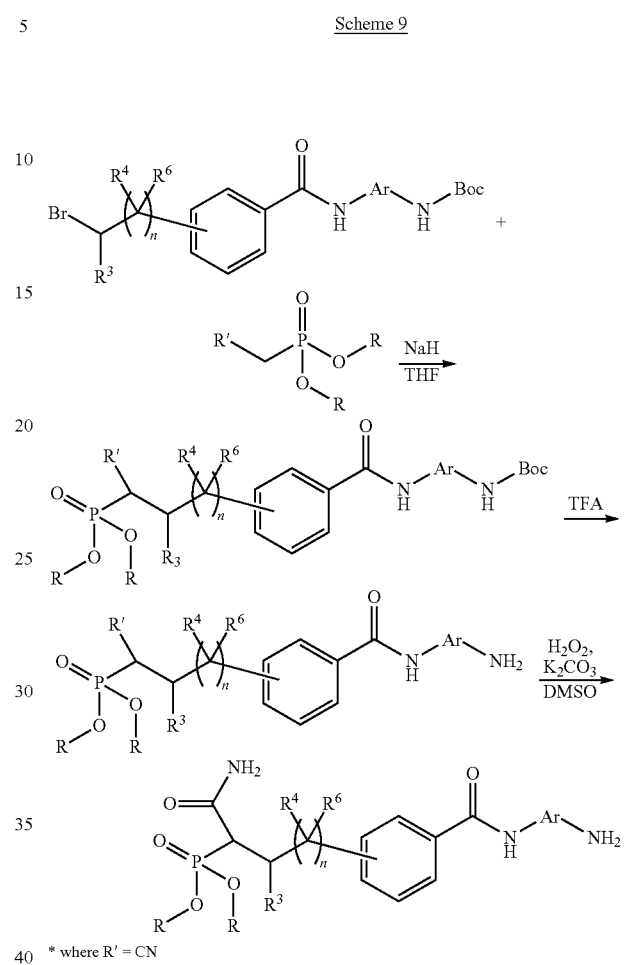
Scheme 10 illustrates an alternative synthetic route to phosphonates and phosphinates derived from methyl 6-methylnicotinate.
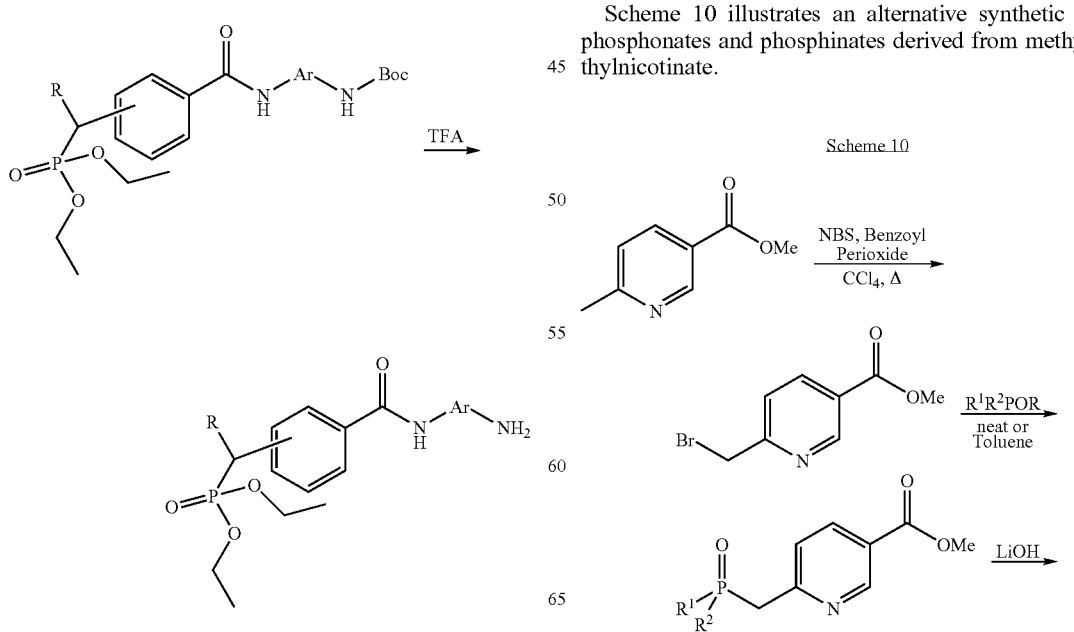

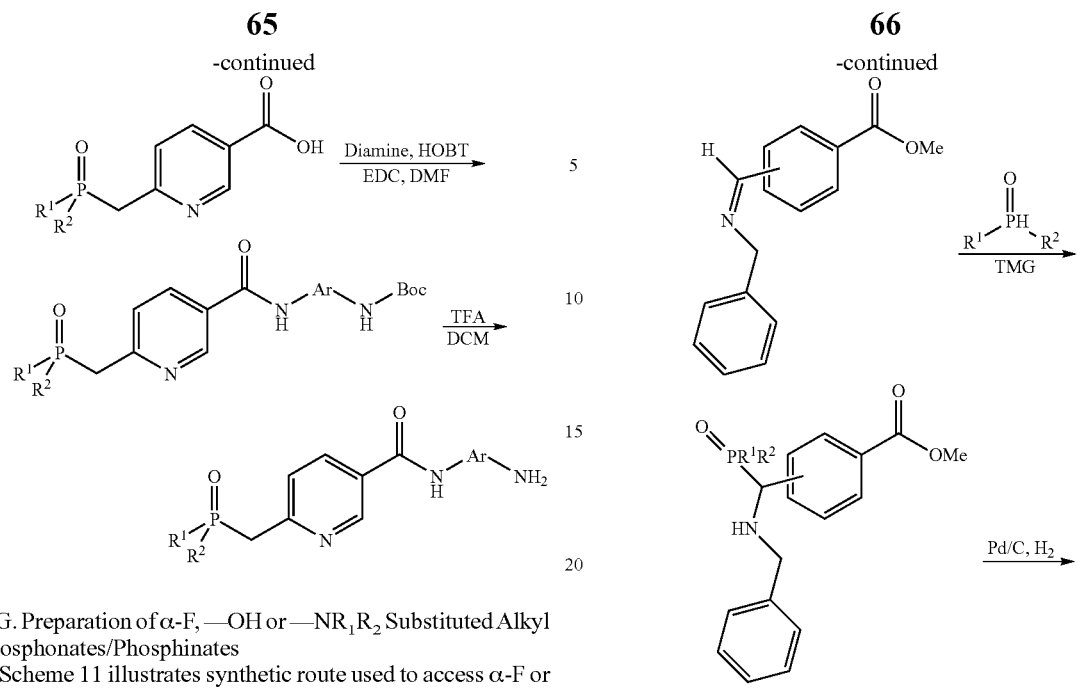
F/G. Preparation of α-F, —OH or —NR₁R₂ Substituted Alkyl Phosphonates/Phosphinates
Scheme 11 illustrates synthetic route used to access α-F or -OH substituted alkyl phosphonates or phosphinates.
Scheme 11
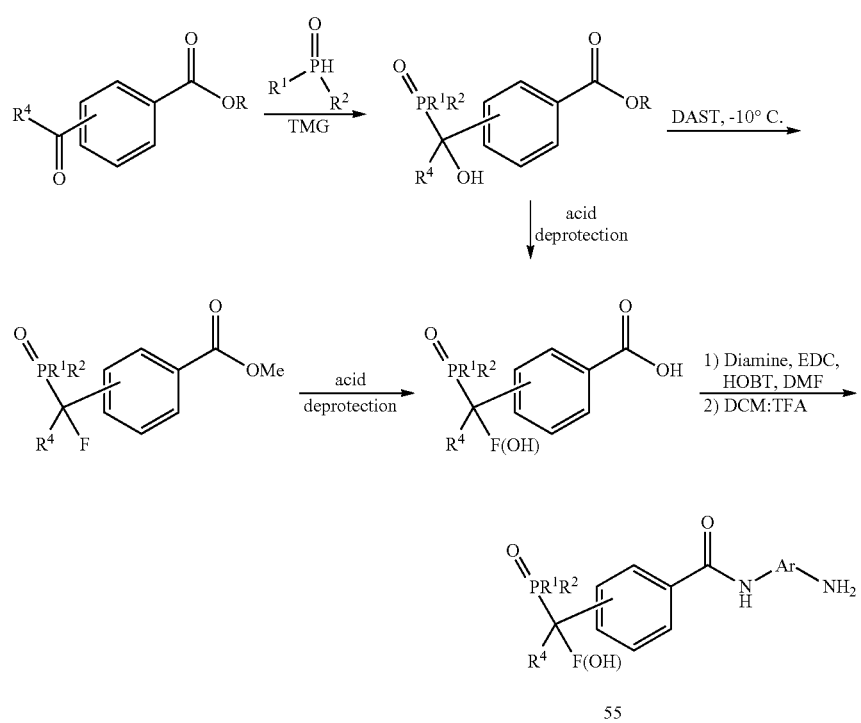
Scheme 12 illustrates the synthetic route used to access alkyl phosphonates or phosphinates with an α-amino group.
Scheme 12
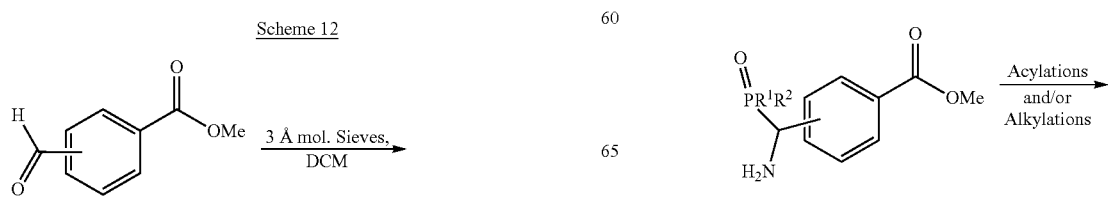

-continued

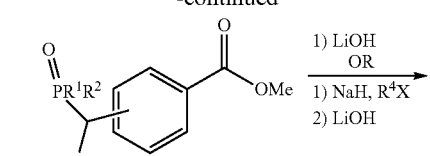

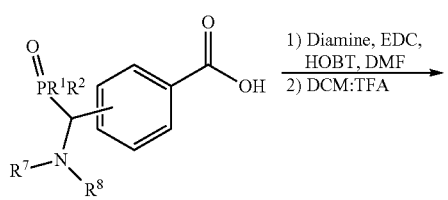

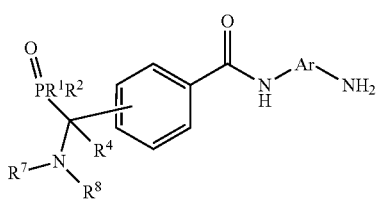

H. Preparation of Alkyl Phosphine Oxides

Scheme 13 illustrates the synthetic route used to access alkyl phosphine oxides.

Scheme 13

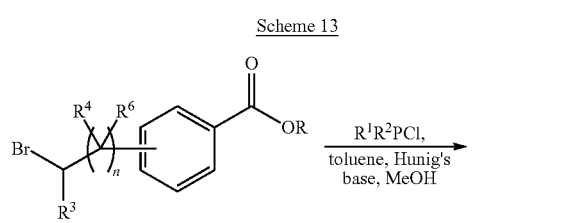

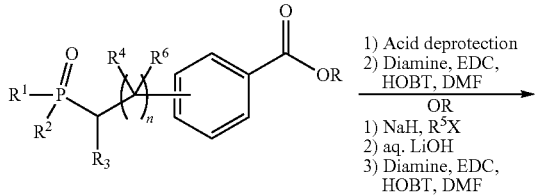

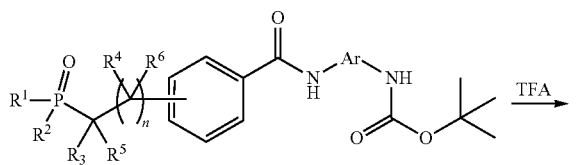

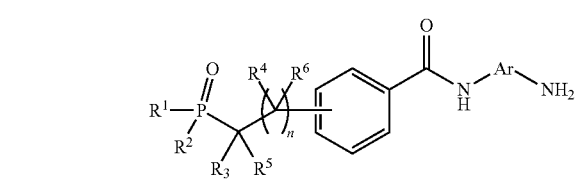

I. Scheme 14 Illustrates the Synthesis of N-Arylpyrazoles.

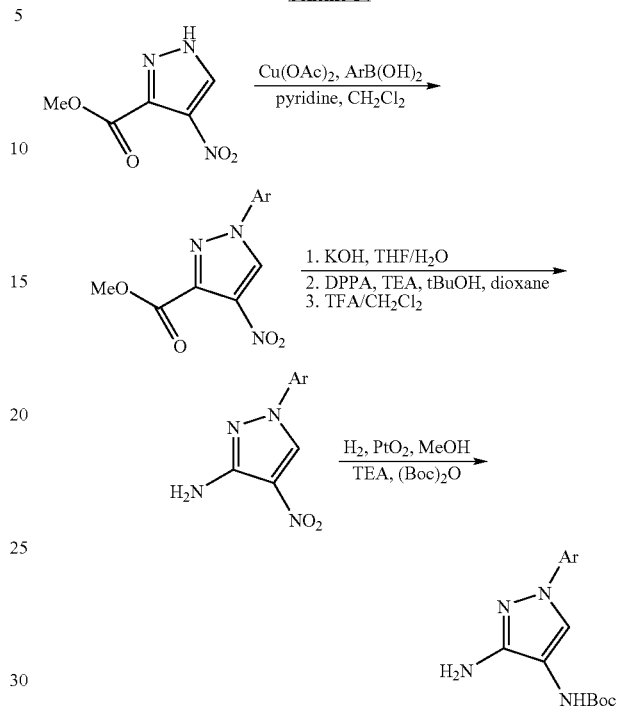

J/K/L. Preparation of Spirocyclic Phosphonates, β-Aminophosphine Oxides, and Phosphopiperidines Scheme 15 illustrates the synthetic route used to access phosphonate-containing spirocyclic amine intermediates.

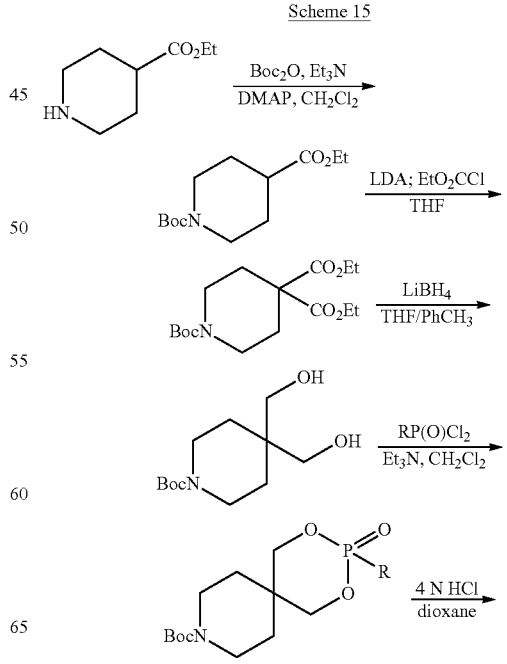

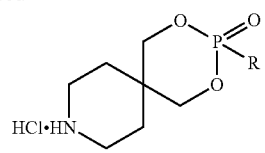

Scheme 16 illustrates the synthetic routes used to access β-aminophosphine oxide intermediates.

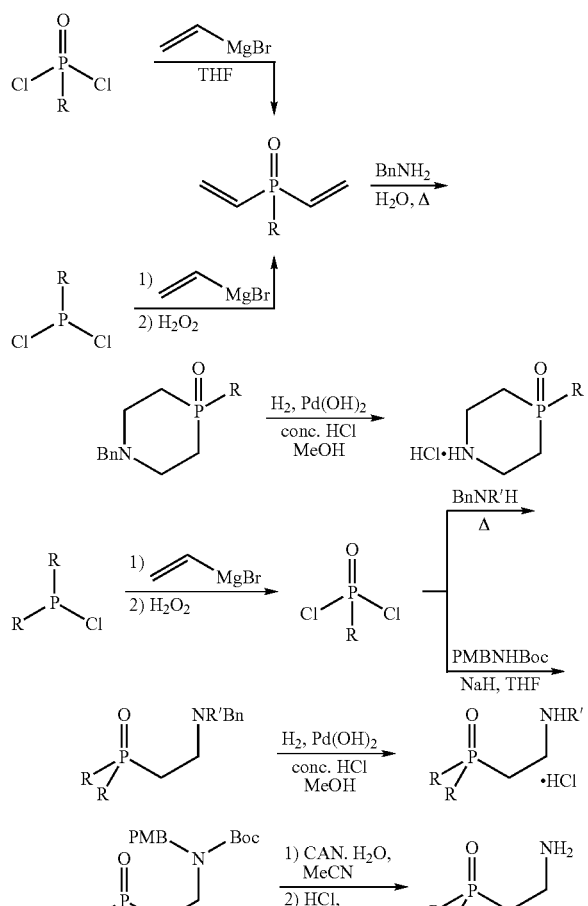

Scheme 17 illustrates the synthetic route used to access diethyl piperidin-4-ylphosphonate.

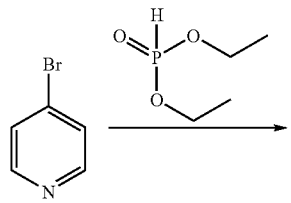

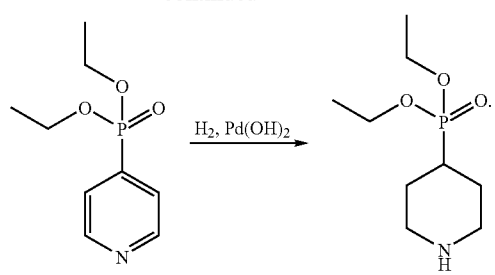

Scheme 18 illustrates the synthetic routes used to access nicotinamide, benzyl amine, phenethyl amine, benzamide, and phenylacetamide derivatives of the amines prepared in Schemes 15-17.

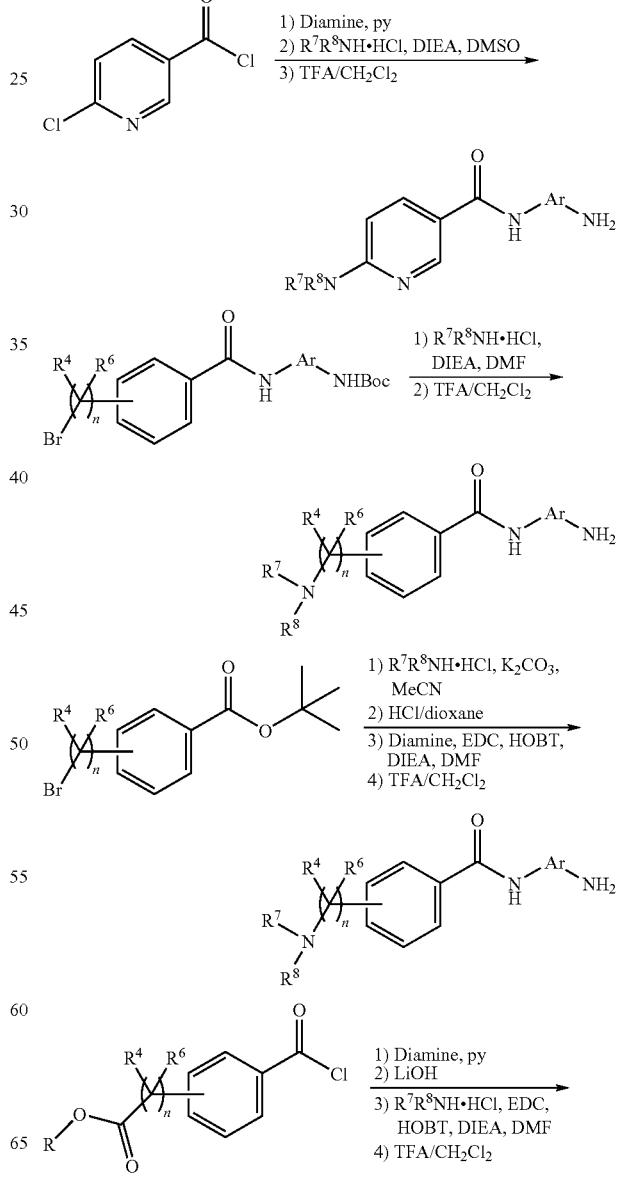

71
-continued

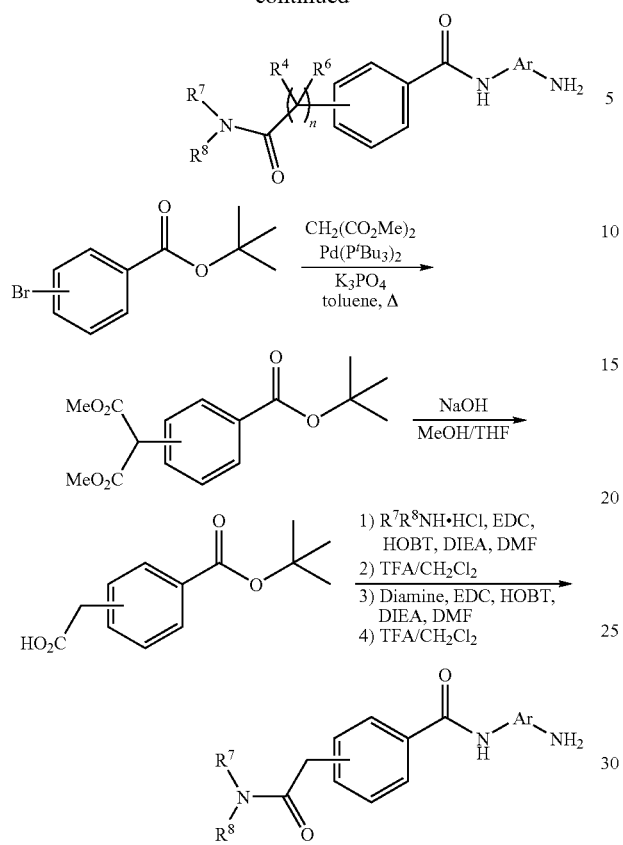

M. Preparation of Alkyloxy Phosphonates/Phosphinates/Phosphates.

Scheme 19 illustrates the synthetic route to phosphonates, phosphinates or phosphates derived from alkyl alcohol.

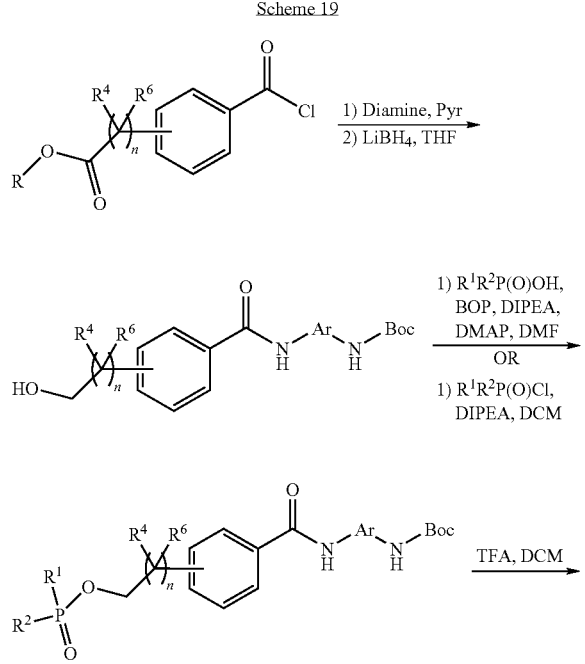

72
-continued

Scheme 20 illustrates an alternative synthetic route to phosphonates, phosphinates or phosphates derived from alkyl alcohols.

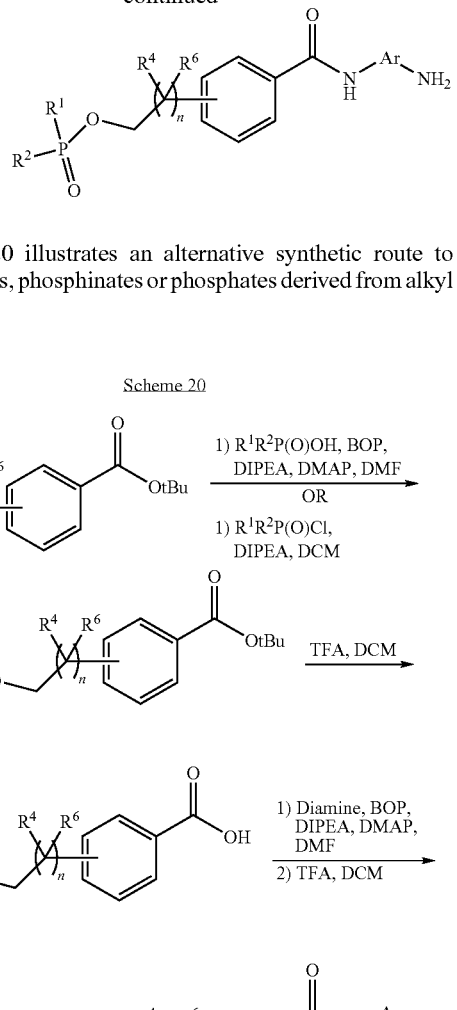

Scheme 21 illustrates an alternative synthetic route to phosphonates, phosphinates or phosphates derived from alcohols.

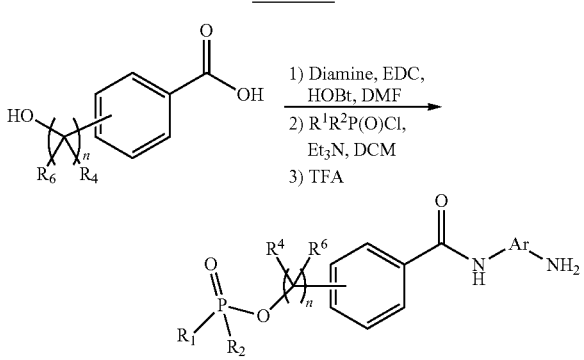

N. Preparation of Arylamino Phosphonawide/Phosphinamide/Phosphoramides.

Scheme 22 illustrates the synthesis of anilino phosphonates

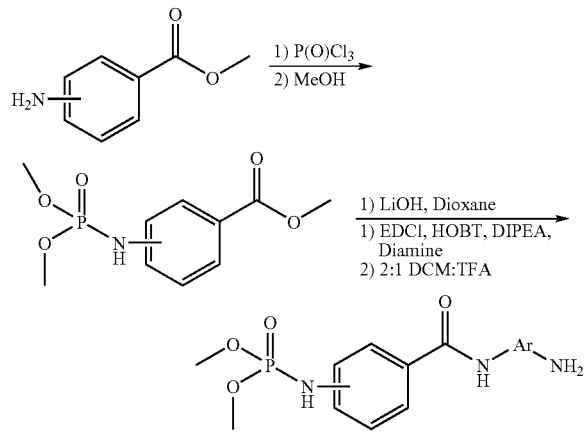

Scheme 23 illustrates the synthesis of aniline phosphinates

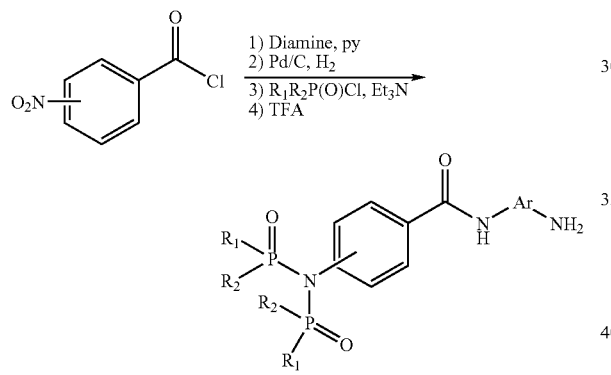

O. Preparation of Alkylamino Phosphonamide/Phosphinamide/Phosphoramides.

Scheme 24 illustrates the synthetic route to phosphonamides, phosphinamides or phosphoramides derived from alkyl amine.

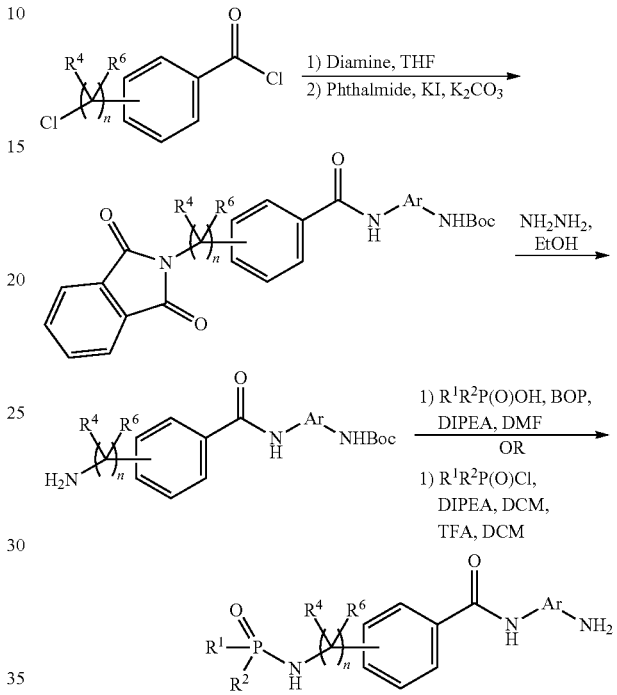

P. Preparation of Alkylamino Phosphorus Containing Carbamates/Ureas.

Scheme 25 illustrates the synthetic route to phosphorus containing ureas/carbamates derived from alkyl amine.

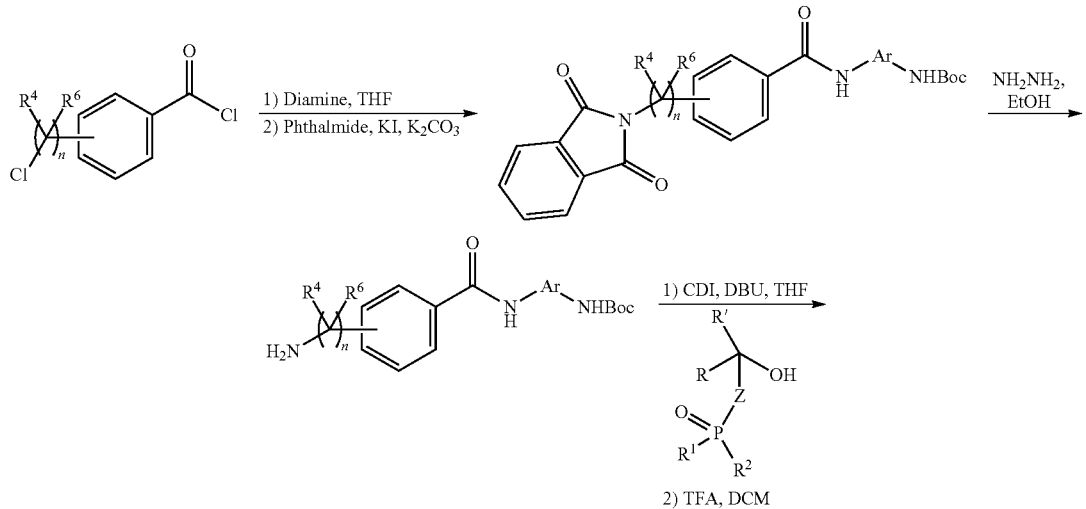

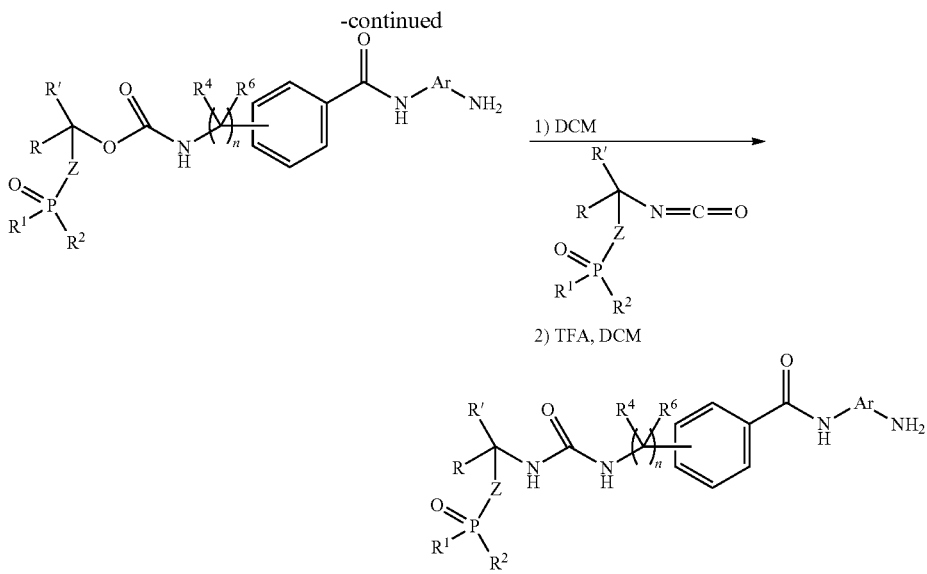
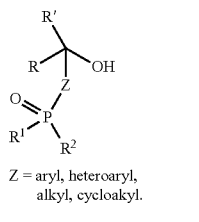
Z = aryl, heteroaryl, alkyl, cycloakyl.
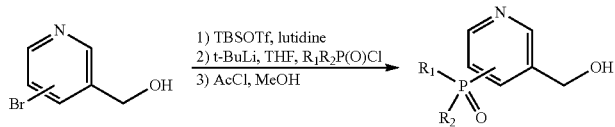
Scheme 26 illustrates an alternative synthetic route to phosphorus containing carbamates derived from alkyl amine.
Scheme 26
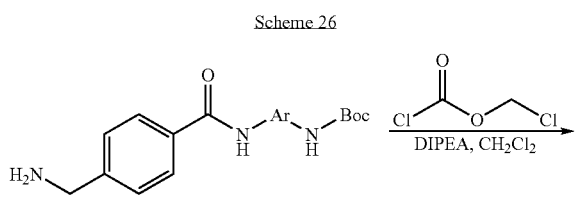
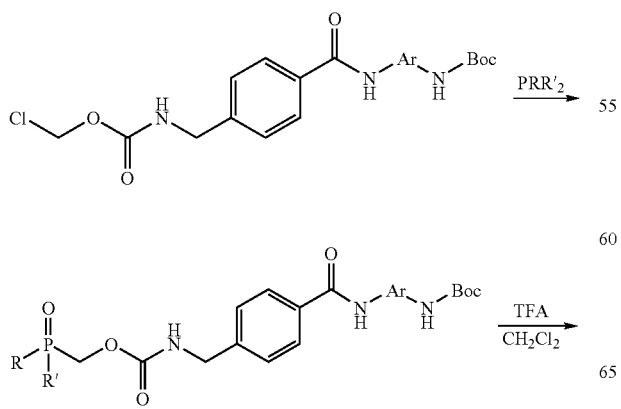
R = Me, Et, OMe, OEt
R' = OMe, OEt
Q. Preparation of Phosphorus Containing Amides.
Scheme 27 illustrates the synthetic route to phosphorus amides.
Scheme 27
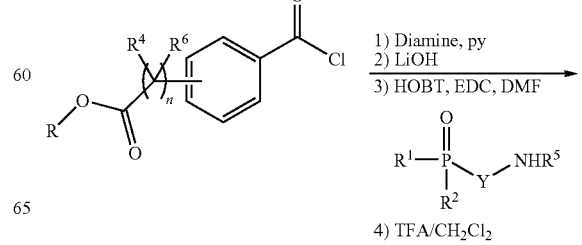

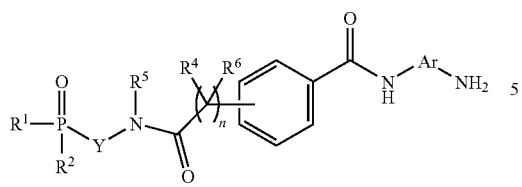

R. Preparation of Cyclic Phosphonates

Scheme 28 illustrates the synthetic route used to prepare cyclic phosphonates

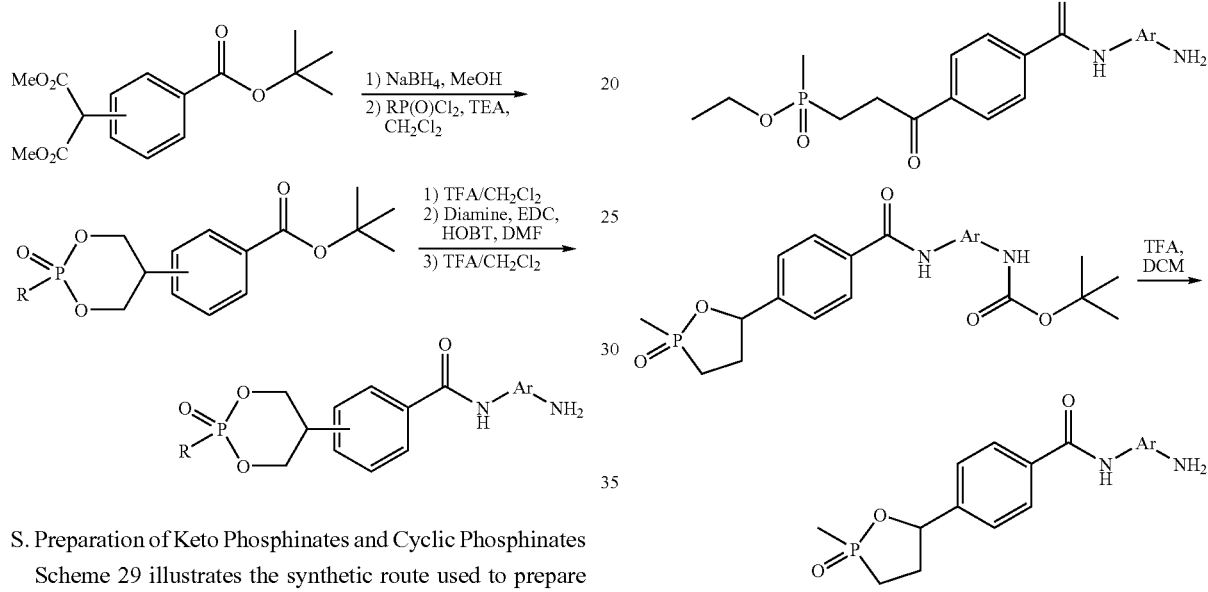

S. Preparation of Keto Phosphinates and Cyclic Phosphinates

Scheme 29 illustrates the synthetic route used to prepare keto phosphinates cyclic phosphinates

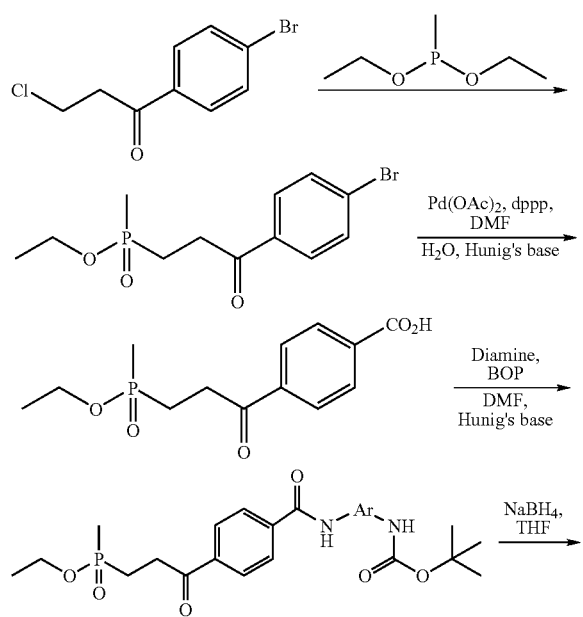

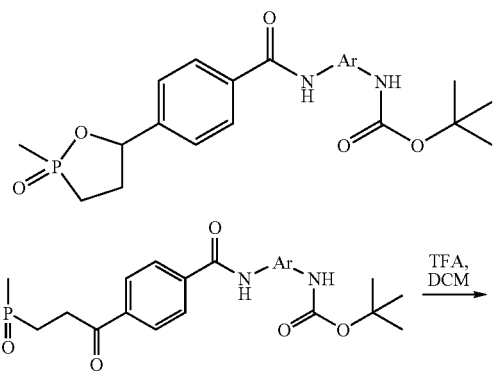

T. Preparation of α,β-Unsaturated Benzamides

Scheme 30 Illustrates the synthesis of a series of α,β-unsaturated benzamides.

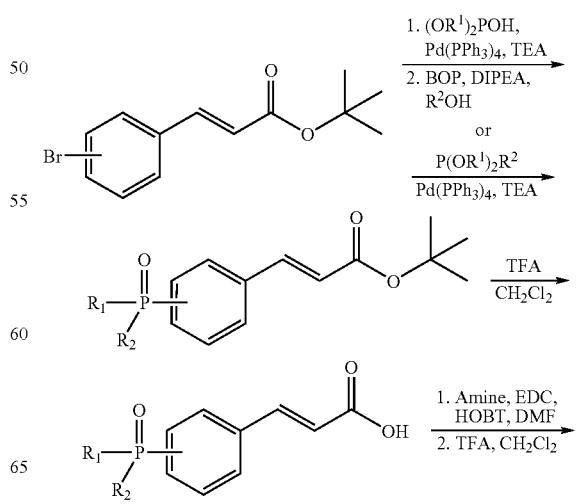

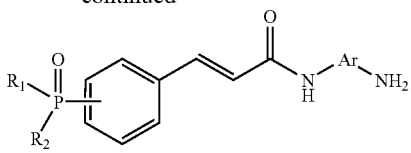

EXPERIMENTAL SECTION

The following examples further describe and demonstrate embodiments within the scope of the present invention. The examples are given solely for the purpose of illustration and are not to be construed as limitations of the present invention as many variations thereof are possible without departing from the spirit and scope of the invention.

Procedures for A. Pregaration of Aryl Phosphonates.

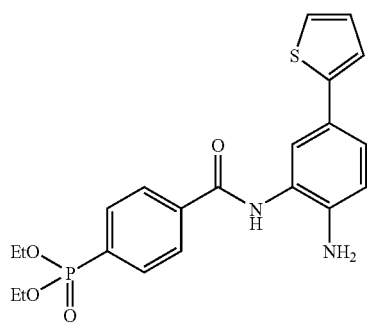

Diethyl [4-({[2-amino-5-(2-thienyl)phenyl]amino}carbonyl)phenyl]phosphonate. A mixture of 4-(diethoxyphosphoryl)benzoic acid (commercially available, 50 mg, 0.194 mmol), EDCI (44.6 mg, 0.233 mmol), HOBT (31.5 mg, 0.233 mmol) and tert-butyl [2-amino-4-(2-thienyl)phenyl]carbamate (67.7 mg, 0.233 mmol) were taken into DMF (0.58 mL) and stirred for 16 h. Approximately 5 mL of TFA was added to the mixture which was stirred for 1 h and concentrated. The product was purified by HPLC (30-90% MeCN in $H_2O$ with 0.025% TFA) to afford the requisite product. $^1$H NMR (DMSO-$d_6$, 600 MHz) δ 9.87 (s, 1H), 8.11 (dd, J=7.9, 3.5 Hz, 2H), 7.83 (dd, J=21.1, 8.2 Hz, 2H), 7.45 (d, J=2.0 Hz, 1H), 7.33 (dd, J=5.0, 0.9 Hz, 1H), 7.29 (dd, J=8.2, 2.0 Hz, 1H), 7.22 (d, J=2.9 Hz, 1H), 7.03 (dd, J=5.0, 3.5 Hz, 1H), 6.79 (d, J=8.5 Hz, 1H), 5.39 (s, 2H), 3.97-4.16 (m, 4H), 1.33 (t, J=7.04 Hz, 6H). MS: cal'd 431 (MH+), exp 431 (MH+).

Ethyl hydrogen [4-({[2-amino-5-(2-thienyl)phenyl]amino}carbonyl)phenyl]phosphonate. A suspension of diethyl [4-({[2-amino-5-(2-thienyl)phenyl]amino}carbonyl)phenyl]phosphonate (24.2 mg, 0.0562 mmol) (24.2 mg, 0.0562 mmol), dioxane (140 uL) and 5N aqueous NaOH (140 uL) was heated to 80° C. (oil bath temperature) for 1 h. The reaction was quenched with TFA (~140 uL) and concentrated. The residue was purified by HPLC (25-80% MeCN in $H_2O$ with 0.025% TFA) to afford the requisite product. $^1$H NMR (DMSO-$d_6$, 600 MHz) δ 9.77 (s, 1H), 8.30 (t, J=8.3 Hz, 2H), 7.69-7.64 (m, 2H), 7.48-7.45 (m, 1H), 7.34-7.31 (m, 1H), 7.26 (dd, J=8.2, 2.0 Hz, 1H), 7.22 (d, J=2.6 Hz, 1H), 7.02 (dd, J=5.0, 3.5 Hz, 1H), 6.79 (d, J=8.5 Hz, 1H), 5.16 (s, 2H), 3.6-3.54 (m, 2H), 1.05 (t, J=7.04 Hz, 3H). MS: cal'd 403 (MH+), exp 403 (MH+).

Additional analogs were prepared in procedures similar to those described for the preparations of the above examples.

TABLE 1

| | A; Aryl Phosphonates | | | |
|---|---|---|---|---|
| Cpd # | | Name | MS | Salt forms |
| 1 | (structure) | Diethyl [4-({[2-amino-5-(2-thienyl)phenyl]amino}carbonyl)phenyl]phosphonate | cal'd 431 (MH+), exp 431 (MH+). | TFA salt |

TABLE 1-continued

A; Aryl Phosphonates

| Cpd # | Structure | Name | MS | Salt forms |
|---|---|---|---|---|
| 2 | 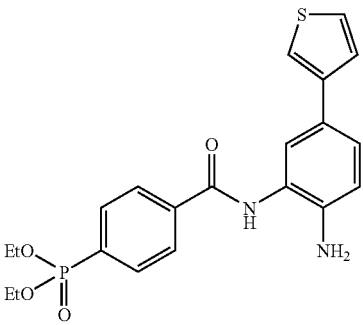 | Diethyl[4-({[2-amino-5-(3-thienyl)phenyl]amino}carbonyl)phenyl]phosphonate | cal'd 431 (MH+), exp 431 (MH$^+$) | Free base |
| 3 | 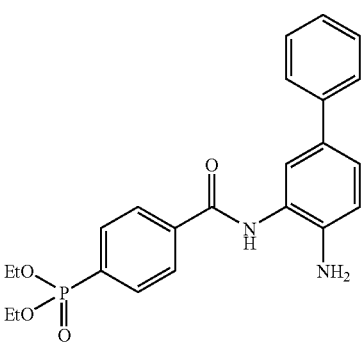 | Diethyl (4-{[(4-aminobiphenyl-3-yl)amino]carbonyl}phenyl)phosphonate | cal'd 425 (MH$^+$), exp 425 (MH$^+$) | Free base |
| 4 | 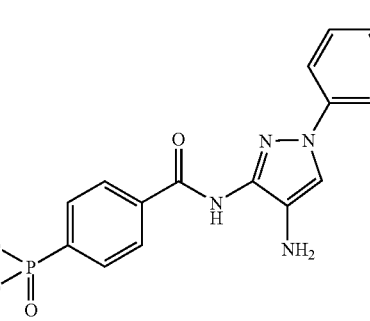 | Diethyl(4-{[(4-amino-1-phenyl-1H-pyrazol-3-yl)amino]carbonyl}phenyl)phosphonate | cal'd 415 (MH$^+$), exp 415 (MH$^+$) | TFA salt |
| 5 | 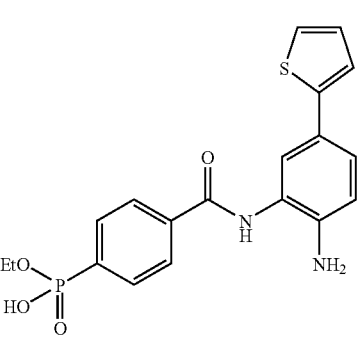 | Ethyl hydrogen [4-({[2-amino-5-(2-thienyl)phenyl]amino}carbonyl)phenyl]phosphonate. | cal'd 403 (MH$^+$), exp 403 (MH$^+$) | TFA salt |

TABLE 1-continued

A: Aryl Phosphonates

| Cpd # | Name | MS | Salt forms |
|---|---|---|---|
| 6 | Ethyl hydrogen(4-{[(4-amino-1-phenyl-1H-pyrazol-3-yl)amino]carbonyl}phenyl)phosphonate | cal'd 387 (MH+), exp 387 (MH+) | TFA salt |

Procedures for B. Preparation of Aryl Phosphinates

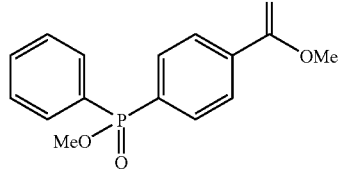

Methyl 4-[methoxy(phenyl)phosphoryl]benzoate. From a related procedure (Helv. Chim. Acta, 2004, 87, 825) a mixture of methyl 4-bromobenzoate (676 mg, 3.14 mmol), anhydrous NiBr$_2$ (34.3 mg, 0.157 mmol), and PhP(OMe)$_2$ (0.500 mL, 3.14 mmol) was added to a pressure vessel and heated to 160° C. (oil bath temperature) for 2 h. The reaction was cooled, diluted with EtOAc and washed with water (3×), brine, dried (MgSO$_4$) and concentrated to afford ~800 mg of a clear, colorless oil that solidified upon standing. The product was purified by MPLC (15-50% EtOAc in CH$_2$Cl$_2$) to afford the requisite product: MS: cal'd 291 (MH+), exp 291 (MH+).

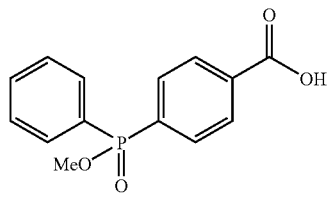

4-[Methoxy(phenyl)phosphoryl]benzoic acid. A solution of methyl 4-[methoxy(phenyl) phosphoryl]benzoate (202 mg, 0.696 mmol) was diluted in THF (2.78 mL) and MeOH (0.696 mL) and treated with LiOH (0.696 mL, 3M solution in water, 2.09 mmol) and stirred for 2 h. The reaction was quenched with 1N aqueous HCl and extracted with EtOAc 3×. The combined organic layers were washed with brine, dried (MgSO$_4$) and concentrated to afford a clear, colorless oil that was used crude in the next step: MS: cal'd 277 (MH+), exp 277 (MH+).

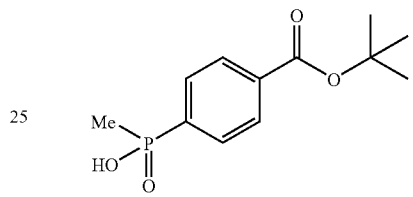

[4-(tert-Butoxycarbonyl)phenyl]methylphosphinic acid]. tert-Butyl 4-[ethoxy(methyl) phosphoryl]benzoate (510 mg, 1.79 mmol) was made 0.25 M in dioxane and to this stirring solution was added potassium hydroxide (5.38 mL, 5.38 mmol). The resulting mixture was stirred at ambient temperature for 10 minutes. The reaction mixture was neutralized with 1 eq aq HCl then concentrated in vacuo. The residue was diluted with MeOH, the inorganic salts were filtered off and the filtrate was concentrated in vacuo. MS: cal'd 257 (MH+), exp 257 (MH+).

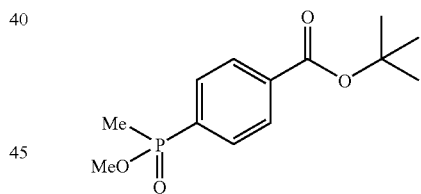

tert-Butyl 4-[methoxy(methyl)phosphoryl]benzoate. 4-(tert-Butoxycarbonyl)phenyl]methylphosphinic acid (500 mg, 1.95 mmol) was made 0.25 M in DMF and to this stirring solution was added MeOH (100 mg, 2.93 mmol), BOP (1.0 g, 2.34 mmol), and DIPEA (750 mg, 5.85 mmol). The resulting mixture was stirred at ambient temperature for 10 minutes then diluted with water and extracted with EtOAc. The organic layer was again washed with dilute aq HCl (2×), brine, then dried over anhydrous MgSO$_4$ and concentrated in vacuo. The residue was purified by MPLC (5-50% EtOAc:DCM), MS: cal'd 271 (MH+), exp 271 (MH+).

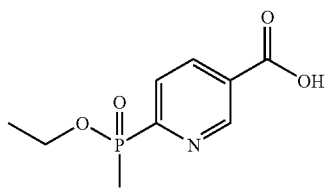

6-[Ethoxy(methyl)phosphoryl]nicotinic acid. 6-Bromonicotinic acid (150 mg, 0.74 mmol) and diethyl methylphosphonite (1.21 g, 8.91 mmol) were dissolved in toluene and the solution was purged with argon for several minutes. The mixture was brought to reflux and a solution of AIBN (40 mg, 0.22 mmol) and tris trimethylsilylsilane (220 mg, 0.89 mmol) in toluene was added dropwise over 4 hours via syringe pump. The initiator was added via syringe pump over 4 hours. The resulting mixture was reluxed for 16 hours then it was concentrated in vacuo and purified directly by MPLC (0-50% EtOAc:Hex). MS: cal'd 230 (MH+), exp 230 (MH+).

Additional analogs were prepared in procedures similar to those described for the preparations of the above examples.

TABLE 2

B; Aryl Phosphinates

| Cpd # | R | Name | MS | Salt forms |
|---|---|---|---|---|
| 1 |  | Methyl [4-({[2-amino-5-(2-thienyl)phenyl]amino}carbonyl)phenyl]phenylphosphinate | cal'd 449 (MH+), exp 449 (MH+) | Free base |
| 2 |  | Methyl [4-({[2-amino-5-(3-thienyl)phenyl]amino}carbonyl)phenyl]phenylphosphinate | cal'd 449 (MH+), exp 449 (MH+) | Free base |
| 3 |  | Methyl (4-{[(4-aminobiphenyl-3-yl)amino]carbonyl}phenyl)phenylphosphinate | cal'd 443 (MH+), exp 443 (MH+) | Free base |
| 4 |  | ethyl[4-({[2-amino-5-(2-thienyl)phenyl]amino}carbonyl)phenyl]methylphosphinate | cal'd 401 (MH+), exp 401 (MH+) | Free base |

TABLE 2-continued

B; Aryl Phosphinates

| Cpd # | R | Name | MS | Salt forms |
|---|---|---|---|---|
| 5 | | ethyl [4-({[2-amino-5-(2-thienyl)phenyl]amino}carbonyl)phenyl]phenylphosphinate | cal'd 463 (MH+), exp 463 (MH+) | Free base |
| 6 | | ethyl (4-{[(4-aminobiphenyl-3-yl)amino]carbonyl}phenyl)methylphosphinate | cal'd 394 (MH+), exp 395 (MH+) | Free base |
| 7 | | methyl[4-({[2-amino-5-(2-thienyl)phenyl]amino}carbonyl)phenyl]methylphosphinate | cal'd 387 (MH+), exp 387 (MH+) | Free Base |
| 8 | | 2-(ethylsulfonyl)ethyl [4-({[2-amino-5-(2-thienyl)phenyl]amino}carbonyl)phenyl]methylphosphinate | cal'd 493 (MH+), exp 493 (MH+) | Free Base |

TABLE 2-continued

B: Aryl Phosphinates

| Cpd # | R | Name | MS | Salt forms |
|---|---|---|---|---|
| 9 | | 3-hydroxy-3-methylbutyl [4-({[2-amino-5-(2-thienyl)phenyl]amino}carbonyl)phenyl]methylphosphinate | cal'd 459 (MH+), exp 459 (MH+) | Free Base |
| 10 | | cyclobutyl [4-({[2-amino-5-(2-thienyl)phenyl]amino}carbonyl)phenyl]methyl phosphinate | cal'd 427 (MH+), exp 427 (MH+) | Free Base |
| 11 | | ethyl [4-({[2-amino-5-(2-thienyl)phenyl]amino}carbonyl)phenyl]ethylphosphinate | cal'd 415 (MH+), exp 415 (MH+) | Free Base |
| 12 | | ethyl [5-({[2-amino-5-(2-thienyl)phenyl]amino}carbonyl)pyridin-2-yl]methylphosphinate | cal'd 402 (MH+), exp 402 (MH+) | Free Base |

Procedures for C. Preparation of Aryl Phosphine Oxides.

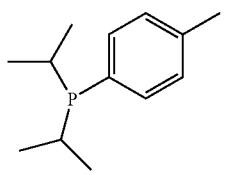

Diisopropyl-p-tolyl-phosphane. To a solution of diisopropylchlorophosphine (2 mL, 12.57 mmol) in THF (25 mL) at −78° C. was added 4-tolylmagnesium bromide (12.57 mL, 12.57 mmol) dropwise. After 1 h at −78° C., the reaction mixture was let warm to RT. The solvent was removed and material was used without further purification. MS: cal'd 209 (MH+), exp 209 (MH+).

(s, 1H), 7.62 (d, J=8.2 Hz, 1H), 7.51 (m, 2H), 7.42 (d, J=3.0 Hz, 1H), 7.21 (dd, j=8.2, 2.5 Hz, 1H), 2.39 (m, 2H), 1.06 (dd, J=15.0, 7.0 Hz, 6H), 0.90 (dd, J=16.07.0 Hz, 6H). MS: cal'd 527 (MH+), exp 527 (MH+).

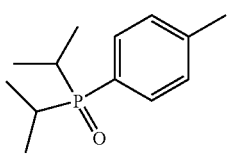

1-(Diisopropyl-phosphinoyl)-4-methyl-benzene. To a solution of diisopropyl-p-tolyl-phosphane (2.6 g, 12.48 mmol) in DCM (5 mL) at 0° C. was added hydrogen peroxide (4.08 mL, 13.31 mmol) dropwise. The reaction mixture was allowed to warm to RT. The reaction was diluted with DCM, washed with water, brine, dried (MgSO$_4$), filtered and the solvent was evaporated under reduced pressure. The material was used without further purification. MS: cal'd 225 (MH+), exp 225 (MH+).

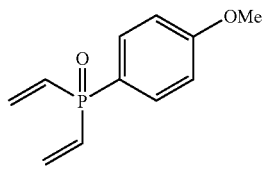

(4-Methoxyphenyl)(divinyl)phosphine oxide. (4-Methoxyphenyl)phosphonic dichloride (2.00 g, 8.89 mmol) was made 0.1 M in 1:1 THF:ether and stirred at −78° C. To this stirring solution vinyl magnesium bromide (17.8 mL, 17.78 mmol, 1M in THF) was added dropwise. The mixture was stirred for 1 h, then quenched with 2M aq. HCl and extracted with DCM (3×). The combined organic extracts were washed with brine, dried (MgSO$_4$) and concentrated to afford the requisite product. MS: cal'd 209 (MH+), exp 209 (MH+)

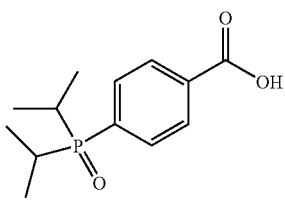

4-(Diisopropyl-phosphinoyl)-benzoic acid. To a solution of 1-(diisopropyl-phosphinoyl)-4-methyl-benzene (2.8 g, 12.48 mmol) in water (21 mL) at 80° C. was added a solution of potassium permanganate (4.74 g, 30.0 mmol) in water (125 mL) slowly and carefully over 1 h. The resultant solution was stirred at 100° C. for 18 h. The brown slurry was filtered hot via a small plug of Celite. The filtrate was washed with ether, acidifed with 1 N HCl and extracted with CHCl$_3$/MeOH. The CHCl$_3$/MeOH fractions were dried (MgSO$_4$), filtered and the solvent was evaporated under reduced pressure. The material was used without further purification. MS: cal'd 432 (MH+), exp 432 (MH+).

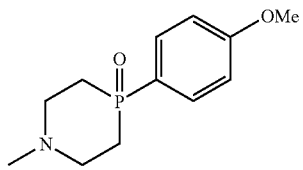

4-(4-Methoxyphenyl)-1-methyl-1,4-azaphosphinane 4-oxide. (4-Methoxyphenyl)(divinyl) phosphine oxide (1.22 g, 5.88 mmol) and methylamine (0.53 mL, 6.18 mmol, 40% in water) was heated to 90° C. for 2 h. The reaction mixture was cooled to ambient temperature then extracted with DCM (3×). The combined organic extracts were dried (MgSO$_4$) then concentrated in vacuo to afford the requisite product. MS: cal'd 240 (MH+), exp 240 (MH+)

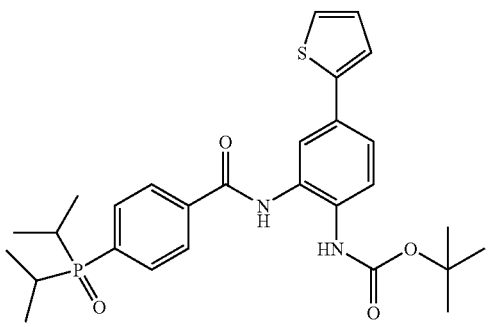

{2-[4-(Diisopropyl-phosphinoyl)-benzoylamino]-4-thiophen-2-yl-phenyl}-carbamic acid tert-butyl ester. To a solution of 4-(diisopropyl-phosphinoyl)-benzoic acid (700 mg, 2.75 mmol), 2-amino-4-thiophen-2-yl-phenyl)-carbamic acid tert-butyl ester (959 mg, 3.30 mmol), and HOBT (558 mg, 4.13 mmol) in DMF (5 mL) was added EDC (792 mg, 4.13 mmol). The reaction mixture was stirred at RT for 4 h. The resultant solid was filtered and washed with MeOH to yield the desired material. $^1$H NMR (CDCl$_3$, 600 MHz) δ 10.02 (s, 1H), 8.75 (br s, 1H), 8.08 (m, 2H), 7.83 (m, 2H), 7.77

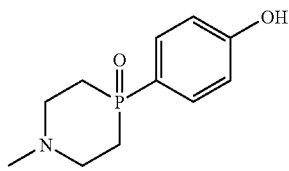

4-(1-Methyl-4-oxido-1,4-azaphosphinan-4-yl)phenol. 4-(4-Methoxyphenyl)-1-methyl-1,4-azaphosphinane 4-oxide (1.05 g, 4.39 mmol) was made 0.16 M in DCM and stirred at −78° C. To this stirring solution was added BBr3 (2.09 g, 8.34 mmol) dropwise. The reaction mixture was slowly warmed to ambient temperature over 16 h. The precipitate was filtered off then dissolved in water. The pH was adjusted to pH=7 with 2N aq HCl. A precipitate was filtered off and the filtrate was concentrated in vacuo. The residue was suspended in 4:1 DCM:MeOH and stirred for 20 mins. The solids were filtered off and the filtrate was concentrated in vacuo to afford the requisite product. MS: cal'd 226 (MH+), exp 226 (MH+)

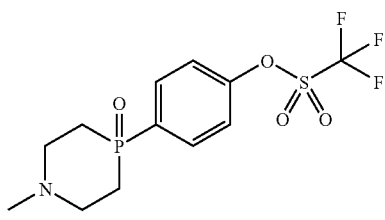

4-(1-Methyl-4-oxido-1,4-azaphosphinan-4-yl)phenyl trifluoromethanesulfonate. 4-(1-Methyl-4-oxido-1,4-azaphosphinan-4-yl)phenol (0.50 g, 2.22 mmol) was made 0.5 M in DMF and N-Phenyl-bis(trifluorometanesulfonamide (1.19 g, 3.33 mmol) was added, followed by TEA (0.62 mL, 4.44 mmol). The mixture was stirred at ambient temperature for 16 h then the precipitate was filtered off and the filtrate was concentrated in vacuo. The residue was purified by HPLC (20-95% MeCN in water w/0.025% TFA). Pure fractions were identified, combined and concentrated in vacuo. The residue was taken up in EtOAc and washed with saturated aqueous sodium bicarbonate (1×) then dried (MgSO$_4$) and concentrated in vacuo to afford the requisite product as a freebase. MS: cal'd 358 (MH+), exp 358 (MH

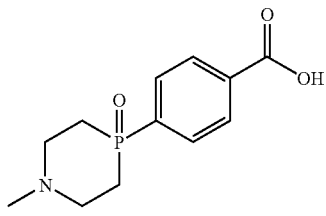

4-(1-Methyl-4-oxido-1,4-azaphosphinan-4-yl)benzoic acid. 4-(1-Methyl-4-oxido-1,4-azaphosphinan-4-yl)phenyl trifluoromethanesulfonate (0.18 g, 0.50 mmol) was made 0.25 M in 4:1 DMF:water and to this stirring solution was added palladium acetate (7 mg, 0.03 mmol), and DPPP (25 mg, 0.06 mmol). The resulting mixture was thoroughly degassed with bubbling carbon monoxide for 20 mins. DIPEA (130 mg, 1.01 mmol) was added and a CO balloon was attached. The resulting mixture was stirred at 70° C. for 16 h. The mixture was then cooled to ambient temperature and carried onto the subsequent reaction without purification. MS: cal'd 254 (MH+), exp 254 (MH+).

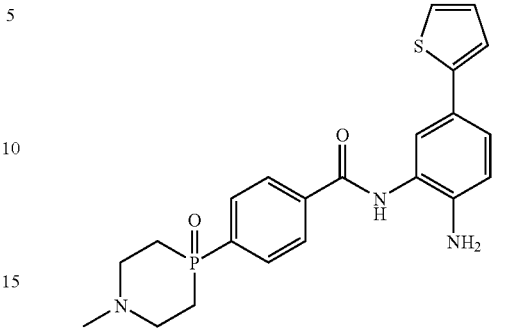

N-[2-Amino-5-(2-thienyl)phenyl]-4-[(1-methyl-4-oxido-1,4-azaphosphinan-4-yl)methyl]benzamide. 4-(1-Methyl-4-oxido-1,4-azaphosphinan-4-yl)benzoic acid (128 mg, 0.51 mmol), 2-amino-4-thiophen-2-yl-phenyl)-carbamic acid tert-butyl ester (176 mg, 0.61 mmol), EDC (116 mg, 0.61 mmol), HOBT (93 mg, 0.61 mmol), and DIPEA (196 mg, 1.52 mmol) were combined and diluted with DMF (2.0 mL). The resulting mixture was stirred at ambient temperature for 18 hours. The reaction mixture was diluted with water and extracted with EtOAc (2×). The combined organic layers were washed again with water (2×) then dried (MgSO$_4$) and concentrated in vacuo. The residue was purified by MPLC (0-8% MeOH in CH$_2$Cl$_2$). Pure fractions were identified, combined, then concentrated in vacuo. The residue was diluted with 2:1 DCM:TFA and stirred at ambient temperature for 1 h. The mixture was then carefully quenched with sat aq sodium bicarbonate and extracted with EtOAc. The organic layer was dried (MgSO$_4$) and concentrated in vacuo to afford the title compound: MS: cal'd 426 (MH+), exp 426 (MH+). $^1$H NMR (CD$_3$OD-d$_4$, 600 MHz) δ 8.18 (d, J=6.2 Hz, 2H), 7.98 (dd, J=11.2 Hz, J=8.2 Hz, 2H), 7.50 (d, J=1.8 Hz, 1H), 7.37 (dd, J=8.2 Hz, J=1.8 Hz, 1H), 7.22 (dd, J=12.6 Hz, J=5.0 Hz, 2H), 7.01 (m, 1H), 6.91 (d, J=8.2 Hz, 1H), 3.06-2.96 (m, 2H), 2.92-2.82 (m, 2H), 2.46-2.36 (m, 5H), 2.17-2.07 (m, 2H).

Additional analogs were prepared in procedures similar to those described for the preparations of the above examples.

TABLE 3

| | C; Aryl Phosphine Oxides | | | |
| --- | --- | --- | --- | --- |
| Cpd # | Structure | Name | MS | Salt Forms |
| 1 | ![structure] | N-(2-Amino-5-thiophen-2-yl-phenyl)-4-(diisopropyl-phosphinoyl)-benzamide | cal'd 427 (MH+), exp 427 | Free base |

TABLE 3-continued

C; Aryl Phosphine Oxides

| Cpd # | Structure | Name | MS | Salt Forms |
|---|---|---|---|---|
| 2 | 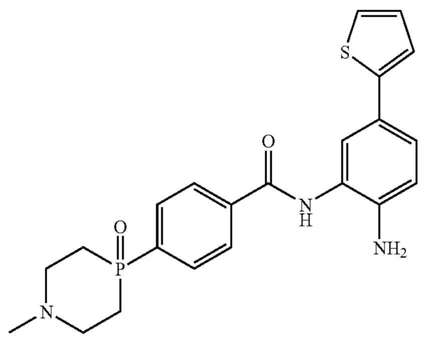 | N-[2-Amino-5-(2-thienyl)phenyl]-4-[(1-methyl-4-oxido-1,4-azaphosphinan-4-yl)methyl]benzamide | cal'd 426 (MH+), exp 426 | Free base |
| 3 | 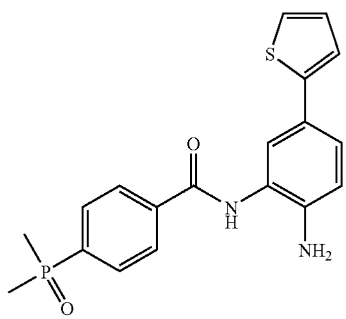 | N-(2-Amino-5-thiophen-2-yl-phenyl)-4-(dimethyl-phosphinoyl)-benzamide | cal'd 371 (MH+), exp 371 | Free base |
| 4 | 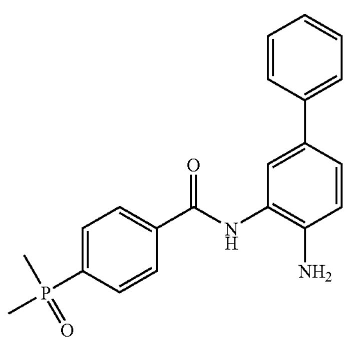 | N-(2-Amino-5-phen-2-yl-phenyl)-4-(dimethyl-phosphinoyl)-benzamide | cal'd 365 (MH+), exp 365 | Free base |

Procedures for D. Preparation of Alkyl Phosphonates

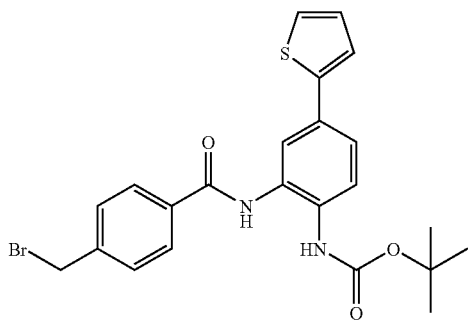

[2-(4-Bromomethyl-benzoylamino)-4-thiophen-2-yl-phenyl]-carbamic acid tert-butyl ester. 4-Bromomethyl-benzoyl bromide (0.70 g, 2.52 mmol) was made 0.21 M in anhydrous DCM and cooled to −78° C. To this stirring solution was added (2-amino-4-thiophen-2-yl-phenyl)-carbamic acid tert-butyl ester (0.73 g, 2.52 mmol) followed by DIPEA (0.98 g, 7.56 mmol). The resulting solution was warmed to ambient temperature and stirred for 18 hours. The reaction mixture was then diluted with 0.1 N HCl and extracted with EtOAc. The organic layer was then washed with saturated aqueous sodium bicarbonate, brine, dried (MgSO$_4$), and concentrated in vacuo to afford the title compound: $^1$H NMR (DMSO-d$_6$, 600 MHz) δ9.90 (s, 1H), 8.72 (s, 1H), 7.94 (d, J=7.8. Hz, 2H), 7.78-7.80 (m, 1H), 7.57-7.62 (m, 3H), 7.47-7.51 (m, 2H), 7.42-7.44 (m, 1H), 7.09-7.12 (m, 1H), 4.77 (s, 2H), 1.43 (s, 9H).

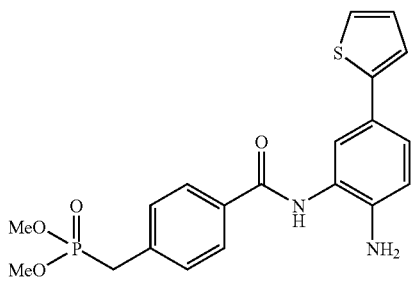

[4-(2-Amino-5-thiophen-2-yl-phenylcarbamoyl)-benzyl]-phosphonic acid dimethyl ester. [2-(4-Bromomethyl-benzoylamino)-4-thiophen-2-yl-phenyl]-carbamic acid tert-butyl ester (0.20 g, 0.41 mmol) was made 2.0 M in anhydrous toluene and to this stirring solution was added trimethylphosphite (0.06 g, 0.45 mmol). The resulting reaction mixture was sealed and stirred at 100° C. for 18 h. The reaction mixture was diluted with EtOAc and washed with saturated aqueous sodium bicarbonate. The organic layer was further washed with brine then dried (MgSO$_4$) and concentrated in vacuo. The residue was dissolved in DMF:MeOH and purified by HPLC (45-95% MeCN in water w/0.025% TFA). Pure fractions were identified, combined, and concentrated in vacuo. The residue was dissolved in 2:1 DCM:TFA and stirred at ambient temperature. After 1 hour the mixture was concentrated in vacuo, diluted with EtOAc, washed with saturated aqueous sodium bicarbonate, brine, dried (MgSO$_4$), then concentrated in vacuo to give the title compound: $^1$H NMR (DMSO-d$_6$, 600 MHz) δ9.68 (s, 1H), 7.92 (d, J=8.4 Hz, 2H), 7.45 (s, 1H), 7.37-7.41 (m, 2H), 7.32-7.34 (m, 1H), 7.26-7.29 (m, 1H), 7.21-7.23 (m, 1H), 7.01-7.04 (m, 1H), 6.78 (d, J=8.4 Hz, 2H), 5.14 (s, 2H), 3.60 (d, J=11.4 Hz, 6H), 3.37 (d, J=22.2 Hz, 2H). MS: cal'd 417 (MH+), exp 417 (MH+)

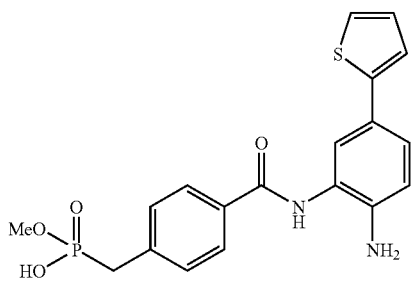

[4-(2-Amino-5-thiophen-2-yl-phenylcarbamoyl)-benzyl]-phosphonic acid monomethyl ester. [4-(2-Amino-5-thiophen-2-yl-phenylcarbamoyl)-benzyl]-phosphonic acid dimethyl ester (35 mg, 0.066 mmol) was made 0.25 M in dioxane and to this stirring solution was added 5N aqueous sodium hydroxide (26 μL, 0.132 mmol). The resulting solution was stirred at 80° C. overnight then diluted with DMF, acidified with TFA, and purified by HPLC (0-60% MeCN in water w/0.025% TFA) to afford the title compound: $^1$H NMR (DMSO-d$_6$, 600 MHz) δ9.80 (s, 1H), 7.91 (d, J=8.4 Hz, 2H), 7.48-7.50 (m, 1H), 7.31-7.42 (m, 4H), 7.26-7.28 (m, 1H), 7.04-7.06 (m, 1H), 6.88 (d, J=8.4 Hz, 1H), 3.52 (d, J=11.4 Hz, 3H), 3.18 (d, J=21.6 Hz, 2H). MS: cal'd 403 (MH+), exp 403 (MH+)

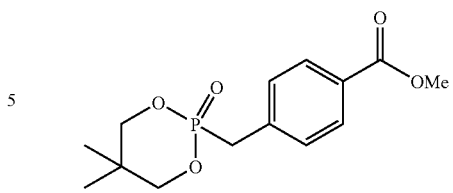

4-(5,5-Dimethyl-2-oxo-2λ$^5$-[1,3,2-]dioxaphosphinan-2-ylmethyl)-benzoic acid methyl ester. 4-Bromomethyl-benzoic acid methyl ester (0.50 g, 2.18 mmol) was made 2.0 M in anhydrous toluene and to this mixture was added 5,5-dimethyl-[1,3,2]dioxaphosphinane 2-oxide (0.66 g, 4.37 mmol) followed by N,N,N',N'-tetramethyl-guanidine (0.25 g, 2.18 mmol). The mixture was stirred at ambient temperature for 18 hours. The reaction mixture was then diluted with 1N aq HCl and extracted with EtOAc. The organic layer was again washed with 1 N aqueous HCl, brine, dried (MgSO$_4$) then concentrated in vacuo. The residue was purified by MPLC (0-70% EtOAc in CH$_2$Cl$_2$) to afford the title compound: MS: cal'd 299 (MH+), exp 299 (MH+)

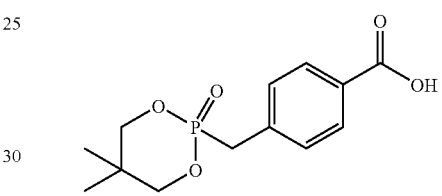

4-(5,5-Dimethyl-2-oxo-2λ$^5$-[1,3,2]dioxaphosphinan-2-ylmethyl)-benzoic acid. 4-(5,5-Dimethyl-2-oxo-2λ$^5$-[1,3,2]dioxaphosphinan-2-ylmethyl)-benzoic acid methyl ester (0.23 g, 0.75 mmol) was made 0.25 M in dioxane and to this stirring solution was added 3 N aq LiOH (0.05 g, 2.26 mmol). The resulting mixture was stirred at ambient temperature for 4 hours. The reaction mixture was concentrated in vacuo and carried directly onto subsequent coupling without further purification: MS: cal'd 285 (MH+), exp 285 (MH+).

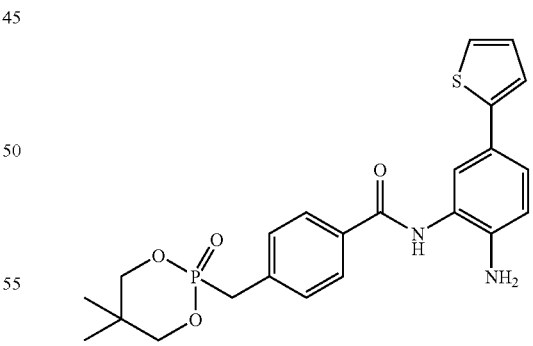

N-(2-Amino-5-thiophen-2-yl-phenyl)-4-(5,5-dimethyl-2-oxo-2λ$^5$-[1,3,2]dioxaphosphinan-2-ylmethyl)-benzamide. 4-(5,5-Dimethyl-2-oxo-2λ$^5$-[1,3,2]dioxaphosphinan-2-ylmethyl)-benzoic acid (100 mg, 0.35 mmol), (2-amino-4-thiophen-2-yl-phenyl)-carbamic acid tert-butyl ester (123 mg, 0.42 mmol), EDC (81 mg, 0.42 mmol), HOBT (54 mg, 0.35 mmol), and DIPEA (136 mg, 1.05 mmol) were combined and diluted with DMF (1.4 mL). The resulting mixture was stirred at ambient temperature for 18 hours. The reaction mixture was purified directly by HPLC (20-85% MeCN in water w/0.025% TFA). Pure fractions were identified, combined and concentrated in vacuo. The residue was diluted with 10:1 DCM:TFA and stirred at ambient temperature for 2 hours. The mixture was then concentrated in vacuo to afford the title compound: $^1$H NMR (DMSO-d$_6$, 600 MHz) δ 9.85 (s, 1H), 7.93 (d, J=7.2 Hz, 2H), 7.50 (s, 1H), 7.43 (d, J=7.2 Hz, 2H), 7.34-7.40 (m, 2H), 7.28-7.30 (m, 1H), 7.03-7.06 (m, 1H), 6.90-6.92 (m, 1H), 4.20-4.25 (m, 2H), 4.01 (br-s, 2H), 3.87-3.94 (m, 2H), 3.52 (d, J=20.4 Hz, 2H), 1.08 (s, 3H), 0.84 (s, 3H). MS: cal'd 457 (MH+), exp 457 (MH+).

Preparation of α-Substituted Alkyl Phosphonates.

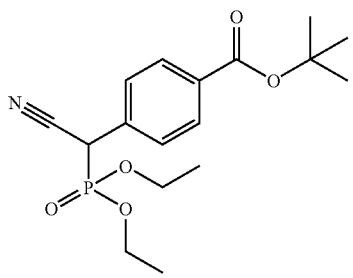

Tert-butyl 4-[cyano(diethoxyphosphoryl)methyl]benzoate. Diethyl cyanomethylphosphonate (0.35 ml, 2.164 mmol), tert-butyl 4-bromobenzoate (0.5096 g, 1.982 mmol), bis(tri-t-butylphosphine)palladium (0.051 g, 0.099 mmol), potassium phosphate, tribasic (1.2381 g, 5.83 mmol) and toluene (6 ml) were combined in a flask. Nitrogen was bubbled through the reaction for approximately two minutes to deoxygenate the reaction. The reaction was allowed to heat at 100° C. until complete (3-24 h). The reaction was filtered over celite. The resulting material was partially purified by column chromatography on silica gel. The partially purified material was further purified by HPLC. $^1$H NMR (CDCl$_3$, 600 MHz) δ 8.01 (d, J=6 Hz, 2H), 7.52 (d, J=6.9 Hz, 2H), 4.30 (d, J$_{P-H}$=26.4 Hz, 1H), 4.19-4.01 (m, 4H), 1.59 (s, 9H), 1.32 (m, 3H), 1.26 (m, 3H). MS: cal'd 354 (MH+), exp 354 (MH+).

Preparation of β-Substituted Alkyl Phosphonates.

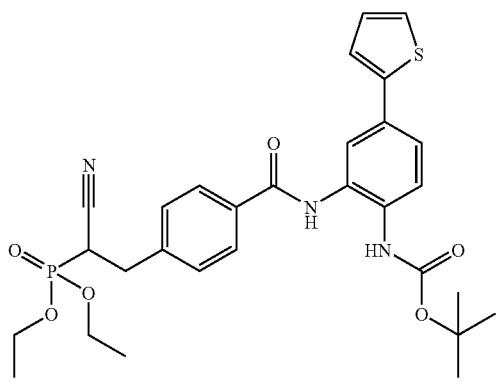

Diethyl {2-[4-({[2-[(tert-butoxycarbonyl)amino]-5-(2-thienyl)phenyl]amino}carbonyl)phenyl]-1-cyanoethyl}phosphonate. Diethyl cyanomethylphosphonate (0.19 ml, 1.175 mmol) was dissolved in THF (7 ml). The solution was cooled to 0° C. Sodium hydride (0.0818 g, 2.045 mmol) was added to the reaction. The reaction was allowed to stir for several minutes. Tert-butyl [2-{[4-(bromomethyl)benzoyl]amino}-4-(2-thienyl)phenyl]carbamate (0.5047 g, 1.035 mmol) was added in a solution of THF. The reaction was allowed to slowly warm to room temperature and stir overnight. The reaction was diluted with ethyl acetate and quenched with saturated aqueous ammonium chloride. The aqueous layer was extracted with ethyl acetate three times. The combined organic layer was dried over sodium sulfate, filtered, and concentrated. The resulting residue was partially purified by column chromatography on silica gel. MS: cal'd 484 (MH+-Boc), exp 484 (MH+-Boc).

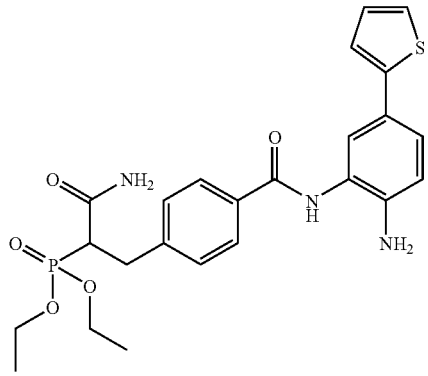

Diethyl {2-amino-1-[4-({[2-amino-5-(2-thienyl)phenyl]amino}carbonyl)benzyl]-2-oxoethyl}phosphate. Diethyl {2-[4-({[2-amino-5-(2-thienyl)phenyl]amino}carbonyl)phenyl]-1-cyanoethyl}phosphonate (0.1333 g, 0.276 mmol) was dissolved in DMSO (3 ml). Potassium carbonate (0.2088 g, 1.511 mmol) and hydrogen peroxide (0.25 ml, 2.86 mmol) were added. The reaction was allowed to stir approximately three hours at 70° C. The reaction was cooled to room temperature and filtered. The filtrate was concentrated and purified by HPLC. $^1$H NMR (DMSO-d$_6$, 600 MHz) δ 9.6 (s, 1H), 7.89 (d, J=8.4 Hz, 1H), 7.44 (d, J=1.8 Hz, 1H), 7.37 (d, J=2.4 Hz, 1H), 7.33 (d,d, J=4.8 Hz, 1.2 Hz, 1H), 7.30 (d, J=7.8 Hz, 2H), 7.27 (d,d, J=8.4 Hz, 1.8 Hz, 1H), 7.21 (d,d, J=3.6 Hz, 1.2 Hz, 1H), 7.02 (m, 2H), 6.78 (d, J=8.4 Hz, 1 H), 5.12 (s, 2H), 4.03 (m, 4H), 3.29-3.16 (m, 2H), 2.94 (m, 1H), 1.24 (m, 6H). MS: cal'd 502 (MH+), exp 502 (MH+).

Additional analogs were prepared in procedures similar to those described for the preparations of the above examples.

TABLE 4

D; Alkyl Phosphonates

| Cpd # | Structure | Name | MS | Salt Forms |
|---|---|---|---|---|
| 1 | 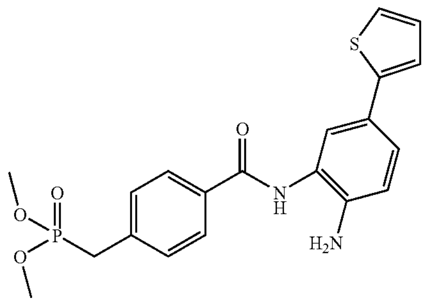 | [4-(2-Amino-5-thiophen-2-yl-phenylcarbamoyl)-benzyl]-phosphonic acid dimethyl ester | cal'd 417 (MH+), exp 417 | TFA Salt |
| 2 | 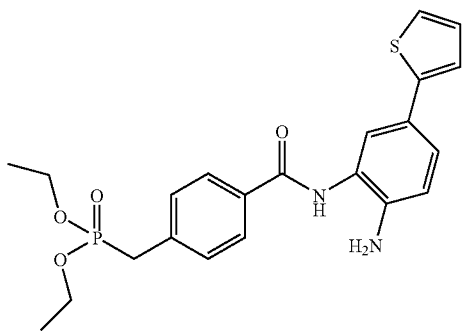 | [4-(2-Amino-5-thiophen-2-yl-phenylcarbamoyl)-benzyl]-phosphonic acid diethyl ester | cal'd 445 (MH+), exp 445 | TFA Salt |
| 3 | 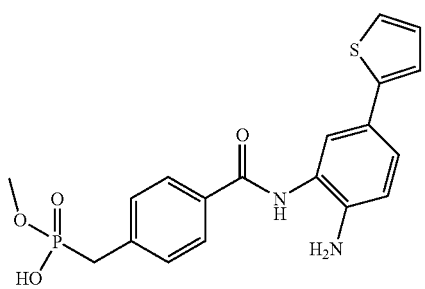 | [4-(2-Amino-5-thiophen-2-yl-phenylcarbamoyl)-benzyl]-phosphonic acid monomethyl ester | cal'd 403 (MH+), exp 403 (MH+) | TFA Salt |
| 4 | 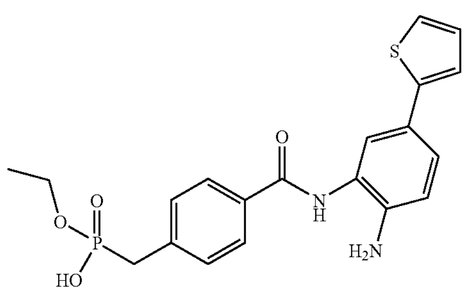 | [4-(2-Amino-5-thiophen-2-yl-phenylcarbamoyl)-benzyl]-phosphonic acid monoethyl ester | cal'd 417 (MH+), exp 417 (MH+) | TFA Salt |
| 5 | 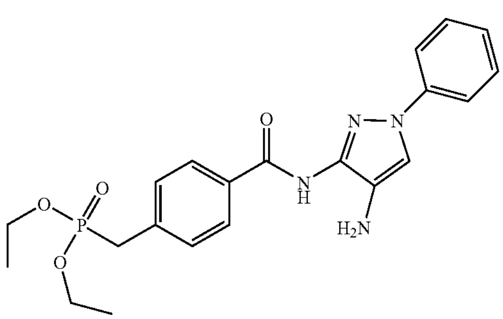 | [4-(4-Amino-1-phenyl-1H-pyrazol-3-ylcarbamoyl)-benzyl]-phosphonic acid diethyl ester | cal'd 429 (MH+), exp 429 (MH+) | TFA Salt |

TABLE 4-continued

| | D; Alkyl Phosphonates | | | |
|---|---|---|---|---|
| Cpd # | Structure | Name | MS | Salt Forms |
| 6 | | [4-(2-Amino-5-thiophen-3-yl-phenylcarbamoyl)-benzyl]-phosphonic acid diethyl ester | cal'd 445 (MH+), exp 445 (MH+) | TFA Salt |
| 7 | | [4-(2-Amino-5-thiophen-2-yl-phenylcarbamoyl)-benzyl]-phosphonic acid diethyl ester | cal'd 445 (MH+), exp 445 (MH+) | Free base |
| 8 | | N-[2-amino-5-(2-thienyl)phenyl]-4-[(5,5-dimethyl-2-oxido-1,3,2-dioxaphosphinan-2-yl)methyl]benzamide | cal'd 457 (MH+), exp 457 (MH+) | TFA Salt |
| 9 | | Diisopropyl [4-({[2-amino-5-(2-thienyl)phenyl]amino}carbonyl)benzyl]phosphonate | cal'd 473 (MH+), exp 473 (MH+) | Free base |

TABLE 4-continued

D; Alkyl Phosphonates

| Cpd # | Structure | Name | MS | Salt Forms |
|---|---|---|---|---|
| 10 | 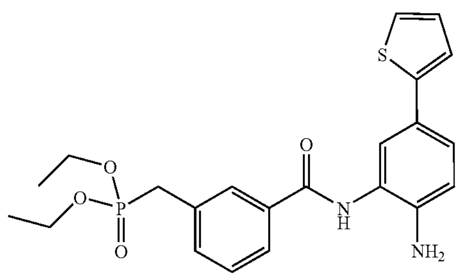 | Diethyl [3-({[2-amino-5-(2-thienyl)phenyl]amino}carbonyl)benzyl]phosphonate | cal'd 445 (MH+), exp 445 (MH+) | Free base |
| 11 | 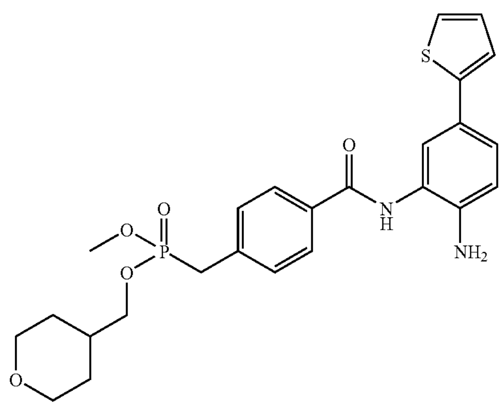 | methyl tetrahydro-2H-pyran-4-ylmethyl[4-({[2-amino-5-(2-thienyl)phenyl]amino}carbonyl)benzyl]phosphonate | cal'd 501 (MH+), exp 501 (MH+) | Free base |
| 12 | 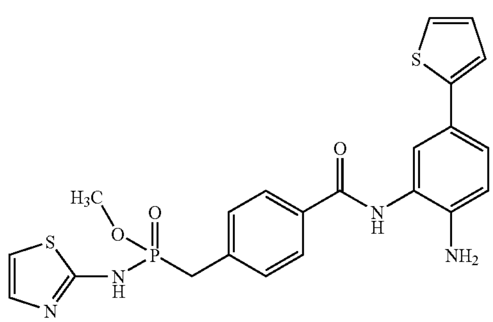 | methyl P-[4-({[2-amino-5-(2-thienyl)phenyl]amino}carbonyl)benzyl]-N-1,3-thiazol-2-ylphosphonamidoate | cal'd 485 (MH+), exp 485 (MH+) | Free base |
| 13 | 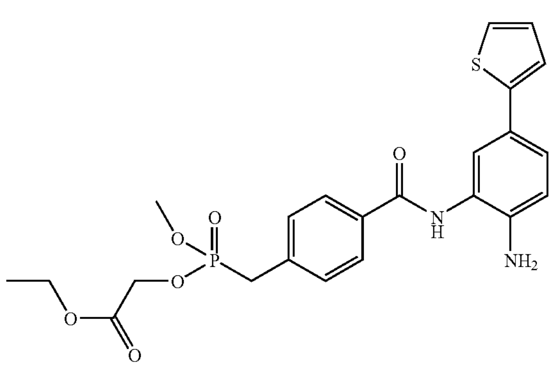 | ethyl {[[4-({[2-amino-5-(2-thienyl)phenyl]amino}carbonyl)benzyl](methoxy)phosphoryl]oxy}acetate | cal'd 489 (MH+), exp 489 (MH+) | Free base |

TABLE 4-continued

D; Alkyl Phosphonates

| Cpd # | Structure | Name | MS | Salt Forms |
|---|---|---|---|---|
| 14 | 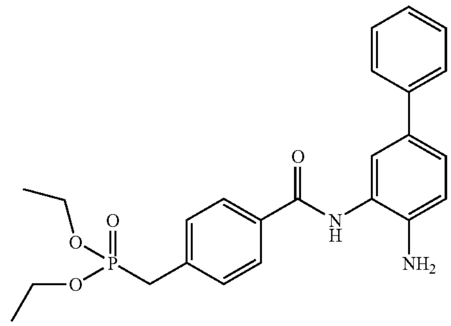 | diethyl (4-{[(4-aminobiphenyl-3-yl)amino]carbonyl}benzyl)phosphonate | cal'd 439 (MH+), exp 439 (MH+) | Free base |
| 15 | 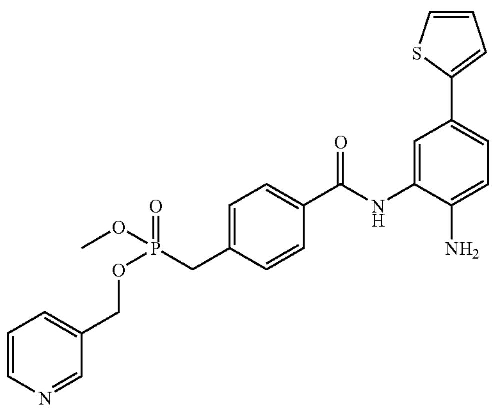 | methyl pyridin-3-ylmethyl[4-({[2-amino-5-(2-thienyl)phenyl]amino}carbonyl)benzyl]phosphonate | cal'd 494 (MH+), exp 494 (MH+) | Free base |
| 16 | 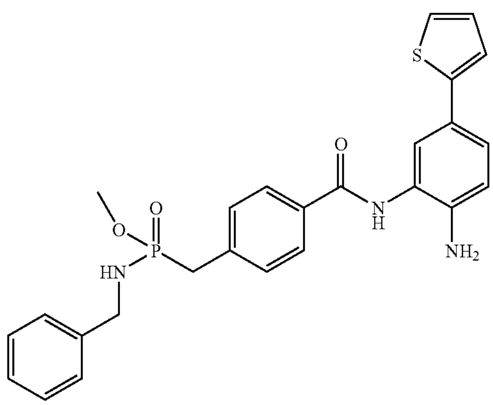 | Methyl P-[4-({[2-amino-5-(2-thienyl)phenyl]amino}carbonyl)benzyl]-N-benzyl phosphonamidoate | cal'd 492 (MH+), exp 492 (MH+) | Free base |
| 17 | 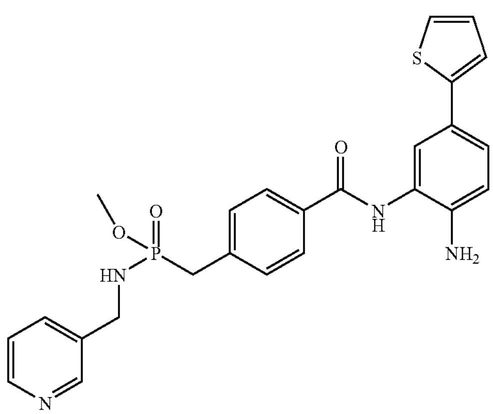 | Methyl P-[4-({[2-amino-5-(2-thienyl)phenyl]amino}carbonyl)benzyl]-N-(pyridin-3-ylmethyl)phosphonamidoate | cal'd 493 (MH+), exp 493 (MH+) | Free base |

TABLE 4-continued

D; Alkyl Phosphonates

| Cpd # | Structure | Name | MS | Salt Forms |
|---|---|---|---|---|
| 18 | 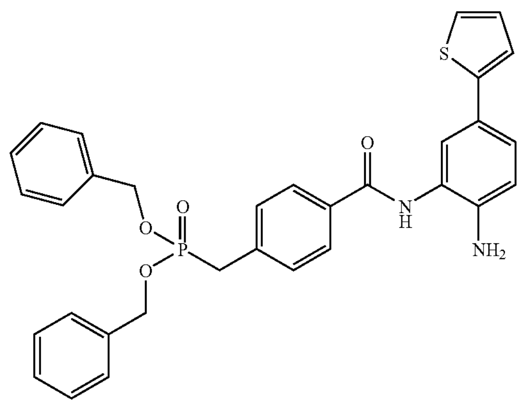 | dibenzyl[4-({[2-amino-5-(2-thienyl)phenyl]amino}carbonyl)benzyl]phosphonate | cal'd 569 (MH+), exp 569 (MH+) | Free base |
| 19 | 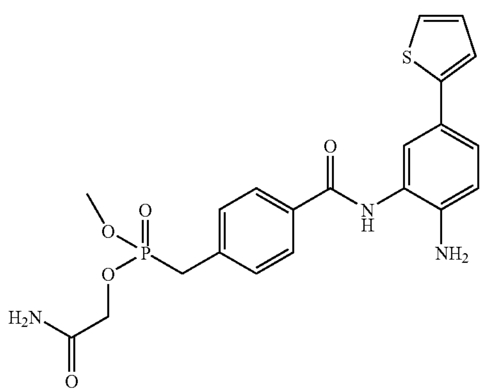 | 2-amino-2-oxoethyl methyl[4-({[2-amino-5-(2-thienyl)phenyl]amino}carbonyl)benzyl]phosphonate | cal'd 460 (MH+), exp 460 (MH+) | Free base |
| 20 | 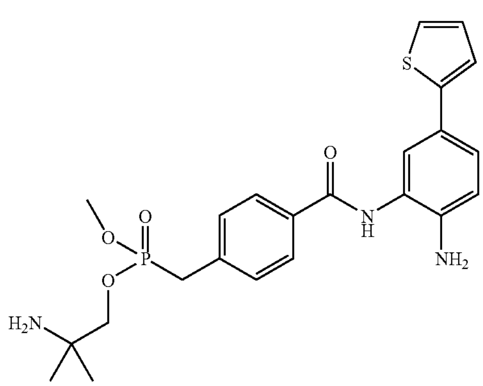 | 2-amino-2-methylpropyl methyl[4-({[2-amino-5-(2-thienyl)phenyl]amino}carbonyl)benzyl]phosphonate | cal'd 474 (MH+), exp 474 (MH+) | Free base |

TABLE 4-continued

D; Alkyl Phosphonates

| Cpd # | Structure | Name | MS | Salt Forms |
|---|---|---|---|---|
| 21 | 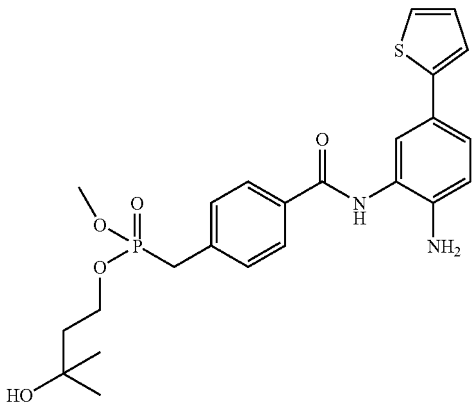 | 3-hydroxy-3-methylbutyl methyl[4-({[2-amino-5-(2-thienyl)phenyl]amino}carbonyl)benzyl]phosphonate | cal'd 489 (MH+), exp 489 (MH+) | Free base |
| 22 | 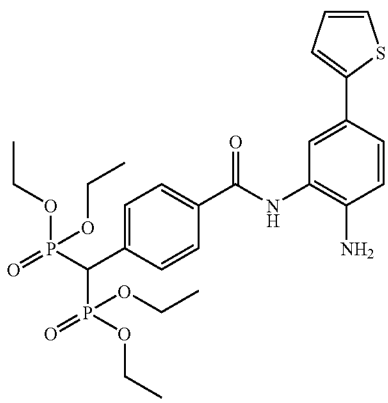 | Tetraethyl {[4-({[2-amino-5-(2-thienyl)phenyl]amino}carbonyl)phenyl]methylene}bis(phosphonate) | cal'd 581 (MH+), exp 581 (MH+) | Free base |
| 23 | 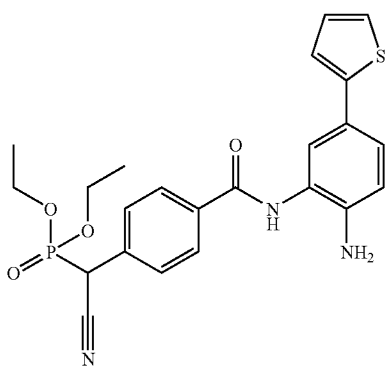 | Diethyl [[4-({[2-amino-5-(2-thienyl)phenyl]amino}carbonyl)phenyl](cyano)methyl]phosphonate | cal'd 470 (MH+), exp 470 (MH+) | Free base |
| 24 | 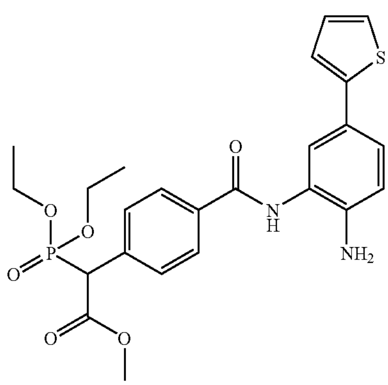 | Methyl [4-({[2-amino-5-(2-thienyl)phenyl]amino}carbonyl)phenyl](diethoxyphosphoryl)acetate | cal'd 503 (MH+), exp 503 (MH+) | Free base |

TABLE 4-continued

D; Alkyl Phosphonates

| Cpd # | Structure | Name | MS | Salt Forms |
|---|---|---|---|---|
| 25 | 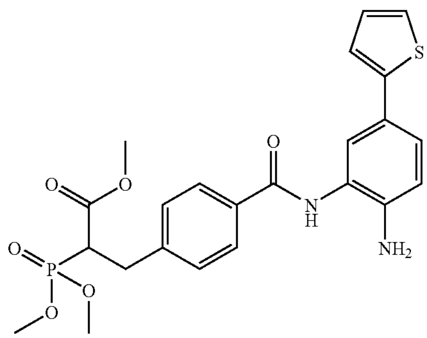 | Methyl 3-[4-({[2-amino-5-(2-thienyl)phenyl]amino}carbonyl)phenyl]-2-(dimethoxyphosphoryl)propanoate | cal'd 489 (MH+), exp 489 (MH+) | Free base |
| 26 | 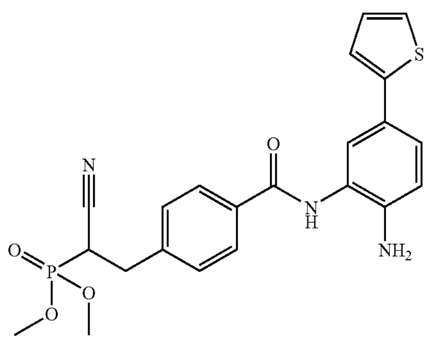 | Diethyl {2-[4-({[2-amino-5-(2-thienyl)phenyl]amino}carbonyl)phenyl]-1-cyanoethyl}phosphonate | cal'd 484 (MH+), exp 484 (MH+) | Free base |
| 27 | 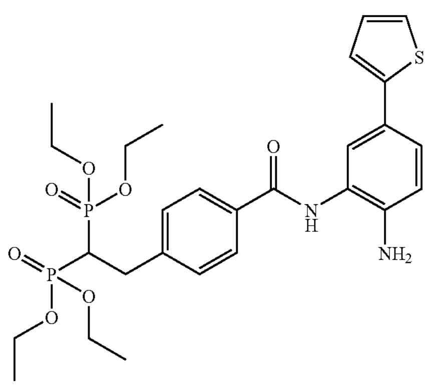 | Tetraethyl {2-[4-({[2-amino-5-(2-thienyl)phenyl]amino}carbonyl)phenyl]ethane-1,1-diyl}bis(phosphonate) | cal'd 595 (MH+), exp 595 (MH+) | Free base |
| 28 | 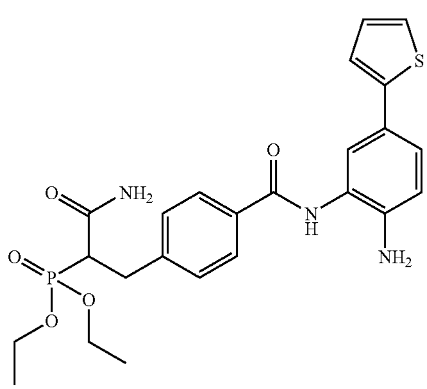 | Diethyl {2-amino-1-[4-({[2-amino-5-(2-thienyl)phenyl]amino}carbonyl)benzyl]-2-oxoethyl}phosphonate | cal'd 502 (MH+), exp 502 (MH+) | Free base |

Procedures for E. Preparation of Alkyl Phosphinates

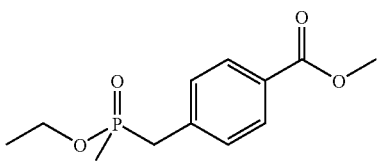

4-(Ethoxy-methyl-phosphinoylmethyl)-benzoic acid methyl ester. A neat solution of 4-bromomethyl-benzoic acid methyl ester (1.80 g, 7.86 mmol) and methyldiethoxyphosphine (1.07 g, 7.86 mmol) were heated in a sealed tube to 100° C. for 1 h. The solution was purified by column chromatography on silica gel, eluting with EtOAc/MeOH to give a colorless solid. $^1$H NMR (CDCl$_3$, 600 MHz) δ 7.98 (d, J=8.2 Hz, 2H), 7.33 (dd, J=8.2, 2.0 Hz, 2H), 4.08-3.96 (m, 2H), 3.90 (s, 3H), 3.19 (d, J=17.6 Hz, 2H), 1.37 (d, J=14.1 Hz, 3H), 1.27 (t, J=7.0 Hz, 3H).
MS: cal'd 257 (MH+), exp 257 (MH+).

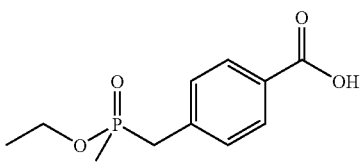

4-(Ethoxy-methyl-phosphinoylmethyl)-benzoic acid. To a solution of 4-(ethoxy-methyl-phosphinoylmethyl)-benzoic acid methyl ester (660 mg, 2.58 mmol) in THF (5 mL) and MeOH (3 mL) was added 1N NaOH (2.58 mL, 2.58 mmol), and the mixture was stirred for 18 h. The mixture was diluted with H$_2$O and washed with EtOAc. The aqueous layer was acidified with 1 N HCl, saturated with NaCl and extracted with a mixture of CHCl$_3$ and MeOH, dried (MgSO$_4$), and filtered. The solvent was evaporated under reduced pressure and the material was used without further purification. $^1$H NMR (CDCl$_3$, 600 MHz) δ 7.98 (d, J=7.9 Hz, 2H), 7.34 (dd, J=7.9, 2.0 Hz, 2H), 4.12-4.03 (m, 2H), 3.26 (dd, J=25.2, 14.2 Hz, 1H), 3.23 (dd, J=25.2, 14.2 Hz, 1H), 1.44 (d, J=13.8 Hz, 3H), 1.30 (t, J=7.0 Hz, 3H). MS: cal'd 243 (MH+), exp 243 (MH+).

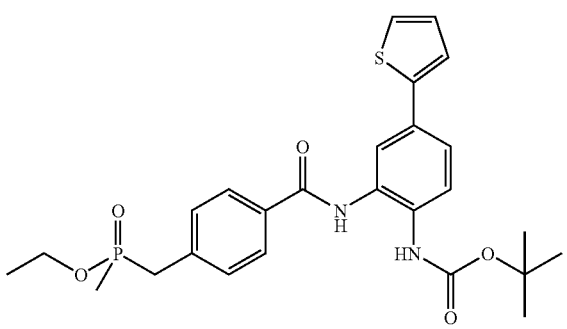

[4-(2-tert-Butoxycarbonylamino-5-thiophen-2-yl-phenyl-carbamoyl)-benzyl]-methyl-phosphinic acid ethyl ester. To a solution of 4-(ethoxy-methyl-phosphinoylmethyl)-benzoic acid (1.0 g, 4.13 mmol) and (2-amino-4-thiophen-2-yl-phenyl)-carbamic acid tert-butyl ester (1.44 g, 4.95 mmol) in DMF (20 mL) was added HOBT (1.27 g, 8.26 mmol) and EDC (1.58 g, 8.26 mmol). The reaction mixture was stirred over the weekend. The solvent was removed and the residue was purified by column chromatography on silica gel, eluting with CHCl$_3$/MeOH (2.5% to 20%) to give a glassy yellow solid. At this stage, the enantiomers can be separated via chiral chromatography and deprotected to generate both enantiomers. Spectral data for Boc-protected racemate; $^1$H NMR (CDCl$_3$, 600 MHz) δ 9.31 (br s, 1H), 8.00 (m, 2H), 7.95 (d, J=8.2 Hz, 2H), 7.40 (dd, J=8.2, 2.0 Hz, 1H), 7.37 (dd, J=8.2, 2.0 Hz, 2H), 7.32 (d, J=8.2 Hz, 1H), 7.28 (dd, J=3.5, 2.3 Hz, 1H), 7.26 (m, 1H), 7.04 (dd, J=5.0, 3.5 Hz, 1H), 6.95 (br s, 1H), 4.05-3.96 (m, 2H), 3.22 (dd, J=18.2, 14.4 Hz, 1H), 3.19 (dd, J=18.2, 14.4 Hz, 1H), 1.37 (d, J=13.8 Hz, 3H), 1.27 (t, J=7.0 Hz, 3H). MS: cal'd 415 (MH+; -Boc), exp 415 (MH+; -Boc).

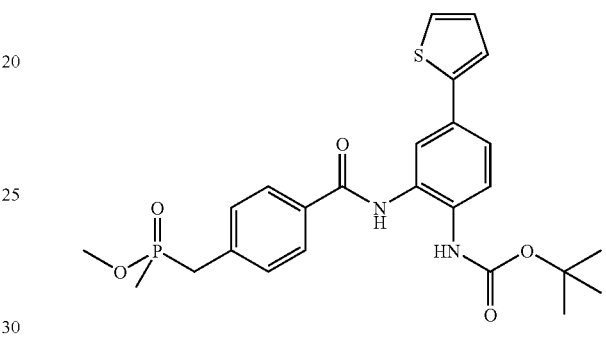

Methyl [4-({[2-[(tert-butoxycarbonyl)amino]-5-(2-thienyl)phenyl]amino}carbonyl)benzyl]methyl-phosphinate. DIEA (30.5 ml, 174 mmol) and MeOH (6.97 ml, 172 mmol) were combined in toluene (120 ml) and cooled to 0° C. Methyldichlorophosphine (7.73 ml, 86 mmol) in toluene (20 ml) was added dropwise over 20 minutes. The solution was then allowed to warm to room temperature and stirred for 1 h. The slurry was filtered to remove the precipitated salt, affording a colorless solution. [2-(4-Bromomethyl-benzoylamino)-4-thiophen-2-yl-phenyl]-carbamic acid tert-butyl ester (10.50 g, 21.54 mmol) was added to the solution, and the mixture was stirred at 100° C. for 4 h. The solvent was removed, and the residue was purified by flash chromatography (Biotage 65i, 0-10% MeOH/EtOAc, then repeated with a fresh column to remove trace coeluting impurities) to afford a colorless solid. $^1$H NMR (DMSO-d$_6$) δ 9.87 (s, 1H), 8.72 (s, 1H), 7.90 (d, J=8.0 Hz, 2H), 7.79 (d, J=1.9 Hz, 1H), 7.59 (d, J=8.9 Hz, 1H), 7.50-7.47 (m, 2H), 7.43-7.40 (m, 3H), 7.09 (dd, J=4.8, 3.7 Hz, 1H), 3.55 (d, J=11.1 Hz, 3H), 3.30 (d, J=18.1 Hz, 2H), 1.42 (s, 9H), 1.32 (d, J=13.9 Hz, 3H). MS: cal'd 523 (MH+), exp 523 (MH+).

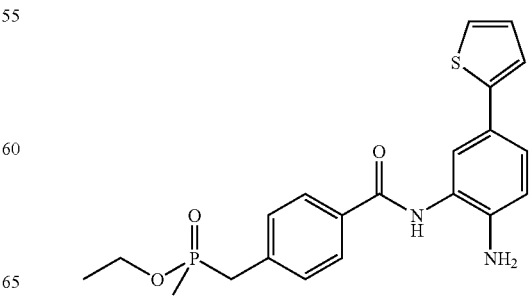

[4-(2-Amino-5-thiophen-2-yl-phenylcarbamoyl)-benzyl]-methyl-phosphinic acid ethyl ester. To a solution of [4-(2-tert-butoxycarbonylamino-5-thiophen-2-yl-phenylcarbamoyl)-benzyl]-methyl-phosphinic acid ethyl ester (500 mg, 0.972 mmol) in DCM (10 mL) was added TFA (5 mL, 64.9 mmol). After 2 h, the solvent was removed, and to the residue was added EtOAc and sat. NaHCO$_3$. The aqueous fraction was extracted further with EtOAc, dried (MgSO$_4$), filtered and the solvent was evaporated under reduced pressure. The material was used without further purification. $^1$H NMR (DMSO-d$_6$) δ 9.69 (br s, 1H), 7.92 (d, J=7.9 Hz, 2H), 7.44 (m, 1H), 7.39 (dd, J=7.9, 2.0 Hz, 1H), 7.33 (dd, J=5.0, 1.8 Hz, 1H), 7.27 (dd, J=8.2, 2.0 Hz, 1H), 7.21 (dd, J=3.5, 1.0 Hz, 1H), 7.02 (dd, J=5.0, 3.5 Hz, 1H), 6.78 (d, J=8.2 Hz, 1H), 5.13 (s, 2H), 3.97-3.88 (m, 2H), 3.40-3.25 (m, 2H), 1.32 (d, J=13.8 Hz, 3H), 1.27 (t, J=7.0 Hz, 3H). MS: cal'd 415 (MH+), exp 415 (MH+).

[4-(2-tert-Butoxycarbonylamino-5-thiophen-2-yl-phenylcarbamoyl)-benzyl]-methyl-phosphinic acid. To a solution [4-(2-tert-butoxycarbonylamino-5-thiophen-2-yl-phenylcarbamoyl)-benzyl]-methyl-phosphinic acid ethyl ester (377 mg, 0.733 mmol) in dioxane (2 mL) was added NaOH (1 mL, 5.00 mmol, 5M) and the solution was heated to 60° C. After 18 h, the reaction was diluted with EtOAc, acidified with 1N HCl. The organic layer was dried (MgSO$_4$), filtered and the solvent was evaporated under reduced pressure. The material was used without further purification. $^1$H NMR (DMSO-d$_6$) δ 9.94 (s, 1H), 8.74 (br s, 1H), 7.91 (d, J=8.2 Hz, 2H), 7.79 (d, J=2.0 Hz, 1H), 7.58 (d, J=8.5 Hz, 1H), 7.50 (dd, J=5.0, 1.2 Hz, 1H), 7.48 (dd, J=8.5, 2.0 Hz, 1H), 7.44-7.39 (m, 3H), 7.10 (dd, J=5.3, 3.5 Hz, 1H), 3.13 (d, J=17.9 Hz, 2H), 1.43 (s, 9H), 1.21 (d, J=13.8 Hz, 3H). MS: cal'd 387 (MH+; -Boc), exp 387 (MH+; -Boc).

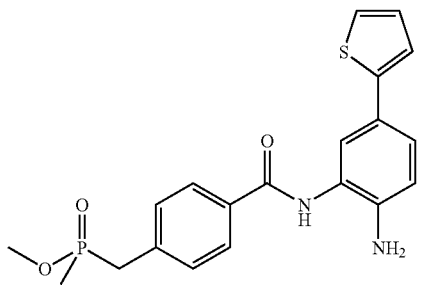

Methyl [4-({[2-amino-5-(2-thienyl)phenyl]amino}carbonyl)benzyl]methylphosphinate. Methyl [4-({[2-[(tert-butoxycarbonyl)amino]-5-(2-thienyl)phenyl]amino}carbonyl)benzyl]methyl-phosphinate (6.69 g, 13.37 mmol) was dissolved in CH$_2$Cl$_2$ (48 ml), and TFA (12 ml) was added. The solution was stirred at room temperature for 3 h and evaporated. The residue was dissolved in CH$_2$Cl$_2$, washed with saturated NaHCO$_3$ and brine, dried (MgSO$_4$), and evaporated. The crude was then slurried in CH$_2$Cl$_2$ and triturated with a small amount of hexanes to precipitate the title compound as a colorless solid. This material was subjected to chiral SFC to provide enantiopure samples of the two enantiomeric forms. Spectral data for racemate: $^1$H NMR (DMSO-d$_6$) δ 9.68 (s, 1H), 7.92 (d, J=7.9 Hz, 2H), 7.44 (d, J=1.6 Hz, 1H), 7.38 (dd, J=8.1, 2.0 Hz, 2H), 7.32 (dd, J=5.2, 0.9 Hz, 1H), 7.27 (dd, J=8.3, 2.2 Hz, 1H), 7.21 (d, J=3.6 Hz, 1H), 7.01 (dd, J=5.0, 3.6 Hz, 1H), 6.78 (d, J=8.7 Hz, 1H), 5.13 (s, 2H), 3.55 (d, J=11.0 Hz, 3H), 3.29 (d, J=18.0 Hz, 2H), 1.32 (d, J=13.7 Hz, 3H). MS: cal'd 401 (MH+), exp 401 (MH+).

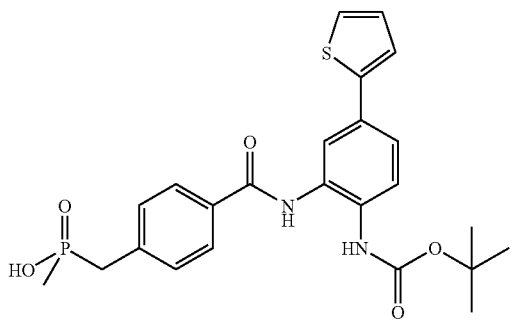

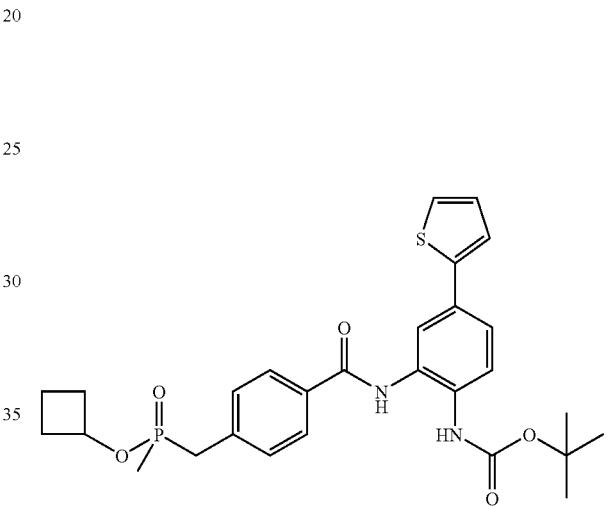

[4-(2-tert-Butoxycarbonylamino-5-thiophen-2-yl-phenylcarbamoyl)-benzyl]-methyl-phosphinic acid cyclobutyl ester. To a solution of [4-(2-tert-butoxycarbonylamino-5-thiophen-2-yl-phenylcarbamoyl)-benzyl]-methyl-phosphinic acid (57 mg, 0.117 mmol), cyclobutanol (0.038 mL, 0.703 mmol), and Hunig's Base (0.031 mL, 0.176 mmol) in DMF (2 mL) was added BOP (78 mg, 0.176 mmol). After 18 h, the reaction was purified by preparative HPLC Reverse phase (C-18), eluting with acetonitrile/water plus 0.025% TFA (40-100%) to give material after extraction of fractions with EtOAc. $^1$H NMR (DMSO-d$_6$) δ 9.88 (s, 1H), 8.74 (br s, 1H), 7.90 (d, J=7.6 Hz, 2H), 7.79 (br s, 1H), 7.58 (d, J=8.5 Hz, 1H), 7.52-7.47 (m, 2H), 7.44-7.39 (m, 3H), 7.12-7.09 (m, 1H), 4.64 (m, 1H), 3.27 (dd, J=23.2, 17.6 Hz, 1H), 3.25 (dd, J=23.2, 17.6 Hz, 1H), 2.25-21.4 (m, 2H), 2.05-1.94 (m, 2H), 1.67-1.60 (m, 1H), 1.49-1.42 (m, 1H), 1.43 (s, 9H), 1.31 (d, J=14.1 Hz, 3H). MS: cal'd 441 (MH+; -Boc), exp 441 (MH+; -Boc).

Additional analogs were prepared in procedures similar to those described for the preparations of the above examples.

TABLE 5

E; Alkyl Phosphinates

| Cpd # | Structure | Name | MS | Salt Forms |
|---|---|---|---|---|
| 1 | 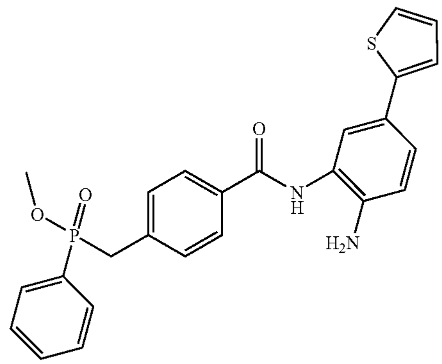 | [4-(2-Amino-5-thiophen-2-yl-phenylcarbamoyl)-benzyl]-phenyl-phosphinic acid methyl ester | cal'd 462 (MH+), exp 462 (MH+) | TFA Salt, Free base |
| 2 | 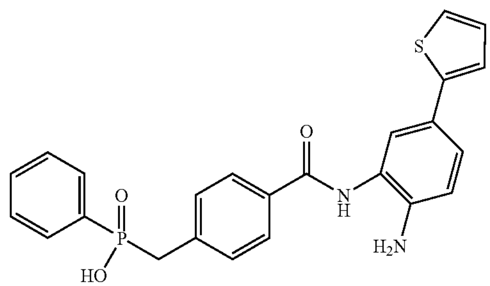 | [4-(2-Amino-5-thiophen-2-yl-phenylcarbamoyl)-benzyl]-phenyl-phosphinic acid | cal'd 448 (MH+), exp 448 (MH+) | TFA Salt |
| 3 | 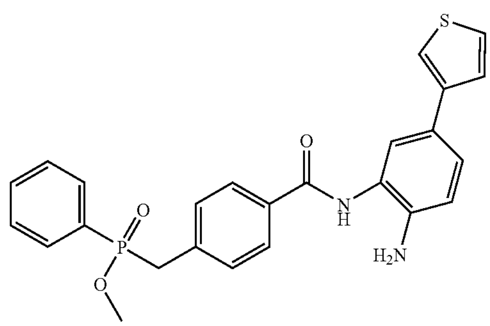 | [4-(2-Amino-5-thiophen-3-yl-phenylcarbamoyl)-benzyl]-phenyl-phosphinic acid methyl ester | cal'd 463 (MH+), exp 463 (MH+) | TFA Salt |
| 4 | 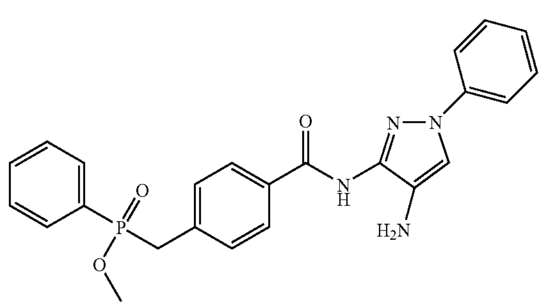 | [4-(4-Amino-1-phenyl-1H-pyrazol-3-ylcarbamoyl)-benzyl]-phenyl-phosphinic acid methyl ester | cal'd 447 (MH+), exp 447 (MH+) | TFA Salt |

TABLE 5-continued

E; Alkyl Phosphinates

| Cpd # | Structure | Name | MS | Salt Forms |
|---|---|---|---|---|
| 5 | 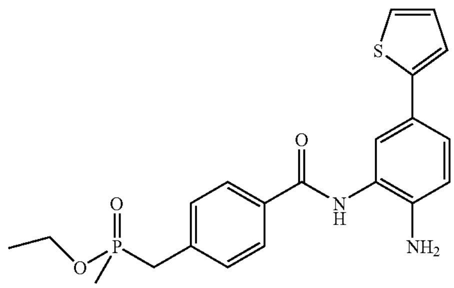 | [4-(2-Amino-5-thiophen-2-yl-phenylcarbamoyl)-benzyl]-methyl-phosphinic acid ethyl ester. | cal'd 415 (MH+), exp 415 (MH+) | Free base |
| 6 | 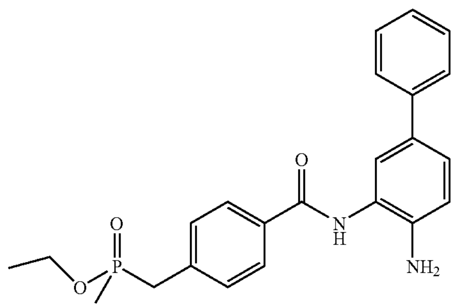 | [4-(4-Amino-biphenyl-3-ylcarbamoyl)-benzyl]-methyl-phosphinic acid ethyl ester | cal'd 409 (MH+), exp 409 (MH+) | Free base |
| 7 | 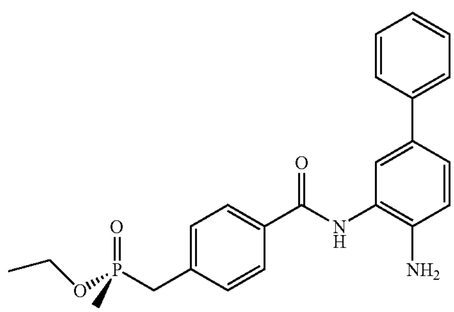 | [4-(4-Amino-biphenyl-3-ylcarbamoyl)-benzyl]-methyl-phosphinic acid ethyl ester | cal'd 409 (MH+), exp 409 (MH+) | Free base |
| 8 | 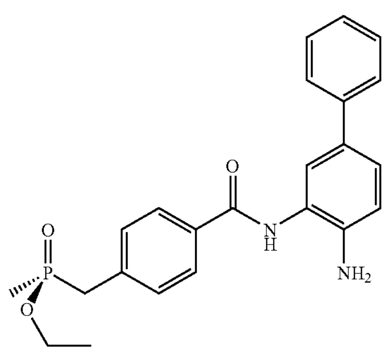 | [4-(4-Amino-biphenyl-3-ylcarbamoyl)-benzyl]-methyl-phosphinic acid ethyl ester | cal'd 409 (MH+), exp 409 (MH+) | Free base |
| 9 | 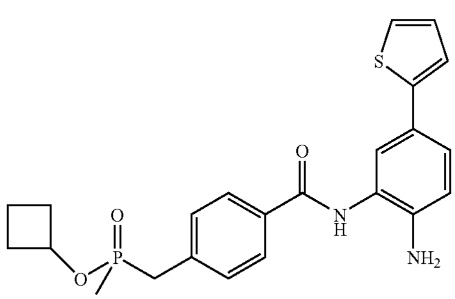 | [4-(2-Amino-5-thiophen-2-yl-phenylcarbamoyl)-benzyl]-methyl-phosphinic acid cyclobutyl ester | cal'd 441 (MH+), exp 441 (MH+) | Free base |

TABLE 5-continued

| | E; Alkyl Phosphinates | | | |
|---|---|---|---|---|
| Cpd # | Structure | Name | MS | Salt Forms |
| 10 | | Methyl [4-({[2-amino-5-(2-thienyl)-phenyl]amino}-carbonyl)benzyl]-methylphosphinate | cal'd 401 (MH+), exp 401 (MH+) | Free base |
| 11 | | Isopropyl [4-({[2-amino-5-(2-thienyl)-phenyl]amino}-carbonyl)benzyl]-methylphosphinate | cal'd 429 (MH+), exp 429 (MH+) | Free base |
| 12 | | N-[2-Amino-5-(2-thienyl)phenyl]-4-({methyl[(pyridin-3-ylmethyl)amino]-phosphoryl}methyl)-benzamide | cal'd 477 (MH+), exp 477 (MH+) | Free base |
| 13 | | Pyridin-3-ylmethyl [4-({[2-amino-5-(2-thienyl)phenyl]amino}-carbonyl)benzyl]methyl-phosphinate | cal'd 478 (MH+), exp 478 (MH+) | Free base |

TABLE 5-continued

| | E; Alkyl Phosphinates | | | |
|---|---|---|---|---|
| Cpd # | Structure | Name | MS | Salt Forms |
| 14 | | Methyl [4-({[2-amino-5-(2-thienyl)-phenyl]amino}-carbonyl)benzyl]-ethylphosphinate | cal'd 415 (MH+), exp 415 (MH+) | Free base |
| 15 | | Ethyl [4-({[2-amino-5-(2-thienyl)-phenyl)amino}-carbonyl)benzyl]-ethylphosphinate | cal'd 429 (MH+), exp 429 (MH+) | Free base |
| 16 | | Isopropyl [4-{{[2-amino-5-(2-thienyl)-phenyl)amino}-carbonyl)benzyl]-ethylphosphinate | cal'd 443 (MH+), exp 443 (MH+) | Free base |
| 17 | | Cyclobutyl [4-({[2-amino-5-(2-thienyl)-phenyl]amino}-carbonyl)benzyl]-ethylphosphinate | cal'd 455 (MH+), exp 455 (MH+) | Free base |

TABLE 5-continued

E; Alkyl Phosphinates

| Cpd # | Structure | Name | MS | Salt Forms |
|---|---|---|---|---|
| 18 | 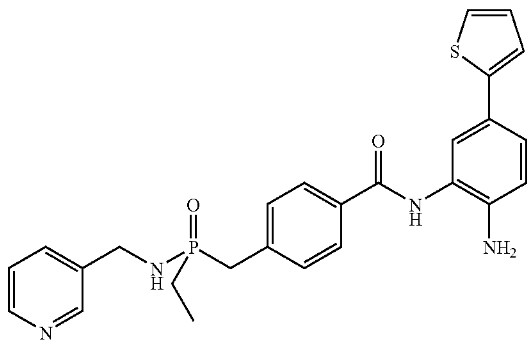 | N-[2-Amino-5-(2-thienyl)phenyl]-4-({ethyl[(pyridin-3-ylmethyl)amino]-phosphoryl}methyl)-benzamide | cal'd 491 (MH+), exp 491 (MH+) | Free base |
| 19 | 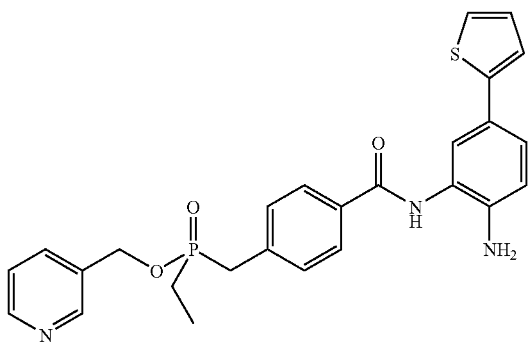 | Pyridin-3-ylmethyl [4-({[2-amino-5-(2-thienyl)phenyl]amino}-carbonyl)benzyl]ethyl-phosphinate | cal'd 492 (MH+), exp 492 (MH+) | Free base |
| 20 | 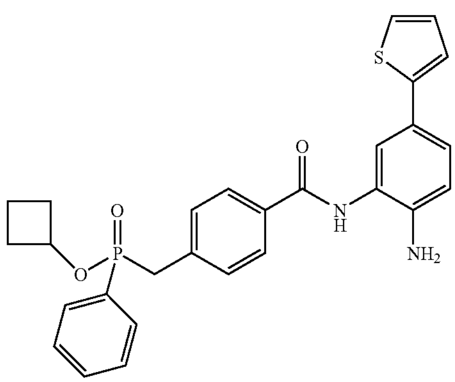 | Cyclobutyl [4-({[2-amino-5-(2-thienyl) phenyl]amino} carbonyl)benzyl]phenyl-phosphinate | cal'd 503 (MH+), exp 503 (MH+) | Free base |
| 21 | 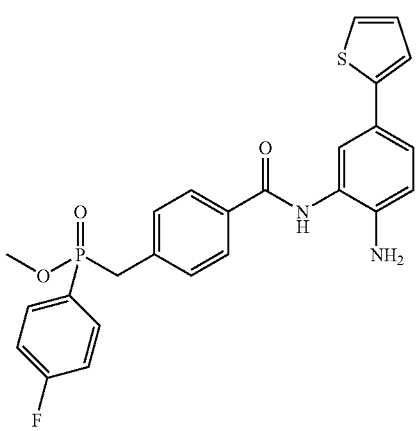 | Methyl [4-({[2-amino-5-(2-thienyl)phenyl]amino}carbonyl)benzyl](4-fluorophenyl) phosphinate | cal'd 481 (MH+), exp 481 (MH+) | Free base |

TABLE 5-continued

E; Alkyl Phosphinates

| Cpd # | Structure | Name | MS | Salt Forms |
|---|---|---|---|---|
| 22 | 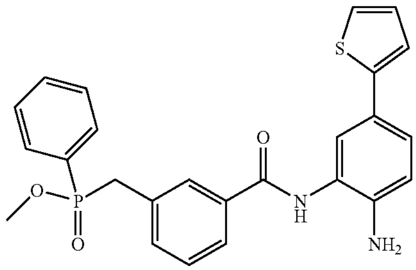 | methyl [3-({[2-amino-5-(2-thienyl)phenyl]amino}carbonyl)benzyl]phenylphosphinate | cal'd 463 (MH+), exp 463 (MH+) | Free base |
| 23 | 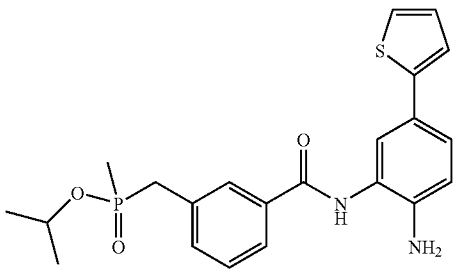 | Isopropyl [3-({[2-amino-5-(2-thienyl)phenyl]amino}carbonyl)benzyl]methylphosphinate | cal'd 429 (MH+), exp 429 (MH+) | Free base |
| 24 | 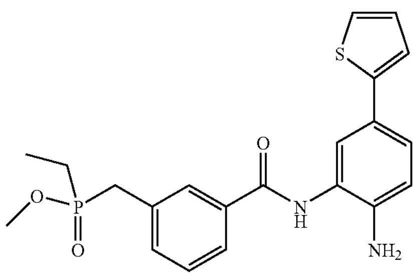 | Methyl [3-({[2-amino-5-(2-thienyl)phenyl]amino}carbonyl)benzyl]ethylphosphinate | cal'd 415 (MH+), exp 415 (MH+) | Free base |
| 25 | 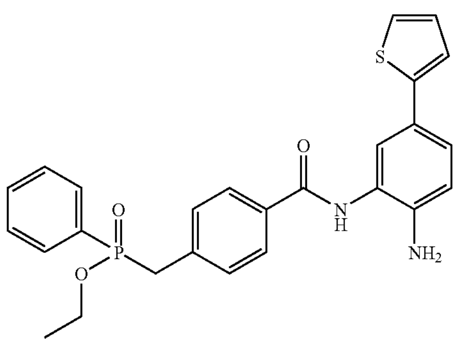 | ethyl[4-({[2-amino-5-(2-thienyl)phenyl]amino}carbonyl)benzyl]phenylphosphinate | cal'd 477 (MH+), exp 477 (MH+) | Free base |
| 26 | 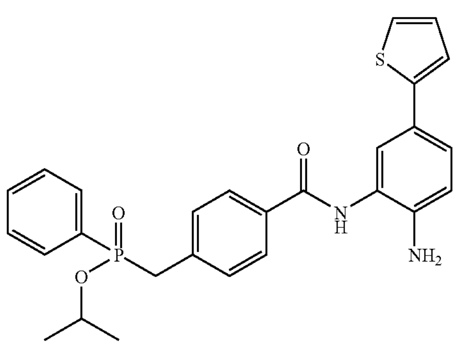 | isopropyl[4-({[2-amino-5-(2-thienyl)phenyl]amino}carbonyl)benzyl]phenylphosphinate | cal'd 491 (MH+), exp 491 (MH+) | Free base |

TABLE 5-continued

E; Alkyl Phosphinates

| Cpd # | Structure | Name | MS | Salt Forms |
|---|---|---|---|---|
| 27 | 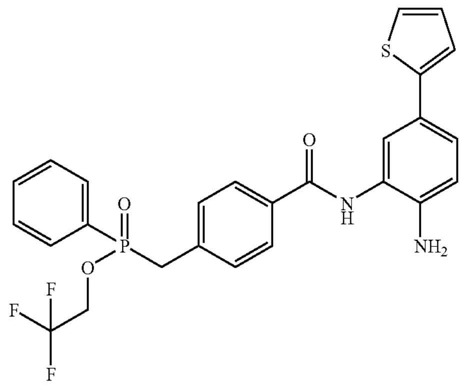 | 2,2,2-trifluoroethyl[4-({[2-amino-5-(2-thienyl)phenyl]amino}carbonyl)benzyl]phenylphosphinate | cal'd 531 (MH+), exp 531 (MH+) | Free base |
| 28 | 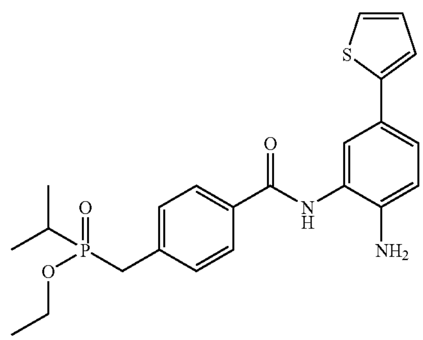 | ethyl[4-({[2-amino-5-(2-thienyl)phenyl]amino}carbonyl)benzyl]isopropyl phosphinate | cal'd 443 (MH+), exp 443 (MH+) | Free base |
| 29 | 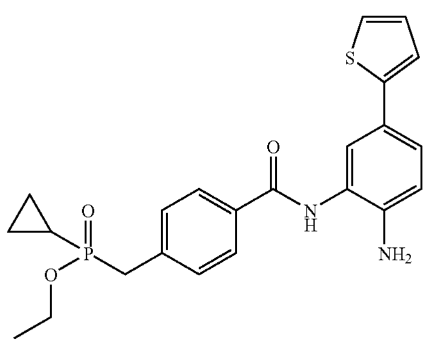 | ethyl[4-({[2-amino-5-(2-thienyl)phenyl]amino}carbonyl)benzyl]cyclopropyl phosphinate | cal'd 441 (MH+), exp 441 (MH+) | Free base |
| 30 | 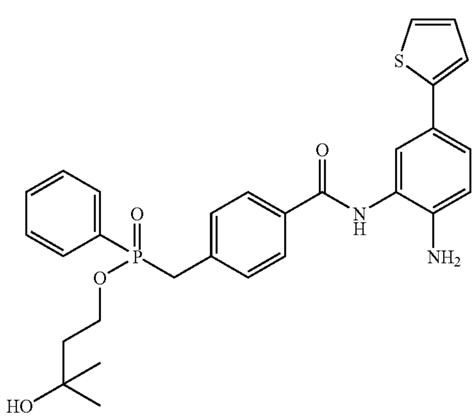 | 3-hydroxy-3-methylbutyl[4-({[2-amino-5-(2-thienyl)phenyl]amino}carbonyl)benzyl]phenylphosphinate | cal'd 535 (MH+), exp 535 (MH+) | Free base |

TABLE 5-continued

E; Alkyl Phosphinates

| Cpd # | Structure | Name | MS | Salt Forms |
|---|---|---|---|---|
| 31 | 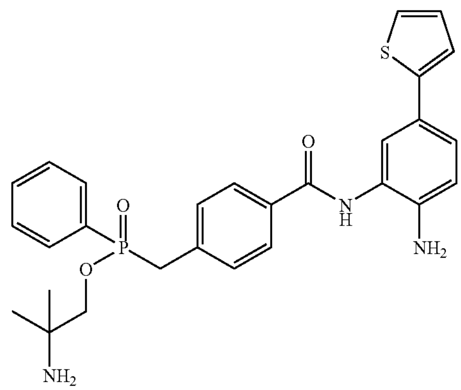 | 2-amino-2-methylpropyl[4-({[2-amino-5-(2-thienyl)phenyl]amino}carbonyl)benzyl]phenylphosphinate | cal'd 520 (MH+), exp 520 (MH+) | Free base |
| 32 | 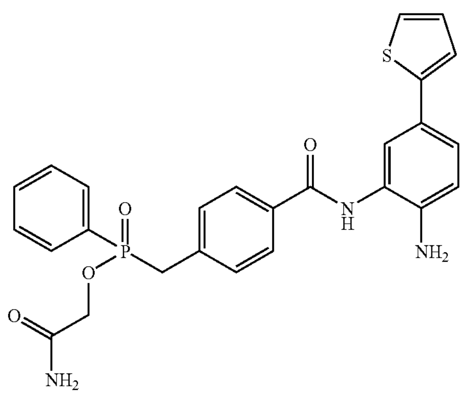 | 2-amino-2-oxoethyl[4-({[2-amino-5-(2-thienyl)phenyl]amino}carbonyl)benzyl]phenylphosphinate | cal'd 506 (MH+), exp 506 (MH+) | Free base |
| 33 | 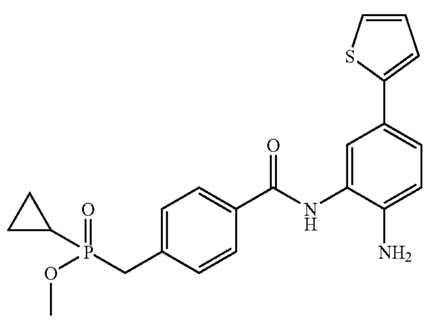 | methyl[4-({[2-amino-5-(2-thienyl)phenyl]amino}carbonyl)benzyl]cyclopropyl phosphinate | cal'd 427 (MH+), exp 427 (MH+) | Free base |
| 34 | 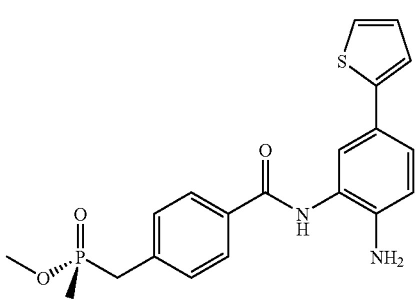 | methyl (S)-[4-({[2-amino-5-(2-thienyl)phenyl]amino}carbonyl)benzyl] methylphosphinate | cal'd 401 (MH+), exp 401 (MH+) | Free base |

TABLE 5-continued

E; Alkyl Phosphinates

| Cpd # | Structure | Name | MS | Salt Forms |
|---|---|---|---|---|
| 35 | 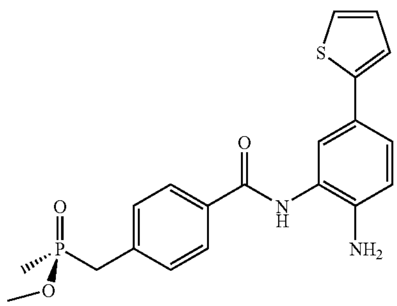 | methyl (R)-[4-({[2-amino-5-(2-thienyl)phenyl]amino}carbonyl)benzyl]methyl phosphinate | cal'd 401 (MH+), exp 401 (MH+) | Free base |
| 36 | 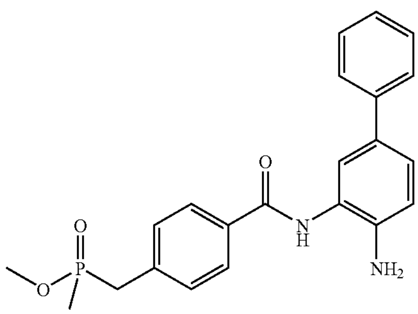 | methyl (4-{[(4-amino biphenyl-3-yl)amino]carbonyl}benzyl)methylphosphinate | cal'd 395 (MH+), exp 395 (MH+) | Free base |
| 37 | 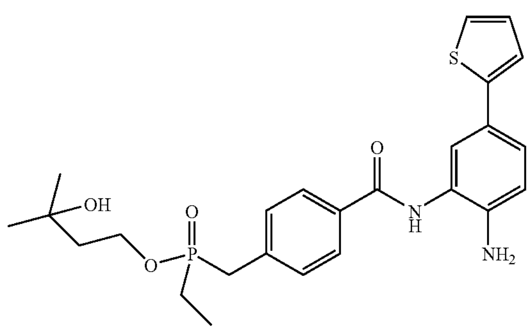 | 3-hydroxy-3-methylbutyl [4-({[2-amino-5-(2-thienyl)phenyl]amino}carbonyl)benzyl]ethylphosphinate | cal'd 487 (MH+), exp 487 (MH+) | Free base |
| 38 | 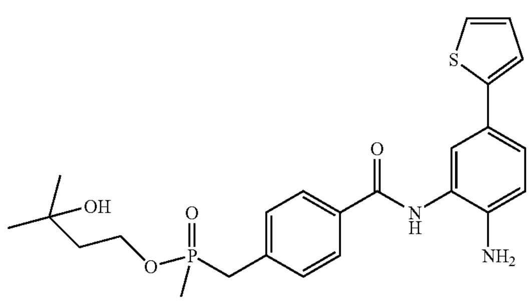 | 3-hydroxy-3-methylbutyl [4-({[2-amino-5-thienyl)phenyl]amino}carbonyl)benzyl]methylphosphinate | cal'd 473 (MH+), exp 473 (MH+) | Free base |
| 39 | 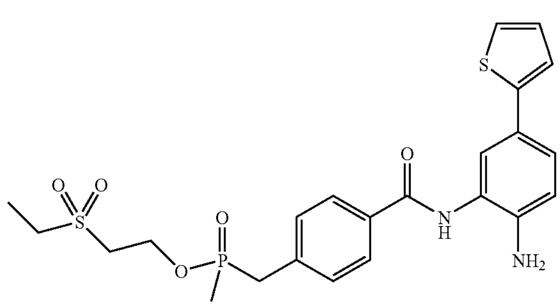 | 2-(ethylsulfonyl)ethyl[4-({[2-amino-5-(2-thienyl)phenyl]amino}carbonyl)benzyl]methylphosphinate | cal'd 507 (MH+), exp 507 (MH+) | Free base |

Procedures for E. Preparation of Benzylnicotinyl Phosphonates and Phosphinates.

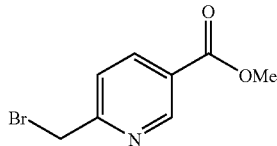

Methyl 6-(bromomethyl)nicotinate. A mixture of methyl 6-methylnicotinate (2.00 g, 13.2 mmol) and CCl₄ (88.2 mL) was treated with NBS (2.57 g, 14.5 μmmol) and benzoyl peroxide (320 mg, 1.32 mmol) and heated to a refluxing temperature overnight. The resulting brown suspension was concentrated and purified by MPLC (10-40% EtOAc in heptane to afford the requisite product as a yellow solid. $^1$H NMR (DMSO-$d_6$, 600 MHz) δ 9.01 (dd, J=2.4, 0.8 Hz, 1H), 8.28 (dd, J=7.9, 2.1 Hz, 1H), 7.68 (dd, J=8.2, 0.9 Hz, 1H), 4.74 (s, 3H), 3.84 (s, 3H).
MS: cal'd 230 and 232 (MH+), exp 230 and 232 (MH+).

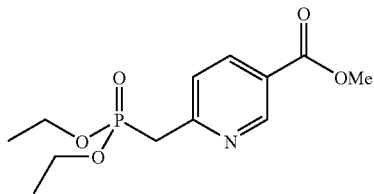

Methyl 6-[(diethoxyphosphoryl)methyl]nicotinate. A mixture of methyl 6-(bromomethyl)nicotinate (153 mg, 0.665 mmol) and triethylphosphine (0.58 mL, 3.33 mmol) were heated to 125° C. for 1 h in a sealed flask via the microwave. The resulting mixture was concentrated via rotovap and purified by MPLC (EtOAc isocratic) to afford the requisite product as a light yellow oil. $^1$H NMR (DMSO-$d_6$, 600 MHz) δ 8.97 (m, 1H), 8.23 (m, 1H), 7.59 (m, 1H), 3.96 (dt, J=15.3, 7.0 Hz, 4H), 3.86 (s, 3H), 3.53 (d, J=22.3 Hz, 2H), 1.15 (t, J=7.0 Hz, 3H). MS: cal'd 288 (MH+), exp 288 (MH+).

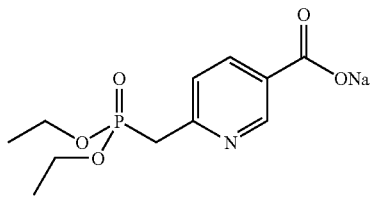

6-[(Diethoxyphosphoryl)methyl]nicotinic acid. A mixture of methyl 6-[(diethoxyphosphoryl)methyl]nicotinate (108 mg, 0.376 mmol), THF (1.13 mL) and MeOH (0.376 mL) was treated with LiOH (0.376 mL, 3.0M in water, 1.13 mmol) and stirred for 2 h. The mixture was concentrated to a white residue used crude in the next step. $^1$H NMR (DMSO-$d_6$, 600 MHz) δ 8.95 (m, 1H), 8.22 (m, 1H), 7.48 (m, 1H), 3.96 (dt, J=15.3, 7.0 Hz, 4H), 3.53 (d, J=22.0 Hz, 2H), 1.15 (t, J=7.0 Hz, 3H). MS: cal'd 274 (MH+), exp 274 (MH+).

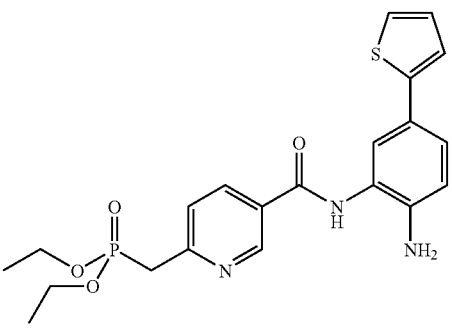

Diethyl {[5-({[2-amino-5-(2-thienyl)phenyl]amino}carbonyl)pyridin-2-yl]methyl}phosphonate. A mixture of 6-[(Diethoxyphosphoryl)methyl]nicotinic acid (55.5 mg, 0.188 mmol), tert-butyl [2-amino-4-(2-thienyl)phenyl]carbamate (65.5 mg, 0.226 mmol) HOBT (30.5 mg, 0.226 mmol), and EDC (43.3 mg, 0.226 mmol) was taken into DMF (1.32 mL) and stirred for 3 days. The mixture was diluted with EtOAc and washed with 50% saturated aqueous NaHCO₃ 3×, brine, dried (MgSO₄) and concentrated to afford a residue taken into DCM (2 mL) and TFA (1 mL) and stirred for 1 h. This mixture was concentrated via rotovap, dissolved in minimum MeOH and purified via HPLC (10-100% MeCN in water with 0.025% TFA) to afford fractions poured into saturated aqueous NaHCO₃ and extracted with EtOAc 2×. The combined organic layers were washed with brine, dried (MgSO₄) and concentrated to afford 36.5 mg of the requisite product as a light yellow solid. $^1$H NMR (DMSO-$d_6$, 600 MHz) δ 9.84 (s, 1H), 9.04 (s, 1H), 8.26 (dd, J=7.9, 2.0 Hz, 1H), 7.47 (dd, J=8.2, 1.8 Hz, 1H), 7.44 (d, J=2.0 Hz, 1H), 7.33 (dd, J=5.0, 0.9 Hz, 1H), 7.28 (dd, J=8.8, 2.3 Hz, 1H), 7.22 (dd, J=3.5, 1.2 Hz, 1H), 7.2 (dd, J=5.0, 3.5 Hz, 1H), 6.78 (d, J=8.2 Hz, 1H), 5.22 (s, 2H), 3.95 (dt, J=7.3, 7.3 Hz, 4H), 3.53 (d, J=22.3 Hz, 2H), 1.19 Hz (t, J=7.0 Hz, 3H). MS: cal'd 446 (MH+), exp 446 (MH+).

TABLE 6

| | | E; Benzylnicotinates | | |
| --- | --- | --- | --- | --- |
| Cpd # | R | Name | MS | Salt forms |
| 1 |  | Diethyl {[5-({[2-amino-5-(2-thienyl)phenyl]amino}carbonyl]methyl}phosphonate | cal'd 446 (MH+), exp 446 (MH+). | Free base |

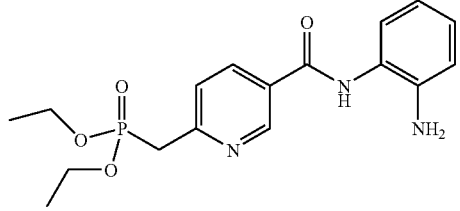

TABLE 6-continued

E: Benzylnicotinates

| Cpd # | R | Name | MS | Salt forms |
|---|---|---|---|---|
| 2 | 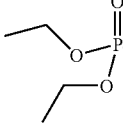 | Diethyl {[5-({[2-amino-5-(3-thienyl)phenyl]amino}carbonyl)pyridin-2-yl]methyl}phosphonate | cal'd 446 (MH+), exp 446 (MH+) | Free base |
| 3 | 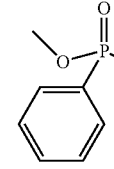 | Methyl {[5-({[2-amino-5-(2-thienyl)phenyl]amino}carbonyl)pyridin-2-yl]methyl}phenylphosphinate | cal'd 464 (MH+), exp 464 (MH+) | Free base |
| 4 | 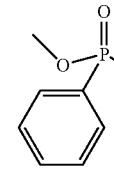 | Methyl {[5-({[2-amino-5-(3-thienyl)phenyl]amino}carbonyl)pyridin-2-yl]methyl}phenylphosphinate | cal'd 464 (MH+), exp 464 (MH+) | Free base |

Procedures for F. Preparation of α-OH, -F or -NR$_1$R$_2$ Substituted Alkyl Phosphonates.

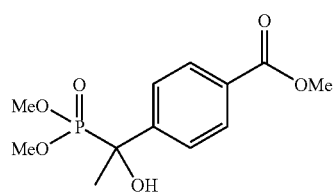

4-[1-(Dimethoxy-phosphoryl)-1-hydroxy-ethyl]-benzoic acid methyl ester. A solution of 4-acetyl-benzoic acid methyl ester (1.0 g, 5.61 mmol) in THF (5.6 mL) was cooled to 0° C. and dimethyl phosphite (0.7 g, 6.17 mmol) and N,N,N'N'-tetramethyl-guanidine (0.07 g, 0.56 mmol) were added dropwise. The reaction mixture was warmed to ambient temperature and stirred for 30 minutes. The reaction mixture was diluted with EtOAc and washed with 1N aqueous HCl (2×), brine, then dried (MgSO$_4$) and concentrated in vacuo. The residue was purified by MPLC (Isocratic CH$_2$Cl$_2$ for 6 CV then 0-7.5% MeOH in CH$_2$Cl$_2$) to afford the title compound: MS: cal'd 289 (MH+), exp 289 (MH+)

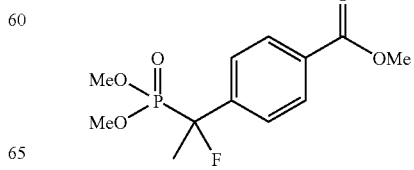

4-[1-(Dimethoxy-phosphoryl)-fluoro-ethyl]-benzoic acid methyl ester. 4-[1-(Dimethoxy-phosphoryl)-1-hydroxy-ethyl]-benzoic acid methyl ester (0.60 g, 2.08 mmol) was added over 30 minutes to a stirring solution of DAST (1M in CH$_2$Cl$_2$) cooled to –78° C. under a dry nitrogen environment. The mixture was warmed to ambient temperature and stirred. After stirring for 90 minutes the reaction mixture was carefully quenched with ethanol containing pyridine (pyr: twice volume of DAST). After stirring for 30 mins the mixture was poured into ice cold water and extracted into DCM (3×). The combined organic extracts were washed with dilute HCl, water, brine, dried (MgSO$_4$) then concentrated in vacuo. The material was carried forward without further purification. MS: cal'd 291 (MH+), exp 291 (MH+)

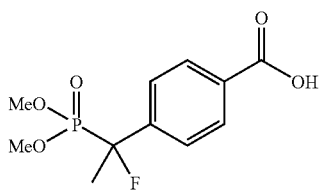

4-[1-(Dimethoxy-phosphoryl)-1-fluoro-ethyl]-benzoic acid. 4-[1-(Dimethoxy-phosphoryl)-1-fluoro-ethyl]-benzoic acid methyl ester (0.56 g, 1.93 mmol) was made 0.25 M in dioxane and to this stirring solution was added 3 M aqueous LiOH (0.14 g, 5.79 mmol). The resulting mixture was stirred at ambient temperature for 18 hours. The mixture was neutralized with 1N aq HCl and concentrated in vacuo. The residue was carried forward without further purification: MS: cal'd 277 (MH+), exp 277 (MH+)

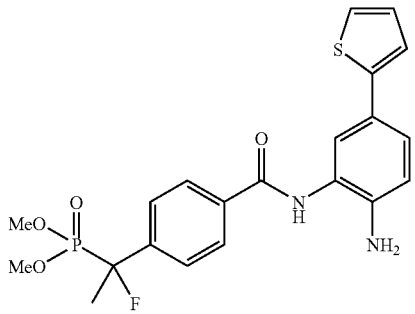

{1-[4-(2-Amino-5-thiophen-2-yl-phenylcarbamoyl)-phenyl]-1-fluoro-ethyl}-phosphonic acid dimethyl ester. 4-[1-(Dimethoxy-phosphoryl)-1-fluoro-ethyl]-benzoic acid (50 mg, 0.18 mmol), (2-Amino-4-thiophen-2-yl-phenyl)-carbamic acid tert-butyl ester (63 mg, 0.22 mmol), BOP (96 mg, 0.22 mmol), and DIPEA (70 mg, 0.54 mmol) were combined and diluted with DMF (0.72 mL). The resulting mixture was stirred at ambient temperature for 18 hours. The reaction mixture was purified directly by HPLC (20-85% MeCN in water w/0.025% TFA). Pure fractions were identified, combined, and concentrated in vacuo. The residue was diluted with 5:1 CH$_2$Cl$_2$:TFA. The resulting solution was stirred at ambient temperature for 1 h then concentrated in vacuo to afford the title compound: $^1$H NMR (DMSO-d$_6$, 600 MHz) δ10.15 (s, 1H), 8.05 (d, J=9.0 Hz, 2H), 7.56-7.62 (m, 3H), 7.43-7.48 (m, 2H), 7.37 (d, J=3.5 Hz, 1H), 7.06-7.09 (m, 2H), 3.72 (d, J=10.8 Hz, 3H), 3.57 (d, J=10.8 Hz, 3H), 1.86-1.96 (m, 3H). MS: cal'd 449 (MH+), exp 449 (MH+)

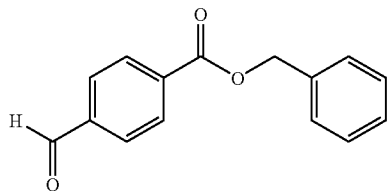

4-Formyl-benzoic acid benzyl ester. 4-Formyl-benzoic acid (2.0 g, 13.3 mmol) was made 0.2 M in 10:1 MeOH:Water and stirred. The stirring slurry was adjusted to pH=8 with 20% aq Cs$_2$CO$_3$. The resulting homogenous solution was stirred at ambient temperature for 20 mins then concentrated to dryness in vacuo. The residue was dried under high vacuum then treated with benzyl bromide (3.4 g, 20.0 mmol) 0.5 M in DMF. The slurry was stirred under nitrogen at ambient temperature for 18 hours. The reaction mixture was diluted with ½ saturated aqueous sodium bicarbonate and extracted with EtOAc. The organic layer was separated and again washed with ½ saturated aqueous sodium bicarbonate, then washed with brine, dried (MgSO$_4$) and concentrated in vacuo. The residue was purified by MPLC (5-45% EtOAc in Hexanes) to afford the title compound: MS: cal'd 241 (MH+), exp 241 (MH+)

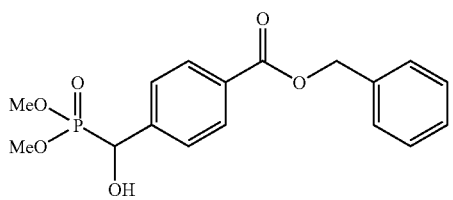

4-[(Dimethoxy-phosphoryl)-hydroxy-methyl]-benzoic acid benzyl ester. A solution of 4-formyl-benzoic acid benzyl ester (0.50 g, 2.08 mmol) in THF (2.0 mL) was cooled to 0° C., then dimethyl phosphite (0.25 g, 2.29 mmol) and N,N,N'M'-tetramethyl-guanidine (0.02 g, 0.21 mmol) was added dropwise. The reaction mixture was warmed to ambient temperature. After stirring for 45 mins the reaction mixture was diluted with EtOAc and washed with 1N aqueous HCl (2×), brine, then dried (MgSO$_4$) and concentrated in vacuo to give the title compound: MS: cal'd 351 (MH+), exp 351 (MH+)

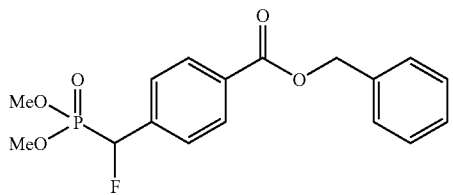

4-[(Dimethoxy-phosphoryl)fluoro-methyl]-benzoic acid benzyl ester. 4-[(Dimethoxy-phosphoryl)-hydroxy-methyl]-benzoic acid benzyl ester (0.20 g, 0.22 mmol) was added over 30 mins to a stirring solution of DAST (1M in CH$_2$Cl$_2$) cooled to –78° C. under a dry nitrogen environment. The mixture was warmed to RT and stirred for 18 hours. The reaction mixture was then quenched with ethanol containing pyridine (pyr: twice volume of DAST). After another 30 mins the mixture was poured into ice cold water and extracted into DCM (3×). The combined organic extracts were washed with dilute aq HCl, water, brine, dried (MgSO$_4$) then concentrated in vacuo. The residue was purified by HPLC (20-85% MeCN in Water w/0.025% TFA) to afford the title compound: MS: cal'd 353 (MH+), exp 353 (MH+)

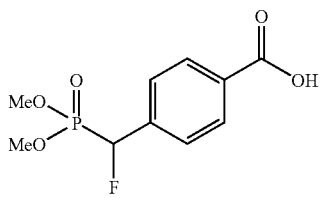

4-[(Dimethoxy-phosphoryl)-fluoro-methyl]-benzoic acid. To a stirring solution of 4-[(dimethoxy-phosphoryl)-fluoro-methyl]-benzoic acid benzyl ester (76 mg, 0.216 mmol) in MeOH (0.21M) was added 20 mol % Pd on Carbon (0.043 mmol). The resulting mixture was degassed with alternating vacuum and hydrogen gas (4×), then stirred under a hydrogen atmosphere (1 atm) at ambient temperature for 18 hours. The reaction mixture was filtered through a nylon syringe filter and concentrated in vacuo to give the title compound: MS: cal'd 263 (MH+), exp 263 (MH+)

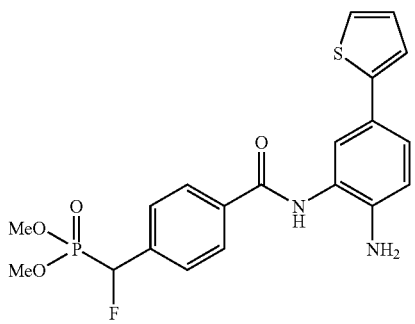

{[4-(2-Amino-5-thiophen-2-yl-phenylcarbamoyl)-phenyl]-fluoro-methyl}-phosphonic acid dimethyl ester. 4-[(Dimethoxy-phosphoryl)-fluoro-methyl]-benzoic acid (52 mg, 0.198 mmol), (2-amino-4-thiophen-2-yl-phenyl)-carbamic acid tert-butyl ester (69 mg, 0.238 mmol), EDC (57 mg, 0.298 mmol), HOBT (36 mg, 0.238 mmol), and DIPEA (77 mg, 0.595 mmol) were combined and diluted with DMF (0.79 mL). The resulting mixture was stirred at ambient temperature for 18 hours. The reaction mixture was purified directly by HPLC (20-85% MeCN in water w/0.025% TFA). Pure fractions were combined and concentrated in vacuo. The residue was diluted with 10:1 DCM:TFA and stirred at ambient temperature. After 2 hours the deprotection was complete and the mixture was concentrated in vacuo to give the title compound: $^1$H NMR (DMSO-$d_6$, 600 MHz) δ 9.87 (br-s, 1H), 8.05 (d, J=8.4 Hz, 2H), 7.56 (d, J=7.8 Hz, 2H), 7.48 (s, 1H), 7.37 (d, J=5.0 Hz, 1H), 7.32 (d, J=8.4 Hz, 1H), 7.24-7.27 (m, 1H), 7.04 (dd, J=3.6 Hz, J=5.0 Hz, 1H), 6.86 (d, J=8.4 Hz, 1H), 6.33 (dd, J=8.4 Hz, J=43.8 Hz, 1H), 3.64-3.71 (m, 6H). MS: cal'd 435 (MH+), exp 435 (MH+)

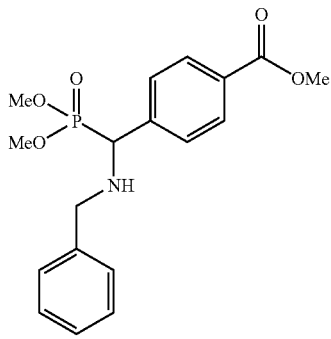

4-[Benzylamino-(dimethoxy-phosphoryl)-methyl]-benzoic acid methyl ester. 4-[(E)-Benzylimino-methyl]-benzoic acid methyl ester (0.50 g, 1.97 mmol) was made 0.3 M in dimethyl phosphite (6.5 mL) and to this stirring solution was added catalytic N,N,N',N'-tetramethyl-guanidine (0.02 g, 0.20 mmol). After stirring at ambient temperature for 4 hours the reaction mixture was diluted with EtOAc and washed with 1M aqueous NaOH (3×). The organic layer was washed further with brine, then dried (MgSO$_4$) and concentrated in vacuo. MPLC purification (10-70% EtOAc in CH$_2$Cl$_2$) gave the title compound: MS: cal'd 364 (MH+), exp 364 (MH+)

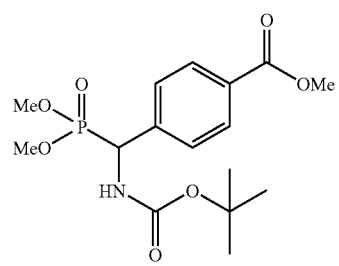

4-[tert-Butoxycarbonylamino-(dimethoxy-phosphoryl)-methyl]-benzoic acid methyl ester. To a solution of 4-[benzylamino-(dimethoxy-phosphoryl)-methyl]-benzoic acid methyl ester (0.40 g, 1.100 mmol) in anhydrous MeOH (14.7 mL) was added BOC anhydride (0.36 g, 1.65 mmol), and 10 mol % Pd on carbon (12 mg, 0.11 mmol). The solution was degassed with alternating vacuum and hydrogen gas (4×). The reaction mixture was stirred at ambient temperature under 1 atm of hydrogen. After stirring for 18 hours the reaction mixture was degassed with alternating vacuum and argon gas, then filtered through a nylon syringe filter and the filtrate was concentrated in vacuo. The residue contained residual BOC anhydride and was purified by MPLC (545% EtOAc in CH$_2$Cl$_2$) to give the title compound: MS: cal'd 374 (MH+), exp (MH+)

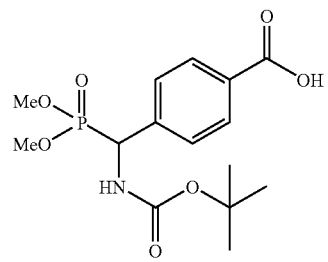

4-[tert-Butoxycarbonylamino(dimethoxy-phosphoryl)-methyl]-benzoic acid. 4-[tert-Butoxycarbonylamino-(dimethoxy-phosphoryl)-methyl]-benzoic acid methyl ester (150 mg, 0.402 mmol) was made 0.25 M in dioxane and to this stirring solution was added 3 M aq LiOH (29 mg, 1.205 mmol). The resulting mixture was stirred at ambient temperature for 18 hours. The reaction mixture was diluted with EtOAc and washed with 1N aq HCl. The organic layer was washed with brine, dried (MgSO$_4$) and concentrated in vacuo. The residue was carried onto subsequent coupling without further purification: $^1$H NMR (DMSO-$d_6$, 600 MHz) δ12.68 (br-s, 1H), 8.07-8.13 (m, 1H), 7.84-7.92 (m, 2H), 7.50-7.61 (m, 2H), 5.15-5.25 (m, 1H), 3.46-3.63 (m, 6H), 1.36 (s, 9H).

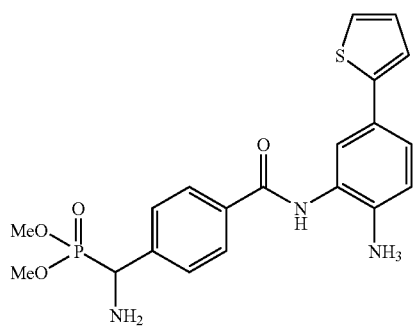

{Amino-[4-(2-amino-5-thiophen-2-yl-phenylcarbamoyl)-phenyl]-methyl}-phosphonic acid dimethyl ester. 4-[tert-Butoxycarbonylamino-(dimethoxy-phosphoryl)-methyl]-benzoic acid (76 mg, 0.212 mmol), (2-amino-4-thiophen-2-yl-phenyl)-carbamic acid tert-butyl ester (74 mg, 0.254 mmol), EDC (61 mg, 0.317 mmol), HOBT (39 mg, 0.254 mmol), and DIPEA (82 mg, 0.635 mmol) were combined and diluted with DMF (0.85 mL). The resulting mixture was stirred at ambient temperature for 18 hours. The reaction mixture was purified directly by HPLC (20-85% MeCN in water w/0.025% TFA). Pure fractions were identified, combined, then concentrated in vacuo. The residue was diluted with 10:1 DCM:TFA and stirred at ambient temperature. After 2 h the mixture was concentrated in vacuo to give the title compound: $^1$H NMR (DMSO-d$_6$, 600 MHz) δ9.81 (s, 1H), 9.06 (br-s, 2H), 8.05 (d, J=9.0 Hz, 2H), 7.62 (d, J=9.0 Hz, 2H), 7.44-7.46 (m, 1H), 7.34-7.36 (m, 1H), 7.29-7.32 (m, 1H), 7.22-7.24 (m, 1H), 7.03-7.05 (m, 1H), 6.82 (d, J=7.8 Hz, 2H), 5.20 (d, J=17.4 Hz, 1H), 3.73 (d, J=10.8 Hz, 3H), 3.58 (d, J=10.8 Hz, 3H). MS: cal'd 432 (MH+), exp 432 (MH+).

Additional analogs were prepared in procedures similar to those described for the preparations of the above examples.

TABLE 7

F; α-F, —OH, —NR$_1$R$_2$ Substituted Alkyl Phosphonates.

| Cpd # | Structure | Name | MS | Salt Forms |
|---|---|---|---|---|
| 1 | 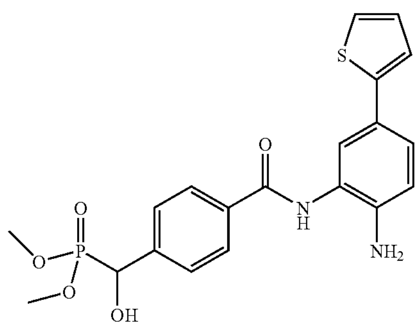 | {[4-(2-Amino-5-thiophen-2-yl-phenylcarbamoyl)-phenyl]-hydroxy-methyl}-phosphonic acid dimethyl ester | cal'd 433 (MH+), exp 433 (MH+) | Free base |
| 2 | 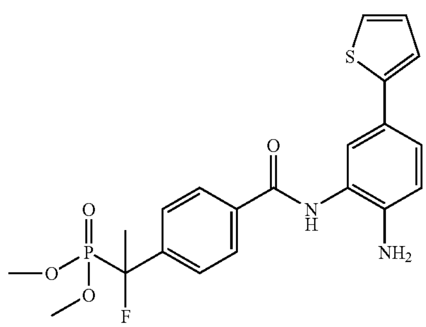 | {1-[4-(2-Amino-5-thiophen-2-yl-phenylcarbamoyl)-phenyl]-1-fluoro-ethyl}-phosphonic acid dimethyl ester | cal'd 449 (MH+), exp 449 (MH+) | TFA Salt |
| 3 | 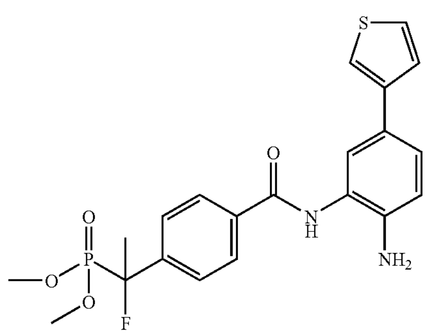 | {1-[4-(2-Amino-5-thiophen-3-yl-phenylcarbamoyl)-phenyl]-1-fluoro-ethyl}-phosphonic acid dimethyl ester | cal'd 449 (MH+), exp 449 (MH+) | TFA Salt |

TABLE 7-continued

F; α-F, —OH, —NR₁R₂ Substituted Alkyl Phosphonates.

| Cpd # | Structure | Name | MS | Salt Forms |
|---|---|---|---|---|
| 4 | 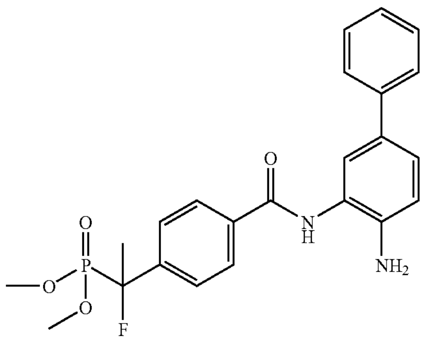 | {1-[4-(4-Amino-biphenyl-3-ylcarbamoyl)-phenyl]-1-fluoro-ethyl}-phosphonic acid dimethyl ester | cal'd 443 (MH+), exp 443 (MH+) | TFA Salt |
| 5 | 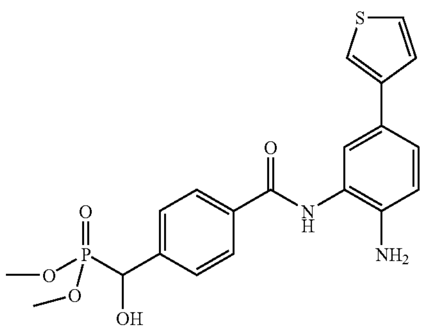 | {[4-(2-Amino-5-thiophen-3-yl-phenylcarbamoyl)-phenyl]-hydroxy-methyl}-phosphonic acid dimethyl ester | cal'd 433 (MH+), exp 433 (MH+) | TFA Salt |
| 6 | 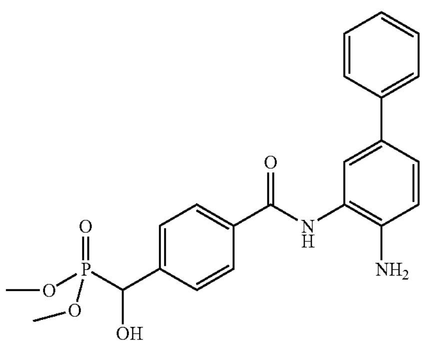 | {[4-(4-Amino-biphenyl-3-ylcarbamoyl)-phenyl]-hydroxy-methyl}-phosphonic acid dimethyl ester | cal'd 427 (MH+), exp 427 (MH+) | TFA Salt |
| 7 | 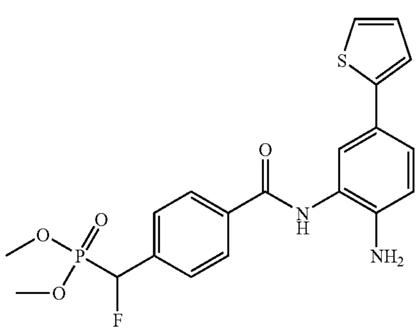 | {[4-(2-Amino-5-thiophen-2-yl-phenylcarbamoyl)-phenyl]-fluoro-methyl}-phosphonic acid dimethyl ester | cal'd 435 (MH+), exp 435 (MH+) | TFA Salt |

TABLE 7-continued

F; α-F, —OH, —NR₁R₂ Substituted Alkyl Phosphonates.

| Cpd # | Structure | Name | MS | Salt Forms |
|---|---|---|---|---|
| 8 | 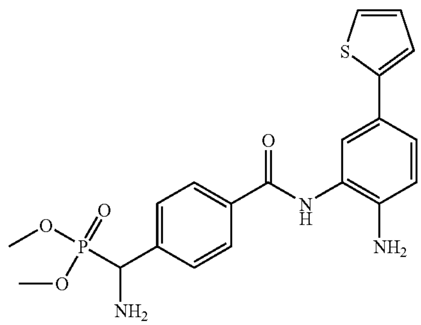 | {Amino-[4-(2-amino-5-thiophen-2-yl-phenylcarbamoyl)-phenyl]-methyl}-phosphonic acid dimethyl ester | cal'd 432 (MH+), exp 432 (MH+) | TFA Salt |

Procedures for G. Preparation of α-F, -OH, -NR₁R₂ Substituted Alkyl Phosphinates.

Additional analogs were prepared in procedures similar to those described for the preparations of the above examples.

TABLE 8

G; α-F, —OH, —NR₁R₂ Substituted Alkyl Phosphinates

| Cpd # | Structure | Name | MS | Salt Forms |
|---|---|---|---|---|
| 1 | 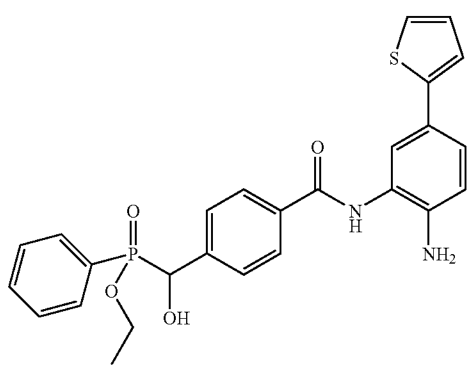 | {[4-(2-Amino-5-thiophen-2-yl-phenylcarbamoyl)-phenyl]-hydroxy-methyl}-phenyl-phosphinic acid ethyl ester | cal'd 493 (MH+), exp 493 (MH+) | Free base |
| 2 | 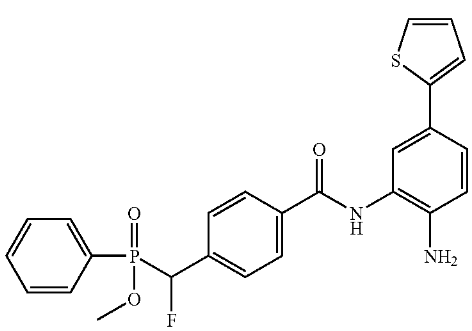 | {1-[4-(2-Amino-5-thiophen-2-yl-phenylcarbamoyl)-phenyl]-1-fluoro-ethyl}-phenyl-phosphinic acid methyl ester | cal'd 495 (MH+), exp 495 (MH+) | Free base |

TABLE 8-continued

G; α-F, —OH, —NR₁R₂ Substituted Alkyl Phosphinates

| Cpd # | Structure | Name | MS | Salt Forms |
|---|---|---|---|---|
| 3 | 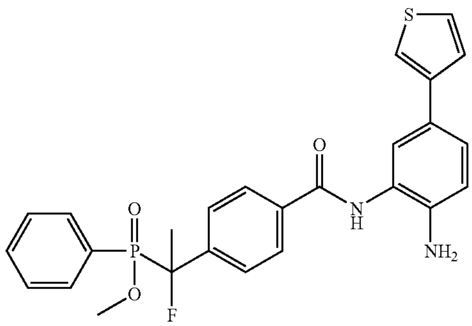 | {1-[4-(2-Amino-5-thiophen-3-yl-phenylcarbamoyl)-phenyl]-1-fluoro-ethyl}-phenyl-phosphinic acid methyl ester | cal'd 495 (MH+), exp 495 (MH+) | Free base |
| 4 | 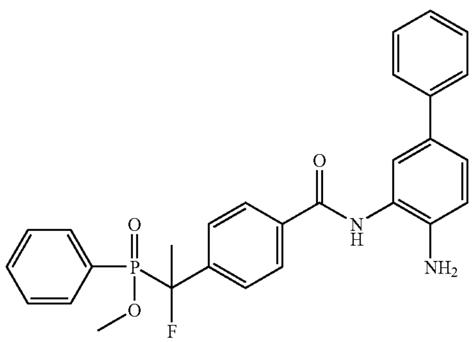 | {1-[4-Amino-biphenyl-3-ylcarbamoyl)-phenyl]-1-fluoro-ethyl}-phenyl-phosphinic acid methyl ester | cal'd 489 (MH+), exp 489 (MH+) | Free base |
| 5 | 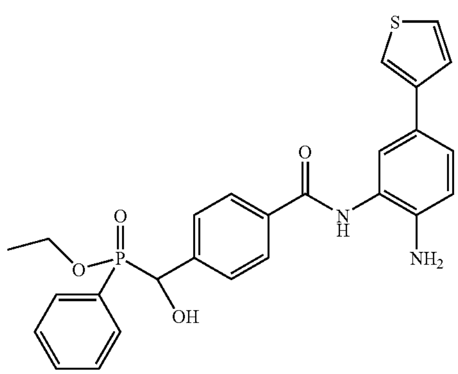 | {[4-(2-Amino-5-thiophen-3-yl-phenylcarbamoyl)-phenyl]-hydroxy-methyl}-phenyl-phosphinic acid ethyl ester | cal'd 493 (MH+), exp 493 (MH+) | TFA Salt |
| 6 | 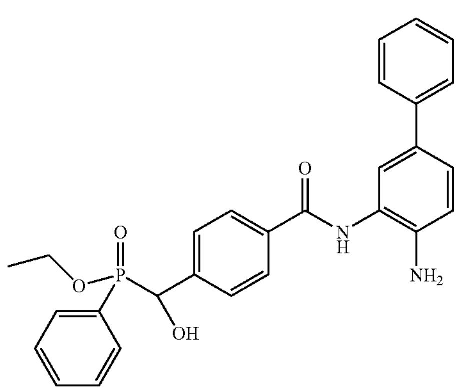 | {[4-(4-Amino-biphenyl-3-ylcarbamoyl)-phenyl]-hydroxy-methyl}-phenyl-phosphinic acid ethyl ester | cal'd 487 (MH+), exp 487 (MH+) | TFA Salt |

Procedures for H. Preparation of Alkyl Phosphine Oxides.

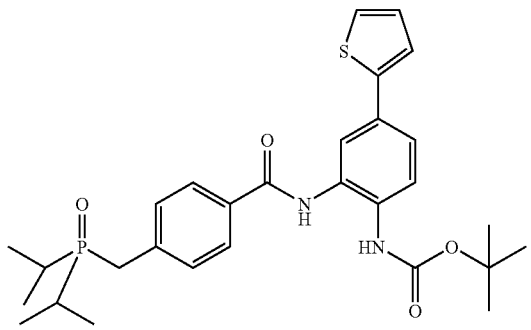

{2-[4-(Diisopropyl-phosphinoylmethyl)-benzoylamino]-4-thiophen-2-yl-phenyl}-carbamic acid tert-butyl ester. To a solution of Hunig's Base (1.451 mL, 8.31 mmol) and MeOH (0.332 mL, 8.21 mmol) in toluene (5 mL) at 0° C. was added diisopropyl chlorophosphine (0.653 mL, 4.10 mmol) in toluene (2 mL) dropwise. The solution was allowed to warm to RT and stirred for 1 h. The slurry was then filtered to remove the salt. To the filtrate was added [2-(4-bromomethyl-benzoylamino)-4-thiophen-2-yl-phenyl]carbamic acid tert-butyl ester (500 mg, 1.026 mmol) and the mixture was stirred at 100° C. for 2 h and then cooled to RT. Once at RT a precipitate formed, which was filtered off and washed with DCM yielding the desired product.

$^1$H NMR (CDCl$_3$, 600 MHz) δ 9.86 (s, 1H), 8.73 (br s, 1H), 7.88 (d, J=8.2 Hz, 2H), 7.79 (d, J=2.0 Hz, 1H), 7.57 (d, J=8.5 Hz, 1H), 7.51-7.46 (m, 4H), 7.43 (dd, J=3.5, 1.2 Hz, 1H), 7.10 (dd, J=5.3, 3.8 Hz, 1H), 3.22 (d, J=12.3 Hz, 2H), 1.93 (m, 2H), 1.08-0.98 (m, 6H). MS: cal'd 541 (MH+), exp 541 (MH+).

Additional analogs were prepared in procedures similar to those described for the preparations of the above examples.

TABLE 9

H; Alkyl Phosphine Oxides

| Cpd # | Structure | Name | MS | Salt Forms |
|---|---|---|---|---|
| 1 | 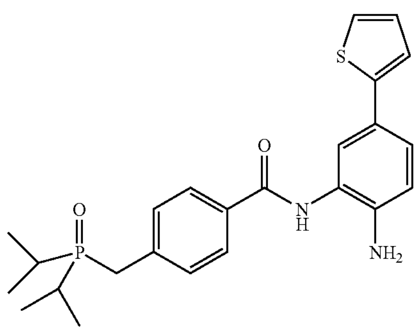 | N-(2-Amino-5-thiophen-2-yl-phenyl)-4-(diisopropyl-phosphinoylmethyl)-benzamide | cal'd 441 (MH+), exp 441 | Free base |
| 2 | 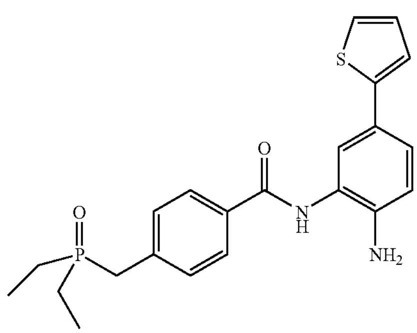 | N-(2-Amino-5-thiophen-2-yl-phenyl)-4-(diethyl-phosphinoylmethyl)-benzamide | cal'd 413 (MH+), exp 413 | Free base |
| 3 | 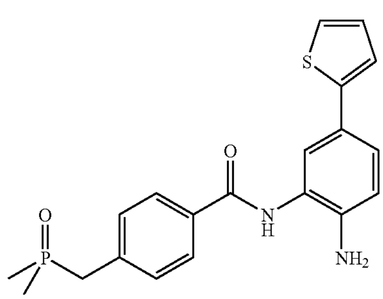 | N-(2-Amino-5-thiophen-2-yl-phenyl)-4-(dimethyl-phosphinoylmethyl)-benzamide | cal'd 385 (MH+), exp 385 | Free base |

TABLE 9-continued

H: Alkyl Phosphine Oxides

| Cpd # | Structure | Name | MS | Salt Forms |
|---|---|---|---|---|
| 4 | 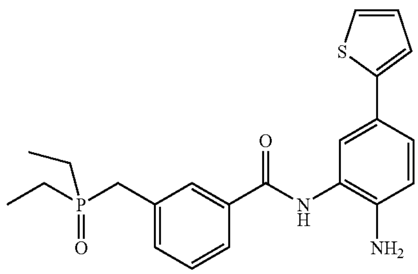 | N-[2-Amino-2-(2-thienyl)phenyl]-3-[(diethylphosphoryl)methyl]benzamide | cal'd 413 (MH+), exp 413 | Free base |
| 5 | 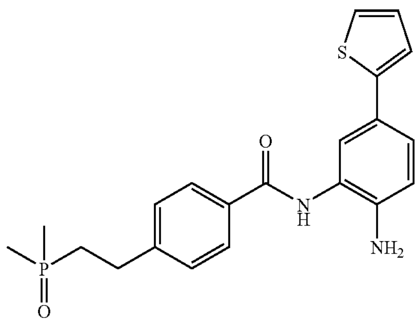 | N-[2-Amino-2-(2-thienyl)phenyl]-4-[2-(dimethylphosphoryl)ethyl]benzamide | cal'd 399 (MH+), exp 399 | Free base |
| 6 | 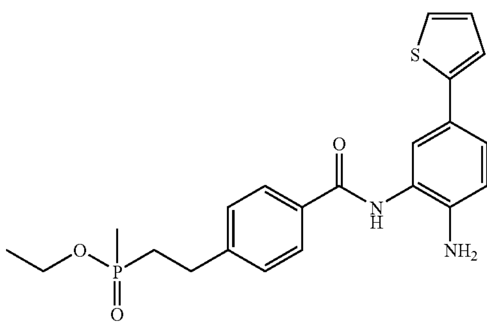 | Ethyl-{2-[4-({[2-amino-5-(2-thienyl)phenyl]amino}carbonyl)phenyl]ethyl}methyl phosphinate | cal'd 429 (MH+), exp 429 | Free base |

Procedures for I. Preparation of N-arylaminopyrazoles

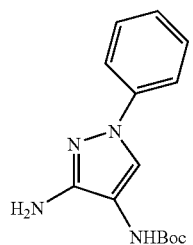

tert-butyl
(3-amino-1-phenyl-1H-pyrazol-4-yl)carbamate

Step A: Copper Coupling

A solution of methyl 4-nitro-1H-pyrazole-3-carboxylate (54.0 g, 315.6 mmol), phenylboronic acid (77.0 g, 631.2 mmol), copper(II) acetate (86.0 g, 473.4 mmol) and pyridine (49.9 g, 631.2 mmol) in methylene chloride (600 mL) was stirred at ambient temperature open to air for 48 hours. The reaction was evaporated in vacuo, diluted with 1000 mL methylene chloride and filtered through a large plug of silica (washing with 2 liters methylene chloride). The solvent was evaporated in vacuo. $^1$H NMR (CDCl$_3$) δ 8.61 (s, 1H), 7.73 (m, 2H), 7.50 (m, 3H), 4.02 (s, 3H).

Step B: Saponification

A solution of methyl 4-nitro-1-phenyl-1H-pyrazole-3-carboxylate (78.1 g, 315.9 mmol) in THF (600 mL) was treated with 4M potassium hydroxide (79 mL, 316 mmol) dropwise and the solution was stirred at ambient temperature for 16 hours. The reaction was evaporated in vacuo and acidified with 6M HCl. After addition of water (500 mL) the solids were filtered off and dried to give 72.1 g (97%, 2 steps) of desired compound as a grayish solid. $^1$H NMR (CD$_3$OD) δ 9.37 (bs, 1H), 7.88 (m, 2H), 7.59 (m, 2H), 7.44 (m, 1H).

Step C: Curtius

A solution of 4-nitro-1-phenyl-1H-pyrazole-3-carboxylic acid (20.0 g, 85.8 mmol), triethylamine (36.0 mL, 257.3 mmol), and diphenylphosphoryl azide (37.8 g, 137.2 mmol) in dioxane (400 mL) and tert-butanol (200 mL) was heated to reflux for 16 hours. The reaction was evaporated to dryness in vacuo, diluted with methylene chloride (400 mL) and treated with trifluoroacetic acid (128 g, 857.7 mmol). The solution was stirred at ambient temperature for 16 hours. The reaction was evaporated in vacuo and the resulting oil diluted with hexanes (750 mL), ethyl acetate (150 mL) and methylene chloride (100 mL). The solids were filtered, washed with above solvent system (hexanes:ethyl acetate; methylene chloride 75:15:10), and dried to give 12.0 g of desired product as yellow solid. $^1$H NMR (CDCl$_3$) δ 8.43 (s, 1H), 7.62 (m, 2H), 7.48 (m, 2H), 7.37 (m, 1H).

Step D: Hydrogenation/Boc Protection

A solution of 4-nitro-1-phenyl-1H-pyrazol-3-amine (0.15 g, 0.74 mmol), di-tertbutyl dicarbonate (0.16 g, 0.74 mmol), triethylamine (0.19 g, 1.84 mmol) in methanol 20 mL was degassed with nitrogen and treated with platinum oxide (17 mg, 10 mol %). The solution was placed under a hydrogen atmosphere and stirred at ambient temperature for 2 hours. The reaction was then degassed with nitrogen, filtered through celite, washed with methanol and evaporated in vacuo. Flash chromatography (20-35% ethyl acetate/hexanes) gave 0.109 g (54%) of title compound as a purplish solid. $^1$H NMR (CDCl$_3$) δ 7.85 (s, 1H), 7.51 (m, 2H), 7.37 (m, 2H), 7.18 (m, 1H), 6.40 (bs, 1H).

Procedures for J. Preparation of Spirocyclic Phosphonates

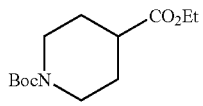

1-tert-Butyl 4-ethyl piperidine-1,4-dicarboxylate. To a solution of ethyl isonipecotate (8.00 g, 50.9 mmol), Et$_3$N (6.18 g, 61.1 mmol), and DMAP (622 mg, 5.09 mmol) in CH$_2$Cl$_2$ (100 mL) at 0° C. was added Boc$_2$O (16.66 g, 76.3 mmol). The reaction was stirred and allowed to warm to room temperature over 90 min. The solution was diluted with additional CH$_2$Cl$_2$, washed with saturated NaHCO$_3$ and brine, dried (MgSO$_4$), and evaporated. The residue was purified by flash chromatography (0-25% EtOAc/hexanes) to give 1-tert-butyl 4-ethyl piperidine-1,4-dicarboxylate as a colorless oil. $^1$H NMR (CDCl$_3$, 600 MHz) δ 4.12 (q, J=7.2 Hz, 2H), 4.08-3.88 (m, 2H), 2.88-2.73 (m, 2H), 2.41 (tt, J=10.9, 3.9 Hz, 1H), 1.89-1.81 (m, 2H), 1.64-1.56 (m, 2H), 1.43 (s, 9H), 1.23 (t, J=7.2 Hz, 3H).

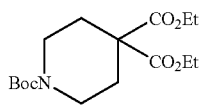

1-tert-Butyl 4,4-diethyl piperidine-1,4,4-tricarboxylate. To a solution of $^i$Pr$_2$NH (4.72 g, 46.6 mmol) at −20° C. in THF (70 mL) was added n-butyllithium (13.99 mL, 35.0 mml, 2.5 M in hexanes). After 15 minutes at −20° C., the solution was cooled to −78° C., and 1-tert-butyl 4-ethyl piperidine-1,4-dicarboxylate (6.00 g, 23.3 mmol) was added. After stirring at −78° C. for 1 h, ethyl chloroformate (7.59 g, 70.0 mmol) was added dropwise. The reaction was then allowed to warm to room temperature over 4 h. The solution was diluted with 1 N HCl and extracted with EtOAc (2×). The combined organic extracts were washed with brine, dried (MgSO$_4$), and evaporated. Flash chromatography of the crude (0-25% EtOAc/hexanes) yielded the desired product as a yellow oil. $^1$H NMR (CDCl$_3$, 600 MHz) δ 4.18 (q, J=7.1 Hz, 4H), 3.43-3.38 (m, 4H), 2.05-2.00 (m, 4H), 1.42 (s, 9H), 1.23 (t, J=7.0 Hz, 6H). MS: cal'd 352 (MNa+), exp 352 (MNa+).

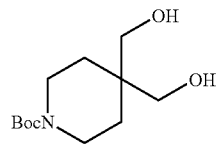

tert-Butyl 4,4-bis(hydroxymethyl)piperidine-1-carboxylate. To a solution of 1-tert-butyl 4,4-diethyl piperidine-1,4,4-tricarboxylate (2.00 g, 6.07 mmol) in 1:1 THF:toluene (50 mL) was added LiBH$_4$ (15.18 mL, 30.4 mmol, 2.0 M in THF). The reaction was stirred at 60° C. for 18 h. It was then quenched with saturated NH$_4$Cl and extracted with EtOAc (2×). The combined organic layers were washed with brine, dried (MgSO$_4$), and evaporated. The residue was purified by flash chromatography (15-100% EtOAc/hexanes) to give tert-butyl 4,4-bis(hydroxymethyl)piperidine-1-carboxylate as a colorless solid. $^1$H NMR (CDCl$_3$, 600 MHz) δ 3.66 (d, J=5.0 Hz, 4H), 3.41-3.37 (m, 4H), 2.29 (t, J=5.1 Hz, 2H), 1.47-1.45 (m, 4H), 1.45 (s, 9H). MS: cal'd 268 (MNa+), exp 268 (MNa+).

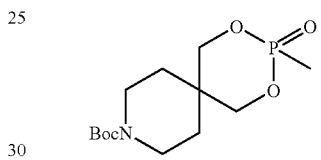

tert-Butyl 3-methyl-2,4-dioxa-9-aza-3-phosphaspiro[5.5]undecane-9-carboxylate 3-oxide. Et$_3$N (943 µL, 6.76 mmol) and tert-butyl 4,4-bis(hydroxymethyl)piperidine-1-carboxylate (790 mg, 3.22 mmol) were combined in CH$_2$Cl$_2$ (25 mL) and cooled to 0° C. A solution of methylphosphonic dichloride (428 mg, 3.22 mmol) in CH$_2$Cl$_2$ (20 mL) was added dropwise over 1 h. The reaction was then allowed to warm to room temperature over 1 h. It was subsequently diluted with saturated NaHCO$_3$ and extracted with CH$_2$Cl$_2$ (2×). The combined organic layers were washed with brine, dried (MgSO$_4$), and evaporated to give the desired product as a colorless solid that was used without purification. MS: cal'd 306 (MH+), exp 306 (MH+).

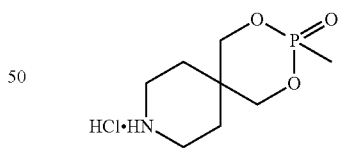

3-Methyl-2,4-dioxa-9-aza-3-phosphaspiro[5.5]undecane 3-oxide hydrochloride. tert-Butyl 3-methyl-2,4-dioxa-9-aza-3-phosphaspiro[5.5]undecane-9-carboxylate 3-oxide (975 mg, 3.19 mmol) was combined with 4.0 M HCl in dioxane (25 mL) and stirred at room temperature for 1 h. The resulting suspension was evaporated to a white solid that was slurried in EtOAc and filtered to give 3-methyl-2,4-dioxa-9-aza-3-phosphaspiro[5.5]undecane 3-oxide hydrochloride as a colorless solid. $^1$H NMR (DMSO-d$_6$, 600 MHz) δ 8.99 (bs, 2H), 4.21-4.11 (m, 4H), 3.12-3.07 (m, 2H), 3.04-2.99 (m, 2H), 1.82-1.78 (m, 2H), 1.59-1.56 (m, 2H), 1.55 (d, J=17.0 Hz, 3H).

MS: cal'd 206 (MH+), exp 206 (MH+).

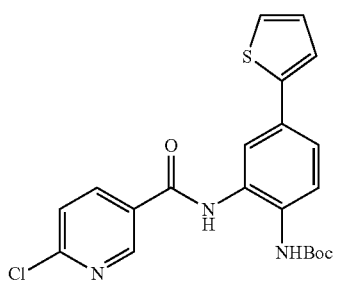

tert-Butyl [2-{[(6-chloropyridin-3-yl)carbonyl]amino}-4-(2-thienyl)phenyl]-carbamate. A mixture of tert-butyl [2-amino-4-(2-thienyl)phenyl]carbamate (600 mg, 2.07 mmol) and 6-chloronicotinyl chloride (380 mg, 2.16 mmol) in 5 mL of pyridine was stirred overnight, poured into EtOAc and washed with saturated NaHCO$_3$, dried (Na$_2$SO$_4$) and concentrated giving the BOC-protected chloronicotinamide. $^1$H NMR (600 MHz, CD$_3$OD): δ 8.95 (d, J=2.3 Hz, 1H), 8.35 (dd, J=8.2 Hz, 2.3 Hz, 1H), 7.85 (br s, 1H), 7.62 (d, J=8.5 Hz, 1H), 7.55-7.51 (m, 2H), 7.37-7.35 (m, 2H), 7.07 (dd, J=5.0 Hz, 3.5 Hz, 1H), 4.59 (s, 1H), 1.49 (s, 9H). MS: cal'd 452 (MNa+), exp 452 (MNa+).

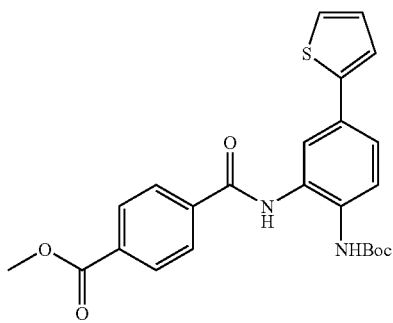

Methyl 4-({[2-[(tert-butoxycarbonyl)amino]-5-(2-thienyl)phenyl]amino}carbonyl)benzoate. Methyl 4-(chlorocarbonyl)benzoate (1.40 g, 7.07 mmol) and tert-butyl [2-amino-4-(2-thienyl)phenyl]carbamate (2.05 g, 7.07 mmol) were combined in pyridine (10 mL) and stirred at room temperature for 18 h. The reaction mixture was poured into 3:1 CHCl$_3$:MeOH, washed with 2 N HCl and 2 N NaOH, dried (Na$_2$SO$_4$), and evaporated to give the desired product as a colorless solid. MS: cal'd 475 (MNa+), exp 475 (MNa+).

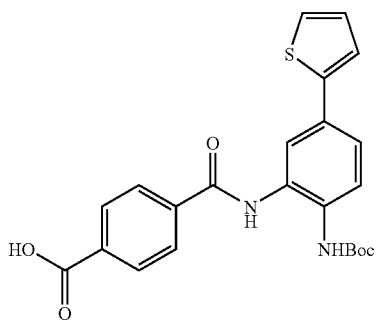

4-({[2-[(tert-Butoxycarbonyl)amino]-5-(2-thienyl)phenyl]amino}carbonyl)benzoic acid. To a solution of methyl 4-({[2-[(tert-butoxycarbonyl)amino]-5-(2-thienyl)phenyl]amino}carbonyl)benzoate (3.20 g, 7.07 mmol) in 1:1:2 H$_2$O:MeOH:THF (80 mL) was added LiOH (1.20 g, 50.1 mmol). The reaction was stirred at room temperature for 18 h, diluted with EtOAc, washed with 2 N HCl, dried (Na$_2$SO$_4$), and evaporated to give the desired product as a red solid. MS: cal'd 461 (MNa+), exp 461 (MNa+).

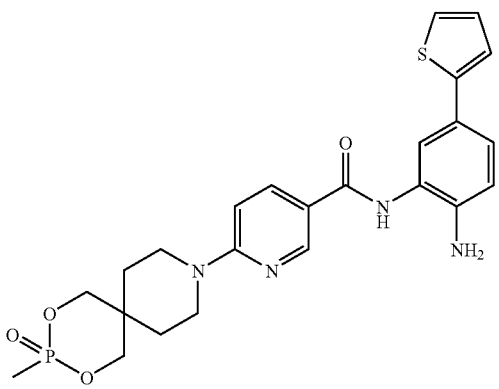

N-[2-Amino-5-(2-thienyl)phenyl]-6-(3-methyl-3-oxido-2,4-dioxa-9-aza-3-phosphaspiro[5.5]undec-9-yl)nicotinamide. tert-Butyl [2-{[(6-chloropyridin-3-yl)carbonyl]amino}-4-(2-thienyl)phenyl]-carbamate (150 mg, 0.35 mmol), 3-methyl-2,4-dioxa-9-aza-3-phosphaspiro[5.5]undecane 3-oxide hydrochloride (169 mg, 0.70 mmol), and DIEA (183 μL, 1.05 mmol) were combined in DMSO (4 mL) and stirred at 90° C. for 24 h. The mixture was directly purified by reverse phase HPLC (35-90% MeCN/water w/0.025% TFA) to afford the desired product as a yellow solid. The solid was dissolved in a mixture of CH$_2$Cl$_2$ (4 mL) and TFA (1 mL) and stirred at room temperature for 2 h. The solution was diluted with 1,2-DCE and evaporated. The resulting residue was purified by reverse phase HPLC (10-70% MeCN/water w/0.025% TFA). Fractions containing the product were diluted with saturated NaHCO$_3$ and extracted with EtOAc (3×). The combined organic layers were washed with brine, dried (MgSO$_4$), and evaporated to give the desired product as a colorless solid. $^1$H NMR (DMSO-d$_6$, 600 MHz) δ 9.48 (d, J=3.3, 1H), 8.72 (t, J=2.7 Hz, 1H), 8.08-8.05 (m, 1H), 7.43 (d, J=2.3 Hz, 1H), 7.33 (dd, J=4.9, 0.9 Hz, 1H), 7.26 (dt, J=8.4, 1.7 Hz, 1H), 7.22 (dd, J=3.6, 1.2 Hz, 1H), 7.02 (dd, J=5.0, 3.6 Hz, 1H), 6.78 (d, J=8.4 Hz, 1H), 6.51 (dd, J=8.9, 6.0 Hz, 1H), 5.10 (s, 2H), 4.15-3.97 (m, 3H), 3.93-3.82 (m, 1H), 3.62-3.50 (m, 3H), 3.36-3.28 (m, 1H), 2.06-1.98 (m, 1H), 1.93-1.80 (m, 3H), 1.50 (d, J=17.4 Hz, 1.5H), 1.49 (d, J=17.4 Hz, 1.5H). MS: cal'd 499 (MH+), exp 499 (MH+).

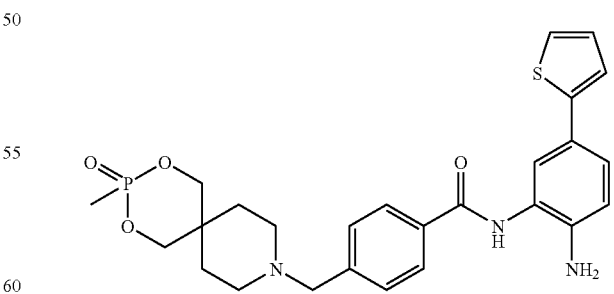

N-[2-Amino-5-(2-thienyl)phenyl]-4-[(3-methyl-3-oxido-2,4-dioxa-9-aza-3-phosphaspiro[5.5]undec-9-yl)methyl]benzamide. [2-(4-Bromomethyl-benzoylamino)-4-thiophen-2-yl-phenyl]-carbamic acid tert-butyl ester (150 mg, 0.31 mmol), 3-methyl-2,4-dioxa-9-aza-3-phosphaspiro[5.5]undecane 3-oxide hydrochloride (89 mg, 0.37 mmol), and DIEA (107 μL, 0.62 mmol) were combined in DMF (4 mL) and stirred at room temperature for 18 h. The solution was diluted with saturated NaHCO₃ and extracted with EtOAc (2×). The combined organic layers were washed with brine, dried (MgSO₄), and evaporated. Flash chromatography of the crude (0-10% MeOH/CH₂Cl₂) afforded the desired product as a colorless solid. The solid was dissolved in a mixture of CH₂Cl₂ (4 mL) and TFA (1 mL) and stirred at room temperature for 2 h. The solution was diluted with 1,2-DCE and evaporated. The crude was taken up in EtOAc, washed with saturated NaHCO₃ and brine, dried (MgSO₄), and evaporated. The residue was triturated with EtOAc and filtered to afford the desired product as a colorless solid ¹H NMR (DMSO-d₆, 600 MHz) δ 9.69 (s, 1H), 7.94 (d, J=7.6 Hz, 2H), 7.44 (s, 1H), 7.41 (d, J=7.8 Hz, 2H), 7.33 (d, J=5.2 Hz, 1H), 7.27 (d, J=8.0 Hz, 1H), 7.22 (d, J=3.5 Hz, 1H), 7.02 (t, J=4.2 Hz, 1H), 6.79 (d, J=8.2 Hz, 1H), 5.13 (s, 2H), 4.16-4.04 (m, 4H), 3.54 (s, 2H), 2.43-2.37 (m, 2H), 2.34-2.28 (m, 2H), 1.68-1.62 (m, 2H), 1.52 (d, J=17.0 Hz, 3H), 1.42-1.38 (m, 2H). MS: cal'd 512 (MH+), exp 512 (MH+).

N-[2-Amino-5-(2-thienyl)phenyl]-4-[(3-methyl-3-oxido-2,4-dioxa-9-aza-3-phosphaspiro[5.5]undec-9-yl)carbonyl]benzamide. 4-({[2-[(tert-Butoxycarbonyl)amino]-5-(2-thienyl)phenyl]amino}carbonyl)-benzoic acid (150 mg, 0.34 mmol), 3-methyl-2,4-dioxa-9-aza-3-phosphaspiro[5.5]undecane 3-oxide hydrochloride (99 mg, 0.41 mmol), EDC (131 mg, 0.68 mmol), HOBT (105 mg, 0.68 mmol), and DIEA (119 μL, 0.68 mmol) were combined in DMF (4 mL) and stirred at room temperature for 18 h. The solution was diluted with saturated NaHCO₃ and extracted with EtOAc (2×). The combined organic extracts were washed with brine, dried (MgSO₄), and evaporated. Purification of the crude by flash chromatography (0-10% MeOH/CH₂Cl₂) afforded the desired product as a yellow solid. The solid was dissolved in a mixture of CH₂Cl₂ (4 mL) and TFA (1 mL) and stirred at room temperature for 2 h. The solution was diluted with 1,2-DCE and evaporated. The crude was taken up in EtOAc, washed with saturated NaHCO₃ and brine, dried (MgSO₄), and evaporated. The residue was dissolved in a minimum amount of MeOH, diluted with EtOAc, concentrated to approximately half-volume, and filtered to isolate the desired product as a colorless solid. ¹H NMR (DMSO-d₆, 600 MHz) δ 9.80 (s, 1H), 8.04 (d, J=7.3 Hz, 2H), 7.50 (d, J=6.4 Hz, 2H), 7.45 (s, 1H), 7.33 (d, J=4.9 Hz, 1H), 7.28 (d, J=8.1 Hz, 1H), 7.22 (bs, 1H), 7.03 (t, J=3.9 Hz, 1H), 6.79 (d, J=8.3 Hz, 1H), 5.17 (s, 2H), 4.29-4.09 (m, 4H), 3.72-3.56 (m, 2H), 3.39-3.23 (m, 2H), 1.77-1.60 (m, 2H), 1.58-1.51 (m, 3H), 1.51-1.36 (m, 2H). MS: cal'd 526 (MH+), exp 526 (MH+).

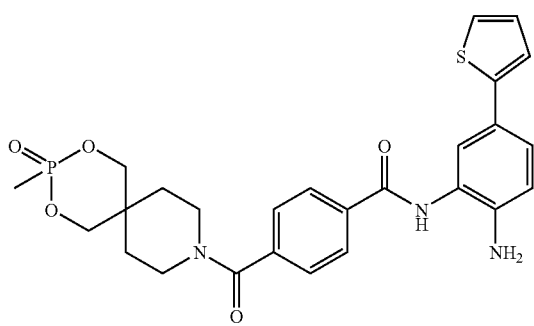

Additional analogs were prepared in procedures similar to those described for the preparations of the above examples.

TABLE 11

| | J; Spirocyclic Phosphonates | | | |
|---|---|---|---|---|
| Cpd # | Structure | Name | MS | Salt Forms |
| 1 | | N-[2-Amino-5-(2-thienyl)phenyl]-4-[(3-methyl-3-oxido-2,4-dioxa-9-aza-3-phosphaspiro[5.5]undec-9-yl)methyl]benzamide | cal'd 512 (MH+), exp 512 | Free base |
| 2 | | N-[2-Amino-5-(2-thienyl)phenyl]-4-[(3-methyl-3-oxido-2,4-dioxa-9-aza-3-phosphaspiro[5.5]undec-9-yl)carbonyl]benzamide | cal'd 526 (MH+), exp 526 | Free base |

TABLE 11-continued

J: Spirocyclic Phosphonates

| Cpd # | Structure | Name | MS | Salt Forms |
|---|---|---|---|---|
| 3 | 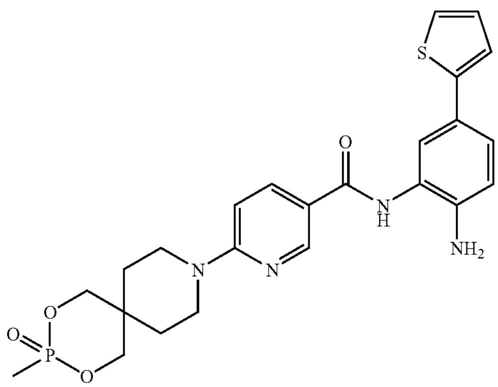 | N-[2-Amino-5-(2-thienyl)phenyl]-6-(3-methyl-3-oxido-2,4-dioxa-9-aza-3-phosphaspiro[5.5]undec-9-yl)nicotinamide | cal'd 499 (MH+), exp 499 | Free base |
| 4 | 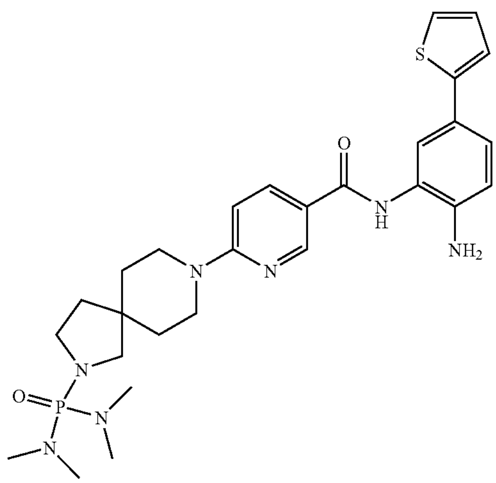 | N-[2-Amino-5-(2-thienyl)phenyl]-6-{2-[bis(dimethylamino)phosphoryl]-2,8-diazaspiro[4.5]dec-8-yl}nicotinamide | cal'd 568 (MH+), exp 568 | TFA Salt |

Procedures for K. Preparation of β-Aminophosphine Oxides

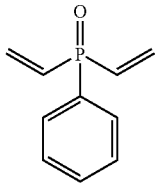

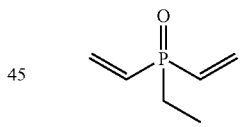

Phenyl(divinyl)phosphine oxide. Phenylphosphonic dichloride (2.00 g, 10.26 mmol) was taken up in 1:1 THF:Et₂O (100 mL) and cooled to −78° C. Vinylmagnesium bromide (21.54 mL, 21.54 mmol, 1.0 M in THF) was added dropwise. After stirring for 2 h at −78° C., the cold reaction was poured into 2 N HCl, and the mixture was extracted with EtOAc (2×). The combined organic extracts were washed with brine, dried (MgSO₄), and evaporated to a yellow oil. Flash chromatography (0-10% MeOH/EtOAc) afforded phenyl(divinyl)phosphine oxide as a colorless solid. $^1$H NMR (CDCl₃, 600 MHz) δ 7.72-7.67 (m, 2H), 7.54-7.50 (m, 1H), 7.49-7.45 (m, 2H), 6.44 (ddd, J=24.5, 18.7, 12.4 Hz, 2H), 6.29-6.18 (m, 4H). MS: cal'd 179 (MH+), exp 179 (MH+).

Ethyl(divinyl)phosphine oxide. A solution of ethyldichlorophosphine (1.00 g, 7.64 mmol) in THF (30 mL) was cooled to −78° C. Vinylmagnesium bromide (16.04 mL, 16.04 mmol, 1.0 M in THF) was added dropwise. The reaction was allowed to warm to room temperature and stirred for 2 h. It was then quenched with saturated NH₄Cl and extracted with CH₂Cl₂ (2×). The combined organic extracts were dried (MgSO₄) and gently concentrated to half-volume. This solution was combined with 30% H₂O₂ (30.00 mL, 343 mmol) and vigorously stirred at room temperature for 60 h. The mixture was extracted with CH₂Cl₂ (2×), dried (MgSO₄), and evaporated. Flash chromatography of the crude (0-10% MeOH/EtOAc) afforded ethyl(divinyl)phosphine oxide as a colorless solid. $^1$H NMR (CDCl₃, 600 MHz) δ 6.29-6.11 (m, 6H), 1.77 (dq, J=12.5, 7.6 Hz, 2H), 1.13 (dt, J=17.7, 7.6 Hz, 3H).

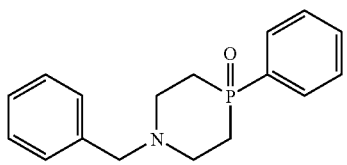

1-Benzyl-4-phenyl-1,4-azaphosphinane 4-oxide. Phenyl (divinyl)phosphine oxide (1.47 g, 8.25 mmol) and benzylamine (901 µL, 8.25 mmol) were combined in water (20 mL) and stirred at 90° C. for 1 h. A second portion of benzylamine (901 mL, 8.25 mmol) was added, and the reaction was stirred at 90° C. for an additional 1 h. The solution was cooled and extracted with EtOAc (2×). The combined organic extracts were washed with brine, dried (MgSO$_4$), and evaporated. The crude residue was purified by flash chromatography (0-10% MeOH/CH$_2$Cl$_2$) to afford the desired product as a colorless solid. $^1$H NMR (CDCl$_3$, 600 MHz) δ 7.79-7.73 (m, 2H), 7.55-7.46 (m, 3H), 7.35-7.30 (m, 4H), 7.27-7.23 (m, 1H), 3.63 (m, 2H), 3.04-2.89 (m, 4H), 2.21-2.14 (m, 2H), 2.08-1.99 (m, 2H). MS: cal'd 286 (MH+), exp 286 (MH+).

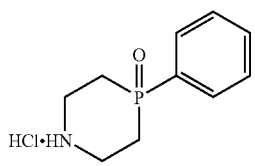

4-Phenyl-1,4-azaphosphinane 4-oxide hydrochloride. A mixture of 1-benzyl-4-phenyl-1,4-azaphosphinane 4-oxide (1.18 g, 4.14 mmol), 20% Pd(OH)$_2$/C (290 mg, 0.41 mmol), and concentrated HCl (0.75 mL) in MeOH (75 mL) was hydrogenated at 45 psi for 18 h. The mixture was filtered through Celite and evaporated. The solid residue was slurried in EtOAc and filtered to give the title compound as an off-white solid. $^1$H NMR (DMSO-d$_6$, 600 MHz) δ 9.87 (bs, 1H), 9.28 (bs, 1H), 7.86-7.79 (m, 2H), 7.66-7.61 (m, 1H), 7.60-7.56 (m, 2H), 3.52-3.34 (m, 4H), 2.75-2.65 (m, 2H), 2.24-2.13 (m, 2H). MS: cal'd 196 (MH+), exp 196 (MH+).

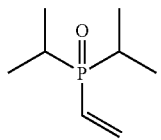

Diisopropyl(vinyl)phosphine oxide. Chlorodiisopropylphosphine (6.00 g, 39.3 mmol) was dissolved in THF (150 mL) and cooled to −78° C. Vinylmagnesium bromide (1 M in THF, 43.2 mL, 43.2 mmol) was added dropwise. The dry ice bath was then removed, and the reaction was allowed to warm to room temperature. After 2 h at room temperature, the reaction was quenched with saturated NH$_4$Cl, and 30% H$_2$O$_2$ (75 mL) was added. The mixture was vigorously stirred at room temperature for 2 h. It was then extracted with CH$_2$Cl$_2$ (2×), dried (MgSO$_4$), and evaporated. Flash chromatography (0-10% MeOH/EtOAc) afforded diisopropyl(vinyl) phosphine oxide as a colorless oil. $^1$H NMR (CDCl$_3$, 600 MHz) δ 6.31 (td, J=18.6, 2.2 Hz, 1H), 6.24 (ddd, J=34.8, 12.8, 2.3 Hz, 1H), 6.03 (ddd, J=27.3, 18.7, 12.8 Hz, 1H), 2.01-1.92 (m, 2H), 1.15 (dd, J=15.0, 7.0 Hz, 6H), 1.06 (dd, J=15.9, 7.4 Hz, 6H). MS: cal'd 161 (MH+), exp 161 (MH+).

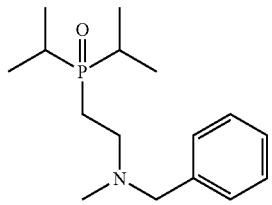

N-Benzyl-2-(diisopropylphosphoryl)-N-methylethanamine. Diisopropyl(vinyl)phosphine oxide (1.00 g, 6.24 mmol) was combined with N-methylbenzylamine (1.61 mL, 12.48 mmol) in a microwave vial and heated at 200° C. for 4 h total (reaction progress checked after 2 h). The crude mixture was directly purified by flash chromatography (0-10% MeOH/CH$_2$Cl$_2$). Coelution of the product with minor impurities required a second column (0-10% MeOH (w/2 N NH$_3$)/CH$_2$Cl$_2$) to give clean product as a yellow oil. $^1$H NMR (CDCl$_3$, 600 MHz) δ 7.30-7.20 (m, 5H), 3.50 (s, 2H), 2.76-2.70 (m, 2H), 2.20 (s, 3H), 2.00-1.92 (m, 2H), 1.90-1.84 (m, 2H), 1.17 (dd, J=14.6, 7.2 Hz, 6H), 1.12 (dd, J=15.1, 7.1 Hz, 6H). MS: cal'd 282 (MH+), exp 282 (MH+).

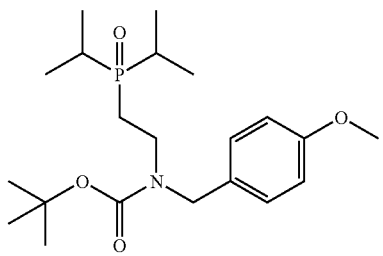

tert-Butyl [2-(diisopropylphosphoryl)ethyl](4-methoxybenzyl)carbamate. To a suspension of NaH (60%, 157 mg, 3.93 mmol) in THF (5 mL) at 0° C. was added tert-butyl (4-methoxybenzyl)carbamate (889 mg, 3.75 mmol) in THF (5 mL). After stirring for 30 minutes at 0° C., diisopropyl (vinyl)phosphine oxide (300 mg, 1.873 mmol) in THF (3 mL) was added. The reaction was allowed to slowly warm to room temperature and subsequently heated to 60° C. for 3 h. The mixture was quenched with saturated NH$_4$Cl and extracted with EtOAc (2×). The combined organic layers were washed with brine, dried (MgSO$_4$), and evaporated. Flash chromatography (0-10% MeOH/EtOAc) afforded the title compound as a pale yellow oil. MS: cal'd 398 (MH+), exp 398 (MH+).

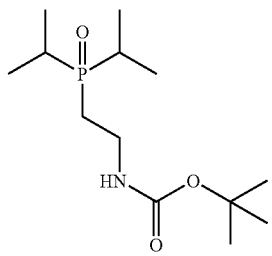

tert-Butyl [2-(diisopropylphosphoryl)ethyl]carbamate. A solution of tert-butyl [2-(diisopropylphosphoryl)ethyl](4- methoxybenzyl)carbamate (1.06 g, 2.68 mmol) in MeCN (20 mL) was cooled to 0° C. CAN (4.40 g, 8.03 mmol) in water (10 mL) was added dropwise via addition funnel over 15 minutes, and the reaction was subsequently stirred at 0° C. for an additional 1 h. The solution was then diluted with water and extracted with EtOAc (4×). The combined organic layers were washed with 10% Na$_2$SO$_3$ (2×). The sodium sulfite layers were then back-extracted with additional EtOAc (2×). All of the organic extracts were combined, dried (MgSO$_4$), and evaporated. Flash chromatography (0-10% MeOH/CH$_2$Cl$_2$) afforded tert-butyl [2-(diisopropylphosphoryl)ethyl]carbamate as a colorless solid. $^1$H NMR (CDCl$_3$, 600 MHz) δ 5.59 (bs, 1H), 3.50-3.42 (dt, J=13.0, 6.5 Hz, 2H), 2.01-1.92 (m, 2H), 1.88-1.83 (m, 2H), 1.39 (s, 9H), 1.18 (dd, J=14.9, 7.2 Hz, 6H), 1.14 (dd, J=15.3, 7.2 Hz, 6H). MS: cal'd 278 (MH+), exp 278 (MH+).

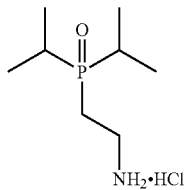

2-(diisopropylphosphoryl)ethanaminehydrochloride. tert-Butyl [2-(diisopropylphosphoryl)ethyl]carbamate (585 mg, 2.11 mmol) was combined with 4.0 M HCl in 1,4-dioxane (10.0 mL, 40.0 mmol) and stirred at room temperature for 30 minutes. The solution was evaporated to dryness to afford 2-(diisopropylphosphoryl)ethanamine hydrochloride as a colorless solid. $^1$H NMR (DMSO-d$_6$, 600 MHz) δ 8.23 (bs, 3H), 2.99-2.90 (m, 2H), 2.08-1.93 (m, 4H), 1.05 (dd, J=14.7, 7.2 Hz, 6H), 1.03 (dd, J=15.2, 7.0 Hz, 6H). MS: cal'd 178 (MH+), exp 178 (MH+).

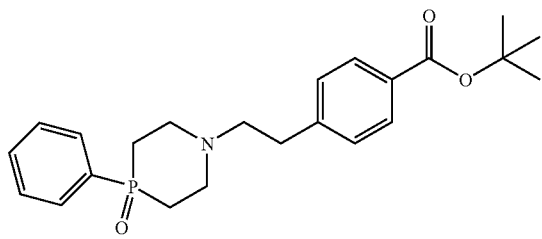

tert-Butyl 4-[2-(4-oxido-4-phenyl-1,4-azaphosphinan-1-yl)ethyl]benzoate. 4-Phenyl-1,4-azaphosphinane 4-oxide hydrochloride (200 mg, 0.863 mmol), tert-butyl 4-(2-bromoethyl)benzoate (246 mg, 0.863 mmol), and K$_2$CO$_3$ (358 mg, 2.59 mmol) were combined in MeCN (10 mL) and stirred at reflux overnight. The reaction was cooled, diluted with EtOAc, washed with water and brine, dried (MgSO$_4$), and evaporated. Flash chromatography (0-10% MeOH/CH$_2$Cl$_2$) afforded the title compound as a colorless solid. $^1$H NMR (CDCl$_3$, 600 MHz) δ 7.88 (d, J=8.4 Hz, 2H), 7.76-7.71 (m, 2H), 7.54-7.45 (m, 3H), 7.21 (d, J=8.2 Hz, 2H), 3.09-2.99 (m, 4H), 2.85-2.80 (m, 2H), 2.77-2.73 (m, 2H), 2.19-2.11 (m, 2H), 2.08-1.98 (m, 2H), 1.55 (s, 9H). MS: cal'd 400 (MH+), exp 400 (MH+).

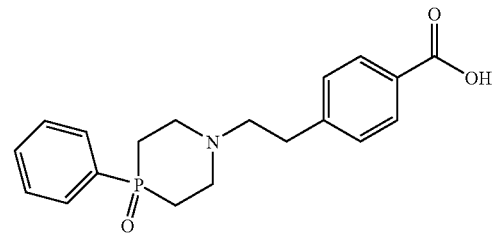

4-[2-(4-Oxido-4-phenyl-1,4-azaphosphinan-1-yl)ethyl]benzoicacid. tert-Butyl 4-[2-(4-oxido-4-phenyl-1,4-azaphosphinan-1-yl)ethyl]benzoate (215 mg, 0.538 mmol) was taken up in 4.0 M HCl in 1,4-dioxane (8.0 mL, 32.0 mmol) and stirred at room temperature overnight. The white slurry was concentrated to dryness, resuspended in MeOH, and concentrated again to afford the title compound as a colorless solid. MS: cal'd 344 (MH+), exp 344 (MH+).

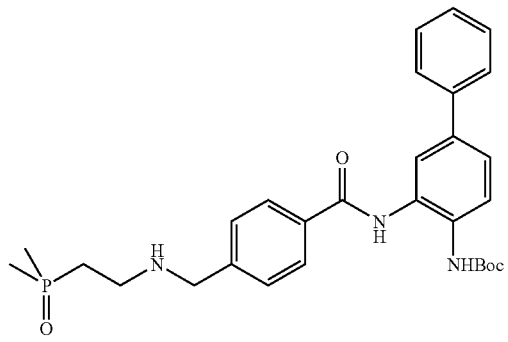

tert-Butyl(3-{[4-({[2-(dimethylphosphoryl)ethyl]amino}methyl)benzoyl]amino}biphenyl-4-yl)carbamate. 2-(Dimethylphosphoryl)ethanamine hydrochloride (393 mg, 2.493 mmol), tert-butyl (3-{[4-(bromomethyl)benzoyl]amino}biphenyl-4-yl)carbamate (400 mg, 0.831 mmol), and DIEA (581 μl, 3.32 mmol) were combined in DMF (8 mL) and water (0.50 mL) and stirred at 60° C. overnight. The solution was diluted with saturated NaHCO$_3$ and extracted with EtOAc (4×). The combined organics were dried (MgSO$_4$), evaporated, and purified by reverse phase HPLC (25-95% MeCN/water w/0.025% TFA). Product fractions were neutralized with saturated NaHCO$_3$, extracted with EtOAc (2×), dried (MgSO$_4$), and evaporated to give a colorless solid.

MS: cal'd 522 (MH+), exp 522 (MH+).

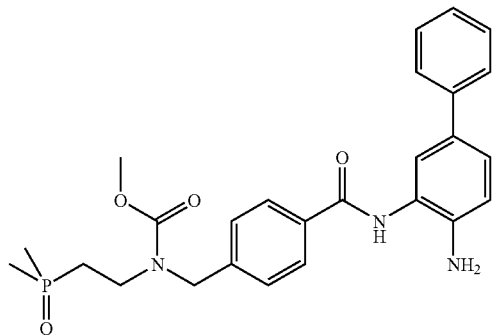

Methyl (4-{[(4-aminobiphenyl-3-yl)amino]carbonyl}benzyl)[2-(dimethylphosphoryl)ethyl]carbamate. To a solution of tert-butyl (3-{[4-({[2-(dimethylphosphoryl)ethyl]amino}methyl)benzoyl]amino}biphenyl-4-yl)carbamate (295 mg, 0.566 mmol) in CH$_2$Cl$_2$ (10 mL) were added DIEA (198 μl, 1.13 mmol) and methyl chloroformate (70 mg, 0.735 mmol). After stirring for 30 min at room temperature, the reaction was diluted with CH$_2$Cl$_2$ and washed with saturated NaHCO$_3$. The aqueous layer was extracted with additional CH$_2$Cl$_2$. The combined organic layers were washed with brine, dried (MgSO$_4$), and evaporated. Flash chromatography (0-10% MeOH/CH$_2$Cl$_2$) afforded a colorless solid. This solid was taken up in CH$_2$Cl$_2$ (5 mL) and TFA (1 mL). After stirring at room temperature for 1 h, the solution was diluted with 1,2-DCE and concentrated. The residue was diluted with EtOAc, washed with saturated NaHCO$_3$ and brine, dried (MgSO$_4$), and evaporated to afford the title compound as a pale yellow solid. NMR (DMSO-d$_6$, 600 MHz) δ 9.70 (bs, 1H), 7.96 (d, J=8.1 Hz, 2H), 7.54-7.50 (m, 2H), 7.50-7.48 (m, 1H), 7.37-7.32 (m, 4H), 7.29 (dd, J=8.2, 2.1 Hz, 1H), 7.20 (t, J=7.4 Hz, 1H), 6.83 (d, J=8.5 Hz, 1H), 5.07 (bs, 2H), 4.52 (s, 2H), 3.69-3.57 (m, 3H), 3.45-3.34 (m, 2H), 1.99-1.87 (m, 2H), 1.34 (d, J=12.9 Hz, 6H). MS: cal'd 480 (MH+), exp 480 (MH+).

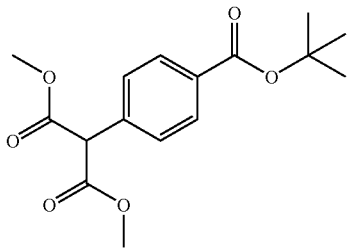

Dimethyl [4-(tert-butoxycarbonyl)phenyl]malonate. Dimethyl malonate (4.24 g, 32.1 mmol), K$_3$PO$_4$ (18.57 g, 88.0 mmol), and tert-butyl-4-bromobenzoate (7.50 g, 29.2 mmol) were placed in a dry 500 mL flask under N$_2$. Bis(tri-t-butylphosphine)palladium(0) (745 mg, 1.46 mmol) and toluene (100 mL) were added, and the slurry was degassed with N$_2$ for 20 minutes. The reaction was subsequently stirred at 80° C. overnight. The slurry was cooled, diluted with water, and extracted with EtOAc (2×). The combined organic layers were washed with brine, dried (MgSO$_4$), and evaporated. Flash chromatography (0-25% EtOAc/hexanes) afforded dimethyl [4-(tert-butoxycarbonyl)phenyl]malonate as a colorless solid. $^1$H NMR (CDCl$_3$, 600 MHz) δ 7.96 (d, J=8.5 Hz, 2H), 7.43 (d, J=8.4 Hz, 2H), 4.68 (s, 1H), 3.73 (s, 6H), 1.56 (s, 9H). MS: cal'd 331 (MNa+), exp 331 (MNa+).

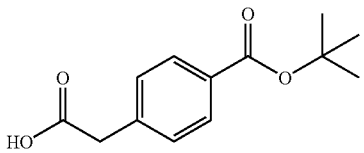

[4-(tert-Butoxycarbonyl)phenyl]acetic acid. Dimethyl [4-(tert-butoxycarbonyl)phenyl]malonate (4.00 g, 13.0 mmol) was taken up in THF (30 mL) and MeOH (10 mL) under N$_2$. NaOH (2 M, 19.5 mL, 39.0 mmol) was added, and the reaction was stirred at room temperature for 45 min. The solution was quenched with 1 M citric acid and extracted with EtOAc (2×). The combined organic extracts were washed with water and brine, dried (MgSO$_4$), and evaporated. The resulting yellow oil was dissolved in 1:1 EtOAc:water (100 mL) and stirred at 85° C. for 2 h. The mixture was diluted with 1 M citric acid and extracted with EtOAc. The organic layer was washed with water and brine, dried (MgSO$_4$), and evaporated to give [4-(tert-Butoxycarbonyl)phenyl]acetic acid as a tan solid. $^1$H NMR (DMSO-d$_6$, 600 MHz) δ 12.42 (bs, 1H), 7.82 (d, J=8.3 Hz, 2H), 7.35 (d, J=8.3 Hz, 2H), 3.64 (s, 2H), 1.51 (s, 9H). MS: cal'd 259 (MNa+), exp 259 (MNa+).

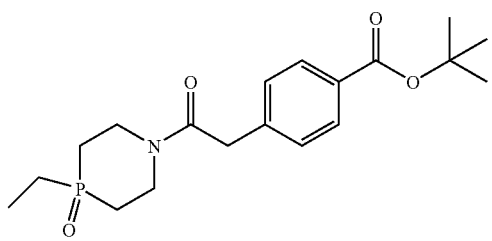

tert-Butyl 4-[2-(4-ethyl-4-oxido-1,4-azaphosphinan-1-yl)-2-oxoethyl]benzoate. 4-Ethyl-1,4-azaphosphinane 4-oxide hydrochloride (233 mg, 1.27 mmol), [4-(tert-butoxycarbonyl)phenyl]acetic acid (200 mg, 0.847 mmol), EDC (325 mg, 1.69 mmol), HOBT (259 mg, 1.69 mmol), and DIEA (296 μl, 1.69 mmol) were combined in DMF (4 mL) and stirred at room temperature overnight. The solution was diluted with saturated NaHCO$_3$ and extracted with EtOAc (2×). The combined organic layers were washed with brine, dried (MgSO$_4$), and evaporated. Flash chromatography (0-10% MeOH/CH$_2$Cl$_2$) afforded the title compound as a colorless oil. MS: cal'd 366 (MH+), exp 366 (MH+).

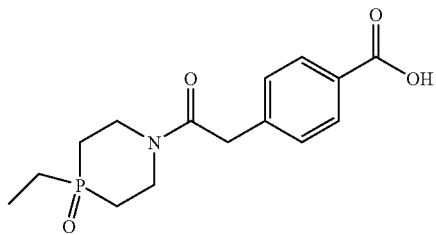

4-[2-(4-Ethyl-4-oxido-1,4-azaphosphinan-1-yl)-2-oxoethyl]benzoic acid. tert-Butyl 4-[2-(4-ethyl-4-oxido-1,4-azaphosphinan-1-yl)-2-oxoethyl]benzoate (270 mg, 0.739 mmol) was dissolved in CH$_2$Cl$_2$ (8 mL) and TFA (2 mL) and stirred at room temperature for 2 h. The solution was concentrated to dryness, redissolved in MeOH, and concentrated again to give the product as a colorless gum that was carried on without purification. MS: cal'd 310 (MH+), exp 310 (MH+).

Additional analogs were prepared in procedures similar to those described for the preparations of the above examples.

TABLE 12

K; β-Aminophosphine Oxides

| Cpd # | Structure | Name | MS | Salt Forms |
|---|---|---|---|---|
| 1 | 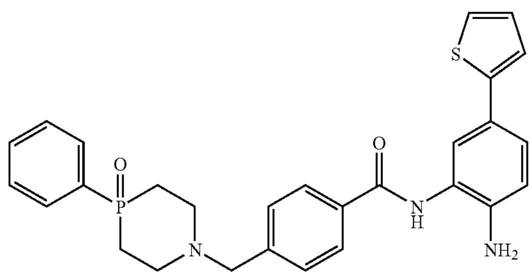 | N-[2-Amino-5-(2-thienyl)phenyl]-4-[(4-oxido-4-phenyl-1,4-azaphosphinan-1-yl)methyl]benzamide | cal'd 502 (MH+), exp 502 | Free base |
| 2 | 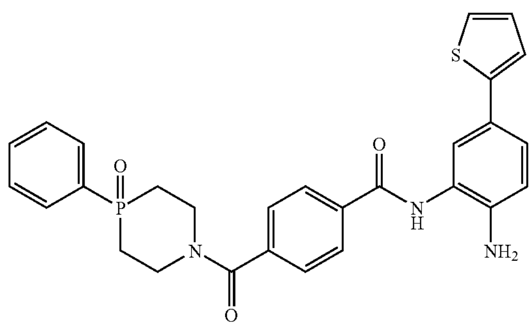 | N-[2-Amino-5-(2-thienyl)phenyl]-4-[(4-oxido-4-phenyl-1,4-azaphosphinan-1-yl)carbonyl]benzamide | cal'd 516 (MH+), exp 516 | Free base |
| 3 | 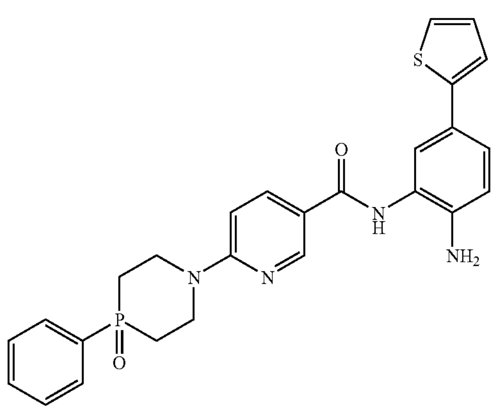 | N-[2-Amino-5-(2-thienyl)phenyl]-6-(4-oxido-4-phenyl-1,4-azaphosphinan-1-yl)nicotinamide | cal'd 489 (MH+), exp 489 | Free base |
| 4 | 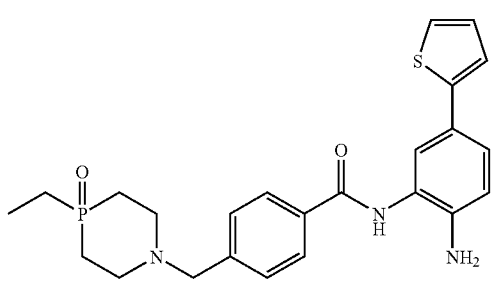 | N-[2-Amino-5-(2-thienyl)phenyl]-4-[(4-ethyl-4-oxido-1,4-azaphosphinan-1-yl)methyl]benzamide | cal'd 454 (MH+), exp 454 | Free base |

TABLE 12-continued

K; β-Aminophosphine Oxides

| Cpd # | Structure | Name | MS | Salt Forms |
|---|---|---|---|---|
| 5 | 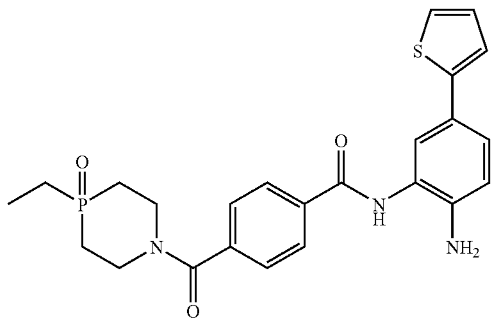 | N-[2-Amino-5-(2-thienyl)phenyl]-4-[(4-ethyl-4-oxido-1,4-azaphosphinan-1-yl)carbonyl]benzamide | cal'd 468 (MH+), exp 468 | Free base |
| 6 | 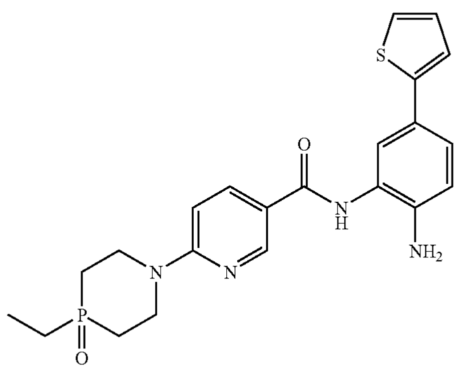 | N-[2-Amino-5-(2-thienyl)phenyl]-6-(4-ethyl-4-oxido-1,4-azaphosphinan-1-yl)nicotinamide | cal'd 441 (MH+), exp 441 | Free base |
| 7 | 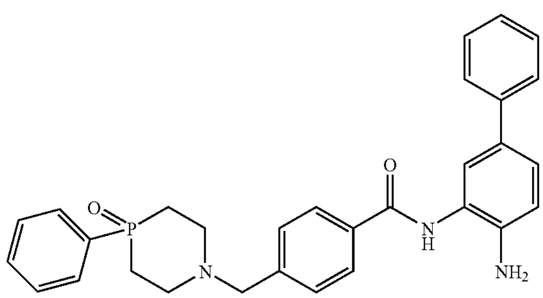 | N-(4-aminobiphenyl-3-yl)-4-[(4-oxido-4-phenyl-1,4-azaphosphinan-1-yl)methyl]benzamide | cal'd 496 (MH+), exp 496 | Free base |
| 8 | 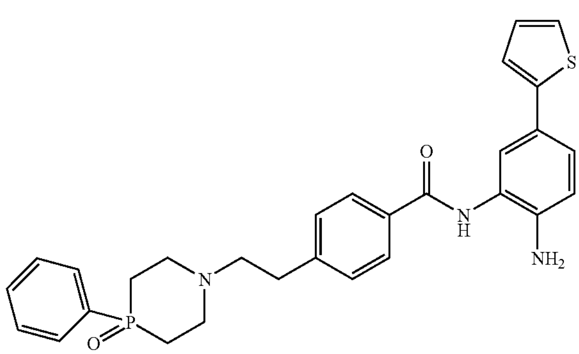 | N-[2-amino-5-(2-thienyl)phenyl]-4-[2-(4-oxido-4-phenyl-1,4-azaphosphinan-1-yl)ethyl]benzamide | cal'd 516 (MH+), exp 516 | Free base |

TABLE 12-continued

K; β-Aminophosphine Oxides

| Cpd # | Structure | Name | MS | Salt Forms |
|---|---|---|---|---|
| 9 | 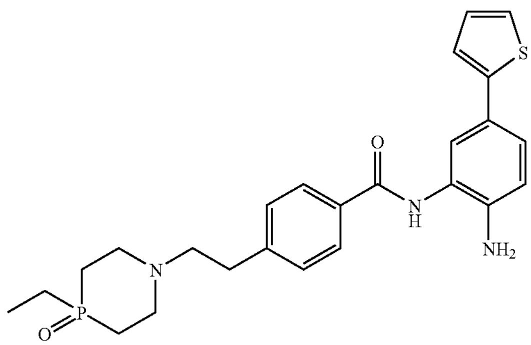 | N-[2-amino-5-(2-thienyl)phenyl]-4-[2-(4-ethyl-4-oxido-1,4-azaphosphinan-1-yl)ethyl]benzamide | cal'd 468 (MH+), exp 468 | Free base |
| 10 | 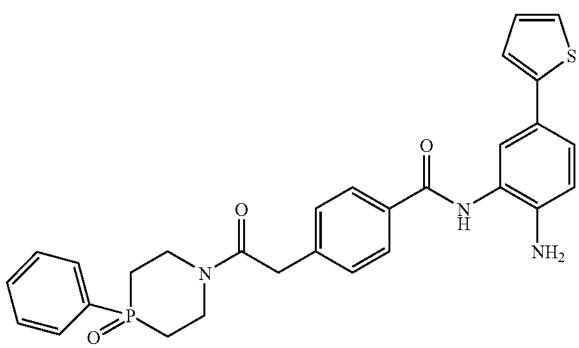 | N-[2-amino-5-(2-thienyl)phenyl]-4-[2-(4-oxido-4-phenyl-1,4-azaphosphinan-1-yl)-2-oxoethyl]benzamide | cal'd 530 (MH+), exp 530 | Free base |
| 11 | 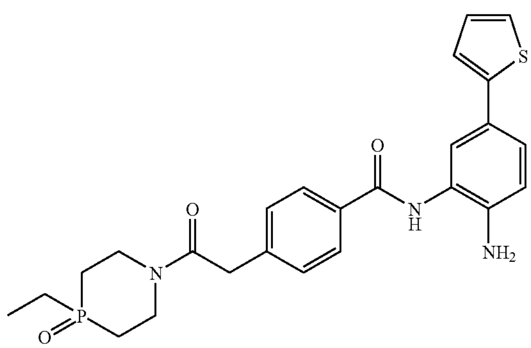 | N-[2-amino-5-(2-thienyl)phenyl]-4-[2-(4-ethyl-4-oxido-1,4-azaphosphinan-1-yl)-2-oxoethyl]benzamide | cal'd 482 (MH+), exp 482 | Free base |
| 12 | 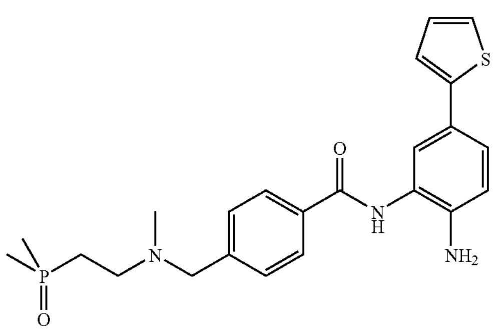 | N-[2-amino-5-(2-thienyl)phenyl]-4-{[[2-(dimethylphosphoryl)ethyl](methyl)amino]methyl}benzamide | cal'd 442 (MH+), exp 442 | Free base |

TABLE 12-continued

K; β-Aminophosphine Oxides

| Cpd # | Structure | Name | MS | Salt Forms |
|---|---|---|---|---|
| 13 | 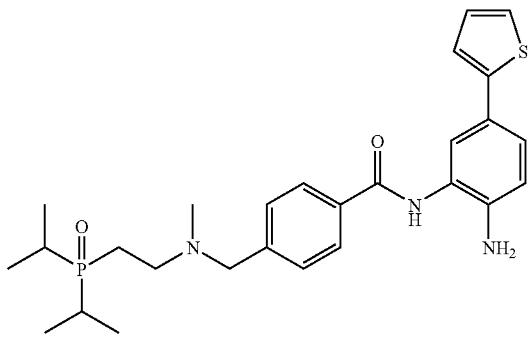 | N-[2-amino-5-(2-thienyl)phenyl]-4-{[[2-(diisopropylphosphoryl)ethyl](methyl)amino]methyl}benzamide | cal'd 498 (MH+), exp 498 | Free base |
| 14 | 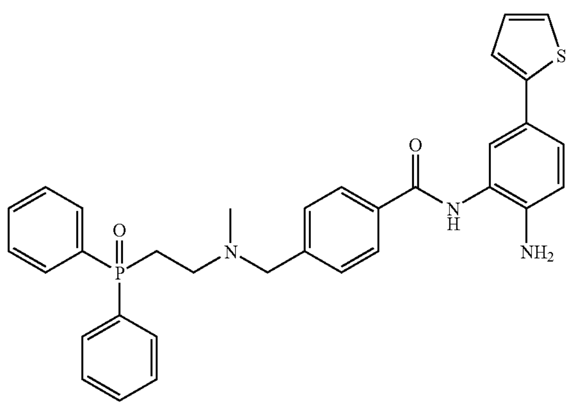 | N-[2-amino-5-(2-thienyl)phenyl]-4-{[[2-(diphenylphosphoryl)ethyl](methyl)amino]ethyl}benzamide | cal'd 566 (MH+), exp 566 | Free base |
| 15 | 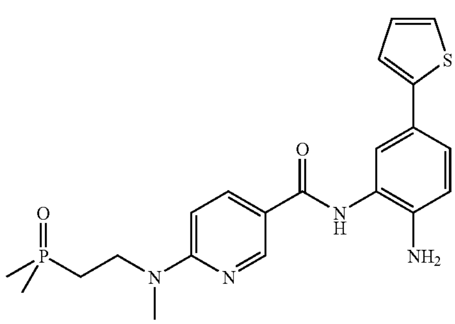 | N-[2-amino-5-(2-thienyl)phenyl]-6-[[2-(dimethylphosphoryl)ethyl](methyl)amino]nicotinamide | cal'd 429 (MH+), exp 429 | Free base |
| 16 | 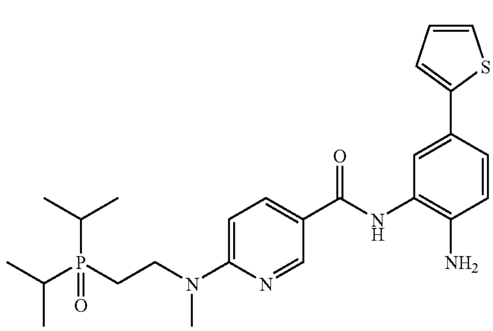 | N-[2-amino-5-(2-thienyl)phenyl]-6-[[2-(diisopropylphosphoryl)ethyl](methyl)amino]nicotinamide | cal'd 485 (MH+), exp 485 | Free base |

TABLE 12-continued

K; β-Aminophosphine Oxides

| Cpd # | Structure | Name | MS | Salt Forms |
|---|---|---|---|---|
| 17 | 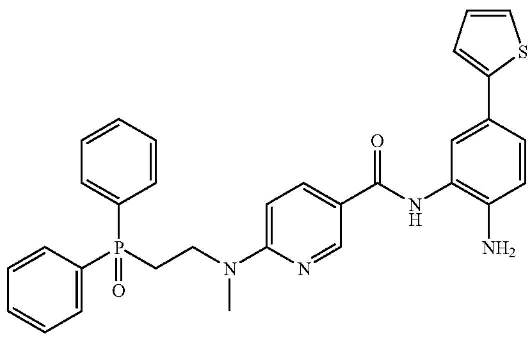 | N-[2-amino-5-(2-thienyl)phenyl]-6-[[2-(diphenylphosphoryl)ethyl](methyl)amino]nicotinamide | cal'd 553 (MH+), exp 553 | Free base |
| 18 | 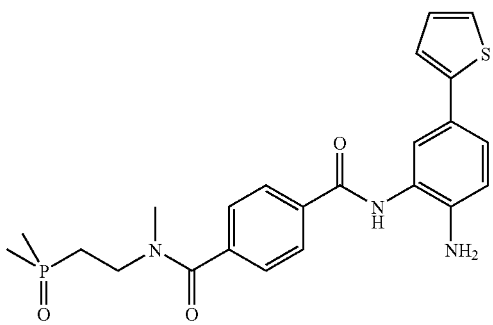 | N'-[2-amino-5-(2-thienyl)phenyl]-N-[2-(dimethylphosphoryl)ethyl]-N-methylterephthalamide | cal'd 456 (MH+), exp 456 | Free base |
| 19 | 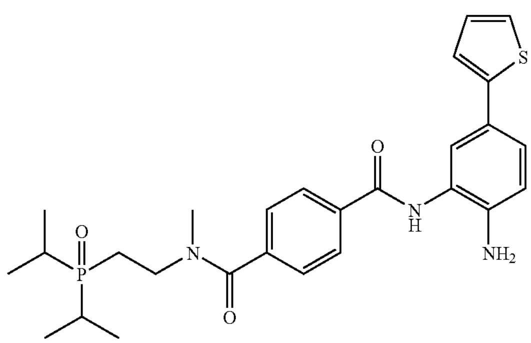 | N'-[2-amino-5-(2-thienyl)phenyl]-N-[2-(diisopropylphosphoryl)ethyl]-N-methylterephthalamide | cal'd 512 (MH+), exp 512 | Free base |
| 20 | 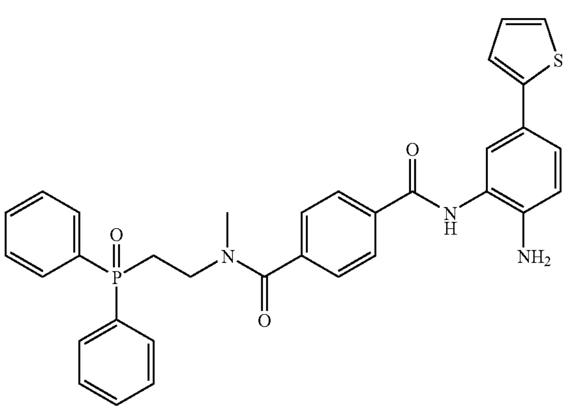 | N'-[2-amino-5-(2-thienyl)phenyl]-N-[2-(diphenylphosphoryl)ethyl]-N-methylterephthalamide | cal'd 580 (MH+), exp 580 | Free base |

TABLE 12-continued

K; β-Aminophosphine Oxides

| Cpd # | Structure | Name | MS | Salt Forms |
|---|---|---|---|---|
| 21 | 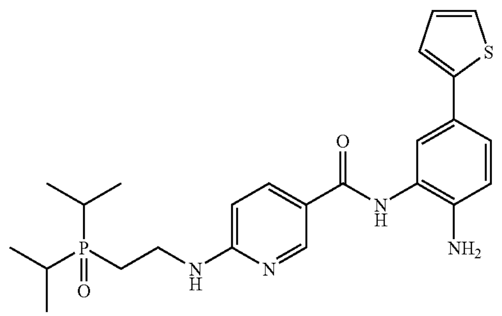 | N-[2-amino-5-(2-thienyl)phenyl]-6-{[2-(diisopropylphosphoryl)ethyl]amino}nicotinamide | cal'd 471 (MH+), exp 471 | Free base |
| 22 | 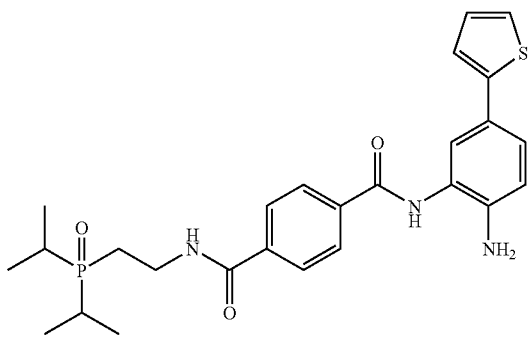 | N-[2-amino-5-(2-thienyl)phenyl]-N'-[2-(diisopropylphosphoryl)ethyl]terephthalamide | cal'd 498 (MH+), exp 498 | Free base |
| 23 | 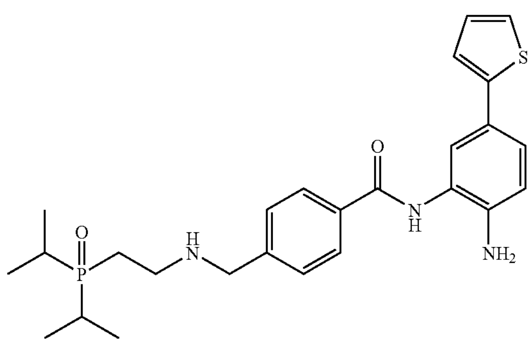 | N-[2-amino-5-(2-thienyl)phenyl]-4-({[2-(diisopropylphosphoryl)ethyl]amino}methyl)benzamide | cal'd 484 (MH+), exp 484 | Free base |
| 24 | 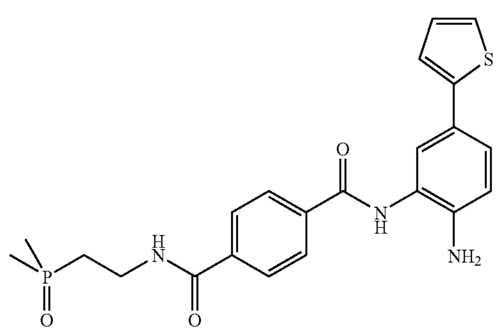 | N-[2-amino-5-(2-thienyl)phenyl]-N'-[2-(dimethylphosphoryl)ethyl]terephthalamide | cal'd 442 (MH+), exp 442 | Free base |

TABLE 12-continued

K: β-Aminophosphine Oxides

| Cpd # | Structure | Name | MS | Salt Forms |
|---|---|---|---|---|
| 25 | 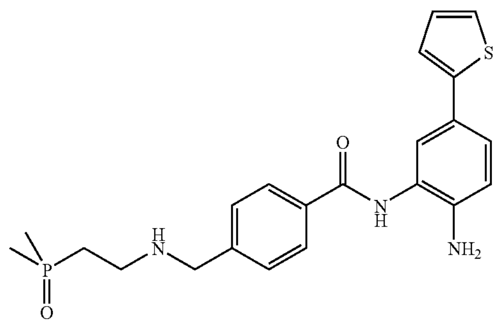 | N-[2-amino-5-(2-thienyl)phenyl]-4-({[2-(dimethylphosphoryl)ethyl]amino}methyl)benzamide | cal'd 428 (MH+), exp 428 | Free base |
| 26 | 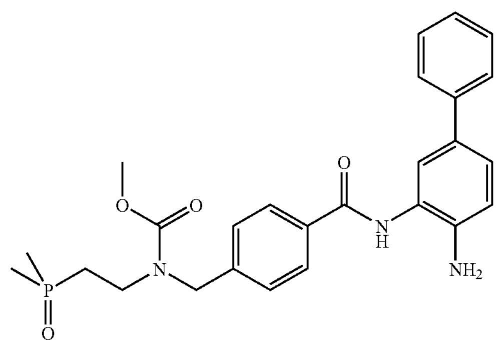 | methyl (4-{[(4-aminobiphenyl-3-yl)amino]carbonyl}benzyl)[2-(dimethylphosphoryl)ethyl]carbamate | cal'd 480 (MH+), exp 480 | Free base |

Procedures for L. Preparation of Phosphopiperidines

Diethyl pyridin-4-ylphosphonate. 4-Bromopyridine hydrochloride (8 g, 41.1 mmol), diethyl phosphite (8.23 mL, 63.8 mmol), tetrakis(triphenylphosphine)palladium(0) (1.189 g, 1.029 mmol) and TEA (17.20 mL, 123 mmol) were stirred in refluxing toluene (160 mL) overnight. Room temperature was attained, water was added and the organic layer separated. The aqueous phase was extracted with EtOAc (×2). The combined organic extracts were washed with brine, dried over $MgSO_4$ and concentrated in vacuo. Purification of the residue by MPLC (EtOAc) gave diethyl pyridin-4-ylphosphonate as a pale yellow oil. $^1$H NMR (DMSO-$d_6$, 600 MHz) δ 8.75 (m, 2H), 7.61 (m, 2H), 4.03 (m, 4H), 1.21 (t, J=7.2 Hz, 6H). MS: cal'd 216 (MH+), exp 216 (MH+).

Diethyl piperidin-4-ylphosphonate hydrochloride. Diethyl pyridin-4-ylphosphonate (3.8 g, 17.66 mmol) and palladium hydroxide on carbon (1.240 g, 1.766 mmol) were taken up in MeOH (90 mL)/HCl (10 mL, 20.00 mmol). The suspension was agitated under $H_2$ @ 40-50 psi for 7 days. The catalyst was removed by filtration and the filtrate concentrated in vacuo to give diethyl piperidin-4-ylphosphonate hydrochloride as a green gum. $^1$H NMR (DMSO-$d_6$, 600 MHz) δ 9.26 (br s, 1H), 8.84 (br s, 1H), 3.96 (m, 4H), 3.20 (m, 2H), 2.80 (m, 2H), 2.10 (m, 1H), 1.84 (m, 2H), 1.68 (m, 2H), 1.19 (t, J=7.2 Hz, 6H). MS: cal'd 222 (MH+), exp 222 (MH+).

Additional analogs were prepared in procedures similar to those described for the preparations of the above examples.

TABLE 13

L; Phosphopiperidines

| Cpd # | Structure | Name | MS | Salt Forms |
|---|---|---|---|---|
| 1 | 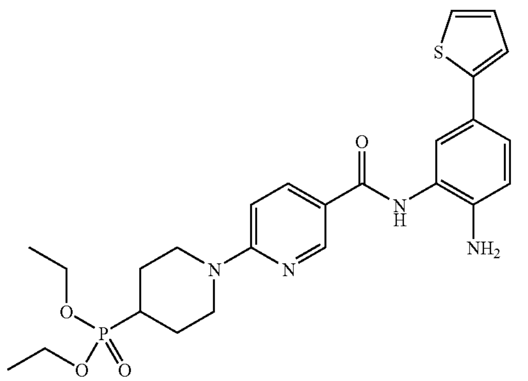 | diethyl {1-[5-({[2-amino-5-(2-thienyl)phenyl]amino}carbonyl)pyridin-2-yl]piperidin-4-yl}phosphonate | cal'd 515 (MH+), exp 515 | Free base |
| 2 | 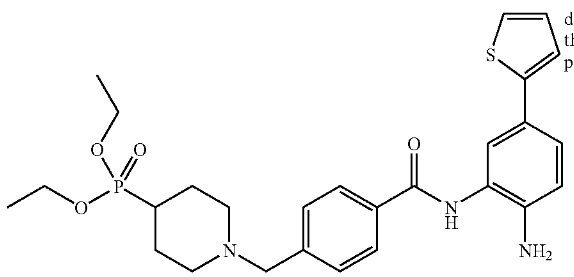 | diethyl (1-{[4-({[2-amino-5-(2-thienyl)phenyl]amino}carbonyl)phenyl]methyl}piperidin-4-yl)phosphonate | cal'd 528 (MH+), exp 528 | Free base |
| 3 | 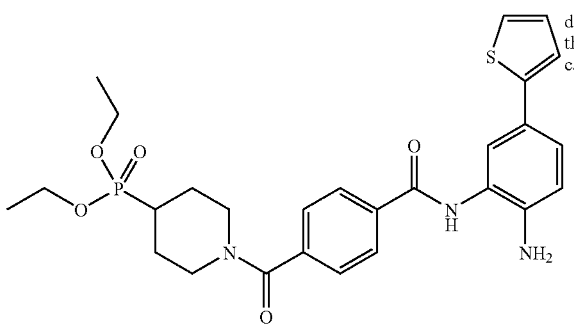 | diethyl (1-{[4-({[2-amino-5-(2-thienyl)phenyl]amino}carbonyl)phenyl]carbonyl}piperidin-4-yl)phosphonate | cal'd 542 (MH+), exp 542 | Free base |

Procedures for M. Preparation of Alkyloxy Phosphonates/Phosphinates/Phosphates.

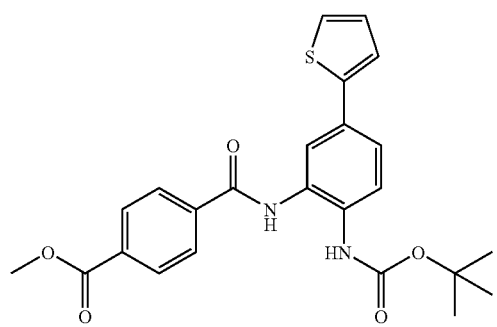

N-(2-tert-Butoxycarbonylamino-5-thiophen-2-yl-phenyl)-terephthalamic acid methyl ester. Methyl 4-(chlorocarbonyl)benzoate (0.75 g, 3.79 mmol) and anhydrous DCM (0.25 M) was treated with tert-butyl 2-amino-4-thien-2-ylphenylcarbamate (1.0 g, 3.44 mmol). The resulting solution was stirred at ambient temperature for 14 hours. The reaction mixture was quenched with a solution of aqueous NaOH (1M) and partitioned between ethyl acetate and water. The organic layer was washed with water, saturated aqueous sodium bicarbonate, brine, dried over anhydrous magnesium sulfate and then concentrated in vacuo. The residue was carried on without further purification.

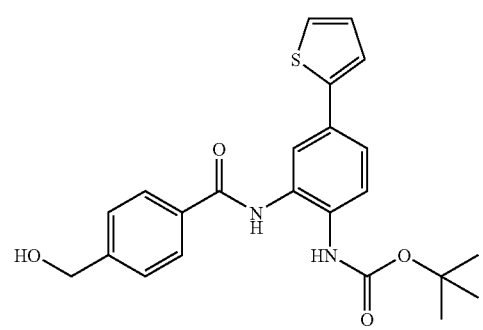

[2-(4-Hydroxymethyl-benzoylamino)-4-thiophen-2-yl-phenyl]-carbamic acid tert-butyl ester. A solution of methyl 4-[({2-[(tert-butoxycarbonyl)amino]-5-thien-2-ylphenyl}amino)carbonyl]benzoate (743 mg, 1.64 mmol) and anhydrous THF (0.10 M) was cooled to 0° C. and a solution of LiBH4 (5.49 mL, 11.0 mmol, 2M in THF) was added dropwise. The resulting solution was allowed to slowly warm to ambient temperature over 14 hours. The reaction was then cooled to 0° C. and quenched with saturated aqueous ammonium cloride. The mixture was diluted with water and extracted with ethyl acetate twice. The combined organic layers were washed with brine, dried over anhydrous magnesium sulfate and concentrated in vacuo. The residue was purified by MPLC (SiO$_2$, 10-80% EtOAc in hexanes) to afford a white glass: $^1$H-NMR (600 mHz, DMSO-d$_6$) δ 9.87 (s, 1H), 8.73 (s, 1H), 7.92 (d, J=9.2 Hz, 2H), 7.81 (d, J=2.1 Hz, 1H), 7.58-7.42 (m, 5H), 7.11 (d, J=3.5 Hz, 1H), 7.10 (d, J=3.5 Hz, 1H), 5.34 (t, J=5.9 Hz, 1H), 4.57 (d, J=5.6 Hz, 2H), 1.43 (s, 9H).

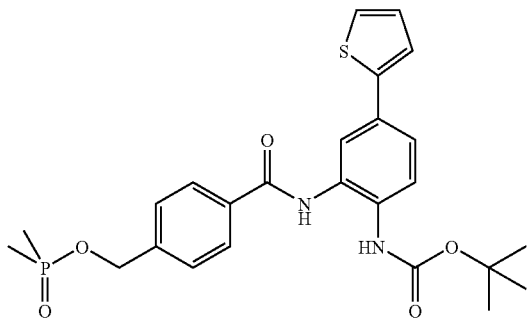

[4-([{2-({[(1,1-dimethylethyl)oxy]carbonyl}amino)-5-(2-thienyl)phenyl]amino}carbonyl)phenyl]methyl dimethylphosphinate. 1,1-dimethylethyl [2-({[4-(hydroxymethyl)phenyl]carbonyl}amino)-4-(2-thienyl)phenyl]carbamate (650 mg, 1.531 mmol), BOP (1016 mg, 2.297 mmol), dimethylphosphinic acid (216 mg, 2.297 mmol), DMAP (10 mg, 0.082 mmol) and DIPEA (0.401 mL, 2.297 mmol) were stirred in DMF (8 mL) at room temperature overnight. Additional BOP (2370 mg, 5.36 mmol), DIPEA (0.936 mL, 5.36 mmol), dimethylphosphinic acid (504 mg, 5.36 mmol) and DMAP (20 mg, 0.164 mmol) were added and stirring continued for 24 hours. Additional BOP (1016 mg, 2.297 mmol), DIPEA (0.401 mL, 2.297 mmol) and dimethylphosphinic acid (216 mg, 2.297 mmol) were added and stirring continued for 6 hours. Saturated NaHCO$_3$ was added and the products extracted into EtOAc (×2). The combined organic extracts were dried over MgSO$_4$ and concentrated in vacuo. Purification of the residue by MPLC (0-20% MeOH-EtOAc) gave [4-({[2-({[(1,1-dimethylethyl)oxy]carbonyl}amino)-5-(2-thienyl)phenyl]amino}carbonyl)phenyl]methyl dimethylphosphinate as a yellow gum. $^1$H-NMR (600 mHz, DMSO-d6) δ 9.90 (s, 1H), 8.72 (s, 1H), 7.96 (d, J=8.4 Hz, 2H), 7.90 (d, J=2.4 Hz, 1H), 7.58 (d, J=8.4 Hz, 1H), 7.53 (d, J=8.4 Hz, 2H), 7.49 (m, 2H), 7.43 (dd, J=3.6 and 1.2 Hz, 1H), 7.10 (dd, J=4.8 and 3.6 Hz, 1H), 5.02 (d, J=8.4 Hz, 2H), 1.46 (d, J=13.8 Hz, 6H), 1.42 (s, 9H). MS: cal'd 401 (MH+-Boc), exp 401 (MH+-Boc).

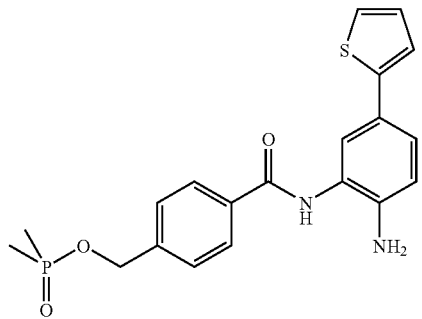

[4-({[2-amino-5-(2-thienyl)phenyl]amino)carbonyl)phenyl]methyl dimethylphosphinate. [4-({[2-({[(1,1-dimethylethyl)oxy]carbonyl}amino)-5-(2-thienyl)phenyl]amino}carbonyl)phenyl]methyl dimethylphosphinate (1.1 g, 2.198 mmol) was taken up in DCM (20 mL)/TFA (8 mL). After 2 hours at room temperature the solvent was removed in vacuo. Saturated NaHCO$_3$ was added and the products extracted into EtOAc (×2). The combined organic extracts were washed with brine, dried over MgSO$_4$ and concentrated in vacuo. The residue was triturated in EtOAc to give [4-({[2-amino-5-(2-thienyl)phenyl]amino}carbonyl)phenyl]methyl dimethylphosphinate as a beige solid. $^1$H-NMR (600 mHz, DMSO-d6) δ 9.72 (s, 1H), 7.98 (d, J=8.4 Hz, 2H), 7.49 (d, J=8.4 Hz, 2H), 7.44 (d, J=1.8 Hz, 1H), 7.32 (dd, J=4.8 and 1.2 Hz, 1H), 7.27 (dd, J=8.4 and 2.4 Hz, 1H), 7.21 (dd, J=3.6 and 1.2 Hz, 1H), 7.01 (dd, J=4.8 and 3.6 Hz, 1H), 6.78 (d, J=8.4 Hz, 1H), 5.13 (s, 2H), 5.01 (d, J=8.4 Hz, 2H), 1.45 (d, J=14.4 Hz, 6H). MS: cal'd 401 (MH+), exp 401 (MH+).

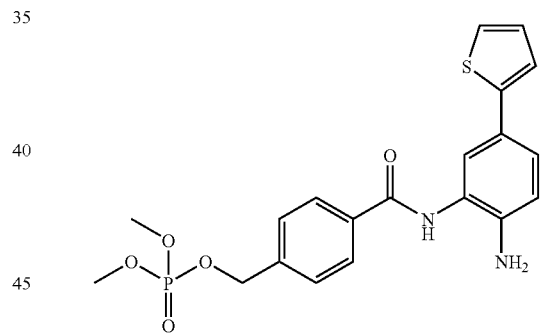

4-({[2-amino-5-(2-thienyl)phenyl]amino}carbonyl)benzyl dimethyl phosphate. [2-(4-Hydroxymethyl-benzoylamino)-4-thiophen-2-yl-phenyl]-carbamic acid tert-butyl ester (60 mg, 0.14 mmol) was made 0.25 M in anhydrous DCM and to this stirring solution was added DIPEA (55 mg, 0.42 mmol), followed by dimethyl phosphochloridate (41 mg, 0.28 mmol). The resulting mixture was stirred at ambient temperature for 16 h. The mixture was diluted with 0.5 mL TFA and stirred for 1 h. The mixture was then diluted with EtOAc and carefully quenched with saturated aqueous sodium bicarbonate. The organic layer was washed again with saturated aqueous sodium bicarbonate, then dried (MgSO$_4$) and concentrated in vacuo. The residue was purified by MPLC (0-8% MeOH in CH$_2$Cl$_2$). Pure fractions were identified, combined, and concentrated to afford the title compound. $^1$H NMR (DMSO-d$_6$, 600 MHz) δ 9.75 (s, 1H), 8.01 (d, J=7.8 Hz, 2H), 7.52 (d, J=7.8 Hz, 1H), 7.45 (s, 1H), 7.34-7.33 (m, 1H), 7.28 (dd, J=8.4 Hz, J=2.4 Hz, 1H), 7.22 (d, J=3.6 Hz, 1H), 7.03 (dd, J=4.8 Hz, J=3.6 Hz, 1H), 6.79 (d, J=8.4 Hz 1H), 5.12 (d, J=8.4 Hz, 2H), 5.15 (br-s, 2H), 3.67 (d, J=11.4 Hz, 6H). MS: cal'd 433 (MH+), exp 433 (MH+).

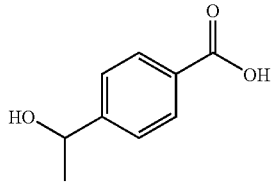

4-(1-hydroxyethyl)benzoic acid. To a solution of methyl-4-(1-hydroxyethyl)benzoate (2.00 g, 11.10 mmol) in a mixture of THF (20 mL) and MeOH (10 mL) was added 1 M KOH (13.32 mL, 13.32 mmol). After stirring at room temperature overnight, the solution was diluted with 2 N HCl and extracted with EtOAc (4×). The combined organic layers were dried (MgSO$_4$) and evaporated to give 4-(1-hydroxyethyl)benzoic acid as a colorless solid. $^1$H NMR (DMSO-d$_6$, 600 MHz) δ 7.86 (d, J=8.6 Hz, 2H), 7.43 (d, J=8.3 Hz, 2H), 4.75 (q, J=6.5 Hz, 1H), 1.30 (d, J=6.6 Hz, 3H). MS: cal'd 167 (MH+), exp 167 (MH+).

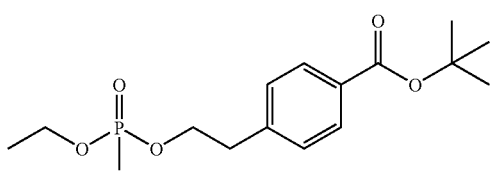

Tert-butyl 4-(2-{[ethoxy(methyl)phosphoryl]oxy}ethyl)benzoate. To a solution of tert-butyl 4-(2-hydroxyethyl)benzoate (100 mg, 0.45 mmol) and diisopropylethyl amine (0.16 mL, 0.90 mmol) in DMF (2 mL) was added DMAP (10 mg, 0.08 mmol) and BOP (400 mg, 0.90 mmol). After stirring at room temperature overnight, the solution was diluted with saturated NaHCO$_3$ solution and extracted with EtOAc. The combined organic layers were dried (Na$_2$SO$_4$) and concentrated in vacuo. The resulting residue was purified by MPLC (0-20% MeOH/EtOAc) to give the title compound as a colorless oil. $^1$H NMR (CDCl$_3$, 600 MHz) δ 7.92 (d, J=8.2 Hz, 2H), 7.27 (d, J=8.2 Hz, 2H), 4.19-4.29 (m, 2H), 3.95-4.04 (m, 2H), 3.02 (t, J=6.7 Hz, 2H) 1.58 (s, 9H), 1.38 (d, J=18.9 Hz), 1.27 (t, J=7.6 Hz). MS: cal'd 272 (MH+-Boc), exp 272 (MH+-Boc).

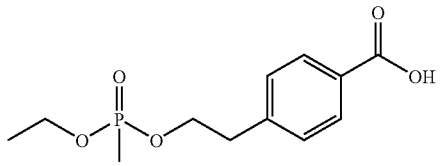

4-(2-{[ethoxy(methyl)phosphoryl]oxy}ethyl)benzoic acid. To a solution of tert-butyl 4-(2-{[ethoxy(methyl)phosphoryl]oxy}ethyl)benzoate (108 mg, 0.33 mmol) in DCM (0.66 mL) was added TFA (0.60 mL, 7.8 mmol). After stirring at room temperature for 30 minutes, the solution was concentrated in vacuo to give the title compound as a colorless oil. $^1$H NMR (CDCl$_3$, 600 MHz) δ 7.85 (d, J=8.2 Hz, 2H), 7.37 (d, J=8.2 Hz, 2H), 4.10-4.16 (m, 2H), 3.80-3.88 (m, 2H), 2.95 (t, J=6.4 Hz, 2H), 1.32 (d, J=17.3 Hz, 3H), 1.13 (t, J=7.1 Hz, 3H). MS cal'd 272 (MH+), exp 272 (MH+).

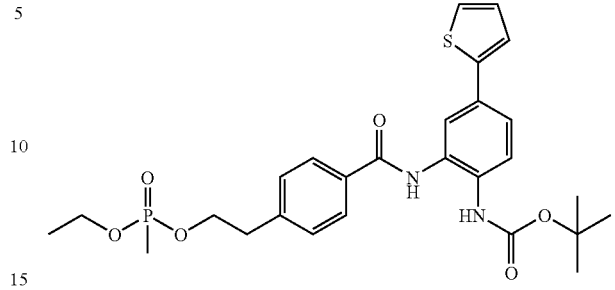

2-[4-({[2-[(tert-butoxycarbonyl)amino]-5-(2-thienyl)phenyl]amino}carbonyl)phenyl]ethyl ethyl methylphosphonate. 1,1-dimethylethyl [2-({[4-(hydroxymethyl)phenyl]carbonyl}amino)-4-(2-thienyl)phenyl]carbamate (140 mg, 0.50 mmol), BOP (440 mg, 0.99 mmol), 4-(2-{[ethoxy(methyl)phosphoryl]oxy}ethyl)benzoic acid (90 mg, 0.33 mmol), and DIPEA (0.17 mL, 0.99 mmol) were stirred in DMF (1.1 mL) at 60° C. for 72 hours. The mixture was then diluted with saturated NaHCO$_3$ solution and extracted with EtOAc. The organic layers were then washed with brine, dried over Na$_2$SO$_4$ and concentrated in vacuo. Purification of the crude reaction mixture by MPLC (0-10% MeOH/DCM) resulted in the title compound as a yellow foam. MS cal'd 445 (MH+-Boc), exp 445 (MH+-Boc).

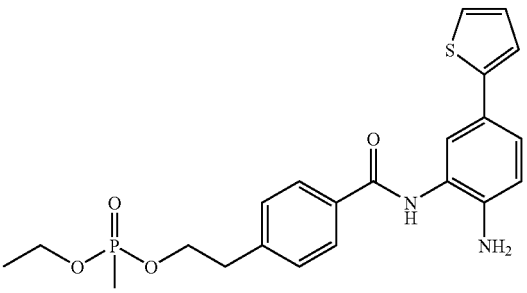

2-[4-({[2-amino-5-(2-thienyl)phenyl]amino}carbonyl)phenyl]ethyl methylphosphonate. To a solution of 2-[4-({[2-[(tert-butoxycarbonyl)amino]-5-(2-thienyl)phenyl]amino}carbonyl)phenyl]ethyl methylphosphonate (180 mg, 0.33 mmol) in DCM (0.66 mL) was added TFA (0.3 mL, 3.9 mmol). After stirring at room temperature for 30 minutes the reaction mixture was concentrated in vacuo and the crude reaction mixture was purified by reverse-phase HPLC (5-65% MeCN/H$_2$O). After purification, the fractions containing the desired product were combined and washed with saturated NaHCO$_3$ solution. The organic layer was then concentrated in vacuo to give the title compound as a pale yellow solid. $^1$H NMR (DMSO-d$_6$, 600 MHz) δ 9.68 (s, 1H), 7.93 (d, J=8.2 Hz, 2H), 7.44 (d, J=1.7 Hz, 1H), 7.39 (d, J=8.2 Hz, 2H), 7.33 (dd, J=1.1, 5.2 Hz, 1H), 7.27 (dd, J=2.1, 8.2 Hz, 1H), 7.22 (dd, J=1.2, 3.5 Hz, 1H), 7.02 (dd, J=3.8, 5.3 Hz, 1H), 6.79 (d, J=8.5 Hz, 1H), 5.12 (s, 2H), 4.11-4.18 (m, 2H), 3.84-3.94 (m, 2H), 2.97 (t, J=6.5 Hz, 2H), 1.35 (d, J=17 Hz, 3H), 1.17 (t, J=7.1 Hz, 3H). MS cal'd 445 (MH+) exp 445 (MH+).

Additional analogs were prepared in procedures similar to those described for the preparations of the above examples.

TABLE 14

| | | | | Salt |
|---|---|---|---|---|
| Cpd # | Structure | Name | MS | Forms |
| 1 | | [4-({[2-amino-5-(2-thienyl)phenyl]amino}carbonyl)phenyl]methyl ethylmethylphosphonate | cal'd 431 (MH+), exp 431 (MH+) | Free base |
| 2 | | [4-({[2-amino-5-(2-thienyl)phenyl]amino}carbonyl)phenyl]methyl methylphenylphosphonate | cal'd 479 (MH+), exp 479 (MH+) | Free base |
| 3 | | N-[2-amino-5-(2-thienyl)phenyl]-4-({[(4R,5R)-4,5-dimethyl-2-oxido-1,3,2-dioxaphospholan-2-yl]oxy}methyl)benzamide | cal'd 459 (MH+), exp 459 (MH+) | Free base |
| 4 | | 4-({[2-amino-5-(2-thienyl)phenyl]amino}carbonyl)benzyl dimethylphosphate | cal'd 433 (MH+), exp 433 (MH+) | Free base |

TABLE 14-continued

M; Alkyloxy Phosphonates/Phosphinates/Phosphates

| Cpd # | Structure | Name | MS | Salt Forms |
|---|---|---|---|---|
| 5 | 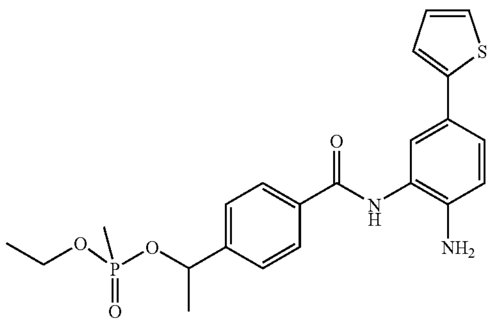 | 1-[4-({[2-amino-5-(2-thienyl)phenyl]amino}carbonyl)phenyl]ethyl ethyl methylphosphonate | cal'd 445 (MH+), exp 445 (MH+) | Free base |
| 6 | 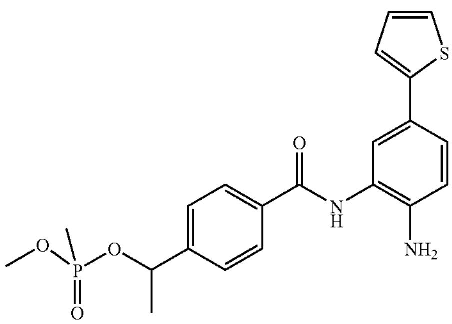 | 1-[4-({[2-amino-5-(2-thienyl)phenyl]amino}carbonyl)phenyl]ethyl methyl methylphosphonate | cal'd 431 (MH+), exp 431 (MH+) | Free base |
| 7 | 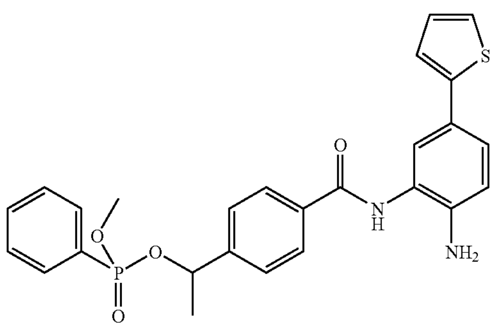 | 1-[4-({[2-amino-5-(2-thienyl)phenyl]amino}carbonyl)phenyl]ethyl methyl phenylphosphonate | cal'd 493 (MH+), exp 493 (MH+) | Free base |
| 8 | 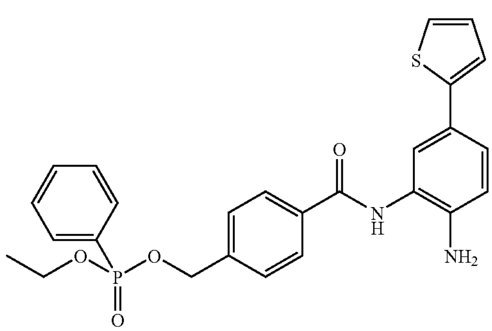 | 4-({[2-amino-5-(2-thienyl)phenyl]amino}carbonyl)benzyl ethylphenylphosphonate | cal'd 493 (MH+), exp 493 (MH+) | Free base |

TABLE 14-continued

M; Alkyloxy Phosphonates/Phosphinates/Phosphates

| Cpd # | Structure | Name | MS | Salt Forms |
|---|---|---|---|---|
| 9 | 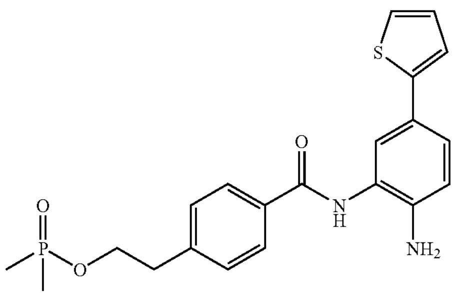 | 2-[4-({[2-amino-5-(2-thienyl)phenyl]amino}carbonyl)phenyl]ethyl dimethylphosphinate | cal'd 415 (MH+), exp 415 (MH+) | Free base |
| 10 | 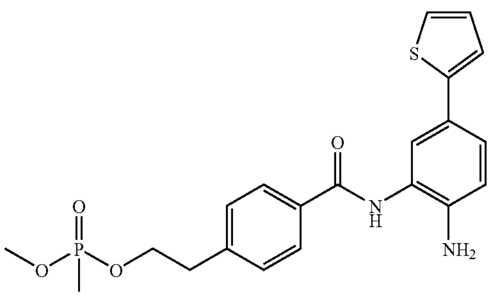 | 2-[4-({[2-amino-5-(2-thienyl)phenyl]amino}carbonyl)phenyl]ethyl methyl methylphosphonate | cal'd 431 (MH+), exp 431 (MH+) | Free base |
| 11 | 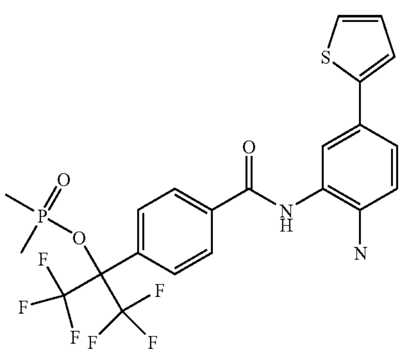 | 1-[4-({[2-amino-5-(2-thienyl)phenyl]amino}carbonyl)phenyl]-2,2,2-trifluoro-1-(trifluoromethyl)ethyl dimethylphosphinate | cal'd 537 (MH+), exp 537 (MH+) | Free base |
| 12 | 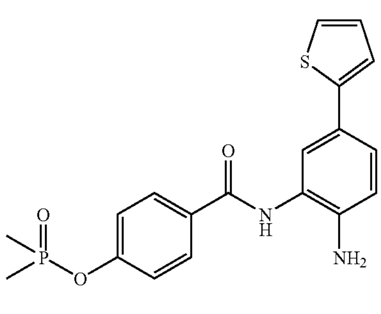 | 4-({[2-amino-5-(2-thienyl)phenyl]amino}carbonyl)phenyl dimethylphosphinate | cal'd 387 (MH+), exp 387 (MH+) | Free base |

TABLE 14-continued

M; Alkyloxy Phosphonates/Phosphinates/Phosphates

| Cpd # | Structure | Name | MS | Salt Forms |
|---|---|---|---|---|
| 13 | 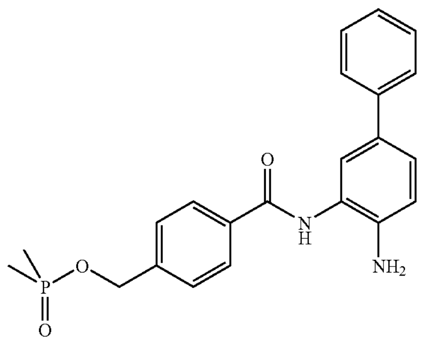 | (4-{[(4-aminobiphenyl-3-yl)amino]carbonyl}phenyl)methyldimethylphosphinate | cal'd 395 (MH+), exp 395 (MH+) | Free base |
| 14 | 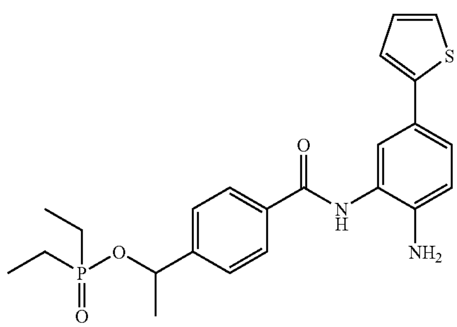 | 1-[4-({[2-amino-5-(2-thienyl)phenyl]amino}carbonyl)phenyl]ethyldiethylphosphinate | cal'd 443 (MH+), exp 443 (MH+) | Free base |
| 15 | 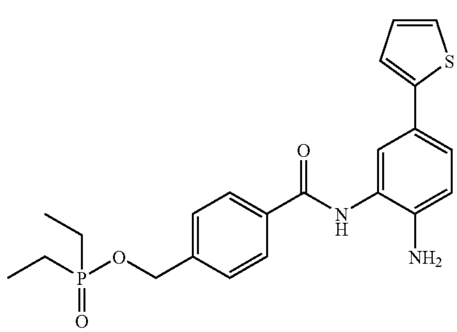 | 4-({[2-amino-5-(2-thienyl)phenyl]amino}carbonyl)benzyldiethylphosphinate | cal'd 429 (MH+), exp 429 (MH+) | Free base |
| 16 | 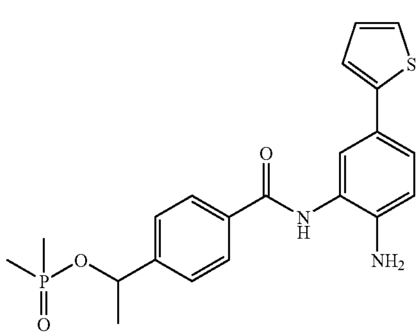 | 1-[4-({[2-amino-5-(2-thienyl)phenyl]amino}carbonyl)phenyl]ethyldimethyl phosphinate | cal'd 415 (MH+), exp 415 (MH+) | Free base |

TABLE 14-continued

M: Alkyloxy Phosphonates/Phosphinates/Phosphates

| Cpd # | Structure | Name | MS | Salt Forms |
|---|---|---|---|---|
| 17 | 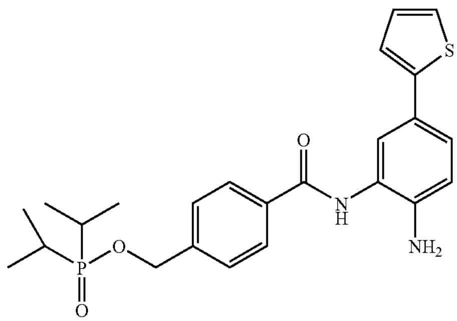 | 4-({[2-amino-5-(2-thienyl)phenyl]amino}carbonyl)benzyldiisopropylphosphinate | cal'd 457 (MH+), exp 457 (MH+) | Free base |
| 18 | 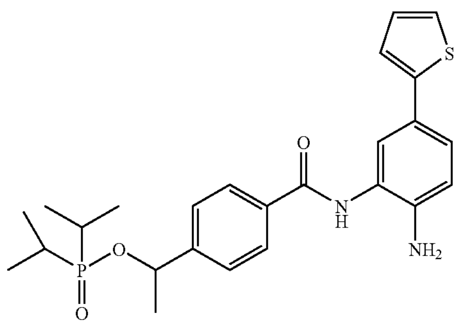 | 1-[4-({[2-amino-5-(2-thienyl)phenyl]amino}carbonyl)phenyl]ethyldiisopropylphosphinate | cal'd 471 (MH+), exp 471 (MH+) | Free base |

Producedures for N. Preparation of Benzylamino Phosphonamides/Phosphinamides/Phosphoramides.

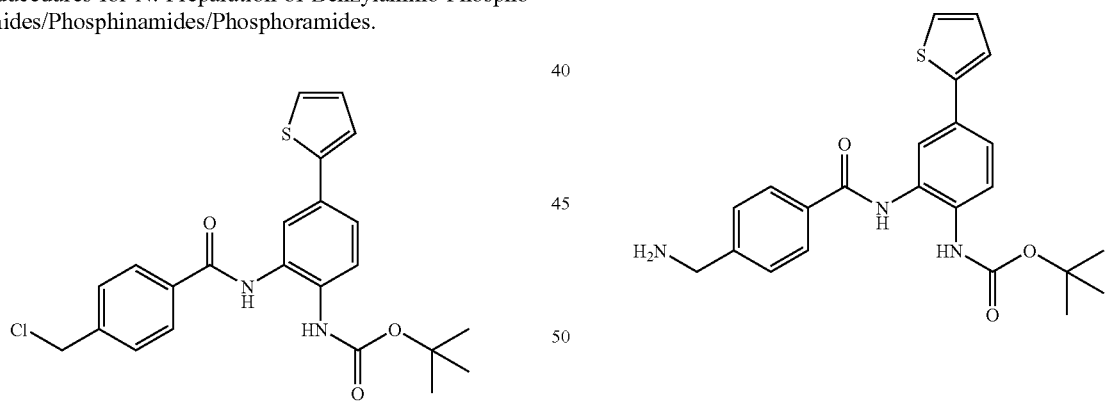

Tert-butyl [2-{[4-(chloromethyl)benzoyl]amino}-4-(2-thienyl)phenyl]carbamate. 4-(chloromethyl)benzoyl chloride (2 g, 10.58 mmol) was dissolved in THF (20 mL) and a solution of tert-butyl [2-amino-4-(2-thienyl)phenyl]carbamate (3.38 g, 11.64 mmol) and DIPEA (2.033 mL, 11.64 mmol) in THF (50 mL) was added dropwise at room temperature. After stirring for 1 hour, saturated NaHCO$_3$ was added and the products extracted into EtOAc (×2). The combined organic extracts were dried over MgSO$_4$ and concentrated in vacuo. The residue was triturated in EtOAc to give tert-butyl [2-{[4-(chloromethyl)benzoyl]amino}-4-(2-thienyl)phenyl] carbamate as a beige powder.

Tert-butyl [2-{[4-(aminomethyl)benzoyl]amino}(2-thienyl)phenyl]carbamate. Tert-butyl [2-({4-[(1,3-dioxo-1,3-dihydro-2H-isoindol-2-yl)methyl]benzoyl}amino)-4-(2-thienyl)phenyl]carbamate (4.4 g, 7.95 mmol) and hydrazine (0.495 mL, 15.90 mmol) were stirred in refluxing EtOH (35 mL) for 5 hours. Room temperature was attained and the white precipitate removed by filtration and washed with EtOH. The filtrate was concentrated in vacuo and purified by MPLC (1-12.5% [MeOH+1% NH$_4$OH]-DCM) to give tert-butyl [2-{[4-(aminomethyl)benzoyl]amino}-4-(2-thienyl)phenyl]carbamate as a white solid.

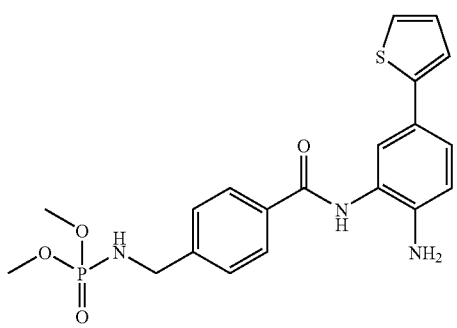

Dimethyl [4-({[2-amino-5-(2-thienyl)phenyl]amino}carbonyl)benzyl]amidophosphate. Tert-butyl [2-{[4-(aminomethyl)benzoyl]amino}-4(2-thienyl)phenyl]carbamate (60 mg, 0.14 mmol) was made 0.25 M in anhydrous DCM and to this stirring solution was added DIPEA (55 mg, 0.42 mmol), followed by dimethyl phosphochloridate (41 mg, 0.28 mmol). The resulting mixture was stirred at ambient temperature for 16 h. The mixture was diluted with 0.5 mL TFA and stirred for 1 h. The mixture was then diluted with EtOAc and carefully quenched with saturated aqueous sodium bicarbonate. The organic layer was washed again with saturated aqueous sodium bicarbonate, then dried (MgSO$_4$) and concentrated in vacuo. The residue was purified by MPLC (0-8% MeOH in CH$_2$Cl$_2$). Pure fractions were identified, combined, and concentrated to afford the title compound. $^1$H NMR (CDCl$_3$-d$_1$, 600 MHz) δ 8.1 (s, 1H), 7.91 (d, J=8.4 Hz, 2H), 7.56 (s, 1H), 7.43 (d, J=7.2 Hz, 2H), 7.34 (dd, J=8.4 Hz, J=1.8 Hz, 2H), 7.19-7.15 (m, 2H), 7.03-7.00 (m, 1H), 6.84 (d J=8.4 Hz, 1H), 4.18-4.13 (m, 2H), 3.71 (d, J=11.4 Hz, 2H), 4.01 (br-s, 2H), 3.08-3.02 (m, 1H). MS: cal'd 432 (MH+), exp 432 (MH+).

Additional analogs were prepared in procedures similar to those described for the preparations of the above examples.

TABLE 15

N; Benzylamino Phosphonamides/Phosphinamides/Phosphoramides

| Cpd # | Structure | Name | MS | Salt Forms |
|---|---|---|---|---|
| 1 | 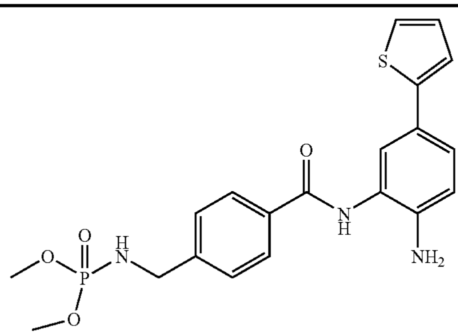 | dimethyl [4-({[2-amino-5-(2-thienyl)phenyl]amino}carbonyl)benzyl]amidophosphate | cal'd 432 (MH+), exp 432 (MH+) | Free base |
| 2 | 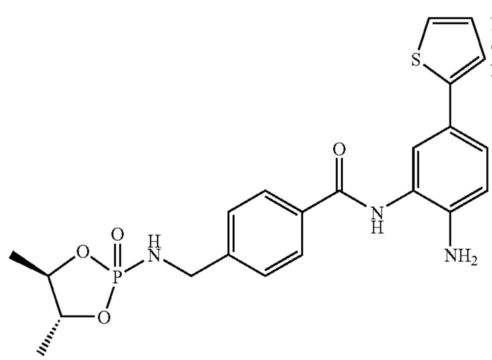 | N-[2-amino-5-(2-thienyl)phenyl]-4-({[(4R,5R)-4,5-dimethyl-2-oxido-1,3,2-dioxaphospholan-2-yl]amino}methyl)benzamide | cal'd 458 (MH+), exp 458 (MH+) | Free base |
| 3 | 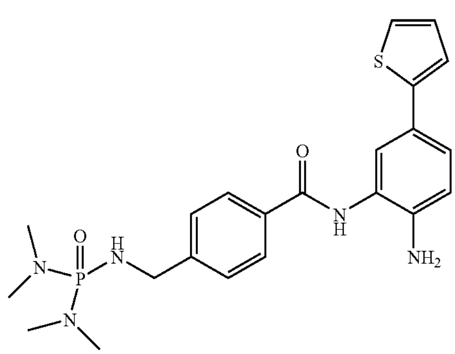 | N-[2-amino-5-(2-thienyl)phenyl]-4-({[bis(dimethylamino)phosphoryl]amino}methyl)benzamide | cal'd 458 (MH+), exp 458 (MH+) | Free base |

Procedures for O. Preparation of Alkylamino Phosphonamide/Phosphinamide/Phosphoramides.

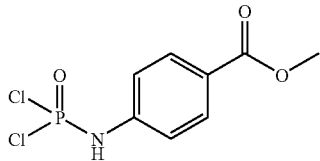

Methyl 4-[(dichlorophosphoryl)amino]benzoate. A suspension of methyl 4-amino benzoate (3.04 g, 19.85 mmol) in phosphorous oxychloride (3.00 g, 19.85 mmol) was heated to 120° C. and stirred for 2 hours. The reaction mixture was cooled to ambient temperature. The solid was filtered and rinsed with pentane. The solid was dried in vacuo to afford the requisite product.

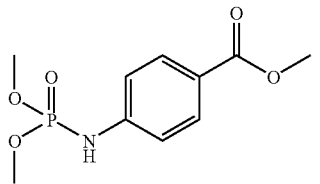

Methyl 4-[(dimethoxyphosphoryl)amino]benzoate. Methyl 4-[(dichlorophosphoryl)amino]benzoate (2.50 g, 9.33 mmol) was made 0.33 M in anhydrous methanol and stirred at ambient temperature for 16 h. The reaction mixture was concentrated in vacuo to afford the requisite product. MS: cal'd 260 (MH+), exp 260 (MH+)

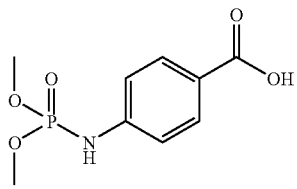

4-[(Dimethoxyphosphoryl)amino]benzoic acid. Methyl 4-[(dimethoxyphosphoryl)amino]benzoate (1.50 g, 5.79 mmol) was made 0.25 M in dioxane and to this stirring solution was added 3M aq LiOH. The resulting solution was stirred at ambient temperature for 16 h. The reaction mixture was then neutralized to pH=7 with 1N aq HCl and concentrated in vacuo to afford the requisite product. MS: cal'd 243 (MH+), exp 243 (MH+)

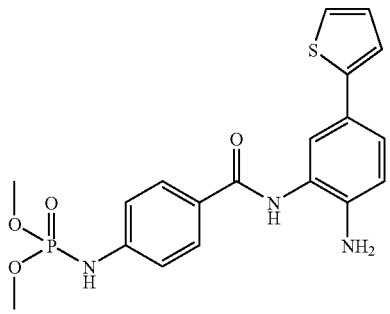

Dimethyl [4-({[2-amino-5-(2-thienyl)phenyl]amino}carbonyl)phenyl]amidophosphate. 4-[(Dimethoxyphosphoryl)amino]benzoic acid (100 mg, 0.41 mmol), 2-amino-4-thiophen-2-yl-phenyl)-carbamic acid tert-butyl ester (142 mg, 0.49 mmol), EDC (94 mg, 0.49 mmol), HOBT (75 mg, 0.49 mmol), and DIPEA (158 mg, 1.22 mmol) were combined and diluted with DMF (1.6 mL). The resulting mixture was stirred at ambient temperature for 18 hours. The reaction mixture was diluted with water and extracted with EtOAc (2×). The combined organic layers were washed again with water (2×) then dried (MgSO$_4$) and concentrated in vacuo. The residue was purified by MPLC (0-8% MeOH in CH$_2$Cl$_2$). Pure fractions were identified, combined, then concentrated in vacuo. The residue was diluted with 2:1 DCM: TFA and stirred at ambient temperature for 1 h. The mixture was then carefully quenched with sat aq sodium bicarbonate and extracted with EtOAc. The organic layer was dried (MgSO$_4$) and concentrated in vacuo to afford the title compound: MS: cal'd 418 (MH+), exp 418 (MH+). $^1$H NMR (DMSO-d, 600 MHz) δ 9.52 (s, 1H), 8.46 (d, J=9.1 Hz, 1H), 7.87 (d, J=8.2 Hz, 2H), 7.42 (s, 1H), 7.33 (d, J=5.0 Hz, 1H), 7.26 (d, J=8.2 Hz, 1H), 7.21 (d, J=3.5 Hz, 1H), 7.08 (d, J=8.5 Hz, 2H), 7.03-7.01 (m, 1H), 6.78 (d, J=8.2 Hz, 1H), 5.09 (s, 2H), 3.65 (d, J=11.2 Hz, 6H). MS: cal'd 418 (MH+), exp 418 (MH+).

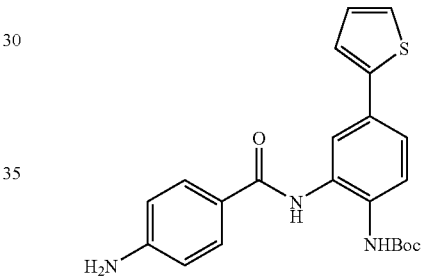

tert-butyl [2-[(4-aminobenzoyl)amino]-4-(2-thienyl)phenyl]carbamate. To a solution of 4-nitrobenzoyl chloride (320 mg, 1.72 mmol) in pyridine (5.0 mL) was added tert-butyl [2-amino-4-(2-thienyl)phenyl]carbamate (500 mg, 1.72 mmol). The reaction mixture was allowed to stir at room temperature for 1 hour. The crude reaction mixture was diluted with EtOAc (20 mL) and washed with 2M HCl (10 mL), 2M NaOH (10 mL) and sat.'d aq. NaHCO$_3$ (1×10 mL). The organic layer was dried over MgSO$_4$, filtered, and concentrated in vacuo and gave the desired tert-butyl[2-[2-(4-nitrobenzoyl)amino]-4-(2-thienyl)phenyl]carbamate which was confirmed by MS: cal'd 462.1 (MHNa+), exp 462.1 (Ma+).

To a solution of tert-butyl [2-[(4-nitrobenzoyl)amino]-4-(2-thienyl)phenyl]carbamate (598 mg, 1.36 mmol) in 1:1 EtOAc/THF was added 10 mol % Pd/C (136 mg, 1.36 mmol). The reaction mixture was evacuated and refilled with hydrogen (2×). The black reaction mixture was stirred in a parr shaker under 50 psi of hydrogen overnight. The mixture was filtered through a pad of celite (with EtOAc then CH$_2$Cl$_2$ washes) and concentrated to provide tert-butyl [2-[(4-aminobenzoyl)amino]-4-(2-thienyl)phenyl]carbamate which was confirmed by MS: cal'd 410.1 (MH+), exp 410.1 (MH+).

TABLE 16

| | | | | Salt |
|---|---|---|---|---|
| Cpd # | Structure | Name | MS | Forms |
| 1 | | dimethyl [4-({[2-amino-5-(2-thienyl)phenyl]amino}carbonyl)phenyl]amidophosphate | cal'd 418 (MH+), exp 418 | Free base |
| 2 | | diethyl [4-({[2-amino-5-(2-thienyl)phenyl]amino}carbonyl)phenyl]amidophosphate | cal'd 446 (MH+), exp 446 | Free base |
| 3 | | dimethyl [4-({[2-amino-5-(2-thienyl)phenyl]amino}carbonyl)phenyl]amidophosphate | cal'd 412 (MH+), exp 412 | Free base |
| 4 | | dimethyl [4-({[2-amino-5-(2-thienyl)phenyl]amino}carbonyl)phenyl]methylamidophosphate | cal'd 432 (MH+), exp 432 | Free base |

TABLE 16-continued

O; Anilino phosphonates

| Cpd # | Structure | Name | MS | Salt Forms |
|---|---|---|---|---|
| 5 | 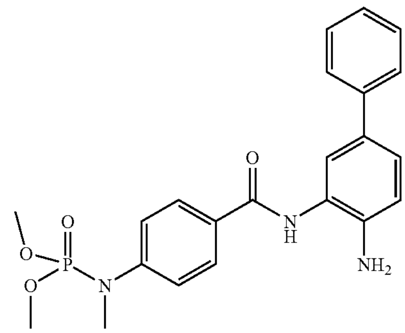 | dimethyl (4-{[(4-aminobiphenyl-3-yl)amino]carbonyl}phenyl)methylamidophosphate | cal'd 426 (MH+), exp 426 | Free base |
| 6. | 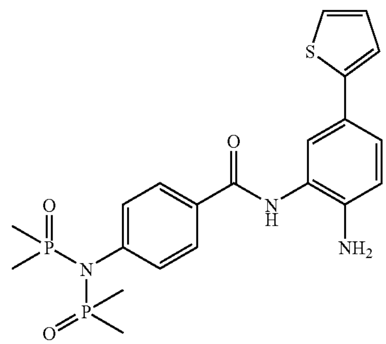 | N-[2-amino-5-(2-thienyl)phenyl]-4-[bis(dimethylphosphoryl)amino]benzamide | cal'd 462 (MH+), exp 462 | Free base |

Procedures for P. Preparation of Alkylamino Phosphorus containing Carbamates/Ureas.

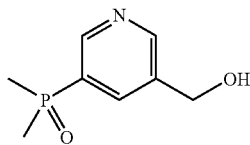

[5-(dimethylphosphoryl)pyridin-3-yl]methanol. Tert-butyldimethylsilyl trifluoromethanesulfonate (1.174 ml, 5.11 mmol) was added to 2,6-lutidine (0.743 ml, 6.38 mmol) and (5-bromopyridin-3-yl)methanol (800 mg, 4.25 mmol) stirred in CH$_2$Cl$_2$ (10 ml) cooled to 0° C. and the mixture was stirred at 0° C. for 1 h. Saturated aqueous sodium hydrogen carbonate was added to the reaction mixture and the mixture was extracted with ethyl acetate. The combined organic fractions were dried (Na$_2$SO$_4$), filtered and the solvent was evaporated under reduced pressure. The residue was purified by column chromatography to provide 3-bromo-5-({[tertbutyl(dimethyl)silyl]oxy}methyl)pyridine: MS: cal'd 325 (MNa+), exp 325 (MNa+).

3-bromo-5-({[tertbutyl(dimethyl)silyl]oxy}methyl)pyridine (600 mg, 1.985 mmol) was dissolved in THF (2 ml) and then cooled to −100° C. (LN$_2$/Et$_2$O). BuLi (0.834 ml, 2.084 mmol) was then added slowly. The reaction mixture was then stirred at −100° C. for 15 minute. Dimethylphosphinic chloride (246 mg, 2.183 mmol) was then added to the reaction and the mixture was stirred as the temperature slowly rose over the course of one hour. After which time, the bath temp was −40° C. At this point, the bath was removed and the clear, pale yellow reaction mixture continued to stir as it warmed to RT. The mixture was then poured into a separatory funnel containing saturated NaHCO$_3$ solution and Et$_2$O. The mixture was extracted with Et$_2$O (3×). The combined organic layers were then washed with brine, dried over Na$_2$SO$_4$ and concentrated in vacuo. Purification of the crude reaction mixture by HPLC provided: 3-({[tert-butyl(dimethyl)silyl]oxy}methyl)-5-(dimethylphosphoryl)pyridine: MS: cal'd 300 (MH+), exp 300 (MH+).

Acetyl chloride (0.044 ml, 0.625 mmol) was added to 3-({[tert-butyl(dimethyl)silyl]oxy}methyl)-5-(dimethylphosphoryl)pyridine (170 mg, 0.568 mmol) stirred in MeOH (1 ml) at 0° C. and the mixture was stirred at 0° C. for 1 h. The reaction was concentrated and left on high vac pump to dry. [5-(dimethylphosphoryl)pyridin-3-yl]methanol was taken on to next reaction crude. MS: cal'd 186 (MH+), exp 186 (MH+).

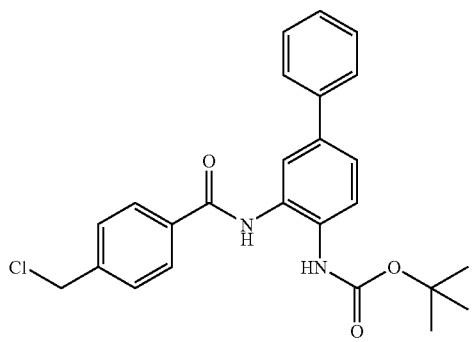

1,1-dimethylethyl [3-({[4-(chloromethyl)phenyl]carbonyl}amino)biphenyl-4-yl]carbamate. 4-(chloromethyl)benzoyl chloride (12 g, 63.5 mmol) was dissolved in THF (120 mL) and a solution of 1,1-dimethylethyl (3-aminobiphenyl-4-yl)carbamate (19.86 g, 69.8 mmol) and DIPEA (12.2 mL, 69.8 mmol) in THF (300 mL) was added dropwise at room temperature. After stirring for 1 hour, saturated NaHCO₃ was added and the products extracted into EtOAc (×2). The combined organic extracts were dried over MgSO₄ and concentrated in vacuo. The residue was triturated in Et₂O to give 1,1-dimethylethyl [3-({[4-(chloromethyl)phenyl]carbonyl}amino)biphenyl-4-yl]carbamate as a white solid. ¹H NMR (d6-DMSO, 600 MHz) δ 9.92 (s, 1H), 8.75 (s, 1H), 7.97 (d, J=8.4 Hz, 2H), 7.83 (s, 1H), 7.63 (m, 3H), 7.59 (d, J=8.4 Hz, 2H), 7.50 (dd, J=8.4 and 1.8 Hz, 1H), 7.44 (t, J=7.2 Hz, 2H), 7.33 (t, J=7.2 Hz, 1H), 4.84 (s, 2H), 1.44 (s, 9H).

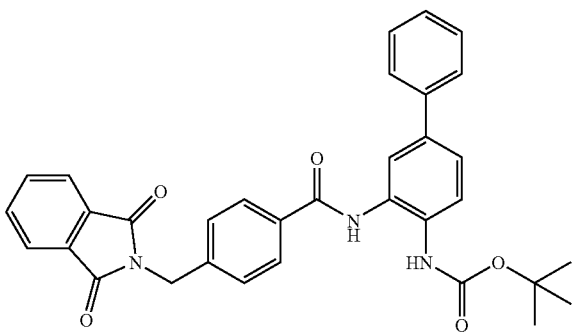

1,1-dimethylethyl {3-[({4-[(1,3-dioxo-1,3-dihydro-2H-isoindol-2-yl)methyl]phenyl}carbonyl)amino]biphenylyl}carbamate. 1,1-dimethylethyl [3-({[4-(chloromethyl)phenyl]carbonyl}amino)biphenyl-4-yl]carbamate (20 g, 45.8 mmol), potassium phthalimide (9.33 g, 50.4 mmol) and potassium iodide (1.52 g, 9.15 mmol) were stirred in DMF (81 mL) at 50° C. overnight. Room temperature was attained, H₂O was added and the products extracted into EtOAc (×2). The combined organic extracts were washed with brine, dried over MgSO₄ and concentrated in vacuo. The residue was triturated in MeOH to give 1,1-dimethylethyl {3-[({4-[(1,3-dioxo-1,3-dihydro-2H-isoindol-2-yl)methyl]phenyl}carbonyl)amino]biphenyl-4-yl}carbamate as a pale yellow solid.

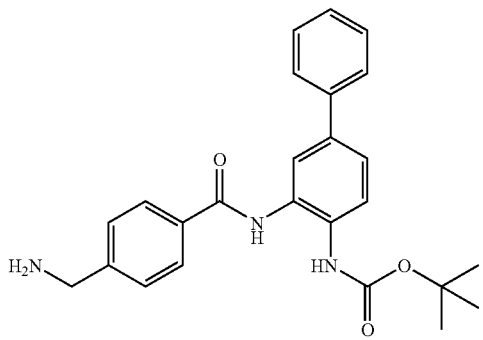

1,1-dimethylethyl [3-({[4-(aminomethyl)phenyl]carbonyl}amino)biphenyl-4-yl]carbamate. 1,1-dimethylethyl {3-[({4-[(1,3-dioxo-1,3-dihydro-2H-isoindol-2-yl)methyl]phenyl}carbonyl)amino]biphenyl-4-yl}carbamate (17 g, 31 mmol) and hydrazine hydrate (3.01 mL, 62.1 mmol) were stirred in refluxing EtOH (135 mL) for 5 hours. Room temperature was attained and the white precipitate removed by filtration and washed with EtOH. The filtrate was concentrated in vacuo and purified by MPLC (10% [MeOH+1% NH₄OH]-DCM) to give 1,1-dimethylethyl [3-({[4-(aminomethyl)phenyl]carbonyl}amino)biphenyl-4-yl]carbamate as a white solid. ¹H NMR (d6-DMSO, 600 MHz) δ 9.86 (s, 1H), 8.77 (s, 1H), 7.90 (d, J=7.8 Hz, 2H), 7.85 (d, J=1.8 Hz, 1H), 7.62 (m, 3H), 7.49 (m, 3H), 7.44 (t, J=7.5 Hz, 2H), 7.33 (t, J=7.5 Hz, 1H), 3.79 (s, 2H), 1.45 (s, 9H).

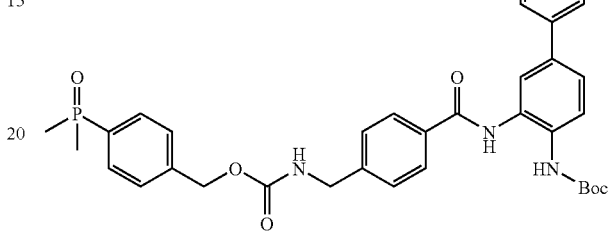

4-(Dimethylphosphoryl)benzyl(4-{[(4-aminobiphenyl-3-yl)amino]carbonyl}benzyl) carbamate. A solution of CDI (117 mg, 0.722 mmol) in dry THF (5 mL) was treated with a solution of [4-(dimethylphosphoryl)phenyl]methanol (133 mg, 0.722 mmol) in DMSO (2 mL) and THF (1 mL) dropwise. The resulting solution was stirred for 1 h and then added dropwise over 5 min. to a solution of 1,1-dimethylethyl [3-({[4-(aminomethyl)phenyl]carbonyl}amino) biphenyl-4-yl]carbamate (301 mg, 0.722 mmol), Et₃N (101 μL, 0.722 mmol) and DBU (109 μL, 0.722 mmol) in dry THF (5 mL). The reaction mixture was stirred at RT overnight. The reaction mixture was concentrated in vacuo, diluted with EtOAc, washed with H₂O, 0.5 N HCl, dried (MgSO₄), filtered and the solvent was evaporated under reduced pressure. The residue was purified by column chromatography on silica gel, eluting with CHCl₃/MeOH (2.5% to 20%) to give a glassy yellow solid. ¹H NMR (CDCl₃, 600 MHz) δ 9.28 (br s, 1H), 8.02 (s, 1H), 7.90 (d, J=8.0 Hz, 2H), 7.75-7.67 (m, 2H), 7.59 (d, J=8.0 Hz, 2H), 7.50-7.46 (m, 2H), 7.42-7.35 (m, 4H), 7.34-7.29 (m, 1H), 7.27 (d, J=8.0 Hz, 2H), 6.98 (s, 1H), 5.49 (br s, 1H), 5.18 (s, 2H), 4.41 (d, J=6.0 Hz, 2H), 1.71 (dd. J=12.9, 3.8 Hz, 6H). MS: cal'd 628 (MH+), exp 628 (MH+).

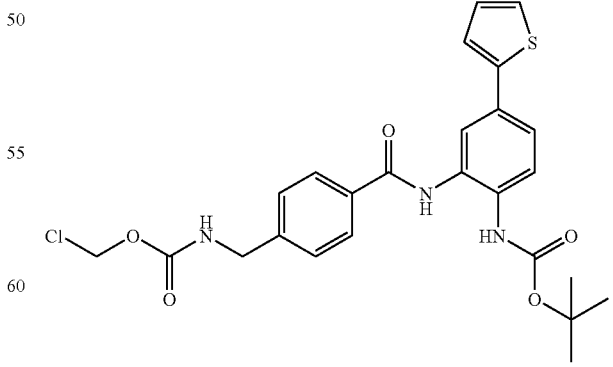

Chloromethyl [4-({[2-[(tert-butoxycarbonyl)amino]-5-(2-thienyl)phenyl]amino}carbonyl)benzyl]carbamate. tert-butyl [2-{[4-(aminomethyl)benzoyl]amino}-4-(2-thienyl)phenyl]carbamate (2.0 g, 4.72 mmol) was suspended in dichloromethane (50 ml). Hunig's Base (1 ml, 5.73 mmol) was added. The solution was cooled to 0° C. Chlorocarbonic acid chloromethyl ester (0.5 ml, 5.68 mmol) was added slowly. The reaction was stirred for approximately 1-2 h. The mixture, while cold, was diluted with dichloromethane and washed with saturated aqueous sodium bicarbonate. The aqueous layer was extracted three times with dichloromethane. The combined organic layers were dried over $Na_2SO_4$, filtered, and the solvent was evaporated under reduced pressure. The residue was purified by column chromatography on silica gel eluting with EtOAc/hexane. MS: calc'd 417 (MH+-Boc), exp 417 (MH+-Boc).

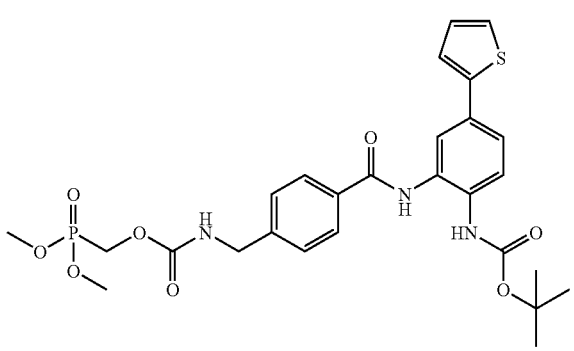

Dimethyl {[({[4-({[2-[(tert-butoxycarbonyl)amino]-5-(2-thienyl)phenyl]amino}carbonyl)benzyl]amino}carbonyl)oxy]methyl}phosphonate. Chloromethyl [4-({[2-[(tert-butoxycarbonyl)amino]-5-(2-thienyl)phenyl]amino}carbonyl)benzyl]carbamate (0.96 g, 1.860 mmol) and trimethyl phosphite (1 ml, 8.48 mmol) were combined in a microwave vial. The vial was capped and the reaction was allowed to heat for 3.5 hours at 100° C. The reaction was cooled and diluted with dichloromethane. The residue was purified by column chromatography on silica gel eluting with EtOAc/hexane. MS: calc'd 490 (MH+-Boc), exp 490 (MH+-Boc).

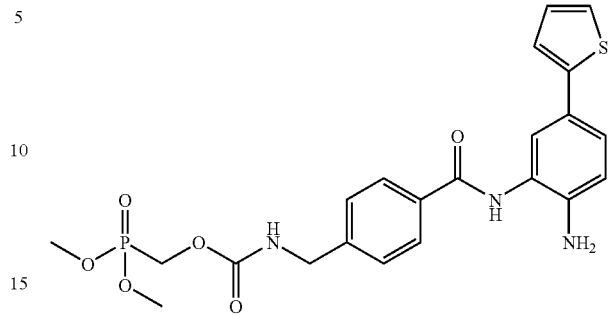

Dimethyl {[({[4-({[2-amino-5-(2-thienyl)phenyl]amino}carbonyl)benzyl]amino}carbonyl) oxy]methyl}phosphonate. Dimethyl {[({[4-({[2-[(tert-butoxycarbonyl)amino]-5-(2-thienyl)phenyl]amino}carbonyl)benzyl]amino}carbonyl)oxy]methyl}phosphonate 0.496 g, 0.841 mmol) was dissolved in DCM (4 ml). TFA (1 ml, 12.98 mmol) was added. The reaction was allowed to stir for ~1 h 15 min. The reaction was diluted with DCM and washed with saturated aqueous sodium hydrogen carbonate. The aqueous layer was extracted three times with DCM. The combined organic layers were dried over $Na_2SO_4$, filtered, and concentrated. $^1$H NMR (DMSO-$d_6$, 600 MHz) δ 9.67 (s, 1H), 8.13 (t, J=6.3 Hz, 1H), 7.93 (d, J=7.9 Hz, 2H), 7.44 (bs, 1H), 7.35 (d, J=7.9 Hz, 2H), 7.32 (dd, J=5.1 Hz, 1.0 Hz, 1H), 7.26 (dd, J=8.4 Hz, 2.2 Hz, 1H), 7.21 (d, J=3.1 Hz, 1H), 7.01 (dd, J=5.1 Hz, 3.7 Hz, 1 H), 6.77 (d, J=8.2 Hz, 1H), 5.11 (s, 2H), 4.39 (d, J=7.9 Hz, 2H), 4.25 (d, J=6.2 Hz, 2H), 3.66 (d, J=10.6 Hz, 6H). MS: calc'd 490 (MH+), exp 490 (MH+).

Additional analogs were prepared in procedures similar to those described for the preparations of the above examples.

TABLE 17

P; Alkylamino Phosphorus containing Carbamates/Ureas

| Cpd # | Structure | Name | MS | Salt Forms |
|---|---|---|---|---|
| 1 | 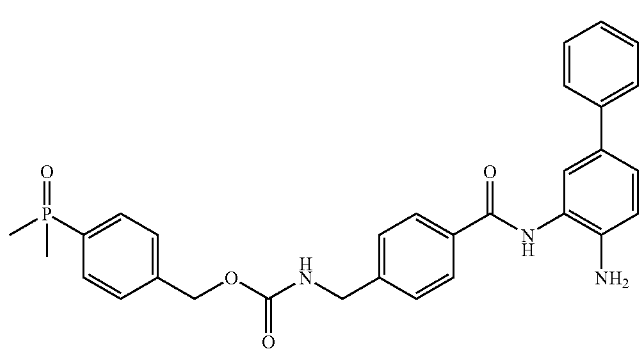 | 4-(dimethylphosphoryl)benzyl (4-{[(4-aminobiphenyl-3-yl)amino]carbonyl}benzyl)carbamate | cal'd 528 (MH+), exp 528 | Free base |

TABLE 17-continued

P; Alkylamino Phosphorus containing Carbamates/Ureas

| Cpd # | Structure | Name | MS | Salt Forms |
|---|---|---|---|---|
| 2 | 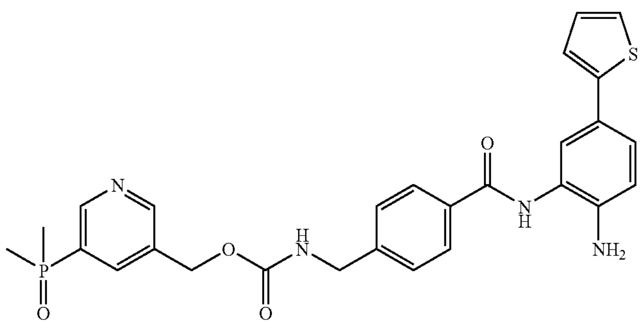 | [5-(dimethylphosphoryl)pyridin-3-yl]methyl[4-({[2-amino-5-(2-thienyl)phenyl]amino}carbonyl)benzyl]carbamate | cal'd 535 (MH+), exp 535 | Free base |
| 3 | 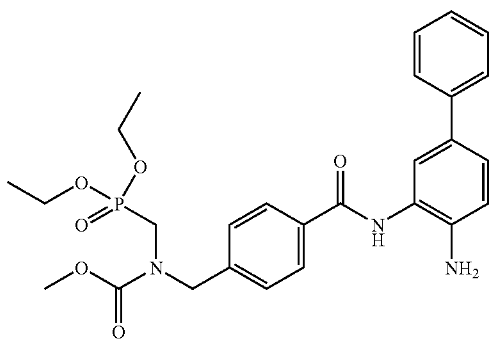 | Diethyl ({[(4-{[(4-aminobiphenyl-3-yl)amino]carbonyl}phenyl)methyl][(methyloxy)carbonyl]amino}methyl)phosphonate | cal'd 526 (MH+), exp 526 | Free base |
| 4 | 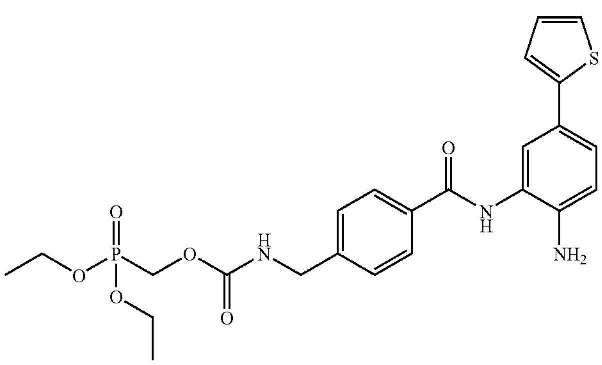 | Diethyl {[({[4-({[2-amino-5-(2-thienyl)phenyl]amino}carbonyl)benzyl]amino}carbonyl)oxy]methyl}phosphonate | cal'd 518 (MH+), exp 518 | Free base |
| 5 | 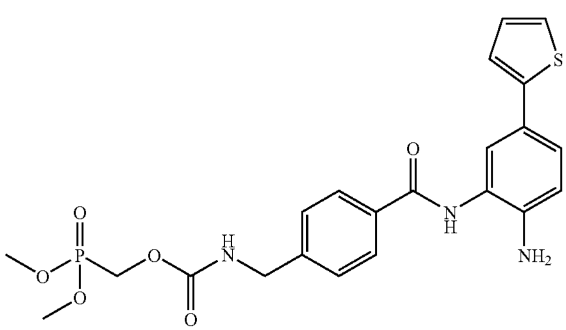 | Dimethyl {[({[4-({[2-amino-5-(2-thienyl)phenyl]amino}carbonyl)benzyl]amino}carbonyl)oxy]methyl}phosphinate | cal'd 490 (MH+), exp 490 | Free base |

TABLE 17-continued

P; Alkylamino Phosphorus containing Carbamates/Ureas

| Cpd # | Structure | Name | MS | Salt Forms |
|---|---|---|---|---|
| 6 | 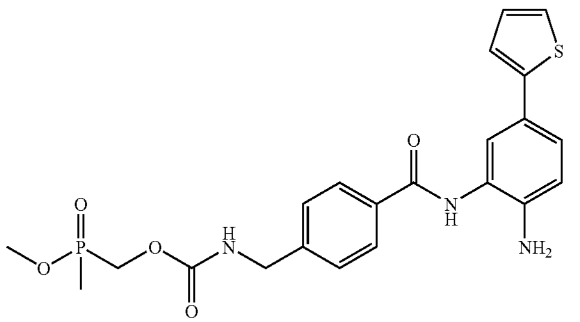 | Methyl {[({[4-({[2-amino-5-(2-thienyl)phenyl]amino}carbonyl)benzyl]amino}carbonyl)oxy]methyl} methylphosphinate | cal'd 474 (MH+), exp 474 | Free base |
| 7 | 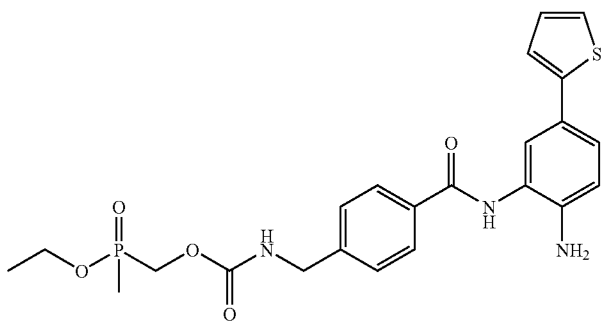 | Ethyl {[({[4-({[2-amino-5-(2-thienyl)phenyl]amino}carbonyl)benzyl]amino}carbonyl)oxy]methyl} methylphosphinate | cal'd 488 (MH+), exp 488 | Free base |
| 8 | 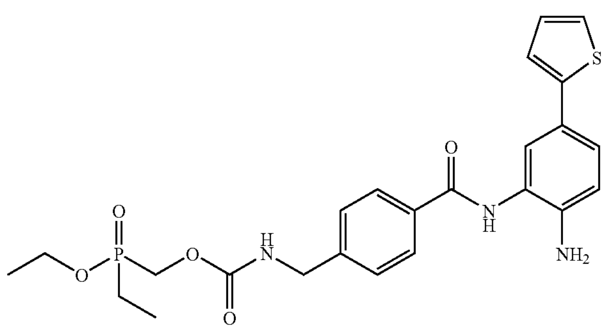 | Ethyl {[({[4-({[2-amino-5-(2-thienyl)phenyl]amino}carbonyl)benzyl]amino}carbonyl)oxy]methyl} ethylphosphinate | cal'd 502 (MH+), exp 502 | Free base |
| 9 | 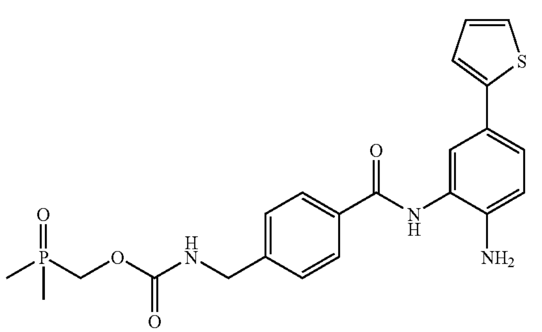 | (dimethylphosphoryl)methyl [4-({[2-amino-5-(2-thienyl)phenyl]amino}carbonyl)benzyl]carbamate | cal'd 458 (MH+), exp 458 | Free base |

Procedures for Q. Preparation of Amino Phosphorus Containing Amines and Amides.

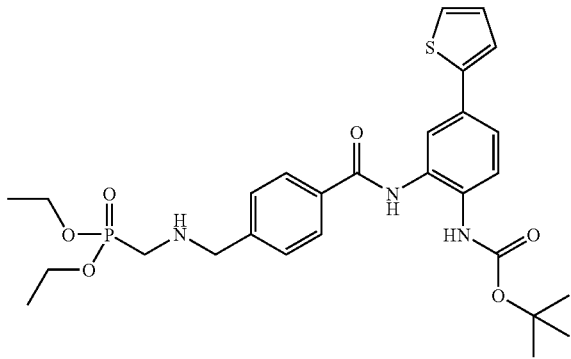

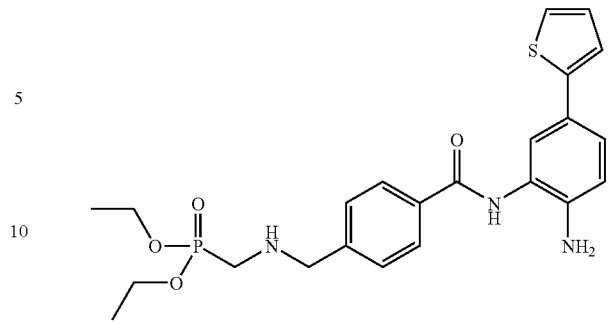

Diethyl [({[4-({[2-({[(1,1-dimethylethyl)oxy]carbonyl}amino)-5-(2-thienyl)phenyl]amino}carbonyl)phenyl]methyl}amino)methyl]phosphonate. 1,1-dimethylethyl [2-({[4-(bromomethyl)phenyl]carbonyl}amino)-4-(2-thienyl)phenyl]carbamate (500 mg, 1.026 mmol), diethyl (aminomethyl)phosphonate oxalate (791 mg, 3.08 mmol), and DIPEA (1.254 mL, 7.18 mmol) were stirred in DMF (6 mL) at 50° C. overnight. Room temperature was attained, H$_2$O: was added and the products extracted into EtOAc (×2). The combined organic extracts were washed with brine, dried over MgSO$_4$ and concentrated in vacuo. Purification of the residue by MPLC (0-10% MeOH-EtOAc) gave diethyl [({[4-({[2-({[(1,1-dimethylethyl)oxy]carbonyl}amino)-5-(2-thienyl)phenyl]amino}carbonyl)phenyl]methyl}amino)methyl]phosphonate as a colourless gum. MS: cal'd 574 (MH+), exp 574.

Diethyl [({[4-({[2-amino-5-(2-thienyl)phenyl]amino)carbonyl}phenyl]methyl}amino) methyl]phosphonate. diethyl [({[4-({[2-({[(1,1-dimethylethyl)oxy]carbonyl}amino)-5-(2-thienyl)phenyl]amino}carbonyl)phenyl]methyl}amino)methyl]phosphonate (360 mg, 0.628 mmol) was taken up in DCM (6 mL)/TFA (2 mL). After 4 hours at room temperature, the solvent was removed in vacuo, saturated NaHCO$_3$ was added and the products extracted into EtOAc (×2). The combined organic extracts were washed with brine, dried over Na$_2$SO$_4$ and concentrated in vacuo to give diethyl [({[4-({[2-amino-5-(2-thienyl)phenyl]amino}carbonyl}phenyl]methyl}amino)methyl]phosphonate as a beige solid. $^1$H NMR (DMSO-d$_6$, 600 MHz) δ 9.67 (s, 1H), 7.93 (d, J=8.4 Hz, 2H), 7.43 (m, 3H), 7.32 (dd, J=4.8 and 0.6 Hz, 1H), 7.26 (dd, J=8.4 and 1.8 Hz, 1H), 7.21 (m, 1H), 7.01 (dd, J=5.4 and 3.6 Hz, 1H), 6.78 (d, J=8.4 Hz, 1H), 5.12 (s, 2H), 3.99 (m, 4H), 3.81 (s, 2H), 2.81 (d, J=12.0 Hz, 2H), 2.40 (br s, 1H), 1.20 (t, J=7.2 Hz, 6H). MS: cal'd 474 (MH+), exp 474.

Additional Analogs were prepared in procedures similar to those described for the preparations of previous examples.

TABLE 18

Q; Amino Phosphorus Containing Amines and Amides

| Cpd # | Structure | Name | MS | Salt Forms |
|---|---|---|---|---|
| 1 | 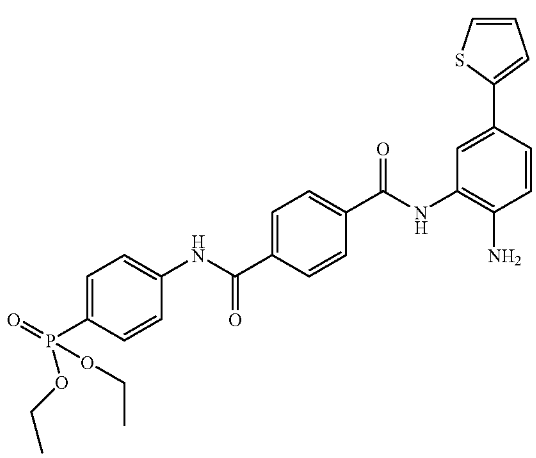 | Diethyl (4-{[4-({[2-amino-5-(2-thienyl)phenyl]amino}carbonyl)benzoyl]amino}phenyl)phosphonate | cal'd 550 (MH+), exp 550 | Free base |

TABLE 18-continued

Q: Amino Phosphorus Containing Amines and Amides

| Cpd # | Structure | Name | MS | Salt Forms |
|---|---|---|---|---|
| 2 | 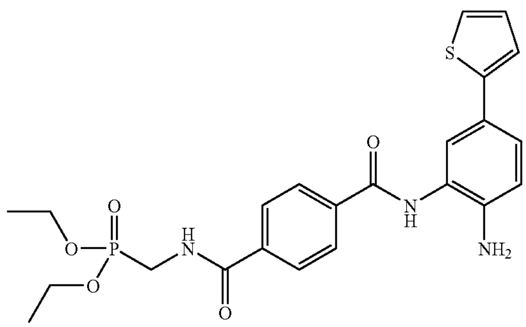 | Diethyl [({[4-({[2-amino-5-(2-thienyl)phenyl]amino}carbonyl)phenyl]carbonyl}amino)methyl]phosphonate | cal'd 488 (MH+), exp 488 | Free base |
| 3 | 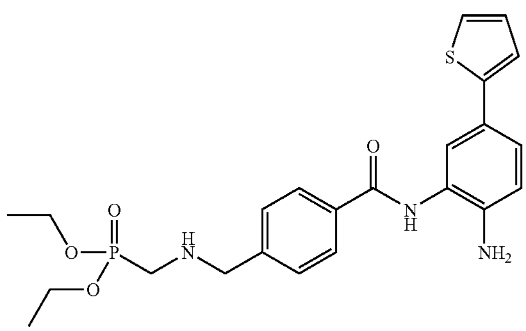 | Diethyl [({[4-({[2-amino-5-(2-thienyl)phenyl]amino}carbonyl)phenyl]methyl}amino)methyl]phosphonate | cal'd 474 (MH+), exp 474 | Free base |

Procedures for R. Preparation of Cyclic Phosphonates

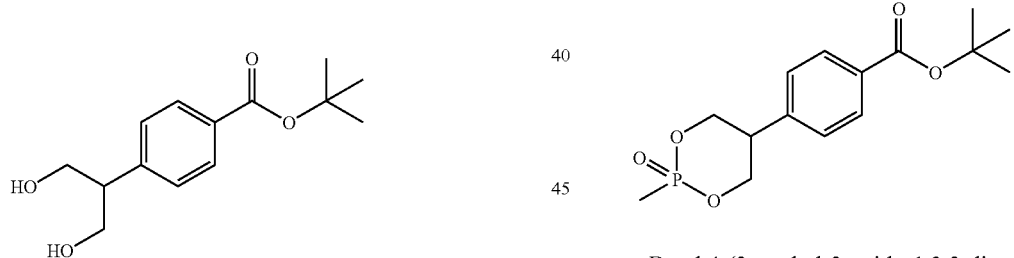

tert-Butyl 4-[2-hydroxy-1-(hydroxymethyl)ethyl]benzoate. To a solution of NaBH$_4$ (1.23 g, 32.4 mmol) in MeOH (20 ml) was added a solution of dimethyl [4-(tert-butoxycarbonyl)phenyl]malonate (2.00 g, 6.49 mmol) in 3:2 MeOH:THF (18 mL). The reaction was stirred at room temperature for 2 h. It was then quenched with saturated NH$_4$Cl and extracted with EtOAc (2×). The combined organic layers were washed with brine, dried (MgSO$_4$), and evaporated. Flash chromatography (0-10% MeOH/CH$_2$Cl$_2$) afforded tert-butyl 4-[2-hydroxy-1-(hydroxymethyl)ethyl]benzoate as a colorless solid. $^1$H NMR (CDCl$_3$, 600 MHz) δ 7.93 (d, J=8.4 Hz, 2H), 7.27 (d, J=8.2 Hz, 2H), 3.99 (ddd, J=10.8, 7.4, 5.1 Hz, 2H), 3.93 (dt, J=10.7, 5.2 Hz, 2H), 3.13 (tt, J=7.6, 5.5 Hz, 1H), 2.14 (t, J=5.3 Hz, 2H), 1.56 (s, 9H). MS: cal'd 275 (MH+), exp 275 (M)H+).

tert-Butyl 4-(2-methyl-2-oxido-1,3,2-dioxaphosphinan-5-yl)benzoate. tert-Butyl 4-[2-hydroxy-1-(hydroxymethyl)ethyl]benzoate (440 mg, 1.74 mmol) and TEA (510 µl, 3.66 mmol) were taken up in CH$_2$Cl$_2$ (20 mL) and cooled to 0° C. Methylphosphonic dichloride (193 µl, 2.09 mmol) in CH$_2$Cl$_2$ (10 mL) was added dropwise over 30 minutes. The reaction was then allowed to warm to room temperature and stirred for 1 h. The mixture was diluted with water and extracted with CH$_2$Cl$_2$ (2×). The combined organic layers were washed with brine, dried (MgSO$_4$), and evaporated. Flash chromatography (0-10% MeOH/CH$_2$Cl$_2$) allowed separation of residual starting material from the diastereomeric products, but the diastereomers coeluted. Flash chromatography of the mixed diastereomers with 25-100% EtOAc/hexanes slowly eluted the first diastereomer, and the same column was flushed with 2-10% MeOH/CH$_2$Cl$_2$ to push off the second diastereomer (both were obtained as colorless solids). $^1$H NMR (CDCl$_3$, 600 MHz) Diastereomer 1: δ 7.95 (d, J=8.5 Hz, 2H), 7.25 (d, J=8.5 Hz, 2H), 4.70-4.65 (m, 2H), 4.24-4.17 (m, 2H), 3.54-3.47 (m, 1H), 1.63 (d, J=18.0 Hz, 3H), 1.56 (s, 9H). Diastereomer 2: δ 7.97 (d, J=8.4 Hz, 2H), 7.31 (d, J=8.3 Hz, 2H), 4.66-4.59 (m, 2H), 4.36-4.30 (m, 2H), 3.50-3.45 (m, 1H), 1.62 (d, J=17-3 Hz, 3H), 1.57 (s, 9H). MS: cal'd 313 (MH+), exp 313 (MH+).

Analogs were prepared in procedures similar to those described for the preparations of the above examples.

TABLE 19

R; Cyclic Phosphonates

| Cpd # | Structure | Name | MS | Salt Forms |
|---|---|---|---|---|
| 1 | 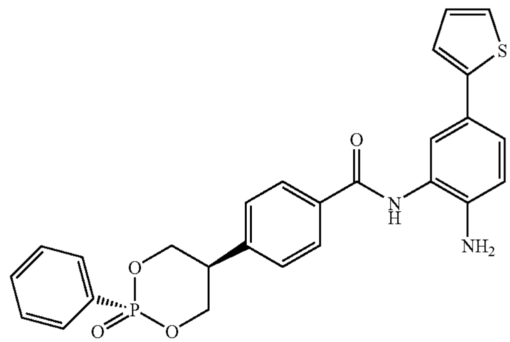 | N-[2-amino-5-(2-thienyl)phenyl]-4-[(2s)-2-oxido-2-phenyl-1,3,2-dioxaphosphinan-5-yl]benzamide | cal'd 491 (MH+), exp 491 | Free base |
| 2 | 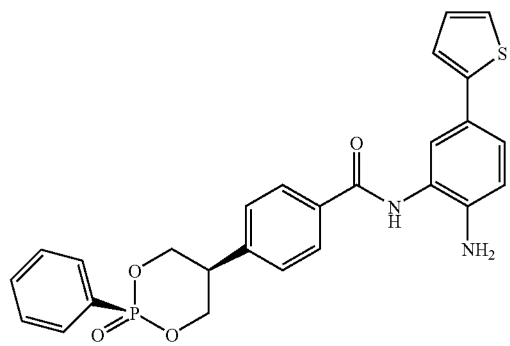 | N-[2-amino-5-(2-thienyl)phenyl]-4-[(2r)-2-oxido-2-phenyl-1,3,2-dioxaphosphinan-5-yl]benzamide | cal'd 491 (MH+), exp 491 | Free base |
| 3 | 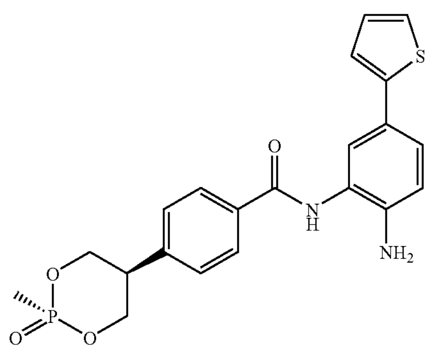 | N-[2-amino-5-(2-thienyl)phenyl]-4-[(2s)-2-methyl-2-oxido-1,3,2-dioxaphosphinan-5-yl]benzamide | cal'd 429 (MH+), exp 429 | Free base |
| 4 | 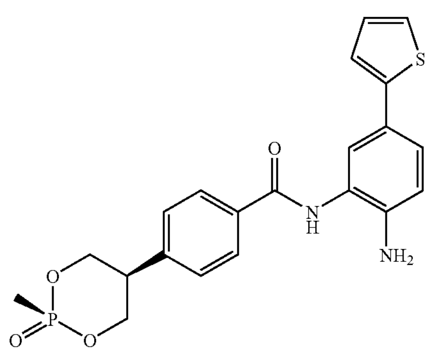 | N-[2-amino-5-(2-thienyl)phenyl]-4-[(2r)-2-methyl-2-oxido-1,3,2-dioxaphosphinan-5-yl]benzamide | cal'd 429 (MH+), exp 429 | Free base |

Procedures for S. Preparation of Keto Phosphinates and Cyclic Phosphinates

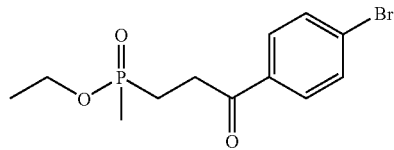

Ethyl [3-(4-bromophenyl)-3-oxopropyl]methylphosphinate. 1-(4-bromophenyl)-3-chloropropan-1-one (4.5 g, 18.18 mmol) and diethyl methylphosphonite (6 g, 44.1 mmol) were stirred in refluxing toluene (9 mL) for 5 hours. Room temperature was attained and the solvent removed in vacuo. Purification of the residue by MPLC (0-10% MeOH-EtOAc) gave ethyl [3-(4-bromophenyl)-3-oxopropyl]methylphosphinate as a pale yellow oil that crystallised on standing.

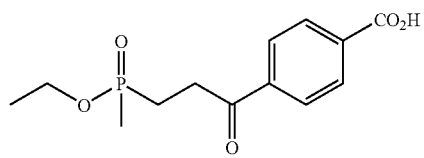

4-{3-[(ethyloxy)(methyl)phosphoryl]propanoyl}benzoic acid. Ethyl [3-(4-bromophenyl)-3-oxopropyl]methylphosphinate (3 g, 9.40 mmol), palladium(II) acetate (0.106 g, 0.470 mmol) and 1,3-bis(diphenylphosphino)propane (0.194 g, 0.470 mmol) were taken up in DMF (24 mL)/water (8 mL). CO was bubbled through for 10 minutes before adding DIPEA (3.28 mL, 18.80 mmol) and stirring at 70° C. under a balloon of CO overnight. Room temperature was attained and saturated NaHCO$_3$ was added. The aqueous phase was extracted with EtOAc (×2) before acidifying with 2N HCl and extracting again with EtOAc (×2). The combined organic extracts from the acidic aqueous were washed with brine, dried over MgSO$_4$ and concentrated in vacuo to give 4-{3-[(ethyloxy)(methyl)phosphoryl]propanoyl}benzoic acid as a pale yellow solid.

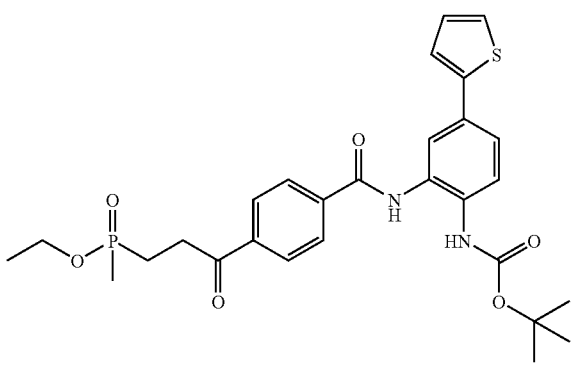

Ethyl {3-[4-({[2-({[(1,1-dimethylethyl)oxy]carbonyl}amino)-5-(2-thienyl)phenyl]amino}carbonyl)phenyl]-3-oxopropyl}methylphosphinate. 4-{3-[(ethyloxy)(methyl)phosphoryl]propanoyl}benzoic acid (1 g, 3.52 mmol), 1,1-dimethylethyl [2-amino-4-(2-thienyl)phenyl]carbamate (1.532 g, 5.28 mmol), DIPEA (0.922 mL, 5.28 mmol) and BOP (2.334 g, 5.28 mmol) were stirred in DMF (10 mL) at room temperature overnight. Saturated NaHCO$_3$ was added and the products extracted into EtOAc (×2). The combined organic extracts were washed with water and brine, dried over MgSO$_4$ and concentrated in vacuo. Purification of the residue by MPLC (0-20% MeOH-EtOAc) gave ethyl {3-[4-({[2-({[(1,1-dimethylethyl)oxy]carbonyl}amino)-5-(2-thienyl)phenyl]amino}carbonyl)phenyl]-3-oxopropyl}methylphosphinate as an orange solid. MS: cal'd 457 (MH+-Boc), exp 457 (MH+-Boc).

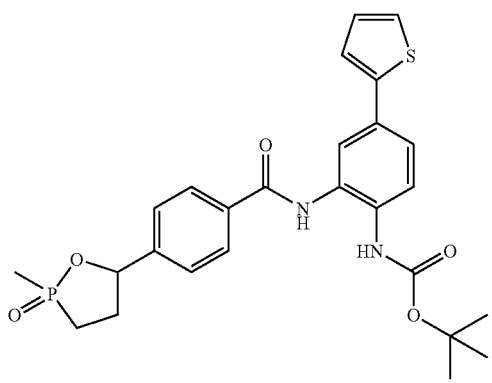

1,1-dimethylethyl [2-({[4-(2-methyl-2-oxido-1,2-oxaphospholan-5-yl)phenyl]carbonyl}amino)-4-(2-thienyl)phenyl]carbamate. Ethyl {3-[4-({[2-({[(1,1-dimethylethyl)oxy]carbonyl}amino)-5-(2-thienyl)phenyl]amino}carbonyl)phenyl]-3-oxopropyl}methylphosphinate (0.7 g, 1.258 mmol) was taken up in THF (6 mL) and sodium borohydride (0.052 g, 1.383 mmol) was added before stirring overnight. Saturated NH$_4$Cl was added and the products extracted into EtOAc (×2). The combined organic extracts were dried over MgSO$_4$ and concentrated in vacuo. Purification of the residue by MPLC followed by HPLC gave 1,1-dimethylethyl [2-({[4-(2-methyl-2-oxido-1,2-oxaphospholan-5-yl)phenyl]carbonyl}amino)-4-(2-thienyl)phenyl]carbamate as a white solid. The title compound was obtained as a ~1:1 mixture of diastereosiomers.

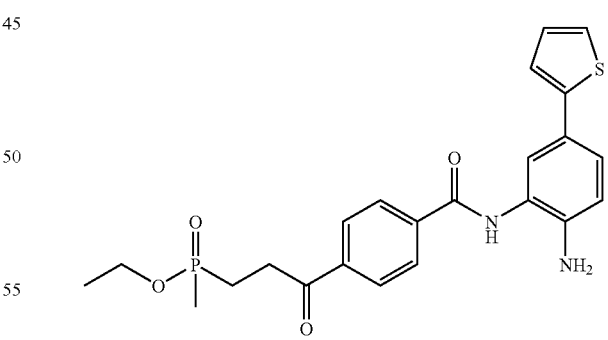

Ethyl {3-[4-({[2-amino-5-(2-thienyl)phenyl]amino}carbonyl)phenyl]-3-oxopropyl}methylphosphinate. Ethyl {3-[4-({[2-({[(1,1-dimethylethyl)oxy]carbonyl}amino)-5-(2-thienyl)phenyl]amino}carbonyl)phenyl]-3-oxopropyl}methylphosphinate (125 mg, 0.225 mmol) was taken up in DCM (5 mL)/TFA (2 mL). After 3 hours, saturated NaHCO$_3$ was added and the products extracted into EtOAc (×2). The combined organic extracts were washed with brine, dried over MgSO$_4$ and concentrated in vacuo to give ethyl {3-[4-({[2-amino-5-(2-thienyl)phenyl]amino}carbonyl)phenyl]-3-oxopropyl}methylphosphinate as an orange solid.

MS: cal'd 457 (MH+), exp 457 (MH+).

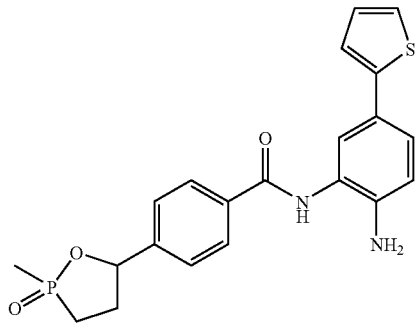

N-[2-amino-5-(2-thienyl)phenyl]-4-(2-methyl-2-oxido-1,2-oxaphospholan-5-yl)benzamide. 1,1-dimethylethyl [2-({[4-(2-methyl-2-oxido-1,2-oxaphospholan-5-yl)phenyl]carbonyl}amino)-4-(2-thienyl)phenyl]carbamate (95 mg, 0.185 mmol) was taken up in DCM (5 mL)/TFA (2 mL). After 3 hours, saturated NaHCO₃ was added and the products extracted into EtOAc (×2). The combined organic extracts were washed with brine, dried over MgSO₄ and concentrated in vacuo to give N-[2-amino-5-(2-thienyl)phenyl]-4-(2-methyl-2-oxido-1,2-oxaphospholan-5-yl)benzamide as a yellow solid. The title compound was obtained as a 1:1 mixture of diastereosiomers. MS: cal'd 413 (MH+), exp 413 (MH+).

Procedures for T. Preparation of α,β-Unsaturated Benzamides.

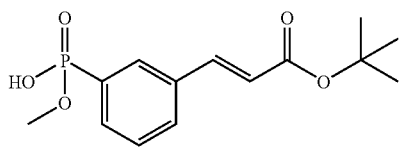

tert-butyl (2E)-3-{3-[hydroxy(methoxy)phosphoryl]phenyl}acrylate. Dimethyl phosphite (0.089 ml, 0.971 mmol), tert-butyl (2E)-3-(3-bromophenyl)acrylate (0.25 g, 0.883 mmol), triethylamine (0.369 ml, 2.65 mmol) and tetrakis(triphenylphosphine)palladium(0) (0.153 g, 0.132 mmol) were combined and allowed to heat for approximately eight hours at 100° C. The reaction was cooled and filtered over celite, washing with ethyl acetate. The filtrate was concentrated under reduced presesure. The residue was purified by column chromatography on silica gel, eluting with EtOAc/hexane, followed by CH₂Cl₂/MeOH. MS: calc'c 299 (MH+), exp 299 (MH+).

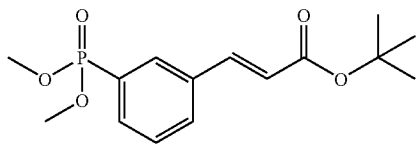

tert-butyl (2E)-3-[3-(dimethoxyphosphoryl)phenyl]acrylate. tert-butyl (2E)-3-{3-[hydroxy(methoxy)phosphoryl]phenyl}acrylate was dissolved in methanol (8 ml). BOP (0.4958 g, 1.121 mmol) and Hunig's base (0.2 ml, 1.145 mmol) were added. DMF (2 ml) was added. The reaction was allowed to stir overnight at room temperature. The reaction was not complete. The reaction was partially concentrated under reduced pressure. BOP (0.4836 g, 1.093 mmol) and Hunig's base (0.2 ml, 1.145 mmol) were added. The reaction was allowed to stir. After several hours additional BOP (0.495 g, 1.119 mmol) and Hunig's base (0.2 ml, 1.145 mmol) were added. The reaction was allowed to stir overnight at room temperature. The reaction was concentrated under reduced pressure. The residue was dissolved in ethyl acetate and washed with saturated aqueous sodium hydrogen carbonate. The residue was purified by column chromatography on silica gel, eluting with EtOAc/hexane. MS: calc'd 313 (MH+), exp 313 (MH+).

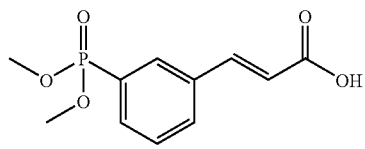

(2E)₃-[3-(dimethoxyphosphoryl)phenyl]acrylic acid. tert-butyl (2E)-3-[3-(dimethoxyphosphoryl)phenyl]acrylate was dissolved in dichloromethane (6 ml). TFA (3 ml, 38.9 mmol) was added. The reaction was allowed to stir for approximately one and a half hours. The reaction was complete as indicated by LCMS. The reaction was diluted with DCM and washed with brine. The aqueous layer was extracted three times with DCM. The combined organic layer was dried over Na₂SO4₂, filtered, and concentrated. MS: calc'd 257 (MH+), exp 257 (MH+)

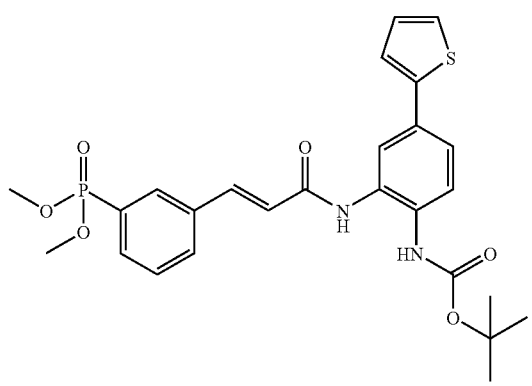

Dimethyl [3-((1E)-3-{[2-[(tert-butoxycarbonyl)amino]-5-(2-thienyl)phenyl]amino}-3-oxoprop-1-en-1-yl)phenyl]phosphonate. (2E)-3-[3-(dimethoxyphosphoryl)phenyl]acrylic acid (0.0735 g, 0.287 mmol) was dissolved in DMF (3 ml). EDC (0.0706 g, 0.368 mmol) and HOBT (0.0993 g, 0.648 mmol) were added. The mixture was allowed to stir briefly. tert-butyl [2-amino-4-(2-thienyl)phenyl]carbamate (0.1333 g, 0.459 mmol) was added. The reaction was allowed to stir at 60° C. After approximately six hours EDC (0.0912 g, 0.476 mmol) and HOBT (0.0906 g, 0.592 mmol) were added. The reaction was allowed to stir over the weekend at 60° C. The reaction was filtered and diluted with methanol. The residue was purified by preparative HPLC Reverse phase (C-18), eluting with Acetonitrile/Water (+0.025% TFA). Fractions containing the product were diluted with ethyl acetate and washed with saturated aqueous sodium hydrogen carbonate. The aqueous layer was extracted three times with ethyl acetate. The combined organic layer was dried over $Na_2SO_4$, filtered, and concentrated. MS: calc'd 429 (MH+-Boc), exp 429 (MH+-Boc).

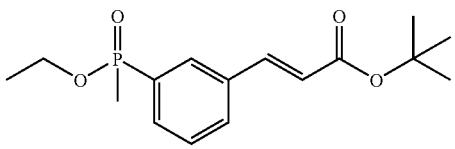

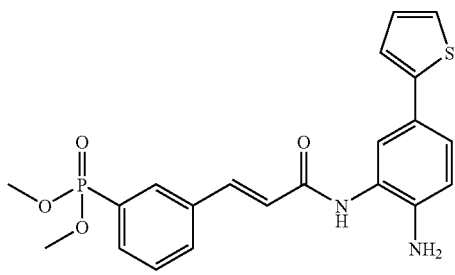

tert-butyl (2E)-3-{3-[ethoxy(methyl)phosphoryl]phenyl}acrylate. Diethyl methylphosphonite (0.15 ml, 0.992 mmol), tert-butyl (2E)-3-(3-bromophenyl)acrylate (0.25 g, 0.883 mmol), triethylamine (0.37 ml, 2.65 mmol), and tetrakis(triphenylphosphine)palladium(0) (0.1559 g, 0.135 mmol) were combined and allowed to heat at 100° C. for approximately eight hours. The reaction was cooled and filtered over celite, washing with ethyl acetate. The filtrate was concentrated under reduced pressure. The residue was purified by column chromatography on silica gel, eluting with EtOAc/hexane. MS: calc'd 311 (MH+), exp 311 (MH+).

TABLE 20

T; α, β-unsaturated benzamides

| Cpd # | Structure | Name | MS | Salt Forms |
|---|---|---|---|---|
| 1 | 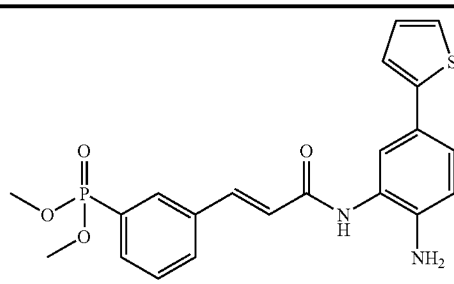 | Dimethyl [3-((1E)-3-{[2-amino-5-(2-thienyl)phenyl]amino}-3-oxoprop-1-en-1-yl)phenyl]phosphonate | cal'd 429 (MH+), exp 429 | Free base |
| 2 | 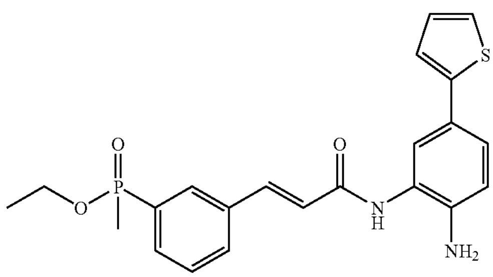 | Ethyl [3-((1E)-3-{[2-amino-5-(2-thienyl)phenyl]amino}-3-oxoprop-1-en-1-yl)phenyl]methylphosphinate | cal'd 427 (MH+), exp 427 | Free base |

Dimethyl [3-((1E)-3-{[2-amino-5-2-thienyl)phenyl]amino}-3-oxoprop-1-en-1-yl)phenyl]phosphonate. Dimethyl [3-((1E)-3-{[2-[(tert-butoxycarbonyl)amino]-5-(2-thienyl)phenyl]amino}-3-oxoprop-1-en-1-yl)phenyl]phosphonate (0.011 g, 0.021 mmol) was dissolved in dichloromethane. TFA (0.5 ml, 6.49 mmol) was added. The reaction was allowed to stir until complete as indicated by LCMS. The reaction was diluted with DCM and washed with saturated aqueous sodium hydrogen carbonate. The aqueous layer was extracted three times with DCM. The combined organic layer was dried over $Na_2SO_4$, filtered, and concentrated. $^1H$ NMR (DMSO-$d_6$, 600 MHz) δ 9.42 (s, 1H) 7.95 (d, J=13.8 Hz, 1H), 7.85 (d, J=7.9 Hz, 1 Hz), 7.70-7.68 (m, 2H), 7.62-7.59 (m, 2H), 7.32 (d, J=4.4 Hz, 1H), 7.21 (dd, J=8.2 Hz, 2.1 Hz, 1H), 7.19 (d, J=3.1 Hz, 1H), 7.03-6.99 (m, 2H), 6.75 (d, J=8.5 Hz, 1H), 5.20 (s, 2H), 3.66 (d, J=11.2 Hz, 6H). MS: calc'd 429 (MH+), exp 429 (MH+).

The compounds in the above tables exhibit histone deacetylase inhibitory activity at concentrations of less than 5 μM.

Example 2

HDAC Inhibition by Novel Compounds

HDAC1-Flag Assay

Novel compounds were tested for their ability to inhibit histone deacetylase, subtype 1 (HDAC1) using an in vitro deacetylation assay. The enzyme source for this assay was an epitope-tagged human HDAC1 complex immuno-purified from stably expressing mammalian cells. The substrate consisted of a commercial product containing an acetylated lysine side chain (BIOMOL Research Laboratories, Inc., Plymouth Meeting, Pa.). Upon deacetylation of the substrate by incubation with the purified HDAC1 complex, a fluorophore is produced that is directly proportional to the level of deacetylation. Using a substrate concentration at the Km for the enzyme preparation, the deacetylation assay was performed in the presence of increasing concentrations of novel compounds to semi-quantitatively determine the concentration of compound required for 50% inhibition (IC50) of the deacetylation reaction.

Example 3

HDAC Inhibition in Cell Lines

ATP Assay

The novel compounds of the present invention were tested for their ability to inhibit proliferation of the human cervical cancer (HeLa) and colon carcinoma (HCT116) cells.

In this assay, also referred to as the Vialight Assay, cellular ATP levels are measured as a means of quantifying cellular proliferation. This assay makes use of a bioluminescent method from Cambrex (ViaLight PLUS, cat. #LT07-121). In the presence of ATP, luciferase converts luciferin to oxyluciferin and light. The amount of light produced (emission at 565 nM) is measured and correlates with a relative amount of proliferation. Human cervical cancer (HeLa) or colon carcinoma (HCT116) cells were incubated with vehicle or increasing concentrations of compound for 48, 72 or 96 hours. Cell proliferation was quantified by adding the cell lysis reagent (provided in the Vialight assay kit) directly to culture wells, followed by addition of the ATP-monitoring reagent (containing luciferase/luciferin). The amount of light produced is then measured (emission at 565 nM). The quantity of light produced, as measured by 565 nM absorbance, is directly proportional to the number of living cells in culture.

While this invention has been particularly shown and described with references to embodiments thereof, it will be understood by those skilled in the art that various changes in form and details may be made therein without departing from the meaning of the invention described. Rather, the scope of the invention is defined by the claims that follow.

What is claimed is:

1. A compound represented by Formula I:

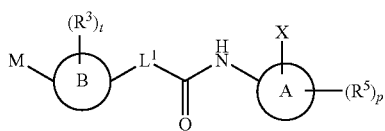

I

Wherein
Ring A is a 5- to 6- membered heteroaryl or 6-membered aryl;
  With the proviso that Ring A is not tetrahydro-dioxo-pyrimidinyl;
Ring B is heteroaryl or aryl;
M is selected from:

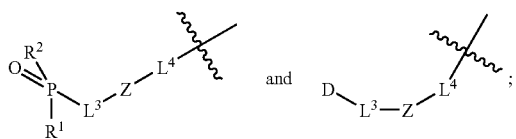

D is a P(O) containing heterocyclyl, wherein the heterocyclyl is optionally substituted with at least one $R^{11}$;
$R^1$ and $R^2$ are independently selected from —OR, —$NR^7R^8$, substituted or unsubstituted $C_1$-$C_{10}$ alkyl, substituted or unsubstituted $C_1$-$C_{10}$ alkenyl, substituted or unsubstituted $C_1$-$C_{10}$alkynyl, substituted or unsubstituted $C_3$-$C_{10}$ cycloalkyl, —$(CR^a_2)_rR^9$, —ORC(O)OR, —O$(CR^a_2)_rR^9$, —O$(CR^a_2)_rC(O)NR^7R^8$, —O$(CR^a_2)_r NR^7R^8$, and —O$(CR^a_2)_rOR$;
or $R^1$ and $R^2$ together with the phosphorous atom to which they are attached form a phosphorous-containing heterocyclic ring, wherein the heterocyclic ring is optionally substituted with at least one $R^{11}$;
or $R^2$ and $R^6$ together with the phosphorous and C atom to which they are respectively attached, form a heterocyclic ring, wherein the heterocyclic ring is optionally substituted with at least one $R^{11}$;
or $R^1$ and $R^4$ together with the phosphorous and C atom to which they are respectively attached, form a heterocyclic ring, wherein the heterocyclic ring is optionally substituted with at least one $R^{11}$;
$R^3$ is independently selected from hydrogen, —OR, —$NR^7R^8$, —$NO_2$, —CN, —C(O)$NR^7R^8$, —$NR^7R^8$C(O)R, C(O), $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl—C(=O)O—, $C_1$-$C_7$ alkyl-C(=O)—, $C_1$-$C_7$ alkynyl, halo, hydroxyalkoxy, $C_1$-$C_7$ alkyl-$NHSO_2$-, $C_1$-$C_7$ alkyl—$SO_2NH$—, $C_1$-$C_7$ alkylsulfonyl, $C_1$-$C_7$ alkylamino and di($C_1$-$C_7$) alkylamino;
$R^4$ and $R^6$ are independently of each other hydrogen, —OR, —$NR^7R^8$, halo, —CN, —C(O)$NR^7R^8$, —$NR^7R^8$C(O)R, —C(O)OR, —P(O)(OR)$_2$, oxo, substituted or unsubstituted $C_1$-$C_6$ alkyl, substituted or unsubstituted $C_1$-$C_4$ alkenyl, substituted or unsubstituted $C_1$-$C_4$ alkynyl, substituted or unsubstituted cycloalkyl, substituted or unsubstituted heteroaryl, substituted or unsubstituted heterocyclic or substituted or unsubstituted aryl;
or $R^4$ and $R^6$ together with the C atom to which they are attached form a heterocyclic or carbocyclic ring, which can be optionally substituted with at least one $R^{11}$;
$R^5$ is independently selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl—C(=O)O—, $C_1$-$C_7$ alkyl—C(=O)—, $C_1$-$C_7$ alkynyl, halo, hydroxyalkoxy, $C_1$-$C_7$ alkyl—$NHSO_2$—, $C_1$-$C_7$ alkyl—$SO_2NH$—, $C_1$-$C_7$ alkylsulfonyl, $C_1$-$C_7$ alkylamino, di($C_1$-$C_7$)alkylamino and $L^2$-$R^9$,
$R^7$ and $R^8$ are independently selected from hydrogen, $C_1$-$C_7$ alkyl, —C(O)O—$C_1$—$C_7$alkyl, —P(O)$CR^a_2$, —P(O)(OR)$_2$, —$(CR^a_2)_r$heteroaryl, —$(CR^a_2)_r$heterocyclic, —$(CR^a_2)_r$ $C_3$-$C_8$ cycloalkyl and —$(CR^a_2)_r$aryl, where alkyl, heteroaryl, heterocyclic, aryl or cycloalkyl is optionally substituted with at least one $R^{11}$;
$R^9$ is independently selected from hydrogen, $C_1$-$C_7$ alkyl, heteroaryl, heterocyclic, aryl, and $C_3$-$C_8$ cycloalkyl, where alkyl, heteroaryl, heterocyclic, aryl or cycloalkyl is optionally substituted with at least one $R^{11}$;
$R^{11}$ is independently selected from OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl- C(=O)—, C$_1$-C$_7$ alkynyl, halo, hydroxyalkoxy, C$_1$-C$_7$ alkyl—NHSO$_2$—, C$_1$-C$_7$ alkyl—SO$_2$NH—, C$_1$-C$_7$ alkylsulfonyl, C$_1$-C$_7$ alkylamino and di(C$_1$-C$_7$) alkylamino;

R is independently H, C$_1$-C$_7$ alkyl, or C$_3$-C$_{10}$ cycloalkyl, where alkyl or cycloalkyl is optionally substituted with at least one R$^{11}$;

R$^a$ is independently selected from H and C$_1$-C$_7$ alkyl, where C$_1$-C$_7$ alkyl is optionally substituted with at least one R$^{11}$;

L$^1$ is (CH$_2$)$_r$, ethenyl or cyclopropyl;

L$^2$ is independently selected from a bond, C$_1$-C$_4$ alkylene, C$_1$-C$_4$ alkynyl, C$_1$-C$_4$ alkenyl, —O—, —S—, —N—, —C(=O)NH—, —NHC(=O)—, —NHC(=O)NH—, —SO$_2$NH—, —NHSO$_2$—, —SO$_2$—, —C(=O)—and —C(=O)O—;

L$^3$ is a bond, —(CR$^a_2$)$_r$C(O)(CR$^a_2$)$_r$—, —(CR$^a_2$)$_r$O(CR$^a_2$)$_r$—, —(CR$^a_2$)$_r$C(O)NR$^7$(CR$^a_2$)$_r$—, —(CR$^a_2$)$_r$NR$^7$C(O)(CR$^a_2$)$_r$—, —(CR$^a_2$)$_r$NR$^7$C(O)NR$^7$(CR$^a_2$)$_r$—, —(CR$^a_2$)$_r$OC(O)NR$^7$(CR$^a_2$)$_r$—, —(CR$^a_2$)$_r$ NR$^7$C(O)O(CR$^a_2$)$_r$—, —(CR$^a_2$)$_r$NR$^7$(CR$^a_2$)$_r$—, or —(CR$^4$R$^6$)$_n$—;

L$^4$ is a bond, —(CR$^a_2$)$_r$C(O)(CR$^a_2$)$_r$—, —(CR$^a_2$)$_r$O(CR$^a_2$)$_r$—, —(CR$^a_2$)$_r$C(O)NR$^7$(CR$^a_2$)$_r$—, —(CR$^a_2$)$_r$NR$^7$C(O)(CR$^a_2$)$_r$—, —(CR$^a_2$)$_r$NR$^7$C(O)NR$^7$(CR$^a_2$)$_r$—, —(CR$^a_2$)$_r$OC(O)NR$^7$(CR$^a_2$)$_r$—, —(CR$^a_2$)$_r$ NR$^7$C(O)O(CR$^a_2$)$_r$—, —(CR$^a_2$)$_r$NR$^7$(CR$^a_2$)$_r$—, or —(CR$^4$R$^6$)$_n$—;

X is NH$_2$;

Z is a bond, heteroaryl, heterocyclic, aryl, or C$_3$-C$_8$ cycloalkyl, where heteroaryl, heterocyclic, aryl or cycloalkyl is optionally substituted with at least one R$^{11}$;

n is 0, 1, 2, 3 or 4;

p is 1, 2, 3 or 4;

r is independently 0, 1 or 2 or 3;

t is 1, 2, 3, or 4;

or a stereoisomer or pharmaceutically acceptable salt thereof.

2. The compound of claim 1,

Wherein

Ring A is a 5- to 6- membered heteroaryl or 6-membered aryl;

With the proviso that Ring A is not tetrahydro-dioxo-pyrimidinyl;

Ring B is heteroaryl or aryl;

M is selected from:

R$_1$ and R$^2$ are independently selected from —OR, —NR$^7$R$^8$, substituted or unsubstituted C$_1$-C$_{10}$ alkyl, substituted or unsubstituted C$_1$-C$_{10}$ alkenyl, substituted or unsubstituted C$_1$-C$_{10}$alkynyl, substituted or unsubstituted C$_3$-C$_{10}$ cycloalkyl, —(CR$^a_2$)$_r$R$^9$, —ORC(O)OR, —O(CR$^a_2$)$_r$R$^9$, —O(CR$^a_2$)$_r$C(O)NR$^7$R$^8$, —O(CR$^a_2$)$_r$NR$^7$R$^8$, and —O(CR$^a_2$)$_r$OR;

or R$_1$ and R$^2$ together with the phosphorous atom to which they are attached form a phosphorous-containing heterocyclic ring, optionally substituted with at least one R$^{11}$;

or R$^2$ and R$^6$ together with the phosphorous and C atom to which they are respectively attached, form a heterocyclic ring, optionally substituted with at least one R$^{11}$;

or R$^1$ and R$^4$ together with the phosphorous and C atom to which they are respectively attached, form a heterocyclic ring, optionally substituted with at least one R$^{11}$;

R$^3$ is independently selected from hydrogen, —OR, —NR$^7$R$^8$, —NO$_2$, —CN, —C(O)NR$^7$R$^8$, —NR$^7$R$^8$C(O)R, C(O), C$_1$—C$_7$ alkyl, C$_1$-C$_7$ haloalkyl, C$_1$-C$_7$ haloalkyloxy, C$_1$-C$_7$ hydroxyalkyl, C$_1$-C$_7$ alkenyl, C$_1$-C$_7$ alkyl—C(=O)O—, C$_1$-C$_7$ alkyl—C(=O)—, C$_1$-C$_7$ alkynyl, halo, hydroxyalkoxy, C$_1$-C$_7$ alkyl—NHSO$_2$—, C$_1$-C$_7$ alkyl—SO$_2$NH—, C$_1$-C$_7$ alkylsulfonyl, C$_1$-C$_7$ alkylamino and di(C$_1$-C$_7$)alkylamino;

R$^4$ and R$^6$ are independently of each other hydrogen, —OR, —NR$^7$R$^8$, halo, —CN, —C(O)NR$^7$R$^8$, —NR$^7$R$^8$C(O)R, C(O)OR, —P(O)(OR)$_2$, oxo, substituted or unsubstituted C$_1$-C$_6$ alkyl, substituted or unsubstituted C$_1$-C$_4$ alkenyl, substituted or unsubstituted C$_1$-C$_4$ alkynyl, substituted or unsubstituted cycloalkyl, substituted or unsubstituted heteroaryl, substituted or unsubstituted heterocyclic or substituted or unsubstituted aryl;

233 or R⁴ and R⁶ together with the C atom to which they are attached form a heterocyclic or carbocyclic ring, optionally substituted with at least one $R^{11}$;

$R^5$ is independently selected from hydrogen, OH, NH₂, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl—C(=O)O—, $C_1$-$C_7$ alkyl—C(=O)—, $C_1$-$C_7$ alkynyl, halo, hydroxyalkoxy, $C_1$-$C_7$ alkyl—NHSO₂—, $C_1$—$C_7$ alkyl—SO₂NH—, $C_1$-$C_7$ alkylsulfonyl, $C_1$-$C_7$ alkylamino, di($C_1$-$C_7$)alkylamino and $L^2$-$R^9$, $R^7$ and $R^8$ are independently selected from hydrogen, $C_1$-$C_7$ alkyl, —C(O)O—$C_1$-$C_7$alkyl, —P(O)$CR^a{}_2$, —P(O)(OR)₂, —($CR^a{}_2$)ᵣheteroaryl, —($CR^a{}_2$)ᵣheterocyclic, —($CR^a{}_2$)ᵣ $C_3$-$C_8$ cycloalkyl and —($CR^a{}_2$)ᵣaryl, where alkyl, heteroaryl, heterocyclic, aryl or cycloalkyl is optionally substituted with at least one $R^{11}$;

$R^9$ is independently selected from hydrogen, $C_1$-$C_7$ alkyl, heteroaryl and aryl, where alkyl, heteroaryl or aryl is optionally substituted with at least one $R^{11}$;

$R^{10}$ is independently selected from hydrogen, $C_1$-$C_7$ alkyl, —($CR^a{}_2$)ᵣheteroaryl, —($CR^a{}_2$)ᵣheterocyclic, -($CR^a{}_2$)ᵣ $C_3$-$C_8$ cycloalkyl and —($CR^a{}_2$)ᵣaryl, where alkyl, heteroaryl, heterocyclic, aryl or cycloalkyl is optionally substituted with at least one $R^{11}$;

$R^{11}$ is independently selected from OH, NH₂, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl—C(=O)O—, $C_1$-$C_7$ alkyl—C(=O)—, $C_1$-$C_7$ alkynyl, halo, hydroxyalkoxy, $C_1$-$C_7$ alkyl—NHSO₂—, $C_1$-$C_7$ alkyl—SO₂NH—, $C_1$-$C_7$ alkylsulfonyl, $C_1$-$C_7$ alkylamino and di($C_1$-$C_7$)alkylamino;

R is independently H, $C_1$-$C_7$ alkyl, or $C_3$-$C_{10}$ cycloalkyl, where alkyl or cycloalkyl is optionally substituted with at least one $R^{11}$;

$R^a$ is independently selected from H and $C_1$-$C_7$ alkyl, where $C_1$-$C_7$ alkyl is optionally substituted with at least one $R^{11}$;

$R^b$ is independently selected from H and $C_1$-$C_7$ alkyl, where $C_1$-$C_7$ alkyl is optionally substituted with at least one $R^{11}$;

$L^1$ is (CH₂)ᵣ, ethenyl or cyclopropyl;

$L^2$ is independently selected from a bond, $C_1$-$C_4$ alkylene, $C_1$-$C_4$ alkynyl, $C_1$-$C_4$ alkenyl, —O—, —S—, —N—, —C(=O)NH—, —NHC(=O)—, —NHC(=O)NH—, —SO₂NH—, —NHSO₂—, —SO₂—, —C(=O)— and —C(=O)O—;

$L^3$ is a bond, —($CR^a{}_2$)ᵣC(O)($CR^a{}_2$)ᵣ—, —($CR^a{}_2$)ᵣO($CR^a{}_2$)ᵣ, —($CR^a{}_2$)ᵣC(O)$NR^7$($CR^a{}_2$)ᵣ—, —($CR^a{}_2$)ᵣ$NR^7$C(O)($CR^a{}_2$)ᵣ—, —($CR^a{}_2$)ᵣ$NR^7$C(O)$NR^7$($CR^a{}_2$)ᵣ—, —($CR^a{}_2$)ᵣOC(O)$NR^7$($CR^a{}_2$)ᵣ—, —($CR^a{}_2$)ᵣ $NR^7$C(O)O($CR^a{}_2$)ᵣ—, —($CR^a{}_2$)ᵣ$NR^7$($CR^a{}_2$)ᵣ—, or —($CR^4R^6$)ₙ—;

$L^4$ is a bond, —($CR^a{}_2$)ᵣC(O)($CR^a{}_2$)ᵣ—, —($CR^a{}_2$)ᵣO($CR^a{}_2$)ᵣ, —($CR^a{}_2$)ᵣC(O)$NR^7$($CR^a{}_2$)ᵣ—, —($CR^a{}_2$)ᵣ$NR^7$C(O)($CR^a{}_2$)ᵣ—, —($CR^a{}_2$)ᵣ$NR^7$C(O)$NR^7$($CR^a{}_2$)ᵣ—, —($CR^a{}_2$)ᵣOC(O)$NR^7$($CR^a{}_2$)ᵣ—, —($CR^a{}_2$)ᵣ $NR^7$C(O)O($CR^a{}_2$)ᵣ—, —($CR^a{}_2$)ᵣ$NR^7$($CR^a{}_2$)ᵣ—, or —($CR^4R^6$)ₙ—;

X is NH₂;

Z is a bond, heteroaryl, heterocyclic, aryl, or $C_3$-$C_8$ cycloalkyl, where heteroaryl, heterocyclic, aryl or cycloalkyl is optionally substituted with at least one $R^{11}$;

234 n is 0, 1, 2, 3 or 4;
p is 1, 2, 3 or 4;
q is 1 or 2;
r is independently 0, 1, 2 or 3;
t is 1, 2, 3, or 4;
or a stereoisomer or pharmaceutically acceptable salt thereof.

3. The compound of claim 2,
Wherein
Ring A is a 5- to 6- membered heteroaryl or 6-membered aryl;
  With the proviso that Ring A is not tetrahydro-dioxopyrimidinyl;
Ring B is heteroaryl or aryl;
M is selected from:

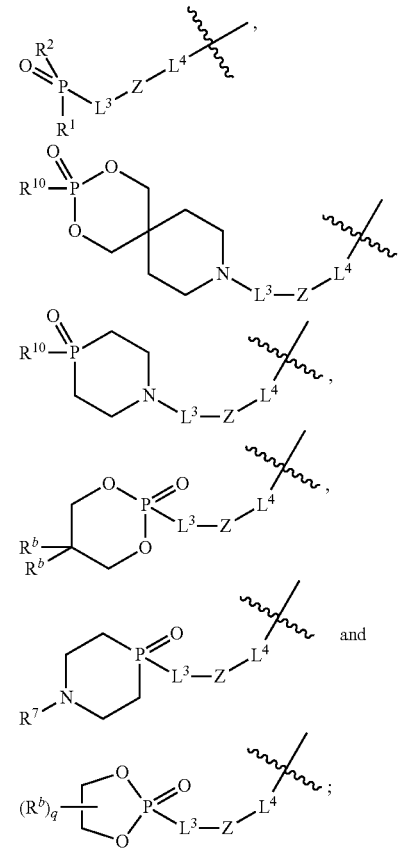

$R^1$ and $R^2$ are independently selected from —OR, —$NR^7R^8$, substituted or unsubstituted $C_1$-$C_{10}$ alkyl, substituted or unsubstituted $C_1$-$C_{10}$ alkenyl, substituted or unsubstituted $C_1$-$C_{10}$alkynyl, substituted or unsubstituted $C_3$-$C_{10}$ cycloalkyl, —($CR^a{}_2$)ᵣ$R^9$, —ORC(O)OR, —O($CR^a{}_2$)ᵣ$R^9$, —O($CR^a{}_2$)ᵣC(O)$NR^7R^8$, —O($CR^a{}_2$)ᵣ$NR^7R^8$, and —O($CR^a{}_2$)ᵣOR;
  or $R^1$ and $R^2$ together with the phosphorous atom to which they are attached form a phosphorous-containing heterocyclic ring;
  or $R^2$ and $R^6$ together with the phosphorous and C atom to which they are respectively attached, form a heterocyclic ring;
  or $R^1$ and $R^4$ together with the phosphorous and C atom to which they are respectively attached, form a heterocyclic ring;
$R^3$ is independently selected from hydrogen, —OR, —$NR^7R^8$, —NO₂, —CN, —C(O)$NR^7R^8$, —NR$^7$R$^8$C(O)R, C(O), C$_1$-C$_7$ alkyl, C$_1$-C$_7$ haloalkyl, C$_1$-C$_7$ haloalkyloxy, C$_1$-C$_7$ hydroxyalkyl, C$_1$-C$_7$ alkenyl, C$_1$-C$_7$ alkyl—C(=O)O—, C$_1$-C$_7$ alkyl—C(=O)—, C$_1$-C$_7$ alkynyl, halo, hydroxyalkoxy, C$_1$-C$_7$ alkyl—NHSO$_2$—, C$_1$-C$_7$ alkyl—SO$_2$NH—, C$_1$-C$_7$ alkylsulfonyl, C$_1$-C$_7$ alkylamino and di(C$_1$-C$_7$)alkylamino;

R$^4$ and R$^6$ are independently of each other hydrogen, —OR, —NR$^7$R$^8$, halo, —CN, —C(O)NR$^7$R$^8$, —NR$^7$R$^8$C(O)R, —C(O)OR, —P(O)(OR)$_2$, oxo, substituted or unsubstituted C$_1$-C$_6$ alkyl, substituted or unsubstituted C$_1$-C$_4$ alkenyl, substituted or unsubstituted C$_1$-C$_4$ alkynyl, substituted or unsubstituted cycloalkyl, substituted or unsubstituted heteroaryl, substituted or unsubstituted heterocyclic or substituted or unsubstituted aryl;

or R$^4$ and R$^6$ together with the C atom to which they are attached form a heterocyclic or carbocyclic ring;

R$^5$ is independently selected from hydrogen, OH, NH$_2$, nitro, CN, amide, carboxyl, C$_1$-C$_7$ alkoxy, C$_1$-C$_7$ alkyl, C$_1$-C$_7$ haloalkyl, C$_1$-C$_7$ haloalkyloxy, C$_1$-C$_7$ hydroxyalkyl, C$_1$-C$_7$ alkenyl, C$_1$-C$_7$ alkyl—C(=O)O—, C$_1$-C$_7$ alkyl—C(=O)—, C$_1$-C$_7$ alkynyl, halo, hydroxyalkoxy, C$_1$-C$_7$ alkyl—NHSO$_2$—, C$_1$-C$_7$ alkyl—SO$_2$NH—, C$_1$-C$_7$ alkylsulfonyl, C$_1$-C$_7$ alkylamino, di(C$_1$-C$_7$)alkylamino and L$^2$-R$^9$;

R$^7$ and R$^8$ are independently selected from hydrogen, C$_1$-C$_7$ alkyl, —(CR$^a_2$)$_r$heteroaryl, —(CR$^a_2$)$_r$heterocyclic, —(CR$^a_2$)$_r$ C$_3$-C$_8$ cycloalkyl and —(CR$^a_2$)$_r$aryl, where alkyl, heteroaryl, heterocyclic, aryl or cycloalkyl is optionally substituted with at least one R$^{11}$;

R$^9$ is independently selected from hydrogen, C$_1$-C$_7$ alkyl, heteroaryl, heterocyclic, aryl, and C$_3$-C$_8$ cycloalkyl, where alkyl, heteroaryl, heterocyclic, aryl or cycloalkyl is optionally substituted with at least one R$^{11}$;

R$^{10}$ is independently selected from hydrogen, C$_1$-C$_7$ alkyl, —(CR$^a_2$)$_r$heteroaryl, —(CR$^a_2$)$_r$heterocyclic, —(CR$^a_2$)$_r$C$_3$-C$_8$ cycloalkyl and —(CR$^a_2$)$_r$aryl, where alkyl, heteroaryl, heterocyclic, aryl or cycloalkyl is optionally substituted with at least one R$^{11}$;

R$^{11}$ is independently selected from OH, NH$_2$, nitro, CN, amide, carboxyl, C$_1$-C$_7$ alkoxy, C$_1$-C$_7$ alkyl, C$_1$-C$_7$ haloalkyl, C$_1$-C$_7$ haloalkyloxy, C$_1$-C$_7$ hydroxyalkyl, C$_1$-C$_7$ alkenyl, C$_1$-C$_7$ alkyl—C(=O)O—, C$_1$-C$_7$ alkyl—C(=O)—, C$_1$-C$_7$ alkynyl, halo, hydroxyalkoxy, C$_1$-C$_7$ alkyl—NHSO$_2$—, C$_1$-C$_7$ alkyl—SO$_2$NH—, C$_1$-C$_7$ alkylsulfonyl, C$_1$-C$_7$ alkylamino and di(C$_1$-C$_7$)alkylamino;

R is independently H, C$_1$-C$_7$ alkyl, or C$_3$-C$_{10}$ cycloalkyl, where alkyl or cycloalkyl is optionally substituted with at least one R$^{11}$;

R$^a$ is independently selected from H and C$_1$-C$_7$ alkyl, where C$_1$-C$_7$ alkyl is optionally substituted with at least one R$^{11}$;

R$^b$ is independently selected from H and C$_1$-C$_7$ alkyl, where C$_1$-C$_7$ alkyl is optionally substituted with at least one R$^{11}$;

L$^1$ is (CH$_2$)$_r$, ethenyl or cyclopropyl;

L$^2$ is independently selected from a bond, C$_1$-C$_4$ alkylene, C$_1$-C$_4$ alkynyl, C$_1$-C$_4$ alkenyl, —O—, —S—, —N—, —C(=O)NH—, —NHC(=O)—, —NHC(=O)NH—, —SO$_2$NH—, —NHSO$_2$—, —SO$_2$—, —C(=O)— and —C(=O)O—;

L$^3$ is a bond, —(CR$^a_2$)$_r$C(O)—, —(CR$^a_2$)$_r$O—, —(CR$^a_2$)$_r$C(O)NR$^7$—, —(CR$^a_2$)$_r$NR$^7$C(O)—, —(CR$^a_2$)$_r$NR$^7$C(O)NR$^7$—, —(CR$^a_2$)$_r$OC(O)NR$^7$—, —(CR$^a_2$)$_r$NR$^7$C(O)O—, —(CR$^a_2$)$_r$NR$^7$—, or —(CR$^4$R$^6$)$_n$—;

L$^4$ is a bond, —(CR$^a_2$)$_r$C(O)—, —(CR$^a_2$)$_r$O—, —(CR$^a_2$)$_r$C(O)NR$^7$—, —(CR$^a_2$)$_r$NR$^7$C(O)—, —(CR$^a_2$)$_r$NR$^7$C(O)NR$^7$—, —(CR$^a_2$)$_r$OC(O)NR$^7$—, —(CR$^a_2$)$_r$NR$^7$C(O)O—, —(CR$^a_2$)$_r$NR$^7$—, or —(CR$^4$R$^6$)$_n$—;

X is NH$_2$;

Z is a bond, heteroaryl, heterocyclic, aryl, or C$_3$-C$_8$ cycloalkyl, where heteroaryl, heterocyclic, aryl or cycloalkyl is optionally substituted with at least one R$^{11}$;

n is 0,1,2,3or 4;

p is 1, 2, 3 or 4;

q is 1 or 2;

r is independently 0, 1, 2 or 3;

t is 1, 2, 3, or 4;

or a stereoisomer or pharmaceutically acceptable salt thereof.

4. The compound of claim 3,

Wherein

Ring A is a 5- to 6- membered heteroaryl or 6-membered aryl;
  With the proviso that Ring A is not tetrahydro-dioxo-pyrimidinyl;

Ring B is heteroaryl or aryl;

M is selected from:

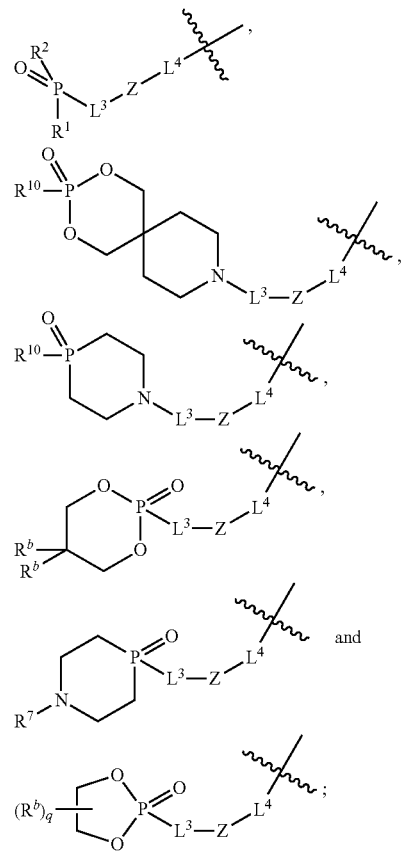

R$^1$ and R$^2$ are independently selected from —OR, —NR$^7$R$^8$, unsubstituted C$_1$-C$_{10}$ alkyl, unsubstituted C$_3$-C$_{10}$ cycloalkyl, —(CR$^a_2$)$_r$R$^9$, —ORC(O)OR, —O(CR$^a_2$)$_r$R$^9$, —O(CR$^a_2$)$_r$C(O)NR$^7$R$^8$, —O(CR$^a_2$)$_r$NR$^7$R$^8$, and —O(CR$^a_2$)$_r$OR;

or R$^1$ and R$^2$ together with the phosphorous atom to which they are attached form a phosphorous-containing heterocyclic ring;

R$^3$ is hydrogen;

R$^4$ and R$^6$ are independently of each other hydrogen, —OR, —NH$_2$, halo, —CN, —C(O)NH$_2$, —NH$_2$C(O)R, —C(O)OR, —P(O)(OR)$_2$, oxo, or unsubstituted C$_1$-C$_6$ alkyl;

R$^5$ is L$^2$-R$^9$;

R$^7$ and R$^8$ are independently selected from hydrogen, C$_1$-C$_7$ alkyl —(CR$^a_2$)$_r$heteroaryl, —(CR$^a_2$)$_r$heterocyclic, —(CR$^a_2$)$_r$ C$_3$—C$_8$ cycloalkyl and —(CR$^a_2$)$_r$aryl, where alkyl, heteroaryl, heterocyclic, aryl or cycloalkyl is optionally substituted with at least one R$^{11}$;

R$^9$ is independently selected from hydrogen, C$_1$-C$_7$ alkyl, heteroaryl and aryl, where heteroaryl, aryl or alkyl is optionally substituted with at least one R$^{11}$;

R$^{10}$ is independently selected from unsubstituted C$_1$-C$_7$ alkyl and unsubstituted aryl;

R$^{11}$ is independently selected from C$_1$-C$_7$ alkyl, halo, CF$_3$, OH and C$_1$-C$_7$ alkoxy;

R is independently H, C$_1$-C$_7$ alkyl, or C$_3$-C$_{10}$ cycloalkyl, where alkyl or cycloalkyl is optionally substituted with at least one R$^{11}$;

R$^a$ is independently selected from H and C$_1$-C$_7$ alkyl, where C$_1$-C$_7$ alkyl is optionally substituted with at least one R$^{11}$;

R$^b$ is independently selected from H and C$_1$-C$_7$ alkyl, where C$_1$-C$_7$ alkyl is optionally substituted with at least one R$^{11}$;

L$^1$ is (CH$_2$)$_r$ or ethenyl;

L$^2$ is a bond;

L$^3$ is a bond, —(CR$^a_2$)$_r$O—, —(CR$^a_2$)$_r$C(O)—, —(CR$^a_2$)$_r$NR$^7$—, —(CR$^4$R$^6$)$_n$—;

L$^4$ is a bond or —(CR$^4$R$^6$)$_n$—;

X is NH$_2$;

Z is a bond, heteroaryl, heterocyclic, aryl, or C$_3$-C$_8$ cycloalkyl, where heteroaryl, heterocyclic, aryl or cycloalkyl is optionally substituted with at least one R$^{11}$;

n is 0, 1 or 2;

p is 1, 2, 3 or 4;

q is 1 or 2;

r is independently 0, 1, 2 or 3;

t is 1, 2, 3, or 4;

or a stereoisomer or pharmaceutically acceptable salt thereof.

5. A compound represented by Formula II:

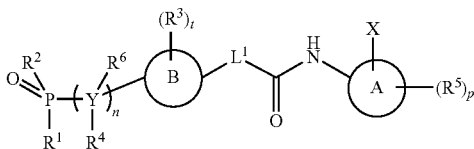

wherein R$^1$ and R$^2$ are independently selected from OH, NR$^7$R$^8$, substituted or unsubstituted C$_1$-C$_{10}$ alkyl, substituted or unsubstituted C$_1$-C$_{10}$ alkenyl, substituted or unsubstituted C$_1$-C$_{10}$ alkynyl, substituted or unsubstituted C$_1$-C$_{10}$ alkoxy, substituted or unsubstituted cycloalkyl, substituted or unsubstituted heteroaryl, substituted or unsubstituted heterocyclic and substituted or unsubstituted aryl;

or R$^1$ and R$^2$ together with the phosphorous atom to which they are attached form a phosphorous-containing heterocyclic ring;

or R$^2$ and R$^6$ together with the phosphorous and Y atom to which they are respectively attached, form a heterocyclic ring;

or R$^1$ and R$^4$ together with the phosphorous and Y atom to which they are respectively attached, form a heterocyclic ring;

R$^3$ is independently selected from hydrogen, OH, NH$_2$, nitro, CN, amide, carboxyl, C$_1$-C$_7$ alkoxy, C$_1$-C$_7$ alkyl, C$_1$-C$_7$ haloalkyl, C$_1$-C$_7$ haloalkyloxy, C$_1$-C$_7$ hydroxyalkyl, C$_1$-C$_7$ alkenyl, C$_1$-C$_7$ alkyl—C(=O)O—, C$_1$-C$_7$ alkyl—C(=O)—, C$_1$-C$_7$ alkynyl, halo, hydroxyalkoxy, C$_1$-C$_7$ alkyl—NHSO$_2$—, C$_1$-C$_7$ alkyl—SO$_2$NH—, C$_1$-C$_7$ alkylsulfonyl, C$_1$-C$_7$ alkylamino and di(C$_1$-C$_7$) alkylamino;

R$^4$ and R$^6$ are independently of each other hydrogen, OH, NR$^7$R$^8$, halo or substituted or unsubstituted C$_1$-C$_4$ alkyl, substituted or unsubstituted C$_1$-C$_4$ alkenyl, substituted or unsubstituted C$_1$-C$_4$ alkynyl, substituted or unsubstituted cycloalkyl, substituted or unsubstituted heteroaryl, substituted or unsubstituted heterocyclic or substituted or unsubstituted aryl;

or R$^4$ and R$^6$ together with the Y atom to which they are attached form a heterocyclic or carbocyclic ring;

R$^5$ is independently selected from hydrogen, OH, NH$_2$, nitro, CN, amide, carboxyl, C$_1$-C$_7$ alkoxy, C$_1$-C$_7$ alkyl, C$_1$-C$_7$ haloalkyl, C$_1$-C$_7$ haloalkyloxy, C$_1$-C$_7$ hydroxyalkyl, C$_1$-C$_7$ alkenyl, C$_1$-C$_7$ alkyl—C(=O)O—, C$_1$-C$_7$ alkyl—C(=O)—, C$_1$-C$_7$ alkynyl, halo, hydroxyalkoxy, C$_1$-C$_7$ alkyl—NHSO$_2$—, C$_1$-C$_7$ alkyl—SO$_2$NH—, C$_1$-C$_7$ alkylsulfonyl, C$_1$-C$_7$ alkylamino, di(C$_1$-C$_7$)alkylamino and L$^2$-R$^9$, wherein R$^9$ is substituted or unsubstituted heteroaryl, substituted or unsubstituted heterocyclic, substituted or unsubstituted aryl, or substituted or unsubstituted C$_3$-C$_8$ cycloalkyl, L$^2$ is selected from a bond, C$_1$-C$_4$ alkylene, C$_1$-C$_4$ alkynyl, C$_1$-C$_4$ alkenyl, —O—, —S—, —N—, —C(=O)NH—, —NHC(=O)—, —NHC(=O)NH—, —SO$_2$NH—, —NHSO$_2$—, —SO$_2$—, —C(=O)— and —C(=O)O—;

R$^7$ and R$^8$ are independently selected from hydrogen, substituted or unsubstituted C$_1$-C$_{10}$ alkyl, substituted or unsubstituted cycloalkyl, substituted or unsubstituted heteroaryl, substituted or unsubstituted heterocyclic and substituted or unsubstituted aryl;

Ring A is a 5- to 6- membered heteroaryl or 6-membered aryl;

Ring B is heteroaryl or aryl;

n is 0, 1, 2, 3 or 4;

p is 1, 2, 3 or 4;

t is 1, 2, 3 or 4;

L$^1$ is (CH$_2$)$_r$, ethenyl or cyclopropyl, wherein r is 0, 1 or 2;

X is NH$_2$;

Y is C or N;

With the proviso that Ring A is not tetrahydro-dioxo-pyrimidinyl;

or a stereoisomer or pharmaceutically acceptable salt thereof.

6. The compound of claim 5, wherein R$^1$ and R$^2$ are independently selected from OH, NR$^7$R$^8$, substituted or unsubstituted $C_1$-$C_4$ alkyl, substituted or unsubstituted $C_1$-$C_4$ alkoxy, substituted or unsubstituted heteroaryl and substituted or unsubstituted aryl;

or $R^1$ and $R^2$ together with the phosphorous atom to which they are attached form a phosphorous-containing heterocyclic ring;

$R^3$ is independently selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl—C(=O)O—, $C_1$-$C_7$ alkyl—C(=O)—, $C_1$-$C_7$ alkynyl, halo, hydroxyalkoxy, $C_1$-$C_7$ alkyl—NHSO$_2$—, $C_1$-$C_7$ alkyl—SO$_2$NH—, $C_1$-$C_7$ alkylsulfonyl, $C_1$-$C_7$ alkylamino and di($C_1$-$C_7$) alkylamino;

$R^4$ and $R^6$ are independently of each other hydrogen, OH, $NH_2$, halo or unsubstituted $C_1$-$C_4$ alkyl;

or $R^4$ and $R^6$ together with the Y atom to which they are attached form a heterocyclic or carbocyclic ring;

$R^5$ is independently selected from hydrogen, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl—C(=O)O—, $C_1$-$C_7$ alkyl—C(=O)—, $C_1$-$C_7$ alkynyl, halo, hydroxyalkoxy, $C_1$-$C_7$ alkyl—NHSO$_2$—, $C_1$-$C_7$ alkyl—SO$_2$NH—, $C_1$-$C_7$ alkylsulfonyl, $C_1$-$C_7$ alkylamino, di($C_1$-$C_7$)alkylamino and $L^2$-$R^9$, wherein $R^9$ is substituted or unsubstituted heteroaryl, or substituted or unsubstituted aryl, $L^2$ is selected from a bond, $C_1$-$C_4$ alkylene, $C_1$-$C_4$ alkynyl, $C_1$-$C_4$ alkenyl, —O—, —S—, —N—, —C(=O)NH—, —NHC(=O)—, —NHC(=O)NH—, —SO$_2$NH—, —NHSO$_2$—, —SO$_2$—, —C(=O)—and —C(=O)O—;

$R^7$ and $R^8$ are independently selected from hydrogen, substituted or unsubstituted $C_1$-$C_4$ alkyl, substituted or unsubstituted heteroaryl and substituted or unsubstituted aryl;

Ring A is a 5- to 6- membered monocyclic heteroaryl or 6-membered monocyclic aryl;

Ring B is heteroaryl or aryl;

n is 0, 1, 2, 3 or 4;

p is 1, 2, 3 or 4;

t is 1, 2, 3 or 4;

$L^1$ is (CH$_2$)$_r$, ethenyl or cyclopropyl, wherein r is 0, 1 or 2;

X is $NH_2$;

Y is C or N;

With the proviso that Ring A is not tetrahydro-dioxo-pyrimidinyl;

or a stereoisomer or pharmaceutically acceptable salt thereof.

7. The compound of claim 3, represented by the Formula IA:

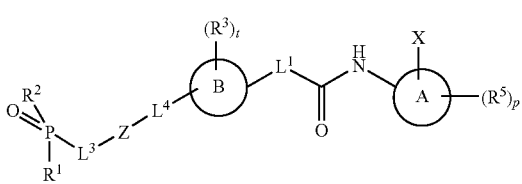

IA

Ring A is phenyl, pyridyl or pyrimidinyl;
Ring B is heteroaryl or aryl;
$R^1$ and $R^2$ are independently selected from —OR, unsubstituted $C_1$-$C_{10}$ alkyl, unsubstituted $C_3$-$C_{10}$ cycloalkyl, —(CR$^a{}_2$)$_r$R$^9$ and —O(CR$^a{}_2$)$_r$R$^9$;

$R^3$ is hydrogen;

$R^4$ and $R^6$ are independently of each other hydrogen, —OR, —NH$_2$, halo, —CN, —C(O)NH$_2$, —NH$_2$C(O)R, —C(O)OR, —P(O)(OR)$_2$, oxo, unsubstituted $C_1$-$C_6$ alkyl;

$R^5$ is L2-R9;

$R^7$ is selected from hydrogen, $C_1$-$C_7$ alkyl, —C(O)O—$C_1$-$C_7$alkyl, —P(O)CR$^a{}_2$, —P(O)(OR)$_2$, —(CR$^a{}_2$)$_r$heteroaryl, —(CR$^a{}_2$)$_r$heterocyclic, —(CR$^a{}_2$)$_r$ $C_3$-$C_8$ cycloalkyl and —(CR$^a{}_2$)$_r$aryl, where alkyl, heteroaryl, heterocyclic, aryl or cycloalkyl is optionally substituted with at least one $R^{11}$;

$R^9$ is independently selected from hydrogen, $C_1$-$C_7$ alkyl, heteroaryl and aryl, where heteroaryl, aryl or alkyl is optionally substituted with at least one $R^{11}$;

$R^{11}$ is independently selected from $C_1$-$C_7$ alkyl, halo, haloalkyl, OH and $C_1$-$C_7$ alkoxy;

R is independently H, $C_1$-$C_7$ alkyl, or $C_3$-$C_{10}$ cycloalkyl, where alkyl or cycloalkyl is optionally substituted with at least one $R^{11}$;

$R^a$ is independently selected from H and $C_1$-$C_7$ alkyl, where $C_1$-$C_7$ alkyl is optionally substituted with at least one $R^{11}$;

$L^1$ is (CH$_2$)$_r$ or ethenyl;

$L^2$ is a bond;

$L^3$ is a bond, —(CR$^a{}_2$)$_r$C(O)NR$^7$—, —(CR$^a{}_2$)$_r$NR$^7$C(O)—, —(CR$^a{}_2$)$_r$NR$^7$C(O)NR$^7$—, —(CR$^a{}_2$)$_r$OC(O)NR$^7$—, —(CR$^a{}_2$)$_r$NR$^7$C(O)O—, —(CR$^a{}_2$)$_r$NR$^7$— or —(CR$^4$R$^6$)$_n$—;

$L^4$ is a bond or —(CR$^4$R$^6$)$_n$—;

X is $NH_2$;

Z is a bond;

n is 0, 1 or 2;

p is 1;

r is independently 0, 1, 2 or 3;

t is 1, 2, 3, or 4;

or a stereoisomer or pharmaceutically acceptable salt thereof.

8. The compound of claim 7, represented by Formula IB,

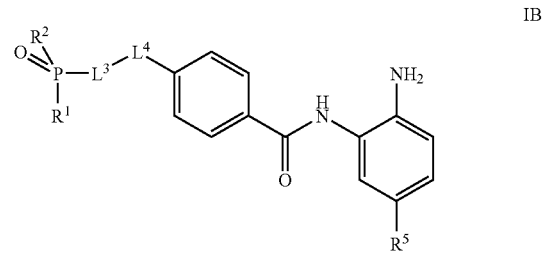

IB $R^1$ and $R^2$ are independently selected from —OR and unsubstituted $C_1$-$C_4$ alkyl;

$R^4$ and $R^6$ are hydrogen;

$R^5$ is L$^2$-R$^9$;

$R^7$ is selected from hydrogen, $C_1$-$C_7$ alkyl, —C(O)O—$C_1$-$C_7$alkyl, —P(O)CR$^a{}_2$, —P(O)(OR)$_2$, —(CR$^a{}_2$)$_r$heteroaryl, —(CR$^a{}_2$)$_r$heterocyclic, —(CR$^a{}_2$)$_r$ $C_3$-$C_8$ cycloalkyl and —(CR$^a{}_2$)$_r$aryl, where alkyl, heteroaryl, heterocyclic, aryl or cycloalkyl is optionally substituted with at least one $R^{11}$;

$R^9$ is independently selected from hydrogen, heteroaryl and aryl, where heteroaryl or aryl is optionally substituted with at least one $R^{11}$;

$R^a$ is independently selected from H and unsubstituted $C_1$-$C_4$ alkyl;

R is unsubstituted $C_1$-$C_4$ alkyl;
$L^3$ is —$(CR^a_2)_rC(O)NR^7$—, —$(CR^a_2)_rOC(O)NR^7$—, or —$(CR^a_2)_rNR^7$—;
$L^4$ is a bond or —$(CR^4R^6)_n$—;
n is 0, 1 or 2;
r is independently 0, 1, 2 or 3;
or a stereoisomer or pharmaceutically acceptable salt thereof.

9. The compound of claim 7, wherein

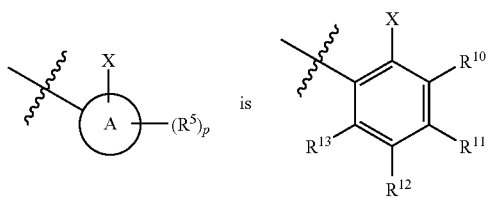

$R^{10}$, $R^{11}$, and $R^{13}$ are independently of each other hydrogen or fluoro;
$R^{12}$ is hydrogen, substituted or unsubstituted phenyl or substituted or unsubstituted thienyl and X is amino.

10. The compound of claim 7, wherein the

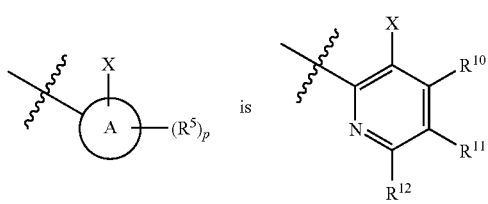

$R^{10}$ and $R^{11}$ are independently of each other hydrogen or fluoro;
$R^{12}$ is hydrogen, substituted or unsubstituted phenyl or substituted or unsubstituted thienyl and X is amino.

11. The compound of claim 9 or 10, wherein $R^{12}$ is

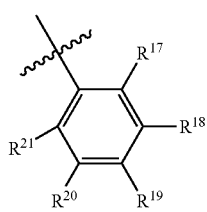

$R^{17}$ and $R^{21}$ are independently selected from hydrogen and fluoro;
$R^{18}$, $R^{19}$ or $R^{20}$ are independently selected from hydrogen, halo, methyl, methoxy and halomethyl.

12. The compound of claim 9 or 10, wherein $R^{12}$ is

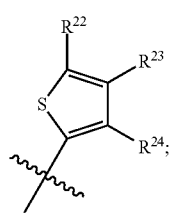

$R^{22}$, $R^{23}$ and $R^{24}$ are independently selected from hydrogen, methyl, amino, hydroxyl, and halo.

13. The compound of claim 9 or 10, wherein $R^{12}$ is

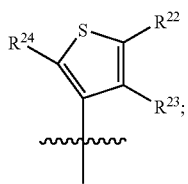

$R^{22}$, $R^{23}$ and $R^{24}$ are independently selected from hydrogen, methyl, amino, hydroxyl and halo.

14. The compound of claim 12, wherein Ring B is selected from phenyl, benzothiophenyl, benzofuranyl, thiazolyl, benzothiazolyl, furanyl, pyridyl, pyrimidyl, quinolinyl, thiophenyl, benzodioxyl, benzooxadiazolyl, quinoxalinyl, benzotriazolyl, benzoimidazolyl and benzooxazolyl.

15. The compound of claim 1 selected from:
Diethyl [4-({[2-amino-5-(2-thienyl)phenyl]amino}carbonyl)phenyl]phosphonate;
Diethyl [4 -({[2 -amino-5 -(3 -thienyl)phenyl]amino}carbonyl)phenyl]phosphonate;
Diethyl (4- {[(4-aminobiphenyl-3-yl)amino]carbonyl}phenyl)phosphonate;
Diethyl(4- {[(4-amino- 1 -phenyl-1H-pyrazol-3 -yl)amino]carbonyl}phenyl)phosphonate;
Ethyl hydrogen [4-({[2-amino-5-(2-thienyl)phenyl]amino}carbonyl)phenyl]phosphonate;
Ethyl hydrogen (4- {[(4-amino-l-phenyl-1H-pyrazol-3 -yl)amino]carbonyl}phenyl) phosphonate;
Methyl [4-({[2-amino-5-(2-thienyl)phenyl]amino}carbonyl)phenyl]phenylphosphinate;
Methyl [4-({[2-amino-5 -(3 -thienyl)phenyl]amino }carbonyl)phenyl]phenylphosphinate;
Methyl (4- {[(4-aminobiphenyl-3-yl)amino]carbonyl}phenyl)phenylphosphinate;
Ethyl [4 -({[2 -amino-5 -(2 -thienyl)phenyl]amino}carbonyl)phenyl]methylphosphinate;
Ethyl [4-({[2-amino-5-(2-thienyl)phenyl]amino}carbonyl)phenyl]phenylphosphinate;
Ethyl (4- {[(4-aminobiphenyl-3-yl)amino]carbonyl}phenyl)methylphosphinate;
Methyl [4-({[2-amino-5 -(2-thienyl)phenyl]amino}carbonyl)phenyl]methylphosphinate;
2-(ethylsulfonyl)ethyl [4-({[2-amino-5-(2-thienyl)phenyl]amino}carbonyl)phenyl]methylphosphinate;
3-hydroxy-3-methylbutyl [4-({[2-amino-5-(2-thienyl)phenyl]amino}carbonyl)phenyl]methylphosphinate;
Cyclobutyl [4-({[2-amino-5-(2-thienyl)phenyl]amino}carbonyl)phenyl]methylphosphinate;
Ethyl [4-({[2-amino-5-(2-thienyl)phenyl]amino}carbonyl)phenylethylphosphinate;
Ethyl [5-({[2-amino-5-(2-thienyl)phenyl]amino}carbonyl)pyridin-2-yl]methylphosphinate;
N-(2-Amino-5-thiophen-2-yl-phenyl)-4-(diisopropylphosphinoyl)-benzamide;
N42-Amino-5-(2-thienyl)phenyl]-4-[(1-methyl-4-oxido-1,4-azaphosphinan-4-yl)methyl]benzamide;
N-(2-Amino-5-thiophen-2-yl-phenyl)-4-(dimethyl-phosphinoyl)-benzamide;
N-(2-Amino-5-phen-2-yl-phenyl)-4-(dimethyl-phosphinoyl)-benzamide;
[4-(2-Amino-5-thiophen-2-yl-phenylcarbamoyl)-benzyl]-phosphonic acid dimethyl ester;

[4-(2-Amino-5-thiophen-2-yl-phenylcarbamoyl)-benzyl]-phosphonic acid diethyl ester;
[4-(2-Amino-5-thiophen-2-yl-phenylcarbamoyl)-benzyl]-phosphonic acid monomethyl ester;
[4-(2-Amino-5-thiophen-2-yl-phenylcarbamoyl)-benzyl]-phosphonic acid monoethyl ester;
[4-(4-Amino-1-phenyl-1H-pyrazol-3-ylcarbamoyl)-benzyl]-phosphonic acid diethyl ester;
[4-(2-Amino-5-thiophen-3-yl-phenylcarbamoyl)-benzyl]-phosphonic acid diethyl ester;
[4-(2-Amino-5-thiophen-2-yl-phenylcarbamoyl)-benzyl]-phosphonic acid diethyl ester;
N2-amino-5-(2-thienyl)phenyl]-4-[(5,5-dimethyl-2-oxido-1,3,2-dioxaphosphinan-2-yl)methyl]benzamide;
Diisopropyl [4-({[2-amino-5-(2-thienyl)phenyl]amino}carbonyl)benzyl]phosphonate;
Diethyl [3-({[2-amino-5-(2-thienyl)phenyl]amino}carbonyl)benzyl]phosphonate;
Methyl tetrahydro-2H-pyran-4-ylmethyl[4-({[2-amino-5-(2-thienyl)phenyl]amino}carbonyl) benzyl]phosphonate;
Methyl P-[4-({[2-amino-5-(2-thienyl)phenyl]amino}carbonyl)benzyl]-N -1,3-thiazo 1-2-ylphosphonamidoate;
Ethyl {[[4-({[2-amino-5-(2-thienyl)phenyl]amino}carbonyl)benzyl](methoxy)phosphoryl]oxy}acetate;
Diethyl (4- {[(4-aminobiphenyl-3-yl)amino]carbonyl}benzyl)phosphonate;
Methyl pyridin-3-ylmethyl[4-({[2-amino-5-(2-thienyl)phenyl]amino}carbonyl)benzyl]phosphonate;
Methyl P-[4-({[2-amino-5 -(2-thienyl)phenyl]amino 1 carbonyl)benzyl]- N-benzylphosphonamidoate;
Methyl P-[4-({[2-amino-5 -(2-thienyl)phenyl]amino 1 carbonyl)benzyl]-N-(pyridin-3-ylmethyl) phosphonamidoate;
Dib enzyl [4-({[2-amino-5 -(2-thienyl)phenyl]amino}carbonyl)benzyl]phosphonate;
2-amino-2-oxoethyl methyl[4-({[2-amino-5 -(2-thienyl)phenyl]amino 1 carbonyl)benzyl]phosphonate;
2-amino-2-methylpropyl methyl[4-({[2-amino-5 -(2-thienyl)phenyl]amino 1 carbonyl)benzyl]phosphonate;
3 -hydroxy-3 -methylbutyl methyl[4-({[2-amino-5 -(2-thienyl)phenyl]amino 1 carbonyl)benzyl]phosphonate;
Tetraethyl {[4-({[2-amino-5 -(2-thienyl)phenyl]amino 1 carbonyl)phenyl]methylene}bis (phosphonate);
Diethyl [[4-({[2-amino-5-(2-thienyl)phenyl]amino}carbonyl)phenyl](cyano)methyl]phosphonate;
Methyl [4-({[2-amino-5-(2-thienyl)phenyl]amino}carbonyl)phenyl](diethoxyphosphoryl)acetate;
Methyl 3-[4-({[2-amino-5 -(2-thienyl)phenyl]amino }carbonyl)phenyl]-2-(dimethoxyphosphoryl) propanoate;
Diethyl {2-[4-({[2-amino-5-(2-thienyl)phenyl]amino}carbonyl)phenyl]-1-cyanoethyl}phosphonate;
Tetraethyl {2- [4-({[2 -amino-5 -(2-thienyl)phenyl]amino 1 carbonyl)phenyl]ethane-1 , 1 -diyl }bis(phosphonate);
Diethyl {2-amino- 1 - [4-({[2-amino-5 -(2-thienyl)phenyl]amino 1 carbonyl)b enzyl]-2-oxoethyl }phosphonate;
[4-(2-Amino-5-thiophen-2-yl-phenylcarbamoyl)-benzyl]-phenyl-phosphinic acid methyl ester;
[4-(2-Amino-5-thiophen-2-yl-phenylcarbamoyl)-benzyl]-phenyl-phosphinic acid;
[4-(2-Amino-5-thiophen-3-yl-phenylcarbamoyl)-benzyl]-phenyl-phosphinic acid methyl ester;
[4-(4-Amino-l-phenyl-1H-pyrazol-3-ylcarbamoyl)-benzyl]-phenyl-phosphinic acid methyl ester;
[4-(2-Amino-5-thiophen-2-yl-phenylcarbamoyl)-benzyl]-methyl-phosphinic acid ethyl ester;
[4-(4-Amino-biphenyl-3-ylcarbamoyl)-benzyl]-methyl-phosphinic acid ethyl ester;
[4-(4-Amino-biphenyl-3-ylcarbamoyl)-benzyl]-methyl-phosphinic acid ethyl ester;
[4-(4-Amino-biphenyl-3-ylcarbamoyl)-benzyl]-methyl-phosphinic acid ethyl ester;
[4-(2-Amino-5-thiophen-2-yl-phenylcarbamoyl)-benzyl]-methyl-phosphinic acid cyclobutyl ester;
Methyl [4-({[2-amino-5-(2-thienyl)-phenyl]amino}-carbonyl)benzyl]-methylphosphinate;
Isopropyl [4-({[2-amino-5 -(2-thienyl)-p henyl]amino }-c arbonyl)b enzyl]-methylpho sphinate;
N-[2-Amino-5 -(2-thienyl)phenyl]-4-({methyl [(pyridin-3 -ylmethyl)amino]-phosphoryl}methyl)-benzamide;
Pyridin-3 -ylmethyl [4-({[2-amino-5 -(2-thienyl)phenyl]amino }-carbonyl)benzyl]methyl-phosphinate;
Methyl [4-({[2-amino-5 -(2-thienyl)-phenyl]amino }-carbonyl)benzyl]-ethylphosphinate;
Ethyl [4-({[2-amino-5 -(2-thienyl)-phenyl]amino}-carbonyl)benzyl]-ethylphosphinate;
Isopropyl [4-({[2-amino-5 -(2-thienyl)-phenyl]amino }-carbonyl)benzyl]-ethylphosphinate;
Cyclobutyl [4-({[2-amino-5 -(2-thienyl)-phenyl]amino }-carbonyl)benzyl]-ethylphosphinate;
N-[2-Amino-5 -(2-thienyl)phenyl]-4-({ethyl [(pyridin-3 -ylmethyl)amino]-phosphoryl}methyl)-benzamide;
Pyridin-3 -ylmethyl [4-({[2-amino-5 -(2-thienyl)phenyl]amino }-carbonyl)benzyllethyl-phosphinate;
Cyclobutyl [4-({[2-amino-5-(2-thienyl)phenyl]amino}carbonyl)benzyl]phenylphosphinate;
Methyl [4-({[2-amino-5-(2-thienyl)phenyl]amino}carbonyl)benzyl](4-fluorophenyl)phosphinate;
Methyl [3 -({[2-amino-5 -(2-thienyl)phenyl]amino }carbonyl)benzyl]phenylphosphinate;
Isopropyl [3 -({[2-amino-5 -(2-thienyl)phenyl]amino }carbonyl)benzyl]methylphosphinate;
Methyl [3 -({[2-amino-5 -(2-thienyl)phenyl]amino }carbonyl)benzyl]ethylphosphinate;
Ethyl [4-({[2-amino-5 -(2-thienyl)phenyl]amino}carbonyl)benzyl]phenylphosphinate;
Isopropyl [4-({[2-amino-5-(2-thienyl)phenyl]amino}carbonyl)benzyl]phenylphosphinate;
2,2,2-trifluoroethyl[4-({[2-amino-5-(2-thienyl)phenyl]amino}carbonyl)benzyl]phenylphosphinate;
Ethyl [4-({[2-amino-5 -(2-thienyl)phenyl]amino}carbonyl)benzyl]isopropylphosphinate;
Ethyl [4-({[2-amino-5 -(2-thienyl)phenyl]amino}carbonyl)benzyl]cyclopropylphosphinate;
3 -hydroxy-3 -methylbutyl [4-({[2-amino-5 -(2-thienyl)phenyl]amino}carbonyl)benzyl]phenylphosphinate;
2-amino-2-methylpropyl[4-({[2-amino-5 -(2-thienyl)phenyl]amino}carbonyl)benzyl]phenylphosphinate;
2-amino-2-oxoethyl[4-({[2-amino-5 -(2-thienyl)phenyl]amino }carbonyl)benzyl]phenylphosphinate;
Methyl [4-({[2-amino-5-(2-thienyl)phenyl]amino}carbonyl)benzyl]cyclopropylphosphinate;
Methyl (S)- [4-({[2-amino-5 -(2-thienyl)phenyl]amino }carbonyl)benzyl]methylphosphinate;
Methyl (R)-[4-({[2-amino-5-(2-thienyl)phenyl]amino}carbonyl)benzyl]methylphosphinate;
Methyl (4- {[(4-aminobiphenyl-3 -yl)amino]carbonyl}benzyl)methylphosphinate;
3 -hydroxy-3 -methylbutyl [4-({[2-amino-5-(2-thienyl)phenyl]amino}carbonyl)benzyl]ethylphosphinate;

3-hydroxy-3-methylbutyl [4-({[2-amino-5-(2-thienyl)phenyl]amino}carbonyl)benzyl]methylphosphinate;

2-(ethylsulfonyl)ethyl[4-({[2-amino-5-(2-thienyl)phenyl]amino}carbonyl)benzyl]methylphosphinate;

Diethyl {[5-({[2-amino-5-(2-thienyl)phenyl]amino}carbonyl)pyridin-2-yl]methyl}phosphonate;

Diethyl {[5-({[2-amino-5-(3-thienyl)phenyl]amino}carbonyl)pyridin-2-yl]methyl}phosphonate;

Methyl {[5-({[2-amino-5-(2-thienyl)phenyl]amino}carbonyl)pyridin-2-yl]methyl}phenylphosphinate;

Methyl {[5-({[2-amino-5-(3-thienyl)phenyl]amino}carbonyl)pyridin-2-yl]methyl}phenylphosphinate;

{[4-(2-Amino-5-thiophen-2-yl-phenylcarbamoyl)-phenyl]-hydroxy-methyl}-phosphonic acid dimethyl ester;

{1[4-(2-Amino-5-thiophen-2-yl-phenylcarbamoyl)-phenyl]-1-fluoro-ethyl}-phosphonic acid dimethyl ester;

{1-[4-(2-Amino-5-thiophen-3-yl-phenylcarbamoyl)-phenyl]-1-fluoro-ethyl}-phosphonic acid dimethyl ester;

{1-[4-(4-Amino-biphenyl-3-ylcarbamoyl)-phenyl]-1-fluoro-ethyl}-phosphonic acid dimethyl ester;

{[4-(2-Amino-5-thiophen-3-yl-phenylcarbamoyl)-phenyl]-hydroxy-methyl}-phosphonic acid dimethyl ester;

{[4-(4-Amino-biphenyl-3-ylcarbamoyl)-phenyl]-hydroxy-methyl}-phosphonic acid dimethyl ester;

{[4-(2-Amino-5-thiophen-2-yl-phenylcarbamoyl)-phenyl]-fluoro-methyl}-phosphonic acid dimethyl ester;

{Amino-[4-(2-amino-5-thiophen-2-yl-phenylcarbamoyl)-phenyl]-methyl}-phosphonic acid dimethyl ester;

{[4-(2-Amino-5-thiophen-2-yl-phenylcarbamoyl)-phenyl]-hydroxy-methyl}-phenyl-phosphinic acid ethyl ester;

{1- [4-(2-Amino-5-thiophen-2-yl-phenylcarbamoyl)-phenyl]-1-fluoro-ethyl}-phenyl-phosphinic acid methyl ester;

{1-[4-(2-Amino-5-thiophen-3-yl-phenylcarbamoyl)-phenyl]-1-fluoro-ethyl}-phenyl-phosphinic acid methyl ester;

{1-[4-(4-Amino-biphenyl-3-ylcarbamoyl)-phenyl]-1-fluoro-ethyl}-phenyl-phosphinic acid methyl ester;

{[4-(2-Amino-5-thiophen-3-yl-phenylcarbamoyl)-phenyl]-hydroxy-methyl}-phenyl-phosphinic acid ethyl ester;

{[4-(4-Amino-biphenyl-3-ylcarbamoyl)-phenyl]-hydroxy-methyl}-phenyl-phosphinic acid ethyl ester;

N-(2-Amino-5-thiophen-2-yl-phenyl)-4-(diisopropyl-phosphinoylmethyl)-benzamide;

N-(2-Amino-5-thiophen-2-yl-phenyl)-4-(diethyl-phosphinoylmethyl)-benzamide;

N-(2-Amino-5-thiophen-2-yl-phenyl)-4-(dimethyl-phosphinoylmethyl)-benzamide;

N-[2-Amino-5-(2-thienyl)phenyl]-3-[(diethylphosphoryl)methyl]benzamide;

N2-amino-5-(2-thienyl)phenyl]-4-[2-(dimethylphosphoryl)ethyl]benzamide;

Ethyl- {2-[4-({[2-amino-5-(2-thienyl)phenyl]amino}carbonyl)phenyl]ethyl}methyl phosphinate;

N-[2-Amino-5-(2-thienyl)phenyl]-4-[(3-methyl-3-oxido-2,4-dioxa-9-aza-3-phosphaspiro[5.5]undec-9-yl)methyl]benzamide;

N-[2-Amino-5-(2-thienyl)phenyl]-4-[(3-methyl-3-oxido-2,4-dioxa-9-aza-3-phosphaspiro[5.5]undec-9-yl)carbonyl]benzamide;

N-[2-Amino-5-(2-thienyl)phenyl]-6-(3-methyl-3-oxido-2,4-dioxa-9-aza-3-phosphaspiro[5.5]undec-9-yl) nicotinamide;

N-[2-amino-5-(2-thienyl)phenyl]-6- {2-[bis(dimethylamino)phosphoryl]-2,8-diazaspiro[4.5]dec-8-yl}nicotinamide;

N-[2-Amino-5-(2-thienyl)phenyl]-4-[(4-oxido-4-phenyl-1,4-azaphosphinan-l-yl)methyl]benzamide;

N-[2-Amino-5-(2-thienyl)phenyl]-4-[(4-oxido-4-phenyl-1,4-azaphosphinan-l-yl)carbonyl]benzamide;

N-[2-Amino-5-(2-thienyl)phenyl]-6-(4-oxido-4-phenyl-1,4-azaphosphinan-l-yl)nicotinamide;

N-[2-Amino-5-(2-thienyl)phenyl]-4-[(4-ethyl-4-oxido-1,4-azaphosphinan-l-yl)methyl]benzamide;

N-[2-Amino-5-(2-thienyl)phenyl]-4-[(4-ethyl-4-oxido-1,4-azaphosphinan-l-yl)carbonyl]benzamide;

N-[2-Amino-5-(2-thienyl)phenyl]-6-(4-ethyl-4-oxido-1,4-azaphosphinan-l-yl)nicotinamide;

N-(4-aminobiphenyl-3-yl)-4-[(4-oxido-4-phenyl-1,4-azaphosphinan-l-yl)methyl]benzamide;

N42-amino-5-(2-thienyl)phenyl]-4-[2-(4-oxido-4-phenyl-1,4-azaphosphinan-l-yl)ethyl]benzamide;

N42-amino-5-(2-thienyl)phenyl]-4-[2-(4-ethyl-4-oxido-1,4-azaphosphinan-l-yl)ethyl]benzamide;

N42-amino-5-(2-thienyl)phenyl]-4-2-(4-oxido-4-phenyl-1,4-azaphosphinan-l-yl)-2-oxoethyl]benzamide;

N42-amino-5-(2-thienyl)phenyl]-4-2-(4-ethyl-4-oxido-1,4-azaphosphinan-l-yl)-2-oxoethyl]benzamide;

N-[2-amino-5-(2-thienyl)phenyl]-4- {[[2-(dimethylphosphoryl)ethyl](methyl)amino]methyl}benzamide;

N-[2-amino-5-(2-thienyl)phenyl]-4- {[[2-(diisopropylphosphoryl) ethyl](methyl) amino]methyl}benzamide;

N-[2-amino-5-(2-thienyl)phenyl]-4- {[[2-(diphenylphosphoryl) ethyl](methyl)amino]ethyl}benzamide;

N42-amino-5-(2-thienyl)phenyl]-6-[[2-(dimethylphosphoryl) ethyl](methyl)amino]nicotinamide;

N42-amino-5-(2-thienyl)phenyl]-6-[[2-(diisopropylphosphoryl) ethyl](methyl)amino]nicotinamide;

N42-amino-5-(2-thienyl)phenyl]-6-[[2-(diphenylphosphoryl) ethyl](methyl)amino]nicotinamide;

N-[2-amino-5-(2-thienyl)phenyl]-N- [2-(dimethylphosphoryl)ethyl]-N-methylterephthalamide;

N-[2-amino-5-(2-thienyl)phenyl]-N-[2-(diisopropylphosphoryl) ethyl]-N-methylterephthalamide;

N-[2-amino-5-(2-thienyl)phenyl]-N- [2-(diphenylphosphoryl)ethyl]-N-methylterephthalamide;

N-[2-amino-5-(2-thienyl)phenyl]-6- {[2-(diisopropylphosphoryl) ethyl]amino}nicotinamide;

N42-amino-5-(2-thienyl)phenyl]-N-[2-(diisopropylphosphoryl) ethyl]terephthalamide;

N42-amino-5-(2-thienyl)phenyl]-4-({[2-(diisopropylphosphoryl) ethyl]amino}methyl) benzamide;

N-[2-amino-5-(2-thienyl)phenyl]-N-[2-(dimethylphosphoryl)ethyl]terephthalamide;

N42-amino-5-(2-thienyl)phenyl]-4-({[2-(dimethylphosphoryl) ethyl]amino}methyl) benzamide;

Methyl (4- {[(4-aminobiphenyl-3-yl)amino]carbonyl}benzyl)[2-(dimethylphosphoryl)ethyl]carbamate;

Diethyl {1 - [5-({[2-amino-5-(2-thienyl)phenyl]amino}carbonyl)pyridin-2-yl]piperidin-4-yl}phosphonate;

Diethyl (1- {[4-({[2-amino-5-(2-thienyl)phenyl]amino}carbonyl)phenyl]methyl}piperidin-4-yl) phosphonate;

Diethyl (1- {[4-({[2-amino-5-(2-thienyl)phenyl]amino}carbonyl)phenyl]carbonyl}piperidin-4-yl) phosphonate;

[4-({[2-amino-5-(2-thienyl)phenyl]amino}carbonyl)phenyl]methyl dimethylphosphinate;

2-[4-({[2-amino-5-(2-thienyl)phenyl]amino}carbonyl)phenyl]ethyl ethyl methylphosphonate;
[4-({[2-amino-5-(2-thienyl)phenyl]amino}carbonyl)phenyl]methyl ethylmethylphosphonate;
[4-({[2-amino-5-(2-thienyl)phenyl]amino}carbonyl)phenyl]methyl methylphenylphosphonate;
N42-amino-5-(2-thienyl)phenyl]-4-({[(4R, 5 R)-4,5-dimethyl-2-oxido-1,3,2-dioxaphospholan-2-yl]oxy}methyl)benzamide;
4-({[2-amino-5-(2-thienyl)phenyl]amino}carbonyl)benzyl dimethylphosphate;
1-[4-({[2-amino-5-(2-thienyl)phenyl]amino}carbonyl)phenyl]ethyl ethyl methylphosphonate;
1-[4-({[2-amino-5-(2-thienyl)phenyl]amino}carbonyl)phenyl]ethyl methyl methylphosphonate;
1-[4-({[2-amino-5-(2-thienyl)phenyl]amino}carbonyl)phenyl]ethyl methyl phenylphosphonate;
4-({[2-amino-5-(2-thienyl)phenyl]amino}carbonyl)benzyl ethylphenylphosphonate;
2-[4-({[2-amino-5-(2-thienyl)phenyl]amino}carbonyl)phenyl]ethyl dimethylphosphinate;
2-[4-({[2-amino-5-(2-thienyl)phenyl]amino}carbonyl)phenyl]ethyl methyl methylphosphonate;
1-[4-({[2-amino-5-(2-thienyl)phenyl]amino}carbonyl)phenyl]-2,2,2-trifluoro-1-(trifluoromethyl) ethyl dimethylphosphinate;
4-({[2-amino-5-(2-thienyl)phenyl]amino}carbonyl)phenyl dimethylphosphinate;
(4-{[(4-aminobiphenyl-3-yl)amino]carbonyl}phenyl) methyldimethylphosphinate;
1-[4-({[2-amino-5-(2-thienyl)phenyl]amino}carbonyl)phenyl]ethyldiethylphosphinate;
4-({[2-amino-5-(2-thienyl)phenyl]amino}carbonyl)benzyldiethylphosphinate;
1-[4-({[2-amino-5-(2-thienyl)phenyl]amino}carbonyl)phenyl]ethyldimethylphosphinate;
4-({[2-amino-5-(2-thienyl)phenyl]amino}carbonyl)benzyldiisopropylphosphinate;
1-[4-({[2-amino-5-(2-thienyl)phenyl]amino}carbonyl)phenyl]ethyldiisopropylphosphinate;
Dimethyl [4-({[2-amino-5-(2-thienyl)phenyl]amino}carbonyl)b enzyl]amidophosphate;
N2-amino-5-(2-thienyl)phenyl]-4-({[(4R, 5R)-4,5-dimethyl-2-oxido-1,3,2-dioxaphospholan-2-yl]amino}methyl)benzamide;
N42-amino-5-(2-thienyl)phenyl]-4-({[bis(dimethylamino)pho sphoryl]amino}methyl) benzamide;
Dimethyl [4-({[2-amino-5-(2-thienyl)phenyl]amino}carbonyl)phenyl]amidophosphate;
Diethyl [4-({[2-amino-5-(2-thienyl)phenyl]amino}carbonyl)phenyl]amidophosphate;
Dimethyl [4-({[2-amino-5-(2-thienyl)phenyl]amino}carbonyl)phenyl]amidophosphate;
Dimethyl [4-({[2-amino-5-(2-thienyl)phenyl]amino}carbonyl)phenyl]methylamidophosphate;
Dimethyl (4-{[(4-aminobiphenyl-3-yl)amino]carbonyl}phenyl)methylamidophosphate;
N42-amino-5-(2-thienyl)phenyl]-4-[bis (dimethylphosphoryl)amino]b enzamide;
Dimethyl {[({[4-({[2-amino-5-(2-thienyl)phenyl]amino}carbonyl)b enzyl]amino}carbonyl) oxy]methyl}phosphonate;
4-(dimethylphosphoryl)benzyl (4-{[(4-aminobiphenyl-3-yl)amino]carbonyl}benzyl)carbamate;
[5-(dimethylphosphoryl)pyridin-3-yl]methyl [4-({[2-amino-5-(2-thienyl)phenyl]amino}carbonyl)b enzyl]carbamate;
Diethyl ({[(4-{[(4-aminobiphenyl-3-yl)amino]carbonyl}phenyl)methyl][(methyloxy)carbonyl]amino}methyl)phosphonate;
Diethyl {[({[4-({[2-amino-5-(2-thienyl)phenyl]amino}carbonyl)benzyl]amino}carbonyl) oxy]methyl}phosphonate;
Dimethyl {[({[4-({[2-amino-5-(2-thienyl)phenyl]amino}carbonyl)b enzyl]amino}carbonyl) oxy]methyl}phosphonate;
Methyl {[({[4-({[2-amino-5-(2-thienyl)phenyl]amino}carbonyl)b enzyl]amino}carbonyl) oxy]methyl}methylphosphinate;
Ethyl {[({[4-({[2-amino-5-(2-thienyl)phenyl]amino}carbonyl)benzyl]amino}carbonyl) oxy]methyl}methylphosphinate;
Ethyl {[({[4-({[2-amino-5-(2-thienyl)phenyl]amino}carbonyl)benzyl]amino}carbonyl) oxy]methyl}ethylphosphinate;
(dimethylphosphoryl)methyl [4-({[2-amino-5-(2-thienyl)phenyl]amino}carbonyl)b enzyl]carbamate;
Diethyl (4-{[4-({[2-amino-5-(2-thienyl)phenyl]amino}carbonyl)benzoyl]amino}phenyl)phosphonate;
Diethyl [({[4-({[2-amino-5-(2-thienyl)phenyl]amino}carbonyl)phenyl]carbonyl}amino)methyl]phosphonate;
Diethyl [({[4-({[2-amino-5-(2-thienyl)phenyl]amino}carbonyl)phenyl]methyl}amino) methyl]phosphonate;
N-[2-amino-5-(2-thienyl)phenyl]-4-[(2s)-2-oxido-2-phenyl-1,3,2-dioxaphosphinan-5-yl]benzamide;
N42-amino-5-(2-thienyl)phenyl]-4-[(2r)-2-oxido-2-phenyl-1,3,2-dioxaphosphinan-5-yl]benzamide;
N42-amino-5-(2-thienyl)phenyl]-4-[(2s)-2-methyl-2-oxido-1,3,2-dioxaphosphinan-5-yl]benzamide;
N42-amino-5-(2-thienyl)phenyl]-4-[(20-2-methyl-2-oxido-1,3,2-dioxaphosphinan-5-yl]benzamide;
Dimethyl [3-((1E)-3-{[2-amino-5-(2-thienyl)phenyl]amino}-3-oxoprop-1-en-1-yl)phenyl]phosphonate;
Ethyl [3-41E)-3-{[2-amino-5-(2-thienyl)phenyl]amino}-3-oxoprop-1-en-1-yl)phenyl]methylphosphinate;
Ethyl {3-[4-({[2-({[(1, 1-dimethylethyl)oxy]carbonyl}amino)-5-(2-thienyl)phenyl]amino}carbonyl)phenyl]-3-oxopropyl}methylphosphinate; and
N42-amino-5-(2-thienyl)phenyl]-4-(2-methyl-2-oxido-1,2-oxaphospholan-5-yl)benzamide or a pharmaceutically acceptable salt or stereoisomer thereof.

16. A pharmaceutical composition comprising a pharmaceutically effective amount of the compound according to claim 1, and a pharmaceutically acceptable carrier.

17. A method for the treatment of cancer in a mammal comprising the step of administering to the mammal a therapeutically effective amount of the compound of claim 1.

\* \* \* \* \*